(12) United States Patent
Kaiser et al.

(10) Patent No.: US 12,318,439 B2
(45) Date of Patent: Jun. 3, 2025

(54) ATTENUATING VIRAL MUTATIONS IN PROTEIN GENES

(71) Applicant: BOARD OF REGENTS, THE UNIVERSITY OF TEXAS SYSTEM, Austin, TX (US)

(72) Inventors: Jaclyn Kaiser, Galveston, TX (US); Tian Wang, Galveston, TX (US); Alan Barrett, Galveston, TX (US); Kassandra Carpio, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 148 days.

(21) Appl. No.: 17/737,991

(22) Filed: May 5, 2022

(65) Prior Publication Data

US 2022/0354942 A1 Nov. 10, 2022

Related U.S. Application Data

(60) Provisional application No. 63/186,160, filed on May 9, 2021.

(51) Int. Cl.
| | |
|---|---|
| *A61K 39/12* | (2006.01) |
| *A61K 39/00* | (2006.01) |
| *A61P 31/14* | (2006.01) |
| *C07K 14/18* | (2006.01) |
| *C12N 7/00* | (2006.01) |

(52) U.S. Cl.
CPC .............. *A61K 39/12* (2013.01); *A61P 31/14* (2018.01); *C07K 14/18* (2013.01); *C12N 7/00* (2013.01); *A61K 39/00* (2013.01); *A61K 2039/5254* (2013.01); *C12N 2770/24134* (2013.01)

(58) Field of Classification Search
CPC .............. A61K 39/12; A61K 39/00; A61K 2039/5254; A61P 31/14; C07K 14/18; C12N 7/00; C12N 2770/24134
See application file for complete search history.

(56) References Cited

U.S. PATENT DOCUMENTS

| | | | | |
|---|---|---|---|---|
| 7,482,017 B2 * | 1/2009 | Barrett | .................. | C07K 14/005 |
| | | | | 435/69.1 |
| 8,017,754 B2 * | 9/2011 | Wicker | ..................... | C12N 7/00 |
| | | | | 424/199.1 |
| 2003/0148261 A1 * | 8/2003 | Fikrig | ................... | C07K 14/005 |
| | | | | 435/235.1 |
| 2006/0062803 A1 * | 3/2006 | Kinney | .................. | A61P 37/04 |
| | | | | 424/199.1 |
| 2015/0231226 A1 * | 8/2015 | Fink | .......................... | C12N 7/00 |
| | | | | 424/218.1 |
| 2021/0187092 A1 * | 6/2021 | Dhere | ...................... | C12N 7/06 |

FOREIGN PATENT DOCUMENTS

WO WO-2006134433 A1 * 12/2006 ............. A61K 39/12

OTHER PUBLICATIONS

Pybus, O. G. et al. (2012). Unifying the spatial epidemiology and molecular evolution of emerging epidemics. Proceedings of the National Academy of Sciences of the United States of America, 109(37), 15066-15071. (Year: 2012).*
Pybus, O. G. et al. (2012). Unifying the spatial epidemiology and molecular evolution of emerging epidemics. Proceedings of the National Academy of Sciences of the United States of America, 109(37). Supplementary Data. (Year: 2012).*
Gray, V. E., Hause, R. J., & Fowler, D. M. (2017). Analysis of Large-Scale Mutagenesis Data to Assess the Impact of Single Amino Acid Substitutions. Genetics, 207(1), 53-61. (Year: 2017).*
GenScript News and Blogs Posted Apr. 20, 2021, [retrieved on Dec. 12, 2023. <URL: https://www.genscript.com/protein-news/alanine-scanning-mutagenesis-a-versatile-approach-to-map-proteins-hot-spots.html> (Year: 2021).*
Heydenreich, F. M., Miljuš, T., Milić, D., & Veprintsev, D. B. (2020). High-throughput Site-directed Scanning Mutagenesis Using a Two-fragment PCR Approach. Bio-protocol, 10(1), e3484. (Year: 2020).*
Kaiser, J. A., Wang, T., & Barrett, A. D. (2017). Virulence determinants of West Nile virus: how can these be used for vaccine design ?. Future virology, 12(5), 283-295. (Year: 2017).*
Kaiser et al. 2020. Direct Submission. Submitted Aug. 4, 2020. GenBank Accession No. UNN25497.1 (Year: 2020).*
Kaiser et al. 2020. Direct Submission. Submitted Aug. 4, 2020. GenBank Accession No. UNN25505.1 (Year: 2020).*
Chancey et al., Biomed Res. Int. 2015, 1-20.
Mann et al., Int. J. Environ. Res. Public Health 2013, 10, 5111-5129.
CDC West Nile Virus—Symptoms, Diagnosis, & Treatment. Available online: URL www.cdc.gov/westnile/symptoms/index.html (accessed on Jul. 5, 2019).
CDC West Nile Virus—Statistics and Maps Available online: URL www.cdc.gov/westnile/statsmaps/index.html (accessed on Jul. 5, 2019).
Klema et al., Viruses 2015, 7, 4640-4656.
Brinton, Viruses 2013, 6, 13-53.
Zmurko et al., Rev. Med. Virol. 2015, 25, 205-223.
Li et al., BBA—Biomembr. 2015, 1848, 3150-3157.
Li et al., Angew. Chemie—Int. Ed. 2016, 55, 12068-12072.
Zou et al., J. Virol. 2014, 88, 3379-91.
Youn et al., J. Virol. 2012, 86, 7360-71.
Yu et al., Virology 2013, 446, 365-377.
Zou et al., J. Virology 2015, 89, 3471-3483.
Zou et al., J. Virol. 2015, 89, 3455-3470.
Kaufusi et al., PLoS One 2014, 9, e84040.

(Continued)

*Primary Examiner* — Janet L Andres
*Assistant Examiner* — Carey Alexander Stuart

(57) ABSTRACT

Embodiments relate to attenuated flaviviruses for use in vaccines and immunogenic compositions. Embodiments include methods for treating or preventing one or more conditions, for example flavivirus infection, using an attenuated flavivirus. In some embodiments, the provided methods and compositions involve one or more attenuated flaviviruses that are capable of inducing a protective immune response.

19 Claims, 17 Drawing Sheets

Specification includes a Sequence Listing.

(56) References Cited

OTHER PUBLICATIONS

Munoz-Jordan et al., J. Virol. 2005, 79, 8004-8013.
Wang et al., J. Virol. 2005, 79, 1934-1942.
Kakumani et al., J. Virol. 2013, 87, 8870-8883.
Grant et al., J. Virol. 2011, 85, 7775-7787.
Pletnev et al., Proc. Natl. Acad. Sci. 2002, 99, 3036-3041.
Orozco et al., J. Gen. Virol. 2012, 93, 2152-2157.
Dunster et al., Virology 1999, 318, 309-318.
Hahn et al., Proc. Natl. Acad. Sci. U. S. A. 1987, 84, 2019-23.
Gromowski et al., J. Virol. 2015, 89, 6328-6337.
Wicker et al., Virology 2006, 349, 245-253.
Wicker et al., Virology 2012, 426, 22-33.
Davis et al., Virology 2004, 330, 342-350.
Beasley et al., J. Virol. 2005, 79, 8339-8347.
Collins et al., MBio 2018, 9, 1-13.
Bolger et al., Bioinformatics 2014, 30, 2114-2120.
Wilm et al., Nucleic Acids Res. 2012, 40, 11189-11201.
Milne et al., Brief. Bioinform. 2012, 14, 193-202.
Whiteman et al., J. Virol. 2015, 89, 1474-1478.
Welte et al., Vaccine 2011, 29, 4853-4861.
Xie et al., Vaccine 2015, 33, 869-878.
Beck et al., J. Infect. Dis. 2014, 209, 334-344.
Kim et al., Protein Sci. 1999, 8, 1492-1499.
Kumeta et al., J. Cell Sci. 2017, 131.
Xie et al., Virology 2014, 450-451, 250-257.

* cited by examiner

SEQUENCE LISTING

```
<160> NUMBER OF SEQ ID NOS: 33

<210> SEQ ID NO 1
<211> LENGTH: 11029
<212> TYPE: DNA
<213> ORGANISM: West Nile virus
<220> FEATURE:
```

<221> NAME/KEY: CDS
<222> LOCATION: (97)..(10398)

<400> SEQUENCE: 1

```
agtagttcgc ctgtgtgagc tgacaaactt agtagtgttt gtgaggatta acaacaatta      60
acacagtgcg agctgtttct tagcacgaag atctcg atg tct aag aaa cca gga        114
                                        Met Ser Lys Lys Pro Gly
                                        1               5 ggg ccc ggc aag agc cgg gct gtc aat atg cta aaa cgc gga atg ccc        162
Gly Pro Gly Lys Ser Arg Ala Val Asn Met Leu Lys Arg Gly Met Pro
            10                  15                  20 cgc gtg ttg tcc ttg att gga ctg aag agg gct atg ttg agc ctg atc        210
Arg Val Leu Ser Leu Ile Gly Leu Lys Arg Ala Met Leu Ser Leu Ile
        25                  30                  35 gac ggc aag ggg cca ata cga ttt gtg ttg gct ctc ttg gcg ttc ttc        258
Asp Gly Lys Gly Pro Ile Arg Phe Val Leu Ala Leu Leu Ala Phe Phe
    40                  45                  50 agg ttc aca gca att gct ccg acc cga gca gtg ctg gat cga tgg aga        306
Arg Phe Thr Ala Ile Ala Pro Thr Arg Ala Val Leu Asp Arg Trp Arg
55                  60                  65                  70 ggt gtg aac aaa caa aca gcg atg aaa cac ctt ctg agt ttt aag aag        354
Gly Val Asn Lys Gln Thr Ala Met Lys His Leu Leu Ser Phe Lys Lys
                75                  80                  85 gaa cta ggg acc ttg acc agt gct atc aat cgg cgg agc tca aaa caa        402
Glu Leu Gly Thr Leu Thr Ser Ala Ile Asn Arg Arg Ser Ser Lys Gln
            90                  95                  100 aag aaa aga gga gga aag acc gga att gca gtc atg att ggc ctg atc        450
Lys Lys Arg Gly Gly Lys Thr Gly Ile Ala Val Met Ile Gly Leu Ile
        105                 110                 115 gcc agc gta gga gca gtt acc ctc tct aac ttc caa ggg aag gtg atg        498
Ala Ser Val Gly Ala Val Thr Leu Ser Asn Phe Gln Gly Lys Val Met
    120                 125                 130 atg acg gta aat gct act gac gtc aca gat gtc atc acg att cca aca        546
Met Thr Val Asn Ala Thr Asp Val Thr Asp Val Ile Thr Ile Pro Thr
135                 140                 145                 150 gct gct gga aag aac cta tgc att gtc aga gca atg gat gtg gga tac        594
Ala Ala Gly Lys Asn Leu Cys Ile Val Arg Ala Met Asp Val Gly Tyr
                155                 160                 165 atg tgc gat gat act atc act tat gaa tgc cca gtg ctg tcg gct ggt        642
Met Cys Asp Asp Thr Ile Thr Tyr Glu Cys Pro Val Leu Ser Ala Gly
            170                 175                 180 aat gat cca gaa gac atc gac tgt tgg tgc aca aag tca gca gtc tac        690
Asn Asp Pro Glu Asp Ile Asp Cys Trp Cys Thr Lys Ser Ala Val Tyr
        185                 190                 195 gtc agg tat gga aga tgc acc aag aca cgc cac tca aga cgc agt cgg        738
Val Arg Tyr Gly Arg Cys Thr Lys Thr Arg His Ser Arg Arg Ser Arg
    200                 205                 210 agg tca ctg aca gtg cag aca cac gga gaa agc act cta gcg aac aag        786
Arg Ser Leu Thr Val Gln Thr His Gly Glu Ser Thr Leu Ala Asn Lys
215                 220                 225                 230 aag ggg gct tgg atg gac agc acc aag gcc aca agg tat ttg gta aaa        834
Lys Gly Ala Trp Met Asp Ser Thr Lys Ala Thr Arg Tyr Leu Val Lys
                235                 240                 245 aca gaa tca tgg atc ttg agg aac cct gga tat gcc ctg gtg gca gcc        882
Thr Glu Ser Trp Ile Leu Arg Asn Pro Gly Tyr Ala Leu Val Ala Ala
            250                 255                 260 gtc att ggt tgg atg ctt ggg agc aac acc atg cag aga gtt gtg ttt        930
Val Ile Gly Trp Met Leu Gly Ser Asn Thr Met Gln Arg Val Val Phe
        265                 270                 275
```

```
                                                      -continued gtc gtg cta ttg ctt ttg gtg gcc cca gct tac agc ttc aac tgc ctt      978
Val Val Leu Leu Leu Leu Val Ala Pro Ala Tyr Ser Phe Asn Cys Leu
    280                 285                 290 gga atg agc aac aga gac ttc ttg gaa gga gtg tct gga gca aca tgg     1026
Gly Met Ser Asn Arg Asp Phe Leu Glu Gly Val Ser Gly Ala Thr Trp
295                 300                 305                 310 gtg gat ttg gtt ctc gaa ggc gac agc tgc gtg act atc atg tct aag     1074
Val Asp Leu Val Leu Glu Gly Asp Ser Cys Val Thr Ile Met Ser Lys
                315                 320                 325 gac aag cct acc atc gat gtg aag atg atg aat atg gag gcg gcc aac     1122
Asp Lys Pro Thr Ile Asp Val Lys Met Met Asn Met Glu Ala Ala Asn
            330                 335                 340 ctg gca gag gtc cgc agt tat tgc tat ttg gct acc gtc agc gat ctc     1170
Leu Ala Glu Val Arg Ser Tyr Cys Tyr Leu Ala Thr Val Ser Asp Leu
        345                 350                 355 tcc acc aaa gct gcg tgc ccg acc atg gga gaa gct cac aat gac aaa     1218
Ser Thr Lys Ala Ala Cys Pro Thr Met Gly Glu Ala His Asn Asp Lys
360                 365                 370 cgt gct gac cca gct ttt gtg tgc aga caa gga gtg gtg gac agg ggc     1266
Arg Ala Asp Pro Ala Phe Val Cys Arg Gln Gly Val Val Asp Arg Gly
375                 380                 385                 390 tgg ggc aac ggc tgc gga cta ttt ggc aaa gga agc att gcc aca tgc     1314
Trp Gly Asn Gly Cys Gly Leu Phe Gly Lys Gly Ser Ile Ala Thr Cys
                395                 400                 405 gcc aaa ttt gcc tgc tct acc aag gca ata gga aga acc atc ttg aaa     1362
Ala Lys Phe Ala Cys Ser Thr Lys Ala Ile Gly Arg Thr Ile Leu Lys
            410                 415                 420 gag aat atc aag tac gaa gtg gcc att ttt gtc cat gga cca act act     1410
Glu Asn Ile Lys Tyr Glu Val Ala Ile Phe Val His Gly Pro Thr Thr
        425                 430                 435 gtg gag tcg cac gga aat tac tcc aca cag gtt gga gcc act cag gca     1458
Val Glu Ser His Gly Asn Tyr Ser Thr Gln Val Gly Ala Thr Gln Ala
440                 445                 450 ggg aga ttc agc atc act cct gcg gcg cct tca tac aca cta aag ctt     1506
Gly Arg Phe Ser Ile Thr Pro Ala Ala Pro Ser Tyr Thr Leu Lys Leu
455                 460                 465                 470 gga gaa tat gga gag gtg aca gtg gac tgt gaa cca cgg tca ggg att     1554
Gly Glu Tyr Gly Glu Val Thr Val Asp Cys Glu Pro Arg Ser Gly Ile
                475                 480                 485 gac acc aat gca tac tac gtg atg act gtt gga aca aag acg ttc ttg     1602
Asp Thr Asn Ala Tyr Tyr Val Met Thr Val Gly Thr Lys Thr Phe Leu
            490                 495                 500 gtc cat cgt gag tgg ttc atg gac ctc aac ctc cct tgg agc agt gct     1650
Val His Arg Glu Trp Phe Met Asp Leu Asn Leu Pro Trp Ser Ser Ala
        505                 510                 515 gga agt act gtg tgg agg aac aga gag acg tta atg gag ttt gag gaa     1698
Gly Ser Thr Val Trp Arg Asn Arg Glu Thr Leu Met Glu Phe Glu Glu
520                 525                 530 cca cac gcc acg aag cag tct gtg ata gca ttg ggc tca caa gag gga     1746
Pro His Ala Thr Lys Gln Ser Val Ile Ala Leu Gly Ser Gln Glu Gly
535                 540                 545                 550 gct ctg cat caa gct ttg gct gga gcc att cct gtg gaa ttt tca agc     1794
Ala Leu His Gln Ala Leu Ala Gly Ala Ile Pro Val Glu Phe Ser Ser
                555                 560                 565 aac act gtc aag ttg acg tcg ggt cat ttg aag tgt aga gtg aag atg     1842
Asn Thr Val Lys Leu Thr Ser Gly His Leu Lys Cys Arg Val Lys Met
            570                 575                 580 gaa aaa ttg cag ctg aag gga aca acc tat ggc gtc tgt tca aag gct     1890
Glu Lys Leu Gln Leu Lys Gly Thr Thr Tyr Gly Val Cys Ser Lys Ala
        585                 590                 595
```

-continued

| | | |
|---|---|---|
| ttc aag ttt ctt ggg act ccc gca gac aca ggt cac ggc act gtg gtg<br>Phe Lys Phe Leu Gly Thr Pro Ala Asp Thr Gly His Gly Thr Val Val<br>600 605 610 | 1938 | |
| ttg gaa ttg cag tac act ggc acg gat gga cct tgc aaa gtt cct atc<br>Leu Glu Leu Gln Tyr Thr Gly Thr Asp Gly Pro Cys Lys Val Pro Ile<br>615 620 625 630 | 1986 | |
| tcg tca gtg gct tca ttg aac gac cta acg cca gtg ggc aga ttg gtc<br>Ser Ser Val Ala Ser Leu Asn Asp Leu Thr Pro Val Gly Arg Leu Val<br>635 640 645 | 2034 | |
| act gtc aac cct ttt gtt tca gtg gcc acg gcc aac gct aag gtc ctg<br>Thr Val Asn Pro Phe Val Ser Val Ala Thr Ala Asn Ala Lys Val Leu<br>650 655 660 | 2082 | |
| att gaa ttg gaa cca ccc ttt gga gac tca tac ata gtg gtg ggc aga<br>Ile Glu Leu Glu Pro Pro Phe Gly Asp Ser Tyr Ile Val Val Gly Arg<br>665 670 675 | 2130 | |
| gga gaa caa cag atc aat cac cat tgg cac aag tct gga agc agc att<br>Gly Glu Gln Gln Ile Asn His His Trp His Lys Ser Gly Ser Ser Ile<br>680 685 690 | 2178 | |
| ggc aaa gcc ttt aca acc acc ctc aaa gga gcg cag aga cta gcc gct<br>Gly Lys Ala Phe Thr Thr Thr Leu Lys Gly Ala Gln Arg Leu Ala Ala<br>695 700 705 710 | 2226 | |
| cta gga gac aca gct tgg gac ttt gga tca gtt gga ggg gtg ttc acc<br>Leu Gly Asp Thr Ala Trp Asp Phe Gly Ser Val Gly Gly Val Phe Thr<br>715 720 725 | 2274 | |
| tca gtt ggg aag gct gtc cat caa gtg ttc gga gga gca ttc cgc tca<br>Ser Val Gly Lys Ala Val His Gln Val Phe Gly Gly Ala Phe Arg Ser<br>730 735 740 | 2322 | |
| ctg ttc gga ggc atg tcc tgg ata acg caa gga ttg ctg ggg gct ctc<br>Leu Phe Gly Gly Met Ser Trp Ile Thr Gln Gly Leu Leu Gly Ala Leu<br>745 750 755 | 2370 | |
| ctg ttg tgg atg ggc atc aat gct cgt gat agg tcc ata gct ctc acg<br>Leu Leu Trp Met Gly Ile Asn Ala Arg Asp Arg Ser Ile Ala Leu Thr<br>760 765 770 | 2418 | |
| ttt ctc gca gtt gga gga gtt ctg ctc ttc ctc tcc gtg aac gtg cac<br>Phe Leu Ala Val Gly Gly Val Leu Leu Phe Leu Ser Val Asn Val His<br>775 780 785 790 | 2466 | |
| gct gac act ggg tgt gcc ata gac atc agc cgg caa gag ctg aga tgt<br>Ala Asp Thr Gly Cys Ala Ile Asp Ile Ser Arg Gln Glu Leu Arg Cys<br>795 800 805 | 2514 | |
| gga agt gga gtg ttc ata cac aat gat gtg gag gct tgg atg gac cgg<br>Gly Ser Gly Val Phe Ile His Asn Asp Val Glu Ala Trp Met Asp Arg<br>810 815 820 | 2562 | |
| tac aag tat tac cct gaa acg cca caa ggc cta gcc aag atc att cag<br>Tyr Lys Tyr Tyr Pro Glu Thr Pro Gln Gly Leu Ala Lys Ile Ile Gln<br>825 830 835 | 2610 | |
| aaa gct cat aag gaa gga gtg tgc ggt cta cga tca gtt tcc aga ctg<br>Lys Ala His Lys Glu Gly Val Cys Gly Leu Arg Ser Val Ser Arg Leu<br>840 845 850 | 2658 | |
| gag cat caa atg tgg gaa gca gtg aag gac gag ctg aac act ctt ttg<br>Glu His Gln Met Trp Glu Ala Val Lys Asp Glu Leu Asn Thr Leu Leu<br>855 860 865 870 | 2706 | |
| aag gag aat ggt gtg gac ctt agt gtc gtg gtt gag aaa cag gag gga<br>Lys Glu Asn Gly Val Asp Leu Ser Val Val Val Glu Lys Gln Glu Gly<br>875 880 885 | 2754 | |
| atg tac aag tca gca cct aaa cgc ctc acc gcc acc acg gaa aaa ttg<br>Met Tyr Lys Ser Ala Pro Lys Arg Leu Thr Ala Thr Thr Glu Lys Leu<br>890 895 900 | 2802 | |
| gaa att ggc tgg aag gcc tgg gga aag agt att tta ttt gca cca gaa<br>Glu Ile Gly Trp Lys Ala Trp Gly Lys Ser Ile Leu Phe Ala Pro Glu | 2850 | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 905 |     |     |     |     | 910 |     |     |     |     | 915 |     |     |      |
| ctc | gcc | aac | aac | acc | ttt | gtg | gtt | gat | ggt | ccg | gag | acc | aag | gaa | tgt | 2898 |
| Leu | Ala | Asn | Asn | Thr | Phe | Val | Val | Asp | Gly | Pro | Glu | Thr | Lys | Glu | Cys |      |
|     | 920 |     |     |     |     | 925 |     |     |     |     | 930 |     |     |     |     |      |
| ccg | act | cag | aat | cgc | gct | tgg | aat | agc | tta | gaa | gtg | gag | gat | ttt | gga | 2946 |
| Pro | Thr | Gln | Asn | Arg | Ala | Trp | Asn | Ser | Leu | Glu | Val | Glu | Asp | Phe | Gly |      |
| 935 |     |     |     |     | 940 |     |     |     |     | 945 |     |     |     |     | 950 |      |
| ttt | ggt | ctc | acc | agc | act | cgg | atg | ttc | ctg | aag | gtc | aga | gag | agc | aac | 2994 |
| Phe | Gly | Leu | Thr | Ser | Thr | Arg | Met | Phe | Leu | Lys | Val | Arg | Glu | Ser | Asn |      |
|     |     |     |     | 955 |     |     |     |     | 960 |     |     |     |     | 965 |     |      |
| aca | act | gaa | tgt | gac | tcg | aag | atc | att | gga | acg | gct | gtc | aag | aac | aac | 3042 |
| Thr | Thr | Glu | Cys | Asp | Ser | Lys | Ile | Ile | Gly | Thr | Ala | Val | Lys | Asn | Asn |      |
|     |     | 970 |     |     |     |     | 975 |     |     |     |     | 980 |     |     |     |      |
| ttg | gcg | atc | cac | agt | gac | ctg | tcc | tat | tgg | att | gaa | agc | agg | ctc | aat | 3090 |
| Leu | Ala | Ile | His | Ser | Asp | Leu | Ser | Tyr | Trp | Ile | Glu | Ser | Arg | Leu | Asn |      |
|     |     |     | 985 |     |     |     |     | 990 |     |     |     |     | 995 |     |     |      |
| gat | acg | tgg | aag | ctt | gaa | agg | gca | gtt | ctg | ggt | gaa | | gtc | aaa | tca | 3135 |
| Asp | Thr | Trp | Lys | Leu | Glu | Arg | Ala | Val | Leu | Gly | Glu | | Val | Lys | Ser |      |
|     | 1000 |   |     |     |     | 1005 |   |     |     |     | 1010 |  |     |     |     |      |
| tgt | acg | tgg | cct | gag | acg | cat | | acc | ttg | tgg | ggc | gat | | gga | atc | ctt | 3180 |
| Cys | Thr | Trp | Pro | Glu | Thr | His | | Thr | Leu | Trp | Gly | Asp | | Gly | Ile | Leu |      |
|     | 1015 |  |     |     |     | 1020 | |     |     |     | 1025 |  |    |     |     |      |
| gag | agt | gac | ttg | ata | ata | cca | gtc | aca | ctg | gcg | gga | | cca | cga | agc | 3225 |
| Glu | Ser | Asp | Leu | Ile | Ile | Pro | Val | Thr | Leu | Ala | Gly | | Pro | Arg | Ser |      |
|     | 1030 |  |     |     |     | 1035 |   |     |     |     | 1040 | |     |     |     |      |
| aat | cac | aat | cgg | aga | cct | ggg | tac | aag | aca | caa | aac | | cag | ggc | cca | 3270 |
| Asn | His | Asn | Arg | Arg | Pro | Gly | Tyr | Lys | Thr | Gln | Asn | | Gln | Gly | Pro |      |
|     | 1045 |  |    |     |     | 1050 |   |     |     |     | 1055 | |    |     |     |      |
| tgg | gac | gaa | ggc | cgg | gta | gag | att | gac | ttc | gat | tac | | tgc | cca | gga | 3315 |
| Trp | Asp | Glu | Gly | Arg | Val | Glu | Ile | Asp | Phe | Asp | Tyr | | Cys | Pro | Gly |      |
|     | 1060 |  |    |     |     | 1065 |   |     |     |     | 1070 | |    |     |     |      |
| act | acg | gtc | acc | ctg | agt | gag | agc | tgc | gga | cac | cgt | | gga | cct | gcc | 3360 |
| Thr | Thr | Val | Thr | Leu | Ser | Glu | Ser | Cys | Gly | His | Arg | | Gly | Pro | Ala |      |
|     | 1075 |  |    |     |     | 1080 |   |     |     |     | 1085 | |     |     |     |      |
| act | cgc | acc | acc | aca | gag | agc | gga | aag | ttg | ata | aca | | gat | tgg | tgc | 3405 |
| Thr | Arg | Thr | Thr | Thr | Glu | Ser | Gly | Lys | Leu | Ile | Thr | | Asp | Trp | Cys |      |
|     | 1090 |  |    |     |     | 1095 |   |     |     |     | 1100 | |    |     |     |      |
| tgc | agg | agc | tgc | acc | tta | cca | cca | ctg | cgc | tac | caa | | act | gac | agc | 3450 |
| Cys | Arg | Ser | Cys | Thr | Leu | Pro | Pro | Leu | Arg | Tyr | Gln | | Thr | Asp | Ser |      |
|     | 1105 |  |    |     |     | 1110 |   |     |     |     | 1115 | |    |     |     |      |
| ggc | tgt | tgg | tat | ggt | atg | gag | atc | aga | cca | cag | aga | | cat | gat | gaa | 3495 |
| Gly | Cys | Trp | Tyr | Gly | Met | Glu | Ile | Arg | Pro | Gln | Arg | | His | Asp | Glu |      |
|     | 1120 |  |    |     |     | 1125 |   |     |     |     | 1130 | |    |     |     |      |
| aag | acc | ctc | gtg | cag | tca | caa | gtg | aat | gct | tat | aat | | gct | gat | atg | 3540 |
| Lys | Thr | Leu | Val | Gln | Ser | Gln | Val | Asn | Ala | Tyr | Asn | | Ala | Asp | Met |      |
|     | 1135 |  |    |     |     | 1140 |   |     |     |     | 1145 | |    |     |     |      |
| att | gac | cct | ttt | cag | ttg | ggc | ctt | ctg | gtc | gtg | ttc | | ttg | gcc | acc | 3585 |
| Ile | Asp | Pro | Phe | Gln | Leu | Gly | Leu | Leu | Val | Val | Phe | | Leu | Ala | Thr |      |
|     | 1150 |  |    |     |     | 1155 |   |     |     |     | 1160 | |    |     |     |      |
| cag | gag | gtc | ctt | cgc | aag | agg | tgg | aca | gcc | aag | atc | | agc | atg | cca | 3630 |
| Gln | Glu | Val | Leu | Arg | Lys | Arg | Trp | Thr | Ala | Lys | Ile | | Ser | Met | Pro |      |
|     | 1165 |  |    |     |     | 1170 |   |     |     |     | 1175 | |    |     |     |      |
| gct | ata | ctg | att | gct | ctg | cta | gtc | ctg | gtg | ttt | ggg | | ggc | att | act | 3675 |
| Ala | Ile | Leu | Ile | Ala | Leu | Leu | Val | Leu | Val | Phe | Gly | | Gly | Ile | Thr |      |
|     | 1180 |  |    |     |     | 1185 |   |     |     |     | 1190 | |    |     |     |      |
| tac | act | gat | gtg | tta | cgc | tat | gtc | atc | ttg | gtg | ggg | | gca | gct | ttc | 3720 |
| Tyr | Thr | Asp | Val | Leu | Arg | Tyr | Val | Ile | Leu | Val | Gly | | Ala | Ala | Phe |      |
|     | 1195 |  |    |     |     | 1200 |   |     |     |     | 1205 | |    |     |     |      |
| gca | gaa | tct | aat | tcg | gga | gga | gac | gtg | gta | cac | ttg | | gcg | ctc | atg | 3765 |

```
        Ala Glu Ser Asn Ser Gly Gly Asp Val Val His Leu Ala Leu Met
            1210            1215                1220 gcg acc ttc aag ata caa cca gtg ttt atg gtg gca tcg ttt ctc        3810
Ala Thr Phe Lys Ile Gln Pro Val Phe Met Val Ala Ser Phe Leu
    1225            1230                1235 aaa gcg aga tgg acc aac cag gag aac att ttg ttg atg ttg gcg        3855
Lys Ala Arg Trp Thr Asn Gln Glu Asn Ile Leu Leu Met Leu Ala
    1240            1245                1250 gct gtt ttc ttt caa atg gct tat tac gat gcc cgc caa att ctg        3900
Ala Val Phe Phe Gln Met Ala Tyr Tyr Asp Ala Arg Gln Ile Leu
    1255            1260                1265 ctc tgg gag atc cct gat gtg ttg aat tca ctg gcg gta gct tgg        3945
Leu Trp Glu Ile Pro Asp Val Leu Asn Ser Leu Ala Val Ala Trp
    1270            1275                1280 atg ata ctg aga gcc ata aca ttc aca acg aca tca aac gtg gtt        3990
Met Ile Leu Arg Ala Ile Thr Phe Thr Thr Thr Ser Asn Val Val
    1285            1290                1295 gtt ccg ctg cta gcc ctg cta aca ccc ggg ctg aga tgc ttg aat        4035
Val Pro Leu Leu Ala Leu Leu Thr Pro Gly Leu Arg Cys Leu Asn
    1300            1305                1310 ctg gat gtg tac agg ata ctg ctg ttg atg gtc gga ata ggc agc        4080
Leu Asp Val Tyr Arg Ile Leu Leu Leu Met Val Gly Ile Gly Ser
    1315            1320                1325 ttg atc agg gag aag agg agt gca gct gca aaa aag aaa gga gca        4125
Leu Ile Arg Glu Lys Arg Ser Ala Ala Ala Lys Lys Lys Gly Ala
    1330            1335                1340 agt ctg cta tgc ttg gct cta gcc tca aca gga ctt ttc aac ccc        4170
Ser Leu Leu Cys Leu Ala Leu Ala Ser Thr Gly Leu Phe Asn Pro
    1345            1350                1355 atg atc ctt gct gct gga ctg att gca tgt gat ccc aac cgt aaa        4215
Met Ile Leu Ala Ala Gly Leu Ile Ala Cys Asp Pro Asn Arg Lys
    1360            1365                1370 cgc gga tgg ccc gca act gaa gtg atg aca gct gtc ggc cta atg        4260
Arg Gly Trp Pro Ala Thr Glu Val Met Thr Ala Val Gly Leu Met
    1375            1380                1385 ttt gcc atc gtc gga ggg ctg gca gag ctt gac att gac tcc atg        4305
Phe Ala Ile Val Gly Gly Leu Ala Glu Leu Asp Ile Asp Ser Met
    1390            1395                1400 gcc att cca atg act atc gcg ggg ctc atg ttt gct gct ttc gtg        4350
Ala Ile Pro Met Thr Ile Ala Gly Leu Met Phe Ala Ala Phe Val
    1405            1410                1415 att tct ggg aaa tca aca gat atg tgg att gag aga acg gcg gac        4395
Ile Ser Gly Lys Ser Thr Asp Met Trp Ile Glu Arg Thr Ala Asp
    1420            1425                1430 att tcc tgg gaa agt gat gca gaa att aca ggc tcg agc gaa aga        4440
Ile Ser Trp Glu Ser Asp Ala Glu Ile Thr Gly Ser Ser Glu Arg
    1435            1440                1445 gtt gat gtg cgg ctt gat gat gat gga aac ttc cag ctc atg aat        4485
Val Asp Val Arg Leu Asp Asp Asp Gly Asn Phe Gln Leu Met Asn
    1450            1455                1460 gat cca gga gca cct tgg aag ata tgg atg ctc aga atg gtc tgt        4530
Asp Pro Gly Ala Pro Trp Lys Ile Trp Met Leu Arg Met Val Cys
    1465            1470                1475 ctc gcg att agt gcg tac acc ccc tgg gca atc ttg ccc tca gta        4575
Leu Ala Ile Ser Ala Tyr Thr Pro Trp Ala Ile Leu Pro Ser Val
    1480            1485                1490 gtt gga ttt tgg ata act ctc caa tac aca aag aga gga ggc gtg        4620
Val Gly Phe Trp Ile Thr Leu Gln Tyr Thr Lys Arg Gly Gly Val
    1495            1500                1505
```

|   |   |   |   |   |   |   |   |   |   |   |   |   |   |   |      |
|---|---|---|---|---|---|---|---|---|---|---|---|---|---|---|------|
| ttg | tgg | gac | act | ccc | tca | cca | aag | gag | tac | aaa | aag | ggg | gac | acg | 4665 |
| Leu | Trp | Asp | Thr | Pro | Ser | Pro | Lys | Glu | Tyr | Lys | Lys | Gly | Asp | Thr |      |
| 1510 |    |    |    |    | 1515 |    |    |    |    | 1520 |    |    |    |    |      |

| acc | acc | ggc | gtc | tac | agg | atc | atg | act | cgt | ggg | ctg | ctc | ggc | agt | 4710 |
|-----|-----|-----|-----|-----|-----|-----|-----|-----|-----|-----|-----|-----|-----|-----|------|
| Thr | Thr | Gly | Val | Tyr | Arg | Ile | Met | Thr | Arg | Gly | Leu | Leu | Gly | Ser |      |
| 1525 |    |    |    |    | 1530 |    |    |    |    | 1535 |    |    |    |    |      |

| tat | caa | gca | gga | gcg | ggc | gtg | atg | gtt | gaa | ggt | gtt | ttc | cac | acc | 4755 |
|-----|-----|-----|-----|-----|-----|-----|-----|-----|-----|-----|-----|-----|-----|-----|------|
| Tyr | Gln | Ala | Gly | Ala | Gly | Val | Met | Val | Glu | Gly | Val | Phe | His | Thr |      |
| 1540 |    |    |    |    | 1545 |    |    |    |    | 1550 |    |    |    |    |      |

| ctt | tgg | cat | aca | aca | aaa | gga | gcc | gct | ttg | atg | agc | gga | gag | ggc | 4800 |
|-----|-----|-----|-----|-----|-----|-----|-----|-----|-----|-----|-----|-----|-----|-----|------|
| Leu | Trp | His | Thr | Thr | Lys | Gly | Ala | Ala | Leu | Met | Ser | Gly | Glu | Gly |      |
| 1555 |    |    |    |    | 1560 |    |    |    |    | 1565 |    |    |    |    |      |

| cgc | ctg | gac | cca | tac | tgg | ggc | agt | gtc | aag | gag | gat | cga | ctt | tgt | 4845 |
|-----|-----|-----|-----|-----|-----|-----|-----|-----|-----|-----|-----|-----|-----|-----|------|
| Arg | Leu | Asp | Pro | Tyr | Trp | Gly | Ser | Val | Lys | Glu | Asp | Arg | Leu | Cys |      |
| 1570 |    |    |    |    | 1575 |    |    |    |    | 1580 |    |    |    |    |      |

| tac | gga | gga | ccc | tgg | aaa | ttg | cag | cac | aag | tgg | aac | ggg | cag | gat | 4890 |
|-----|-----|-----|-----|-----|-----|-----|-----|-----|-----|-----|-----|-----|-----|-----|------|
| Tyr | Gly | Gly | Pro | Trp | Lys | Leu | Gln | His | Lys | Trp | Asn | Gly | Gln | Asp |      |
| 1585 |    |    |    |    | 1590 |    |    |    |    | 1595 |    |    |    |    |      |

| gag | gtg | cag | atg | att | gtg | gtg | gaa | cct | ggc | agg | aac | gtt | aag | aac | 4935 |
|-----|-----|-----|-----|-----|-----|-----|-----|-----|-----|-----|-----|-----|-----|-----|------|
| Glu | Val | Gln | Met | Ile | Val | Val | Glu | Pro | Gly | Arg | Asn | Val | Lys | Asn |      |
| 1600 |    |    |    |    | 1605 |    |    |    |    | 1610 |    |    |    |    |      |

| gtc | cag | acg | aaa | cca | ggg | gtg | ttc | aaa | aca | cct | gaa | gga | gaa | atc | 4980 |
|-----|-----|-----|-----|-----|-----|-----|-----|-----|-----|-----|-----|-----|-----|-----|------|
| Val | Gln | Thr | Lys | Pro | Gly | Val | Phe | Lys | Thr | Pro | Glu | Gly | Glu | Ile |      |
| 1615 |    |    |    |    | 1620 |    |    |    |    | 1625 |    |    |    |    |      |

| ggg | gcc | gtg | act | ttg | gac | ttc | ccc | act | gga | aca | tca | ggc | tca | cca | 5025 |
|-----|-----|-----|-----|-----|-----|-----|-----|-----|-----|-----|-----|-----|-----|-----|------|
| Gly | Ala | Val | Thr | Leu | Asp | Phe | Pro | Thr | Gly | Thr | Ser | Gly | Ser | Pro |      |
| 1630 |    |    |    |    | 1635 |    |    |    |    | 1640 |    |    |    |    |      |

| ata | gtg | gac | aaa | aac | ggt | gat | gtg | att | ggg | ctt | tat | ggc | aat | gga | 5070 |
|-----|-----|-----|-----|-----|-----|-----|-----|-----|-----|-----|-----|-----|-----|-----|------|
| Ile | Val | Asp | Lys | Asn | Gly | Asp | Val | Ile | Gly | Leu | Tyr | Gly | Asn | Gly |      |
| 1645 |    |    |    |    | 1650 |    |    |    |    | 1655 |    |    |    |    |      |

| gtc | ata | atg | ccc | aac | ggc | tca | tac | ata | agc | gcg | ata | gtg | cag | ggt | 5115 |
|-----|-----|-----|-----|-----|-----|-----|-----|-----|-----|-----|-----|-----|-----|-----|------|
| Val | Ile | Met | Pro | Asn | Gly | Ser | Tyr | Ile | Ser | Ala | Ile | Val | Gln | Gly |      |
| 1660 |    |    |    |    | 1665 |    |    |    |    | 1670 |    |    |    |    |      |

| gaa | agg | atg | gat | gag | cca | atc | cca | gcc | gga | ttc | gaa | cct | gag | atg | 5160 |
|-----|-----|-----|-----|-----|-----|-----|-----|-----|-----|-----|-----|-----|-----|-----|------|
| Glu | Arg | Met | Asp | Glu | Pro | Ile | Pro | Ala | Gly | Phe | Glu | Pro | Glu | Met |      |
| 1675 |    |    |    |    | 1680 |    |    |    |    | 1685 |    |    |    |    |      |

| ctg | agg | aaa | aaa | cag | atc | act | gta | ctg | gat | ctc | cat | ccc | ggc | gcc | 5205 |
|-----|-----|-----|-----|-----|-----|-----|-----|-----|-----|-----|-----|-----|-----|-----|------|
| Leu | Arg | Lys | Lys | Gln | Ile | Thr | Val | Leu | Asp | Leu | His | Pro | Gly | Ala |      |
| 1690 |    |    |    |    | 1695 |    |    |    |    | 1700 |    |    |    |    |      |

| ggt | aaa | aca | agg | agg | att | ctg | cca | cag | atc | atc | aaa | gag | gcc | ata | 5250 |
|-----|-----|-----|-----|-----|-----|-----|-----|-----|-----|-----|-----|-----|-----|-----|------|
| Gly | Lys | Thr | Arg | Arg | Ile | Leu | Pro | Gln | Ile | Ile | Lys | Glu | Ala | Ile |      |
| 1705 |    |    |    |    | 1710 |    |    |    |    | 1715 |    |    |    |    |      |

| aac | aga | aga | ctg | aga | aca | gcc | gtg | cta | gca | cca | acc | agg | gtt | gtg | 5295 |
|-----|-----|-----|-----|-----|-----|-----|-----|-----|-----|-----|-----|-----|-----|-----|------|
| Asn | Arg | Arg | Leu | Arg | Thr | Ala | Val | Leu | Ala | Pro | Thr | Arg | Val | Val |      |
| 1720 |    |    |    |    | 1725 |    |    |    |    | 1730 |    |    |    |    |      |

| gct | gct | gag | atg | gct | gaa | gca | ctg | aga | gga | ctg | ccc | atc | cgg | tac | 5340 |
|-----|-----|-----|-----|-----|-----|-----|-----|-----|-----|-----|-----|-----|-----|-----|------|
| Ala | Ala | Glu | Met | Ala | Glu | Ala | Leu | Arg | Gly | Leu | Pro | Ile | Arg | Tyr |      |
| 1735 |    |    |    |    | 1740 |    |    |    |    | 1745 |    |    |    |    |      |

| cag | aca | tcc | gca | gtg | ccc | aga | gaa | cat | aat | gga | aat | gag | att | gtt | 5385 |
|-----|-----|-----|-----|-----|-----|-----|-----|-----|-----|-----|-----|-----|-----|-----|------|
| Gln | Thr | Ser | Ala | Val | Pro | Arg | Glu | His | Asn | Gly | Asn | Glu | Ile | Val |      |
| 1750 |    |    |    |    | 1755 |    |    |    |    | 1760 |    |    |    |    |      |

| gat | gtc | atg | tgt | cat | gct | acc | ctc | acc | cac | agg | ctg | atg | tct | cct | 5430 |
|-----|-----|-----|-----|-----|-----|-----|-----|-----|-----|-----|-----|-----|-----|-----|------|
| Asp | Val | Met | Cys | His | Ala | Thr | Leu | Thr | His | Arg | Leu | Met | Ser | Pro |      |
| 1765 |    |    |    |    | 1770 |    |    |    |    | 1775 |    |    |    |    |      |

| cac | agg | gtg | ccg | aac | tac | aac | ctg | ttc | gtg | atg | gat | gag | gct | cat | 5475 |
|-----|-----|-----|-----|-----|-----|-----|-----|-----|-----|-----|-----|-----|-----|-----|------|
| His | Arg | Val | Pro | Asn | Tyr | Asn | Leu | Phe | Val | Met | Asp | Glu | Ala | His |      |
| 1780 |    |    |    |    | 1785 |    |    |    |    | 1790 |    |    |    |    |      |

| ttc | acc | gac | cca | gct | agc | att | gca | gca | aga | ggt | tac | att | tcc | aca | 5520 |
|-----|-----|-----|-----|-----|-----|-----|-----|-----|-----|-----|-----|-----|-----|-----|------|
| Phe | Thr | Asp | Pro | Ala | Ser | Ile | Ala | Ala | Arg | Gly | Tyr | Ile | Ser | Thr |      |
| 1795 |    |    |    |    | 1800 |    |    |    |    | 1805 |    |    |    |    |      |

-continued

| | | | | | | | | | | |
|---|---|---|---|---|---|---|---|---|---|---|
| aag | gtc | gag | cta | ggg | gag | gcg | gcg | gca | ata | ttc | atg | aca | gcc | acc | 5565 |
| Lys | Val | Glu | Leu | Gly | Glu | Ala | Ala | Ala | Ile | Phe | Met | Thr | Ala | Thr | |
| | 1810 | | | | 1815 | | | | | 1820 | | | | | |

| cca | cca | ggc | act | tca | gat | cca | ttc | cca | gag | tcc | aat | tca | cca | att | 5610 |
| Pro | Pro | Gly | Thr | Ser | Asp | Pro | Phe | Pro | Glu | Ser | Asn | Ser | Pro | Ile | |
| | 1825 | | | | 1830 | | | | | 1835 | | | | | |

| tcc | gac | tta | cag | act | gag | atc | ccg | gat | cga | gct | tgg | aac | tct | gga | 5655 |
| Ser | Asp | Leu | Gln | Thr | Glu | Ile | Pro | Asp | Arg | Ala | Trp | Asn | Ser | Gly | |
| | 1840 | | | | 1845 | | | | | 1850 | | | | | |

| tac | gaa | tgg | atc | aca | gaa | tac | acc | ggg | aag | acg | gtt | tgg | ttt | gtg | 5700 |
| Tyr | Glu | Trp | Ile | Thr | Glu | Tyr | Thr | Gly | Lys | Thr | Val | Trp | Phe | Val | |
| | 1855 | | | | 1860 | | | | | 1865 | | | | | |

| cct | agt | gtc | aag | atg | ggg | aat | gag | att | gcc | ctt | tgc | cta | caa | cgt | 5745 |
| Pro | Ser | Val | Lys | Met | Gly | Asn | Glu | Ile | Ala | Leu | Cys | Leu | Gln | Arg | |
| | 1870 | | | | 1875 | | | | | 1880 | | | | | |

| gct | gga | aag | aaa | gta | gtc | caa | ttg | aac | aga | aag | tcg | tac | gag | acg | 5790 |
| Ala | Gly | Lys | Lys | Val | Val | Gln | Leu | Asn | Arg | Lys | Ser | Tyr | Glu | Thr | |
| | 1885 | | | | 1890 | | | | | 1895 | | | | | |

| gag | tac | cca | aaa | tgt | aag | aac | gat | gat | tgg | gac | ttt | gtt | atc | aca | 5835 |
| Glu | Tyr | Pro | Lys | Cys | Lys | Asn | Asp | Asp | Trp | Asp | Phe | Val | Ile | Thr | |
| | 1900 | | | | 1905 | | | | | 1910 | | | | | |

| aca | gac | ata | tct | gaa | atg | ggg | gct | aac | ttc | aag | gcg | agc | agg | gtg | 5880 |
| Thr | Asp | Ile | Ser | Glu | Met | Gly | Ala | Asn | Phe | Lys | Ala | Ser | Arg | Val | |
| | 1915 | | | | 1920 | | | | | 1925 | | | | | |

| att | gac | agc | cgg | aag | agt | gtg | aaa | cca | acc | atc | ata | aca | gaa | gga | 5925 |
| Ile | Asp | Ser | Arg | Lys | Ser | Val | Lys | Pro | Thr | Ile | Ile | Thr | Glu | Gly | |
| | 1930 | | | | 1935 | | | | | 1940 | | | | | |

| gaa | ggg | aga | gtg | atc | ctg | gga | gaa | cca | tct | gca | gtg | aca | gca | gct | 5970 |
| Glu | Gly | Arg | Val | Ile | Leu | Gly | Glu | Pro | Ser | Ala | Val | Thr | Ala | Ala | |
| | 1945 | | | | 1950 | | | | | 1955 | | | | | |

| agt | gcc | gcc | cag | aga | cgt | gga | cgt | atc | ggt | aga | aat | ccg | tcg | caa | 6015 |
| Ser | Ala | Ala | Gln | Arg | Arg | Gly | Arg | Ile | Gly | Arg | Asn | Pro | Ser | Gln | |
| | 1960 | | | | 1965 | | | | | 1970 | | | | | |

| gtt | ggt | gat | gag | tac | tgt | tat | ggg | ggg | cac | acg | aat | gaa | gac | gac | 6060 |
| Val | Gly | Asp | Glu | Tyr | Cys | Tyr | Gly | Gly | His | Thr | Asn | Glu | Asp | Asp | |
| | 1975 | | | | 1980 | | | | | 1985 | | | | | |

| tcg | aac | ttc | gcc | cat | tgg | act | gag | gca | cga | atc | atg | ctg | gac | aac | 6105 |
| Ser | Asn | Phe | Ala | His | Trp | Thr | Glu | Ala | Arg | Ile | Met | Leu | Asp | Asn | |
| | 1990 | | | | 1995 | | | | | 2000 | | | | | |

| atc | aac | atg | cca | aac | gga | ctg | atc | gct | caa | ttc | tac | caa | cca | gag | 6150 |
| Ile | Asn | Met | Pro | Asn | Gly | Leu | Ile | Ala | Gln | Phe | Tyr | Gln | Pro | Glu | |
| | 2005 | | | | 2010 | | | | | 2015 | | | | | |

| cgt | gag | aag | gta | tat | acc | atg | gat | ggg | gaa | tac | cgg | ctc | aga | gga | 6195 |
| Arg | Glu | Lys | Val | Tyr | Thr | Met | Asp | Gly | Glu | Tyr | Arg | Leu | Arg | Gly | |
| | 2020 | | | | 2025 | | | | | 2030 | | | | | |

| gaa | gag | aga | aaa | aac | ttt | ctg | gaa | ctg | ttg | agg | act | gca | gat | ctg | 6240 |
| Glu | Glu | Arg | Lys | Asn | Phe | Leu | Glu | Leu | Leu | Arg | Thr | Ala | Asp | Leu | |
| | 2035 | | | | 2040 | | | | | 2045 | | | | | |

| cca | gtt | tgg | ctg | gct | tac | aag | gtt | gca | gcg | gct | gga | gtg | tca | tac | 6285 |
| Pro | Val | Trp | Leu | Ala | Tyr | Lys | Val | Ala | Ala | Ala | Gly | Val | Ser | Tyr | |
| | 2050 | | | | 2055 | | | | | 2060 | | | | | |

| cac | gac | cgg | agg | tgg | tgc | ttt | gat | ggt | cct | agg | aca | aac | aca | att | 6330 |
| His | Asp | Arg | Arg | Trp | Cys | Phe | Asp | Gly | Pro | Arg | Thr | Asn | Thr | Ile | |
| | 2065 | | | | 2070 | | | | | 2075 | | | | | |

| tta | gaa | gac | aac | aac | gaa | gtg | gaa | gtc | atc | acg | aag | ctt | ggt | gaa | 6375 |
| Leu | Glu | Asp | Asn | Asn | Glu | Val | Glu | Val | Ile | Thr | Lys | Leu | Gly | Glu | |
| | 2080 | | | | 2085 | | | | | 2090 | | | | | |

| agg | aag | att | ctg | agg | ccg | cgc | tgg | att | gac | gcc | agg | gtg | tac | tcg | 6420 |
| Arg | Lys | Ile | Leu | Arg | Pro | Arg | Trp | Ile | Asp | Ala | Arg | Val | Tyr | Ser | |

-continued

|  |  |  |  |
|---|---|---|---|
| 2095 | 2100 | 2105 | |
| gat cac cag gca cta aag gcg ttc aag gac ttc gcc tcg gga aaa<br>Asp His Gln Ala Leu Lys Ala Phe Lys Asp Phe Ala Ser Gly Lys<br>2110 2115 2120 | | | 6465 |
| cgt tct cag ata ggg ctc att gag gtt ctg gga aag atg cct gag<br>Arg Ser Gln Ile Gly Leu Ile Glu Val Leu Gly Lys Met Pro Glu<br>2125 2130 2135 | | | 6510 |
| cac ttc atg ggg aag aca tgg gaa gca ctt gac acc atg tac gtt<br>His Phe Met Gly Lys Thr Trp Glu Ala Leu Asp Thr Met Tyr Val<br>2140 2145 2150 | | | 6555 |
| gtg gcc act gca gag aaa gga gga aga gct cac aga atg gcc ctg<br>Val Ala Thr Ala Glu Lys Gly Gly Arg Ala His Arg Met Ala Leu<br>2155 2160 2165 | | | 6600 |
| gag gaa ctg cca gat gct ctt cag aca att gcc ttg att gcc tta<br>Glu Glu Leu Pro Asp Ala Leu Gln Thr Ile Ala Leu Ile Ala Leu<br>2170 2175 2180 | | | 6645 |
| ttg agt gtg atg acc atg gga gta ttc ttc ctc ctc atg cag cgg<br>Leu Ser Val Met Thr Met Gly Val Phe Phe Leu Leu Met Gln Arg<br>2185 2190 2195 | | | 6690 |
| aag ggc att gga aag ata ggt ttg gga ggc gct gtc ttg gga gtc<br>Lys Gly Ile Gly Lys Ile Gly Leu Gly Gly Ala Val Leu Gly Val<br>2200 2205 2210 | | | 6735 |
| gcg acc ttt ttc tgt tgg atg gct gaa gtt cca gga acg aag atc<br>Ala Thr Phe Phe Cys Trp Met Ala Glu Val Pro Gly Thr Lys Ile<br>2215 2220 2225 | | | 6780 |
| gcc gga atg ttg ctg ctc tcc ctt ctc ttg atg att gtg cta att<br>Ala Gly Met Leu Leu Leu Ser Leu Leu Leu Met Ile Val Leu Ile<br>2230 2235 2240 | | | 6825 |
| cct gag cca gag aag caa cgt tcg cag aca gac aac cag cta gcc<br>Pro Glu Pro Glu Lys Gln Arg Ser Gln Thr Asp Asn Gln Leu Ala<br>2245 2250 2255 | | | 6870 |
| gtg ttc ctg att tgt gtc atg acc ctt gtg agc gca gtg gca gcc<br>Val Phe Leu Ile Cys Val Met Thr Leu Val Ser Ala Val Ala Ala<br>2260 2265 2270 | | | 6915 |
| aac gag atg ggt tgg cta gat aag acc aag agt gac ata agc agt<br>Asn Glu Met Gly Trp Leu Asp Lys Thr Lys Ser Asp Ile Ser Ser<br>2275 2280 2285 | | | 6960 |
| ttg ttt ggg caa aga att gag gtc aag gag aat ttc agc atg gga<br>Leu Phe Gly Gln Arg Ile Glu Val Lys Glu Asn Phe Ser Met Gly<br>2290 2295 2300 | | | 7005 |
| gag ttt ctt ttg gac ttg agg cct gca aca gcc tgg tca ctg tac<br>Glu Phe Leu Leu Asp Leu Arg Pro Ala Thr Ala Trp Ser Leu Tyr<br>2305 2310 2315 | | | 7050 |
| gct gtg aca aca gcg gtc ctc act cca ctg cta aag cat ttg atc<br>Ala Val Thr Thr Ala Val Leu Thr Pro Leu Leu Lys His Leu Ile<br>2320 2325 2330 | | | 7095 |
| acg tca gat tac atc aac acc tca ttg acc tca ata aac gtt cag<br>Thr Ser Asp Tyr Ile Asn Thr Ser Leu Thr Ser Ile Asn Val Gln<br>2335 2340 2345 | | | 7140 |
| gca agt gca cta ttc aca ctc gcg cga ggc ttc ccc ttc gtc gat<br>Ala Ser Ala Leu Phe Thr Leu Ala Arg Gly Phe Pro Phe Val Asp<br>2350 2355 2360 | | | 7185 |
| gtt gga gtg tcg gct ctc ctg cta gca gcc gga tgc tgg gga caa<br>Val Gly Val Ser Ala Leu Leu Leu Ala Ala Gly Cys Trp Gly Gln<br>2365 2370 2375 | | | 7230 |
| gtc acc ctc acc gtt acg gta aca gcg gca aca ctc ctt ttt tgc<br>Val Thr Leu Thr Val Thr Val Thr Ala Ala Thr Leu Leu Phe Cys<br>2380 2385 2390 | | | 7275 |
| cac tat gcc tac atg gtt ccc ggt tgg caa gct gag gca atg cgc | | | 7320 |

```
                His Tyr Ala Tyr Met Val Pro Gly Trp Gln Ala Glu Ala Met Arg
                2395                2400                2405 tca gcc cag cgg cgg aca gcg gcc gga atc atg aag aac gct gta       7365
Ser Ala Gln Arg Arg Thr Ala Ala Gly Ile Met Lys Asn Ala Val
2410                2415                2420 gtg gat ggc atc gtg gcc acg gac gtc cca gaa tta gag cgc acc       7410
Val Asp Gly Ile Val Ala Thr Asp Val Pro Glu Leu Glu Arg Thr
2425                2430                2435 aca ccc atc atg cag aag aaa gtt gga cag atc atg ctg atc ttg       7455
Thr Pro Ile Met Gln Lys Lys Val Gly Gln Ile Met Leu Ile Leu
2440                2445                2450 gtg tct cta gct gca gta gta gtg aac ccg tct gtg aag aca gta       7500
Val Ser Leu Ala Ala Val Val Val Asn Pro Ser Val Lys Thr Val
2455                2460                2465 cga gaa gcc gga att ttg atc acg gcc gca gcg gtg acg ctt tgg       7545
Arg Glu Ala Gly Ile Leu Ile Thr Ala Ala Ala Val Thr Leu Trp
2470                2475                2480 gag aat gga gca agc tct gtt tgg aac gca aca act gcc atc gga       7590
Glu Asn Gly Ala Ser Ser Val Trp Asn Ala Thr Thr Ala Ile Gly
2485                2490                2495 ctc tgc cac atc atg cgt ggg ggt tgg ttg tca tgt cta tcc ata       7635
Leu Cys His Ile Met Arg Gly Gly Trp Leu Ser Cys Leu Ser Ile
2500                2505                2510 aca tgg aca ctc ata aag aac atg gaa aaa cca gga cta aaa aga       7680
Thr Trp Thr Leu Ile Lys Asn Met Glu Lys Pro Gly Leu Lys Arg
2515                2520                2525 ggt ggg gca aaa gga cgc acc ttg gga gag gtt tgg aaa gaa aga       7725
Gly Gly Ala Lys Gly Arg Thr Leu Gly Glu Val Trp Lys Glu Arg
2530                2535                2540 ctc aac cag atg aca aaa gaa gag ttc act agg tac cgc aaa gag       7770
Leu Asn Gln Met Thr Lys Glu Glu Phe Thr Arg Tyr Arg Lys Glu
2545                2550                2555 gcc atc atc gaa gtc gat cgc tca gcg gca aaa cac gcc agg aaa       7815
Ala Ile Ile Glu Val Asp Arg Ser Ala Ala Lys His Ala Arg Lys
2560                2565                2570 gaa ggc aat gtc act gga ggg cat cca gtc tct agg ggc aca gca       7860
Glu Gly Asn Val Thr Gly Gly His Pro Val Ser Arg Gly Thr Ala
2575                2580                2585 aaa ctg aga tgg ctg gtc gaa cgg agg ttt ctc gaa ccg gtc gga       7905
Lys Leu Arg Trp Leu Val Glu Arg Arg Phe Leu Glu Pro Val Gly
2590                2595                2600 aaa gtg att gac ctt gga tgt gga aga ggc ggt tgg tgt tac tat       7950
Lys Val Ile Asp Leu Gly Cys Gly Arg Gly Gly Trp Cys Tyr Tyr
2605                2610                2615 atg gca acc caa aaa aga gtc caa gaa gtc aga ggg tac aca aag       7995
Met Ala Thr Gln Lys Arg Val Gln Glu Val Arg Gly Tyr Thr Lys
2620                2625                2630 ggc ggt ccc gga cat gaa gag ccc caa cta gtg caa agt tat gga       8040
Gly Gly Pro Gly His Glu Glu Pro Gln Leu Val Gln Ser Tyr Gly
2635                2640                2645 tgg aac att gtc acc atg aag agt gga gtg gat gtg ttc tac aga       8085
Trp Asn Ile Val Thr Met Lys Ser Gly Val Asp Val Phe Tyr Arg
2650                2655                2660 cct tct gag tgt tgt gac acc ctc ctt tgt gac atc gga gag tcc       8130
Pro Ser Glu Cys Cys Asp Thr Leu Leu Cys Asp Ile Gly Glu Ser
2665                2670                2675 tcg tca agt gct gag gtt gaa gag cat agg acg att cgg gtc ctt       8175
Ser Ser Ser Ala Glu Val Glu Glu His Arg Thr Ile Arg Val Leu
2680                2685                2690
```

|     |     |     |     |     |     |     |     |     |     |     |     |     |     |     |      |
| --- | --- | --- | --- | --- | --- | --- | --- | --- | --- | --- | --- | --- | --- | --- | ---- |
| gaa | atg | gtt | gag | gac | tgg | ctg | cac | cga | ggg | cca | agg | gaa | ttt | tgc | 8220 |
| Glu | Met | Val | Glu | Asp | Trp | Leu | His | Arg | Gly | Pro | Arg | Glu | Phe | Cys |      |
|     | 2695 |   |     |     | 2700 |   |     |     |     | 2705 |   |     |     |     |      |
| gtg | aag | gtg | ctc | tgc | ccc | tac | atg | ccg | aaa | gtc | ata | gag | aag | atg | 8265 |
| Val | Lys | Val | Leu | Cys | Pro | Tyr | Met | Pro | Lys | Val | Ile | Glu | Lys | Met |      |
| 2710 |   |     |     |     | 2715 |   |     |     |     | 2720 |   |     |     |     |      |
| gag | ctg | ctc | caa | cgc | cgg | tat | ggg | ggg | gga | ctg | gtc | aga | aac | cca | 8310 |
| Glu | Leu | Leu | Gln | Arg | Arg | Tyr | Gly | Gly | Gly | Leu | Val | Arg | Asn | Pro |      |
|     | 2725 |   |     |     | 2730 |   |     |     |     | 2735 |   |     |     |     |      |
| ctc | tca | cgg | aat | tcc | acg | cac | gag | atg | tat | tgg | gtg | agt | cga | gct | 8355 |
| Leu | Ser | Arg | Asn | Ser | Thr | His | Glu | Met | Tyr | Trp | Val | Ser | Arg | Ala |      |
|     | 2740 |   |     |     | 2745 |   |     |     |     | 2750 |   |     |     |     |      |
| tca | ggc | aat | gtg | gta | cat | tca | gtg | aat | atg | acc | agc | cag | gtg | ctc | 8400 |
| Ser | Gly | Asn | Val | Val | His | Ser | Val | Asn | Met | Thr | Ser | Gln | Val | Leu |      |
|     | 2755 |   |     |     | 2760 |   |     |     |     | 2765 |   |     |     |     |      |
| cta | gga | aga | atg | gaa | aaa | agg | acc | tgg | aag | gga | ccc | caa | tac | gag | 8445 |
| Leu | Gly | Arg | Met | Glu | Lys | Arg | Thr | Trp | Lys | Gly | Pro | Gln | Tyr | Glu |      |
|     | 2770 |   |     |     | 2775 |   |     |     |     | 2780 |   |     |     |     |      |
| gaa | gat | gta | aac | ttg | gga | agt | gga | acc | agg | gcg | gtg | gga | aaa | ccc | 8490 |
| Glu | Asp | Val | Asn | Leu | Gly | Ser | Gly | Thr | Arg | Ala | Val | Gly | Lys | Pro |      |
|     | 2785 |   |     |     | 2790 |   |     |     |     | 2795 |   |     |     |     |      |
| ctg | ctc | aac | tca | gac | acc | agt | aaa | atc | aag | aac | agg | att | gaa | cga | 8535 |
| Leu | Leu | Asn | Ser | Asp | Thr | Ser | Lys | Ile | Lys | Asn | Arg | Ile | Glu | Arg |      |
| 2800 |   |     |     |     | 2805 |   |     |     |     | 2810 |   |     |     |     |      |
| ctc | agg | cgt | gag | tac | agt | tcg | acg | tgg | cac | cac | gat | gag | aac | cac | 8580 |
| Leu | Arg | Arg | Glu | Tyr | Ser | Ser | Thr | Trp | His | His | Asp | Glu | Asn | His |      |
|     | 2815 |   |     |     | 2820 |   |     |     |     | 2825 |   |     |     |     |      |
| cca | tat | aga | acc | tgg | aac | tat | cac | ggc | agt | tat | gat | gtg | aag | ccc | 8625 |
| Pro | Tyr | Arg | Thr | Trp | Asn | Tyr | His | Gly | Ser | Tyr | Asp | Val | Lys | Pro |      |
|     | 2830 |   |     |     | 2835 |   |     |     |     | 2840 |   |     |     |     |      |
| aca | ggc | tcc | gcc | agt | tcg | ctg | gtc | aat | gga | gtg | gtc | agg | ctc | ctc | 8670 |
| Thr | Gly | Ser | Ala | Ser | Ser | Leu | Val | Asn | Gly | Val | Val | Arg | Leu | Leu |      |
|     | 2845 |   |     |     | 2850 |   |     |     |     | 2855 |   |     |     |     |      |
| tca | aaa | cca | tgg | gac | acc | atc | acg | aat | gtt | acc | acc | atg | gcc | atg | 8715 |
| Ser | Lys | Pro | Trp | Asp | Thr | Ile | Thr | Asn | Val | Thr | Thr | Met | Ala | Met |      |
|     | 2860 |   |     |     | 2865 |   |     |     |     | 2870 |   |     |     |     |      |
| act | gac | act | act | ccc | ttc | ggg | cag | cag | cga | gtg | ttc | aaa | gag | aag | 8760 |
| Thr | Asp | Thr | Thr | Pro | Phe | Gly | Gln | Gln | Arg | Val | Phe | Lys | Glu | Lys |      |
|     | 2875 |   |     |     | 2880 |   |     |     |     | 2885 |   |     |     |     |      |
| gtg | gac | acg | aaa | gct | cct | gaa | ccg | cca | gaa | gga | gtg | aag | tac | gtg | 8805 |
| Val | Asp | Thr | Lys | Ala | Pro | Glu | Pro | Pro | Glu | Gly | Val | Lys | Tyr | Val |      |
|     | 2890 |   |     |     | 2895 |   |     |     |     | 2900 |   |     |     |     |      |
| ctc | aac | gag | acc | acc | aac | tgg | ttg | tgg | gcg | ttt | ttg | gcc | aga | gaa | 8850 |
| Leu | Asn | Glu | Thr | Thr | Asn | Trp | Leu | Trp | Ala | Phe | Leu | Ala | Arg | Glu |      |
|     | 2905 |   |     |     | 2910 |   |     |     |     | 2915 |   |     |     |     |      |
| aaa | cgt | ccc | aga | atg | tgc | tct | cga | gag | gaa | ttc | ata | aga | aag | gtc | 8895 |
| Lys | Arg | Pro | Arg | Met | Cys | Ser | Arg | Glu | Glu | Phe | Ile | Arg | Lys | Val |      |
|     | 2920 |   |     |     | 2925 |   |     |     |     | 2930 |   |     |     |     |      |
| aac | agc | aat | gca | gct | ttg | ggt | gcc | atg | ttt | gaa | gag | cag | aat | caa | 8940 |
| Asn | Ser | Asn | Ala | Ala | Leu | Gly | Ala | Met | Phe | Glu | Glu | Gln | Asn | Gln |      |
|     | 2935 |   |     |     | 2940 |   |     |     |     | 2945 |   |     |     |     |      |
| tgg | agg | agc | gcc | aga | gaa | gca | gtt | gaa | gat | cca | aaa | ttt | tgg | gag | 8985 |
| Trp | Arg | Ser | Ala | Arg | Glu | Ala | Val | Glu | Asp | Pro | Lys | Phe | Trp | Glu |      |
|     | 2950 |   |     |     | 2955 |   |     |     |     | 2960 |   |     |     |     |      |
| atg | gtg | gat | gag | gag | cgc | gag | gca | cat | ctg | cgg | ggg | gaa | tgt | cac | 9030 |
| Met | Val | Asp | Glu | Glu | Arg | Glu | Ala | His | Leu | Arg | Gly | Glu | Cys | His |      |
|     | 2965 |   |     |     | 2970 |   |     |     |     | 2975 |   |     |     |     |      |
| act | tgc | att | tac | aac | atg | atg | gga | aag | aga | gag | aaa | aaa | ccc | gga | 9075 |
| Thr | Cys | Ile | Tyr | Asn | Met | Met | Gly | Lys | Arg | Glu | Lys | Lys | Pro | Gly |      |
|     | 2980 |   |     |     | 2985 |   |     |     |     | 2990 |   |     |     |     |      |

```
gag ttc gga aag gcc aag gga agc aga gcc att tgg ttc atg tgg        9120
Glu Phe Gly Lys Ala Lys Gly Ser Arg Ala Ile Trp Phe Met Trp
    2995            3000                3005 ctc gga gct cgc ttt ctg gag ttc gag gct ctg ggt ttt ctc aat        9165
Leu Gly Ala Arg Phe Leu Glu Phe Glu Ala Leu Gly Phe Leu Asn
3010                3015                3020 gaa gac cac tgg ctt gga aga aag aac tca gga gga ggt gtc gag        9210
Glu Asp His Trp Leu Gly Arg Lys Asn Ser Gly Gly Gly Val Glu
    3025            3030                3035 ggc ttg ggc ctc caa aaa ctg ggt tac atc ctg cgt gaa gtt ggc        9255
Gly Leu Gly Leu Gln Lys Leu Gly Tyr Ile Leu Arg Glu Val Gly
3040                3045                3050 acc cgg cct ggg ggc aag atc tat gct gat gac aca gct ggc tgg        9300
Thr Arg Pro Gly Gly Lys Ile Tyr Ala Asp Asp Thr Ala Gly Trp
    3055            3060                3065 gac acc cgc atc acg aga gct gac ttg gaa aat gaa gct aag gtg        9345
Asp Thr Arg Ile Thr Arg Ala Asp Leu Glu Asn Glu Ala Lys Val
3070                3075                3080 ctt gag ctg ctt gat ggg gaa cat cgg cgt ctt gcc agg gcc atc        9390
Leu Glu Leu Leu Asp Gly Glu His Arg Arg Leu Ala Arg Ala Ile
    3085            3090                3095 att gag ctc acc tat cgt cac aaa gtt gtg aaa gtg atg cgc ccg        9435
Ile Glu Leu Thr Tyr Arg His Lys Val Val Lys Val Met Arg Pro
3100                3105                3110 gct gct gat gga aga acc gtc atg gat gtt atc tcc aga gaa gat        9480
Ala Ala Asp Gly Arg Thr Val Met Asp Val Ile Ser Arg Glu Asp
    3115            3120                3125 cag agg ggg agt gga caa gtt gtc acc tac gcc cta aac act ttc        9525
Gln Arg Gly Ser Gly Gln Val Val Thr Tyr Ala Leu Asn Thr Phe
3130                3135                3140 acc aac ctg gcc gtc cag ctg gtg agg atg atg gaa ggg gaa gga        9570
Thr Asn Leu Ala Val Gln Leu Val Arg Met Met Glu Gly Glu Gly
    3145            3150                3155 gtg att ggc cca gat gat gtc gag aaa ctc aca aaa ggg aaa gga        9615
Val Ile Gly Pro Asp Asp Val Glu Lys Leu Thr Lys Gly Lys Gly
3160                3165                3170 ccc aaa gtc agg acc tgg ctg ttt gag aat ggg gaa gaa aga ctc        9660
Pro Lys Val Arg Thr Trp Leu Phe Glu Asn Gly Glu Glu Arg Leu
    3175            3180                3185 agc cgc atg gct gtc agt gga gat gac tgt gtg gta aag ccc ctg        9705
Ser Arg Met Ala Val Ser Gly Asp Asp Cys Val Val Lys Pro Leu
3190                3195                3200 gac gat cgc ttt gcc acc tcg ctc cac ttc ctc aat gct atg tca        9750
Asp Asp Arg Phe Ala Thr Ser Leu His Phe Leu Asn Ala Met Ser
    3205            3210                3215 aag gtt cgc aaa gac atc caa gag tgg aaa ccg tca act gga tgg        9795
Lys Val Arg Lys Asp Ile Gln Glu Trp Lys Pro Ser Thr Gly Trp
3220                3225                3230 tat gat tgg cag cag gtt cca ttt tgc tca aac cat ttc act gaa        9840
Tyr Asp Trp Gln Gln Val Pro Phe Cys Ser Asn His Phe Thr Glu
    3235            3240                3245 ttg atc atg aaa gat gga aga aca ctg gtg gtt cca tgc cga gga        9885
Leu Ile Met Lys Asp Gly Arg Thr Leu Val Val Pro Cys Arg Gly
3250                3255                3260 cag gat gaa ttg gta ggc aga gct cgc ata tct cca ggg gcc gga        9930
Gln Asp Glu Leu Val Gly Arg Ala Arg Ile Ser Pro Gly Ala Gly
    3265            3270                3275 tgg aac gtc cgc gac act gct tgt ctg gct aag tct tat gcc cag        9975
Trp Asn Val Arg Asp Thr Ala Cys Leu Ala Lys Ser Tyr Ala Gln
```

|   |   |   |   |   |   |   |   |   |   |   |   |   |   |   |
|---|---|---|---|---|---|---|---|---|---|---|---|---|---|---|
|   |   | 3280 |   |   |   |   | 3285 |   |   |   |   | 3290 |   |   |
| atg | tgg | ctg | ctt | ctg | tac | ttc | cac | aga | aga | gac | ctg | cgg | ctc | atg | 10020 |
| Met | Trp | Leu | Leu | Leu | Tyr | Phe | His | Arg | Arg | Asp | Leu | Arg | Leu | Met |   |
|   | 3295 |   |   |   |   | 3300 |   |   |   |   | 3305 |   |   |   |   |
| gcc | aac | gcc | att | tgc | tcc | gct | gtc | cct | gtg | aat | tgg | gtc | cct | acc | 10065 |
| Ala | Asn | Ala | Ile | Cys | Ser | Ala | Val | Pro | Val | Asn | Trp | Val | Pro | Thr |   |
|   | 3310 |   |   |   |   | 3315 |   |   |   |   | 3320 |   |   |   |   |
| gga | aga | acc | acg | tgg | tcc | atc | cat | gca | gga | gag | tgg | atg | aca | 10110 |
| Gly | Arg | Thr | Thr | Trp | Ser | Ile | His | Ala | Gly | Glu | Trp | Met | Thr |   |
|   | 3325 |   |   |   |   | 3330 |   |   |   |   | 3335 |   |   |   |
| aca | gag | gac | atg | ttg | gag | gtc | tgg | aac | cgt | gtt | tgg | ata | gag | gag | 10155 |
| Thr | Glu | Asp | Met | Leu | Glu | Val | Trp | Asn | Arg | Val | Trp | Ile | Glu | Glu |   |
|   | 3340 |   |   |   |   | 3345 |   |   |   |   | 3350 |   |   |   |   |
| aat | gaa | tgg | atg | gaa | gac | aaa | acc | cca | gtg | gag | aaa | tgg | agt | gac | 10200 |
| Asn | Glu | Trp | Met | Glu | Asp | Lys | Thr | Pro | Val | Glu | Lys | Trp | Ser | Asp |   |
|   | 3355 |   |   |   |   | 3360 |   |   |   |   | 3365 |   |   |   |   |
| gtc | cca | tat | tca | gga | aaa | cga | gag | gac | atc | tgg | tgt | ggc | agc | ctg | 10245 |
| Val | Pro | Tyr | Ser | Gly | Lys | Arg | Glu | Asp | Ile | Trp | Cys | Gly | Ser | Leu |   |
|   | 3370 |   |   |   |   | 3375 |   |   |   |   | 3380 |   |   |   |   |
| att | ggc | aca | aga | gcc | cga | gcc | acg | tgg | gca | gaa | aac | atc | cag | gtg | 10290 |
| Ile | Gly | Thr | Arg | Ala | Arg | Ala | Thr | Trp | Ala | Glu | Asn | Ile | Gln | Val |   |
|   | 3385 |   |   |   |   | 3390 |   |   |   |   | 3395 |   |   |   |   |
| gct | atc | aac | caa | gtc | aga | gca | atc | atc | gga | gat | gag | aag | tat | gtg | 10335 |
| Ala | Ile | Asn | Gln | Val | Arg | Ala | Ile | Ile | Gly | Asp | Glu | Lys | Tyr | Val |   |
|   | 3400 |   |   |   |   | 3405 |   |   |   |   | 3410 |   |   |   |   |
| gat | tac | atg | agt | tca | cta | aag | aga | tat | gaa | gac | aca | act | ttg | gtt | 10380 |
| Asp | Tyr | Met | Ser | Ser | Leu | Lys | Arg | Tyr | Glu | Asp | Thr | Thr | Leu | Val |   |
|   | 3415 |   |   |   |   | 3420 |   |   |   |   | 3425 |   |   |   |   |
| gag | gac | aca | gta | ctg | tag | atatttaatc | aattgtaaat | agacaatata |   |   |   |   |   |   | 10428 |
| Glu | Asp | Thr | Val | Leu |   |   |   |   |   |   |   |   |   |   |   |
|   | 3430 |   |   |   |   |   |   |   |   |   |   |   |   |   |   | agtatgcata aaagtgtagt tttatagtag tatttagtgg tgttagtgta aatagttaag 10488 aaaattttga ggagaaagtc aggccgggaa gttcccgcca ccggaagttg agtagacggt 10548 gctgcctgcg actcaacccc aggaggactg ggtgaacaaa gccgcgaagt gatccatgta 10608 agccctcaga accgtctcgg aaggaggacc ccacatgttg taacttcaaa gcccaatgtc 10668 agaccacgct acggcgtgct actctgcgga gagtgcagtc tgcgatagtg ccccaggagg 10728 actgggttaa caaaggcaaa ccaacgcccc acgcggccct agccccggta atggtgttaa 10788 ccagggcgaa aggactagag gttagaggag accccgcggt ttaaagtgca cggcccagcc 10848 tggctgaagc tgtaggtcag gggaaggact agaggttagt ggagacccccg tgccacaaaa 10908 caccacaaca aaacagcata ttgacacctg ggatagacta ggagatcttc tgctctgcac 10968 aaccagccac acggcacagt gcgccgacaa tggtggctgg tggtgcgaga acacaggatc 11028 t                                                                 11029

<210> SEQ ID NO 2
<211> LENGTH: 3433
<212> TYPE: PRT
<213> ORGANISM: West Nile virus

<400> SEQUENCE: 2

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu

```
                35                  40                  45
Ala Leu Leu Ala Phe Phe Arg Phe Thr Ala Ile Ala Pro Thr Arg Ala
 50                  55                  60

Val Leu Asp Arg Trp Arg Gly Val Asn Lys Gln Thr Ala Met Lys His
 65                  70                  75                  80

Leu Leu Ser Phe Lys Glu Leu Gly Thr Leu Thr Ser Ala Ile Asn
                 85                  90                  95

Arg Arg Ser Ser Lys Gln Lys Lys Arg Gly Gly Lys Thr Gly Ile Ala
                100                 105                 110

Val Met Ile Gly Leu Ile Ala Ser Val Gly Ala Val Thr Leu Ser Asn
                115                 120                 125

Phe Gln Gly Lys Val Met Met Thr Val Asn Ala Thr Asp Val Thr Asp
                130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
                180                 185                 190

Thr Lys Ser Ala Val Tyr Val Arg Tyr Gly Arg Cys Thr Lys Thr Arg
                195                 200                 205

His Ser Arg Arg Ser Arg Arg Ser Leu Thr Val Gln Thr His Gly Glu
                210                 215                 220

Ser Thr Leu Ala Asn Lys Lys Gly Ala Trp Met Asp Ser Thr Lys Ala
225                 230                 235                 240

Thr Arg Tyr Leu Val Lys Thr Glu Ser Trp Ile Leu Arg Asn Pro Gly
                245                 250                 255

Tyr Ala Leu Val Ala Ala Val Ile Gly Trp Met Leu Gly Ser Asn Thr
                260                 265                 270

Met Gln Arg Val Val Phe Val Val Leu Leu Leu Val Ala Pro Ala
                275                 280                 285

Tyr Ser Phe Asn Cys Leu Gly Met Ser Asn Arg Asp Phe Leu Glu Gly
                290                 295                 300

Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                325                 330                 335

Asn Met Glu Ala Ala Asn Leu Ala Glu Val Arg Ser Tyr Cys Tyr Leu
                340                 345                 350

Ala Thr Val Ser Asp Leu Ser Thr Lys Ala Ala Cys Pro Thr Met Gly
                355                 360                 365

Glu Ala His Asn Asp Lys Arg Ala Asp Pro Ala Phe Val Cys Arg Gln
                370                 375                 380

Gly Val Val Asp Arg Gly Trp Gly Asn Gly Cys Gly Leu Phe Gly Lys
385                 390                 395                 400

Gly Ser Ile Ala Thr Cys Ala Lys Phe Ala Cys Ser Thr Lys Ala Ile
                405                 410                 415

Gly Arg Thr Ile Leu Lys Glu Asn Ile Lys Tyr Glu Val Ala Ile Phe
                420                 425                 430

Val His Gly Pro Thr Thr Val Glu Ser His Gly Asn Tyr Ser Thr Gln
                435                 440                 445

Val Gly Ala Thr Gln Ala Gly Arg Phe Ser Ile Thr Pro Ala Ala Pro
                450                 455                 460
```

```
Ser Tyr Thr Leu Lys Leu Gly Glu Tyr Gly Glu Val Thr Val Asp Cys
465                 470                 475                 480

Glu Pro Arg Ser Gly Ile Asp Thr Asn Ala Tyr Tyr Val Met Thr Val
            485                 490                 495

Gly Thr Lys Thr Phe Leu Val His Arg Glu Trp Phe Met Asp Leu Asn
        500                 505                 510

Leu Pro Trp Ser Ser Ala Gly Ser Thr Val Trp Arg Asn Arg Glu Thr
    515                 520                 525

Leu Met Glu Phe Glu Glu Pro His Ala Thr Lys Gln Ser Val Ile Ala
530                 535                 540

Leu Gly Ser Gln Glu Gly Ala Leu His Gln Ala Leu Ala Gly Ala Ile
545                 550                 555                 560

Pro Val Glu Phe Ser Ser Asn Thr Val Lys Leu Thr Ser Gly His Leu
                565                 570                 575

Lys Cys Arg Val Lys Met Glu Lys Leu Gln Leu Lys Gly Thr Thr Tyr
            580                 585                 590

Gly Val Cys Ser Lys Ala Phe Lys Phe Leu Gly Thr Pro Ala Asp Thr
        595                 600                 605

Gly His Gly Thr Val Val Leu Glu Leu Gln Tyr Thr Gly Thr Asp Gly
    610                 615                 620

Pro Cys Lys Val Pro Ile Ser Ser Val Ala Ser Leu Asn Asp Leu Thr
625                 630                 635                 640

Pro Val Gly Arg Leu Val Thr Val Asn Pro Phe Val Ser Val Ala Thr
                645                 650                 655

Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
        675                 680                 685

Lys Ser Gly Ser Ser Ile Gly Lys Ala Phe Thr Thr Thr Leu Lys Gly
    690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                725                 730                 735

Gly Gly Ala Phe Arg Ser Leu Phe Gly Gly Met Ser Trp Ile Thr Gln
            740                 745                 750

Gly Leu Leu Gly Ala Leu Leu Leu Trp Met Gly Ile Asn Ala Arg Asp
        755                 760                 765

Arg Ser Ile Ala Leu Thr Phe Leu Ala Val Gly Gly Val Leu Leu Phe
    770                 775                 780

Leu Ser Val Asn Val His Ala Asp Thr Gly Cys Ala Ile Asp Ile Ser
785                 790                 795                 800

Arg Gln Glu Leu Arg Cys Gly Ser Gly Val Phe Ile His Asn Asp Val
                805                 810                 815

Glu Ala Trp Met Asp Arg Tyr Lys Tyr Tyr Pro Glu Thr Pro Gln Gly
            820                 825                 830

Leu Ala Lys Ile Ile Gln Lys Ala His Lys Glu Gly Val Cys Gly Leu
        835                 840                 845

Arg Ser Val Ser Arg Leu Glu His Gln Met Trp Glu Ala Val Lys Asp
    850                 855                 860

Glu Leu Asn Thr Leu Leu Lys Glu Asn Gly Val Asp Leu Ser Val Val
865                 870                 875                 880
```

```
Val Glu Lys Gln Glu Gly Met Tyr Lys Ser Ala Pro Lys Arg Leu Thr
            885                 890                 895

Ala Thr Thr Glu Lys Leu Glu Ile Gly Trp Lys Ala Trp Gly Lys Ser
        900                 905                 910

Ile Leu Phe Ala Pro Glu Leu Ala Asn Asn Thr Phe Val Val Asp Gly
        915                 920                 925

Pro Glu Thr Lys Glu Cys Pro Thr Gln Asn Arg Ala Trp Asn Ser Leu
    930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
                965                 970                 975

Thr Ala Val Lys Asn Asn Leu Ala Ile His Ser Asp Leu Ser Tyr Trp
            980                 985                 990

Ile Glu Ser Arg Leu Asn Asp Thr Trp Lys Leu Glu Arg Ala Val Leu
            995                 1000                1005

Gly Glu Val Lys Ser Cys Thr Trp Pro Glu Thr His Thr Leu Trp
    1010                1015                1020

Gly Asp Gly Ile Leu Glu Ser Asp Leu Ile Ile Pro Val Thr Leu
    1025                1030                1035

Ala Gly Pro Arg Ser Asn His Asn Arg Arg Pro Gly Tyr Lys Thr
    1040                1045                1050

Gln Asn Gln Gly Pro Trp Asp Glu Gly Arg Val Glu Ile Asp Phe
    1055                1060                1065

Asp Tyr Cys Pro Gly Thr Thr Val Thr Leu Ser Glu Ser Cys Gly
    1070                1075                1080

His Arg Gly Pro Ala Thr Arg Thr Thr Thr Glu Ser Gly Lys Leu
    1085                1090                1095

Ile Thr Asp Trp Cys Cys Arg Ser Cys Thr Leu Pro Pro Leu Arg
    1100                1105                1110

Tyr Gln Thr Asp Ser Gly Cys Trp Tyr Gly Met Glu Ile Arg Pro
    1115                1120                1125

Gln Arg His Asp Glu Lys Thr Leu Val Gln Ser Gln Val Asn Ala
    1130                1135                1140

Tyr Asn Ala Asp Met Ile Asp Pro Phe Gln Leu Gly Leu Leu Val
    1145                1150                1155

Val Phe Leu Ala Thr Gln Glu Val Leu Arg Lys Arg Trp Thr Ala
    1160                1165                1170

Lys Ile Ser Met Pro Ala Ile Leu Ile Ala Leu Leu Val Leu Val
    1175                1180                1185

Phe Gly Gly Ile Thr Tyr Thr Asp Val Leu Arg Tyr Val Ile Leu
    1190                1195                1200

Val Gly Ala Ala Phe Ala Glu Ser Asn Ser Gly Gly Asp Val Val
    1205                1210                1215

His Leu Ala Leu Met Ala Thr Phe Lys Ile Gln Pro Val Phe Met
    1220                1225                1230

Val Ala Ser Phe Leu Lys Ala Arg Trp Thr Asn Gln Glu Asn Ile
    1235                1240                1245

Leu Leu Met Leu Ala Ala Val Phe Phe Gln Met Ala Tyr Tyr Asp
    1250                1255                1260

Ala Arg Gln Ile Leu Leu Trp Glu Ile Pro Asp Val Leu Asn Ser
    1265                1270                1275

Leu Ala Val Ala Trp Met Ile Leu Arg Ala Ile Thr Phe Thr Thr
```

```
                  1280                1285                1290
Thr Ser Asn Val Val Pro Leu Leu Ala Leu Leu Thr Pro Gly
    1295                1300            1305

Leu Arg Cys Leu Asn Leu Asp Val Tyr Arg Ile Leu Leu Met
    1310                1315            1320

Val Gly Ile Gly Ser Leu Ile Arg Glu Lys Arg Ser Ala Ala Ala
    1325                1330            1335

Lys Lys Lys Gly Ala Ser Leu Leu Cys Leu Ala Leu Ala Ser Thr
    1340                1345            1350

Gly Leu Phe Asn Pro Met Ile Leu Ala Ala Gly Leu Ile Ala Cys
    1355                1360            1365

Asp Pro Asn Arg Lys Arg Gly Trp Pro Ala Thr Glu Val Met Thr
    1370                1375            1380

Ala Val Gly Leu Met Phe Ala Ile Val Gly Gly Leu Ala Glu Leu
    1385                1390            1395

Asp Ile Asp Ser Met Ala Ile Pro Met Thr Ile Ala Gly Leu Met
    1400                1405            1410

Phe Ala Ala Phe Val Ile Ser Gly Lys Ser Thr Asp Met Trp Ile
    1415                1420            1425

Glu Arg Thr Ala Asp Ile Ser Trp Glu Ser Asp Ala Glu Ile Thr
    1430                1435            1440

Gly Ser Ser Glu Arg Val Asp Val Arg Leu Asp Asp Gly Asn
    1445                1450            1455

Phe Gln Leu Met Asn Asp Pro Gly Ala Pro Trp Lys Ile Trp Met
    1460                1465            1470

Leu Arg Met Val Cys Leu Ala Ile Ser Ala Tyr Thr Pro Trp Ala
    1475                1480            1485

Ile Leu Pro Ser Val Val Gly Phe Trp Ile Thr Leu Gln Tyr Thr
    1490                1495            1500

Lys Arg Gly Gly Val Leu Trp Asp Thr Pro Ser Pro Lys Glu Tyr
    1505                1510            1515

Lys Lys Gly Asp Thr Thr Thr Gly Val Tyr Arg Ile Met Thr Arg
    1520                1525            1530

Gly Leu Leu Gly Ser Tyr Gln Ala Gly Ala Gly Val Met Val Glu
    1535                1540            1545

Gly Val Phe His Thr Leu Trp His Thr Thr Lys Gly Ala Ala Leu
    1550                1555            1560

Met Ser Gly Glu Gly Arg Leu Asp Pro Tyr Trp Gly Ser Val Lys
    1565                1570            1575

Glu Asp Arg Leu Cys Tyr Gly Gly Pro Trp Lys Leu Gln His Lys
    1580                1585            1590

Trp Asn Gly Gln Asp Glu Val Gln Met Ile Val Val Glu Pro Gly
    1595                1600            1605

Arg Asn Val Lys Asn Val Gln Thr Lys Pro Gly Val Phe Lys Thr
    1610                1615            1620

Pro Glu Gly Glu Ile Gly Ala Val Thr Leu Asp Phe Pro Thr Gly
    1625                1630            1635

Thr Ser Gly Ser Pro Ile Val Asp Lys Asn Gly Asp Val Ile Gly
    1640                1645            1650

Leu Tyr Gly Asn Gly Val Ile Met Pro Asn Gly Ser Tyr Ile Ser
    1655                1660            1665

Ala Ile Val Gln Gly Glu Arg Met Asp Glu Pro Ile Pro Ala Gly
    1670                1675            1680
```

-continued

Phe Glu Pro Glu Met Leu Arg Lys Lys Gln Ile Thr Val Leu Asp
1685                1690                1695

Leu His Pro Gly Ala Gly Lys Thr Arg Arg Ile Leu Pro Gln Ile
1700                1705                1710

Ile Lys Glu Ala Ile Asn Arg Arg Leu Arg Thr Ala Val Leu Ala
1715                1720                1725

Pro Thr Arg Val Val Ala Ala Glu Met Ala Glu Ala Leu Arg Gly
1730                1735                1740

Leu Pro Ile Arg Tyr Gln Thr Ser Ala Val Pro Arg Glu His Asn
1745                1750                1755

Gly Asn Glu Ile Val Asp Val Met Cys His Ala Thr Leu Thr His
1760                1765                1770

Arg Leu Met Ser Pro His Arg Val Pro Asn Tyr Asn Leu Phe Val
1775                1780                1785

Met Asp Glu Ala His Phe Thr Asp Pro Ala Ser Ile Ala Ala Arg
1790                1795                1800

Gly Tyr Ile Ser Thr Lys Val Glu Leu Gly Glu Ala Ala Ala Ile
1805                1810                1815

Phe Met Thr Ala Thr Pro Pro Gly Thr Ser Asp Pro Phe Pro Glu
1820                1825                1830

Ser Asn Ser Pro Ile Ser Asp Leu Gln Thr Glu Ile Pro Asp Arg
1835                1840                1845

Ala Trp Asn Ser Gly Tyr Glu Trp Ile Thr Glu Tyr Thr Gly Lys
1850                1855                1860

Thr Val Trp Phe Val Pro Ser Val Lys Met Gly Asn Glu Ile Ala
1865                1870                1875

Leu Cys Leu Gln Arg Ala Gly Lys Lys Val Val Gln Leu Asn Arg
1880                1885                1890

Lys Ser Tyr Glu Thr Glu Tyr Pro Lys Cys Lys Asn Asp Asp Trp
1895                1900                1905

Asp Phe Val Ile Thr Thr Asp Ile Ser Glu Met Gly Ala Asn Phe
1910                1915                1920

Lys Ala Ser Arg Val Ile Asp Ser Arg Lys Ser Val Lys Pro Thr
1925                1930                1935

Ile Ile Thr Glu Gly Glu Gly Arg Val Ile Leu Gly Glu Pro Ser
1940                1945                1950

Ala Val Thr Ala Ala Ser Ala Ala Gln Arg Arg Gly Arg Ile Gly
1955                1960                1965

Arg Asn Pro Ser Gln Val Gly Asp Glu Tyr Cys Tyr Gly Gly His
1970                1975                1980

Thr Asn Glu Asp Asp Ser Asn Phe Ala His Trp Thr Glu Ala Arg
1985                1990                1995

Ile Met Leu Asp Asn Ile Asn Met Pro Asn Gly Leu Ile Ala Gln
2000                2005                2010

Phe Tyr Gln Pro Glu Arg Glu Lys Val Tyr Thr Met Asp Gly Glu
2015                2020                2025

Tyr Arg Leu Arg Gly Glu Glu Arg Lys Asn Phe Leu Glu Leu Leu
2030                2035                2040

Arg Thr Ala Asp Leu Pro Val Trp Leu Ala Tyr Lys Val Ala Ala
2045                2050                2055

Ala Gly Val Ser Tyr His Asp Arg Arg Trp Cys Phe Asp Gly Pro
2060                2065                2070

-continued

```
Arg Thr Asn Thr Ile Leu Glu Asp Asn Asn Glu Val Glu Val Ile
2075                2080                2085

Thr Lys Leu Gly Glu Arg Lys Ile Leu Arg Pro Arg Trp Ile Asp
2090                2095                2100

Ala Arg Val Tyr Ser Asp His Gln Ala Leu Lys Ala Phe Lys Asp
2105                2110                2115

Phe Ala Ser Gly Lys Arg Ser Gln Ile Gly Leu Ile Glu Val Leu
2120                2125                2130

Gly Lys Met Pro Glu His Phe Met Gly Lys Thr Trp Glu Ala Leu
2135                2140                2145

Asp Thr Met Tyr Val Val Ala Thr Ala Glu Lys Gly Gly Arg Ala
2150                2155                2160

His Arg Met Ala Leu Glu Glu Leu Pro Asp Ala Leu Gln Thr Ile
2165                2170                2175

Ala Leu Ile Ala Leu Leu Ser Val Met Thr Met Gly Val Phe Phe
2180                2185                2190

Leu Leu Met Gln Arg Lys Gly Ile Gly Lys Ile Gly Leu Gly Gly
2195                2200                2205

Ala Val Leu Gly Val Ala Thr Phe Phe Cys Trp Met Ala Glu Val
2210                2215                2220

Pro Gly Thr Lys Ile Ala Gly Met Leu Leu Leu Ser Leu Leu Leu
2225                2230                2235

Met Ile Val Leu Ile Pro Glu Pro Glu Lys Gln Arg Ser Gln Thr
2240                2245                2250

Asp Asn Gln Leu Ala Val Phe Leu Ile Cys Val Met Thr Leu Val
2255                2260                2265

Ser Ala Val Ala Ala Asn Glu Met Gly Trp Leu Asp Lys Thr Lys
2270                2275                2280

Ser Asp Ile Ser Ser Leu Phe Gly Gln Arg Ile Glu Val Lys Glu
2285                2290                2295

Asn Phe Ser Met Gly Glu Phe Leu Leu Asp Leu Arg Pro Ala Thr
2300                2305                2310

Ala Trp Ser Leu Tyr Ala Val Thr Thr Ala Val Leu Thr Pro Leu
2315                2320                2325

Leu Lys His Leu Ile Thr Ser Asp Tyr Ile Asn Thr Ser Leu Thr
2330                2335                2340

Ser Ile Asn Val Gln Ala Ser Ala Leu Phe Thr Leu Ala Arg Gly
2345                2350                2355

Phe Pro Phe Val Asp Val Gly Val Ser Ala Leu Leu Leu Ala Ala
2360                2365                2370

Gly Cys Trp Gly Gln Val Thr Leu Thr Val Thr Val Thr Ala Ala
2375                2380                2385

Thr Leu Leu Phe Cys His Tyr Ala Tyr Met Val Pro Gly Trp Gln
2390                2395                2400

Ala Glu Ala Met Arg Ser Ala Gln Arg Arg Thr Ala Ala Gly Ile
2405                2410                2415

Met Lys Asn Ala Val Val Asp Gly Ile Val Ala Thr Asp Val Pro
2420                2425                2430

Glu Leu Glu Arg Thr Thr Pro Ile Met Gln Lys Lys Val Gly Gln
2435                2440                2445

Ile Met Leu Ile Leu Val Ser Leu Ala Ala Val Val Val Asn Pro
2450                2455                2460

Ser Val Lys Thr Val Arg Glu Ala Gly Ile Leu Ile Thr Ala Ala
```

-continued

```
            2465                2470                2475

Ala Val Thr Leu Trp Glu Asn Gly Ala Ser Ser Val Trp Asn Ala
        2480                2485                2490

Thr Thr Ala Ile Gly Leu Cys His Ile Met Arg Gly Gly Trp Leu
        2495                2500                2505

Ser Cys Leu Ser Ile Thr Trp Thr Leu Ile Lys Asn Met Glu Lys
        2510                2515                2520

Pro Gly Leu Lys Arg Gly Gly Ala Lys Gly Arg Thr Leu Gly Glu
        2525                2530                2535

Val Trp Lys Glu Arg Leu Asn Gln Met Thr Lys Glu Glu Phe Thr
        2540                2545                2550

Arg Tyr Arg Lys Glu Ala Ile Ile Glu Val Asp Arg Ser Ala Ala
        2555                2560                2565

Lys His Ala Arg Lys Glu Gly Asn Val Thr Gly Gly His Pro Val
        2570                2575                2580

Ser Arg Gly Thr Ala Lys Leu Arg Trp Leu Val Glu Arg Arg Phe
        2585                2590                2595

Leu Glu Pro Val Gly Lys Val Ile Asp Leu Gly Cys Gly Arg Gly
        2600                2605                2610

Gly Trp Cys Tyr Tyr Met Ala Thr Gln Lys Arg Val Gln Glu Val
        2615                2620                2625

Arg Gly Tyr Thr Lys Gly Gly Pro Gly His Glu Glu Pro Gln Leu
        2630                2635                2640

Val Gln Ser Tyr Gly Trp Asn Ile Val Thr Met Lys Ser Gly Val
        2645                2650                2655

Asp Val Phe Tyr Arg Pro Ser Glu Cys Cys Asp Thr Leu Leu Cys
        2660                2665                2670

Asp Ile Gly Glu Ser Ser Ser Ala Glu Val Glu Glu His Arg
        2675                2680                2685

Thr Ile Arg Val Leu Glu Met Val Glu Asp Trp Leu His Arg Gly
        2690                2695                2700

Pro Arg Glu Phe Cys Val Lys Val Leu Cys Pro Tyr Met Pro Lys
        2705                2710                2715

Val Ile Glu Lys Met Glu Leu Leu Gln Arg Arg Tyr Gly Gly Gly
        2720                2725                2730

Leu Val Arg Asn Pro Leu Ser Arg Asn Ser Thr His Glu Met Tyr
        2735                2740                2745

Trp Val Ser Arg Ala Ser Gly Asn Val Val His Ser Val Asn Met
        2750                2755                2760

Thr Ser Gln Val Leu Leu Gly Arg Met Glu Lys Arg Thr Trp Lys
        2765                2770                2775

Gly Pro Gln Tyr Glu Glu Asp Val Asn Leu Gly Ser Gly Thr Arg
        2780                2785                2790

Ala Val Gly Lys Pro Leu Leu Asn Ser Asp Thr Ser Lys Ile Lys
        2795                2800                2805

Asn Arg Ile Glu Arg Leu Arg Arg Glu Tyr Ser Ser Thr Trp His
        2810                2815                2820

His Asp Glu Asn His Pro Tyr Arg Thr Trp Asn Tyr His Gly Ser
        2825                2830                2835

Tyr Asp Val Lys Pro Thr Gly Ser Ala Ser Ser Leu Val Asn Gly
        2840                2845                2850

Val Val Arg Leu Leu Ser Lys Pro Trp Asp Thr Ile Thr Asn Val
        2855                2860                2865
```

```
Thr Thr Met Ala Met Thr Asp Thr Thr Pro Phe Gly Gln Gln Arg
2870                2875                2880

Val Phe Lys Glu Lys Val Asp Thr Lys Ala Pro Glu Pro Pro Glu
2885                2890                2895

Gly Val Lys Tyr Val Leu Asn Glu Thr Thr Asn Trp Leu Trp Ala
2900                2905                2910

Phe Leu Ala Arg Glu Lys Arg Pro Arg Met Cys Ser Arg Glu Glu
2915                2920                2925

Phe Ile Arg Lys Val Asn Ser Asn Ala Ala Leu Gly Ala Met Phe
2930                2935                2940

Glu Glu Gln Asn Gln Trp Arg Ser Ala Arg Glu Ala Val Glu Asp
2945                2950                2955

Pro Lys Phe Trp Glu Met Val Asp Glu Glu Arg Glu Ala His Leu
2960                2965                2970

Arg Gly Glu Cys His Thr Cys Ile Tyr Asn Met Met Gly Lys Arg
2975                2980                2985

Glu Lys Lys Pro Gly Glu Phe Gly Lys Ala Lys Gly Ser Arg Ala
2990                2995                3000

Ile Trp Phe Met Trp Leu Gly Ala Arg Phe Leu Glu Phe Glu Ala
3005                3010                3015

Leu Gly Phe Leu Asn Glu Asp His Trp Leu Gly Arg Lys Asn Ser
3020                3025                3030

Gly Gly Gly Val Glu Gly Leu Gly Leu Gln Lys Leu Gly Tyr Ile
3035                3040                3045

Leu Arg Glu Val Gly Thr Arg Pro Gly Gly Lys Ile Tyr Ala Asp
3050                3055                3060

Asp Thr Ala Gly Trp Asp Thr Arg Ile Thr Arg Ala Asp Leu Glu
3065                3070                3075

Asn Glu Ala Lys Val Leu Glu Leu Leu Asp Gly Glu His Arg Arg
3080                3085                3090

Leu Ala Arg Ala Ile Ile Glu Leu Thr Tyr Arg His Lys Val Val
3095                3100                3105

Lys Val Met Arg Pro Ala Ala Asp Gly Arg Thr Val Met Asp Val
3110                3115                3120

Ile Ser Arg Glu Asp Gln Arg Gly Ser Gly Gln Val Val Thr Tyr
3125                3130                3135

Ala Leu Asn Thr Phe Thr Asn Leu Ala Val Gln Leu Val Arg Met
3140                3145                3150

Met Glu Gly Glu Gly Val Ile Gly Pro Asp Asp Val Glu Lys Leu
3155                3160                3165

Thr Lys Gly Lys Gly Pro Lys Val Arg Thr Trp Leu Phe Glu Asn
3170                3175                3180

Gly Glu Glu Arg Leu Ser Arg Met Ala Val Ser Gly Asp Asp Cys
3185                3190                3195

Val Val Lys Pro Leu Asp Asp Arg Phe Ala Thr Ser Leu His Phe
3200                3205                3210

Leu Asn Ala Met Ser Lys Val Arg Lys Asp Ile Gln Glu Trp Lys
3215                3220                3225

Pro Ser Thr Gly Trp Tyr Asp Trp Gln Gln Val Pro Phe Cys Ser
3230                3235                3240

Asn His Phe Thr Glu Leu Ile Met Lys Asp Gly Arg Thr Leu Val
3245                3250                3255
```

```
Val Pro Cys Arg Gly Gln Asp Glu Leu Val Gly Arg Ala Arg Ile
    3260                3265                3270

Ser Pro Gly Ala Gly Trp Asn Val Arg Asp Thr Ala Cys Leu Ala
    3275                3280                3285

Lys Ser Tyr Ala Gln Met Trp Leu Leu Leu Tyr Phe His Arg Arg
    3290                3295                3300

Asp Leu Arg Leu Met Ala Asn Ala Ile Cys Ser Ala Val Pro Val
    3305                3310                3315

Asn Trp Val Pro Thr Gly Arg Thr Thr Trp Ser Ile His Ala Gly
    3320                3325                3330

Gly Glu Trp Met Thr Thr Glu Asp Met Leu Glu Val Trp Asn Arg
    3335                3340                3345

Val Trp Ile Glu Glu Asn Glu Trp Met Glu Asp Lys Thr Pro Val
    3350                3355                3360

Glu Lys Trp Ser Asp Val Pro Tyr Ser Gly Lys Arg Glu Asp Ile
    3365                3370                3375

Trp Cys Gly Ser Leu Ile Gly Thr Arg Ala Arg Ala Thr Trp Ala
    3380                3385                3390

Glu Asn Ile Gln Val Ala Ile Asn Gln Val Arg Ala Ile Ile Gly
    3395                3400                3405

Asp Glu Lys Tyr Val Asp Tyr Met Ser Ser Leu Lys Arg Tyr Glu
    3410                3415                3420

Asp Thr Thr Leu Val Glu Asp Thr Val Leu
    3425                3430

<210> SEQ ID NO 3
<211> LENGTH: 11029
<212> TYPE: DNA
<213> ORGANISM: West Nile virus
<220> FEATURE:
<221> NAME/KEY: CDS
<222> LOCATION: (97)..(10398)

<400> SEQUENCE: 3
agtagttcgc ctgtgtgagc tgacaaactt agtagtgttt gtgaggatta acaacaatta     60
acacagtgcg agctgtttct tagcacgaag atctcg atg tct aag aaa cca gga     114
                                         Met Ser Lys Lys Pro Gly
                                           1               5 ggg ccc ggc aag agc cgg gct gtc aat atg cta aaa cgc gga atg ccc     162
Gly Pro Gly Lys Ser Arg Ala Val Asn Met Leu Lys Arg Gly Met Pro
             10                  15                  20 cgc gtg ttg tcc ttg att gga ctg aag agg gct atg ttg agc ctg atc     210
Arg Val Leu Ser Leu Ile Gly Leu Lys Arg Ala Met Leu Ser Leu Ile
         25                  30                  35 gac ggc aag ggg cca ata cga ttt gtg ttg gct ctc ttg gcg ttc ttc     258
Asp Gly Lys Gly Pro Ile Arg Phe Val Leu Ala Leu Leu Ala Phe Phe
     40                  45                  50 agg ttc aca gca att gct ccg acc cga gca gtg ctg gat cga tgg aga     306
Arg Phe Thr Ala Ile Ala Pro Thr Arg Ala Val Leu Asp Arg Trp Arg
 55                  60                  65                  70 ggt gtg aac aaa caa aca gcg atg aaa cac ctt ctg agt ttt aag aag     354
Gly Val Asn Lys Gln Thr Ala Met Lys His Leu Leu Ser Phe Lys Lys
                 75                  80                  85 gaa cta ggg acc ttg acc agt gct atc aat cgg cgg agc tca aaa caa     402
Glu Leu Gly Thr Leu Thr Ser Ala Ile Asn Arg Arg Ser Ser Lys Gln
             90                  95                 100 aag aaa aga gga gga aag acc gga att gca gtc atg att ggc ctg atc     450
Lys Lys Arg Gly Gly Lys Thr Gly Ile Ala Val Met Ile Gly Leu Ile
```

```
gcc agc gta gga gca gtt acc ctc tct aac ttc caa ggg aag gtg atg    498
Ala Ser Val Gly Ala Val Thr Leu Ser Asn Phe Gln Gly Lys Val Met
    120                 125                 130 atg acg gta aat gct act gac gtc aca gat gtc atc acg att cca aca    546
Met Thr Val Asn Ala Thr Asp Val Thr Asp Val Ile Thr Ile Pro Thr
135                 140                 145                 150 gct gct gga aag aac cta tgc att gtc aga gca atg gat gtg gga tac    594
Ala Ala Gly Lys Asn Leu Cys Ile Val Arg Ala Met Asp Val Gly Tyr
                155                 160                 165 atg tgc gat gat act atc act tat gaa tgc cca gtg ctg tcg gct ggt    642
Met Cys Asp Asp Thr Ile Thr Tyr Glu Cys Pro Val Leu Ser Ala Gly
            170                 175                 180 aat gat cca gaa gac atc gac tgt tgg tgc aca aag tca gca gtc tac    690
Asn Asp Pro Glu Asp Ile Asp Cys Trp Cys Thr Lys Ser Ala Val Tyr
        185                 190                 195 gtc agg tat gga aga tgc acc aag aca cgc cac tca aga cgc agt cgg    738
Val Arg Tyr Gly Arg Cys Thr Lys Thr Arg His Ser Arg Arg Ser Arg
    200                 205                 210 agg tca ctg aca gtg cag aca cac gga gaa agc act cta gcg aac aag    786
Arg Ser Leu Thr Val Gln Thr His Gly Glu Ser Thr Leu Ala Asn Lys
215                 220                 225                 230 aag ggg gct tgg atg gac agc acc aag gcc aca agg tat ttg gta aaa    834
Lys Gly Ala Trp Met Asp Ser Thr Lys Ala Thr Arg Tyr Leu Val Lys
                235                 240                 245 aca gaa tca tgg atc ttg agg aac cct gga tat gcc ctg gtg gca gcc    882
Thr Glu Ser Trp Ile Leu Arg Asn Pro Gly Tyr Ala Leu Val Ala Ala
            250                 255                 260 gtc att ggt tgg atg ctt ggg agc aac acc atg cag aga gtt gtg ttt    930
Val Ile Gly Trp Met Leu Gly Ser Asn Thr Met Gln Arg Val Val Phe
        265                 270                 275 gtc gtg cta ttg ctt ttg gtg gcc cca gct tac agc ttc aac tgc ctt    978
Val Val Leu Leu Leu Leu Val Ala Pro Ala Tyr Ser Phe Asn Cys Leu
    280                 285                 290 gga atg agc aac aga gac ttc ttg gaa gga gtg tct gga gca aca tgg   1026
Gly Met Ser Asn Arg Asp Phe Leu Glu Gly Val Ser Gly Ala Thr Trp
295                 300                 305                 310 gtg gat ttg gtt ctc gaa ggc gac agc tgc gtg act atc atg tct aag   1074
Val Asp Leu Val Leu Glu Gly Asp Ser Cys Val Thr Ile Met Ser Lys
                315                 320                 325 gac aag cct acc atc gat gtg aag atg atg aat atg gag gcg gcc aac   1122
Asp Lys Pro Thr Ile Asp Val Lys Met Met Asn Met Glu Ala Ala Asn
            330                 335                 340 ctg gca gag gtc cgc agt tat tgc tat ttg gct acc gtc agc gat ctc   1170
Leu Ala Glu Val Arg Ser Tyr Cys Tyr Leu Ala Thr Val Ser Asp Leu
        345                 350                 355 tcc acc aaa gct gcg tgc ccg acc atg gga gaa gct cac aat gac aaa   1218
Ser Thr Lys Ala Ala Cys Pro Thr Met Gly Glu Ala His Asn Asp Lys
    360                 365                 370 cgt gct gac cca gct ttt gtg tgc aga caa gga gtg gtg gac agg ggc   1266
Arg Ala Asp Pro Ala Phe Val Cys Arg Gln Gly Val Val Asp Arg Gly
375                 380                 385                 390 tgg ggc aac ggc tgc gga cta ttt ggc aaa gga agc att gac aca tgc   1314
Trp Gly Asn Gly Cys Gly Leu Phe Gly Lys Gly Ser Ile Asp Thr Cys
                395                 400                 405 gcc aaa ttt gcc tgc tct acc aag gca ata gga aga acc atc ttg aaa   1362
Ala Lys Phe Ala Cys Ser Thr Lys Ala Ile Gly Arg Thr Ile Leu Lys
            410                 415                 420 gag aat atc aag tac gaa gtg gcc att ttt gtc cat gga cca act act   1410
```

```
                Glu Asn Ile Lys Tyr Glu Val Ala Ile Phe Val His Gly Pro Thr Thr
                            425                 430                 435 gtg gag tcg cac gga aat tac tcc aca cag gtt gga gcc act cag gca         1458
Val Glu Ser His Gly Asn Tyr Ser Thr Gln Val Gly Ala Thr Gln Ala
        440                 445                 450 ggg aga ttc agc atc act cct gcg gcg cct tca tac aca cta aag ctt         1506
Gly Arg Phe Ser Ile Thr Pro Ala Ala Pro Ser Tyr Thr Leu Lys Leu
455                 460                 465                 470 gga gaa tat gga gag gtg aca gtg gac tgt gaa cca cgg tca ggg att         1554
Gly Glu Tyr Gly Glu Val Thr Val Asp Cys Glu Pro Arg Ser Gly Ile
                475                 480                 485 gac acc aat gca tac tac gtg atg act gtt gga aca aag acg ttc ttg         1602
Asp Thr Asn Ala Tyr Tyr Val Met Thr Val Gly Thr Lys Thr Phe Leu
        490                 495                 500 gtc cat cgt gag tgg ttc atg gac ctc aac ctc cct tgg agc agt gct         1650
Val His Arg Glu Trp Phe Met Asp Leu Asn Leu Pro Trp Ser Ser Ala
505                 510                 515 gga agt act gtg tgg agg aac aga gag acg tta atg gag ttt gag gaa         1698
Gly Ser Thr Val Trp Arg Asn Arg Glu Thr Leu Met Glu Phe Glu Glu
        520                 525                 530 cca cac gcc acg aag cag tct gtg ata gca ttg ggc tca caa gag gga         1746
Pro His Ala Thr Lys Gln Ser Val Ile Ala Leu Gly Ser Gln Glu Gly
535                 540                 545                 550 gct ctg cat caa gct ttg gct gga gcc att cct gtg gaa ttt tca agc         1794
Ala Leu His Gln Ala Leu Ala Gly Ala Ile Pro Val Glu Phe Ser Ser
                555                 560                 565 aac act gtc aag ttg acg tcg ggt cat ttg aag tgt aga gtg aag atg         1842
Asn Thr Val Lys Leu Thr Ser Gly His Leu Lys Cys Arg Val Lys Met
        570                 575                 580 gaa aaa ttg cag ctg aag gga aca acc tat ggc gtc tgt tca aag gct         1890
Glu Lys Leu Gln Leu Lys Gly Thr Thr Tyr Gly Val Cys Ser Lys Ala
585                 590                 595 ttc aag ttt ctt ggg act ccc gca gac aca ggt cac ggc act gtg gtg         1938
Phe Lys Phe Leu Gly Thr Pro Ala Asp Thr Gly His Gly Thr Val Val
                600                 605                 610 ttg gaa ttg cag tac act ggc acg gat gga cct tgc aaa gtt cct atc         1986
Leu Glu Leu Gln Tyr Thr Gly Thr Asp Gly Pro Cys Lys Val Pro Ile
615                 620                 625                 630 tcg tca gtg gct tca ttg aac gac cta acg cca gtg ggc aga ttg gtc         2034
Ser Ser Val Ala Ser Leu Asn Asp Leu Thr Pro Val Gly Arg Leu Val
                635                 640                 645 act gtc aac cct ttt gtt tca gtg gcc acg gcc aac gct aag gtc ctg         2082
Thr Val Asn Pro Phe Val Ser Val Ala Thr Ala Asn Ala Lys Val Leu
        650                 655                 660 att gaa ttg gaa cca ccc ttt gga gac tca tac ata gtg gtg ggc aga         2130
Ile Glu Leu Glu Pro Pro Phe Gly Asp Ser Tyr Ile Val Val Gly Arg
665                 670                 675 gga gaa caa cag atc aat cac cat tgg cac aag tct gga agc agc att         2178
Gly Glu Gln Gln Ile Asn His His Trp His Lys Ser Gly Ser Ser Ile
                680                 685                 690 ggc aaa gcc ttt aca acc acc ctc aaa gga gcg cag aga cta gcc gct         2226
Gly Lys Ala Phe Thr Thr Thr Leu Lys Gly Ala Gln Arg Leu Ala Ala
695                 700                 705                 710 cta gga gac aca gct tgg gac ttt gga tca gtt gga ggg gtg ttc acc         2274
Leu Gly Asp Thr Ala Trp Asp Phe Gly Ser Val Gly Gly Val Phe Thr
                715                 720                 725 tca gtt ggg aag gct gtc cat caa gtg ttc gga gga gca ttc cgc tca         2322
Ser Val Gly Lys Ala Val His Gln Val Phe Gly Gly Ala Phe Arg Ser
        730                 735                 740
```

```
ctg ttc gga ggc atg tcc tgg ata acg caa gga ttg ctg ggg gct ctc      2370
Leu Phe Gly Gly Met Ser Trp Ile Thr Gln Gly Leu Leu Gly Ala Leu
        745                 750                 755 ctg ttg tgg atg ggc atc aat gct cgt gat agg tcc ata gct ctc acg      2418
Leu Leu Trp Met Gly Ile Asn Ala Arg Asp Arg Ser Ile Ala Leu Thr
760                 765                 770 ttt ctc gca gtt gga gga gtt ctg ctc ttc ctc tcc gtg aac gtg cac      2466
Phe Leu Ala Val Gly Gly Val Leu Leu Phe Leu Ser Val Asn Val His
775                 780                 785                 790 gct gac act ggg tgt gcc ata gac atc agc cgg caa gag ctg aga tgt      2514
Ala Asp Thr Gly Cys Ala Ile Asp Ile Ser Arg Gln Glu Leu Arg Cys
                795                 800                 805 gga agt gga gtg ttc ata cac aat gat gtg gag gct tgg atg gac cgg      2562
Gly Ser Gly Val Phe Ile His Asn Asp Val Glu Ala Trp Met Asp Arg
            810                 815                 820 tac aag tat tac cct gaa acg cca caa ggc cta gcc aag atc att cag      2610
Tyr Lys Tyr Tyr Pro Glu Thr Pro Gln Gly Leu Ala Lys Ile Ile Gln
        825                 830                 835 aaa gct cat aag gaa gga gtg tgc ggt cta cga tca gtt tcc aga ctg      2658
Lys Ala His Lys Glu Gly Val Cys Gly Leu Arg Ser Val Ser Arg Leu
840                 845                 850 gag cat caa atg tgg gaa gca gtg aag gac gag ctg aac act ctt ttg      2706
Glu His Gln Met Trp Glu Ala Val Lys Asp Glu Leu Asn Thr Leu Leu
855                 860                 865                 870 aag gag aat ggt gtg gac ctt agt gtc gtg gtt gag aaa cag gag gga      2754
Lys Glu Asn Gly Val Asp Leu Ser Val Val Glu Lys Gln Glu Gly
                875                 880                 885 atg tac aag tca gca cct aaa cgc ctc acc gcc acc acg gaa aaa ttg      2802
Met Tyr Lys Ser Ala Pro Lys Arg Leu Thr Ala Thr Thr Glu Lys Leu
            890                 895                 900 gaa att ggc tgg aag gcc tgg gga aag agt att tta ttt gca cca gaa      2850
Glu Ile Gly Trp Lys Ala Trp Gly Lys Ser Ile Leu Phe Ala Pro Glu
        905                 910                 915 ctc gcc aac aac acc ttt gtg gtt gat ggt ccg gag acc aag gaa tgt      2898
Leu Ala Asn Asn Thr Phe Val Val Asp Gly Pro Glu Thr Lys Glu Cys
920                 925                 930 ccg act cag aat cgc gct tgg aat agc tta gaa gtg gag gat ttt gga      2946
Pro Thr Gln Asn Arg Ala Trp Asn Ser Leu Glu Val Glu Asp Phe Gly
935                 940                 945                 950 ttt ggt ctc acc agc act cgg atg ttc ctg aag gtc aga gag agc aac      2994
Phe Gly Leu Thr Ser Thr Arg Met Phe Leu Lys Val Arg Glu Ser Asn
                955                 960                 965 aca act gaa tgt gac tcg aag atc att gga acg gct gtc aag aac aac      3042
Thr Thr Glu Cys Asp Ser Lys Ile Ile Gly Thr Ala Val Lys Asn Asn
            970                 975                 980 ttg gcg atc cac agt gac ctg tcc tat tgg att gaa agc agg ctc aat      3090
Leu Ala Ile His Ser Asp Leu Ser Tyr Trp Ile Glu Ser Arg Leu Asn
        985                 990                 995 gat acg tgg aag ctt gaa agg gca gtt ctg ggt gaa    gtc aaa tca      3135
Asp Thr Trp Lys Leu Glu Arg Ala Val Leu Gly Glu      Val Lys Ser
        1000                1005                    1010 tgt acg tgg cct gag acg cat  acc ttg tgg ggc gat   gga atc ctt      3180
Cys Thr Trp Pro Glu Thr His  Thr Leu Trp Gly Asp   Gly Ile Leu
        1015                1020                    1025 gag agt gac ttg ata ata cca  gtc aca ctg gcg gga   cca cga agc      3225
Glu Ser Asp Leu Ile Ile Pro  Val Thr Leu Ala Gly   Pro Arg Ser
        1030                1035                    1040 aat cac aat cgg aga cct ggg  tac aag aca caa aac   cag ggc cca      3270
Asn His Asn Arg Arg Pro Gly  Tyr Lys Thr Gln Asn   Gln Gly Pro
        1045                1050                    1055
```

-continued

| | | | | | | | | | | |
|---|---|---|---|---|---|---|---|---|---|---|
| tgg | gat | gaa | ggc | cgg | gta | gag | att | gac | ttc | gat | tac | tgc | cca | gga | 3315 |
| Trp | Asp | Glu | Gly | Arg | Val | Glu | Ile | Asp | Phe | Asp | Tyr | Cys | Pro | Gly | |
| | 1060 | | | | 1065 | | | | 1070 | | | | | | |

```
tgg gat gaa ggc cgg gta gag att gac ttc gat tac tgc cca gga       3315
Trp Asp Glu Gly Arg Val Glu Ile Asp Phe Asp Tyr Cys Pro Gly
    1060            1065            1070 act acg gtc acc ctg agt gag agc tgc gga cac cgt gga cct gcc       3360
Thr Thr Val Thr Leu Ser Glu Ser Cys Gly His Arg Gly Pro Ala
1075            1080            1085 act cgc acc acc aca gag agc gga aag ttg ata aca gat tgg tgc       3405
Thr Arg Thr Thr Thr Glu Ser Gly Lys Leu Ile Thr Asp Trp Cys
    1090            1095            1100 tgc agg agc tgc acc tta cca cca ctg cgc tac caa act gac agc       3450
Cys Arg Ser Cys Thr Leu Pro Pro Leu Arg Tyr Gln Thr Asp Ser
1105            1110            1115 ggc tgt tgg tat ggt atg gag atc aga cca cag aga cat gat gaa       3495
Gly Cys Trp Tyr Gly Met Glu Ile Arg Pro Gln Arg His Asp Glu
    1120            1125            1130 aag acc ctc gtg cag tca caa gtg aat gct tat aat gct gat atg       3540
Lys Thr Leu Val Gln Ser Gln Val Asn Ala Tyr Asn Ala Asp Met
1135            1140            1145 att gac cct ttt cag ttg ggc ctt ctg gtc gtg ttc ttg gcc acc       3585
Ile Asp Pro Phe Gln Leu Gly Leu Leu Val Val Phe Leu Ala Thr
    1150            1155            1160 cag gag gtc ctt cgc aag agg tgg aca gcc aag atc agc atg cca       3630
Gln Glu Val Leu Arg Lys Arg Trp Thr Ala Lys Ile Ser Met Pro
1165            1170            1175 gct ata ctg att gct ctg cta gtc ctg gtg ttt ggg ggc att act       3675
Ala Ile Leu Ile Ala Leu Leu Val Leu Val Phe Gly Gly Ile Thr
    1180            1185            1190 tac act gat gtg tta cgc tat gtc atc ttg gtg ggg gca gct ttc       3720
Tyr Thr Asp Val Leu Arg Tyr Val Ile Leu Val Gly Ala Ala Phe
1195            1200            1205 gca gaa tct aat tcg gga gga gac gtg gta cac ttg gcg ctc atg       3765
Ala Glu Ser Asn Ser Gly Gly Asp Val Val His Leu Ala Leu Met
    1210            1215            1220 gcg acc ttc aag ata caa cca gtg ttt atg gtg gca tcg ttt ctc       3810
Ala Thr Phe Lys Ile Gln Pro Val Phe Met Val Ala Ser Phe Leu
1225            1230            1235 aaa gcg aga tgg acc aac cag gag aac att ttg ttg atg ttg gcg       3855
Lys Ala Arg Trp Thr Asn Gln Glu Asn Ile Leu Leu Met Leu Ala
    1240            1245            1250 gct gtt ttc ttt caa atg gct tat tac gat gcc cgc caa att ctg       3900
Ala Val Phe Phe Gln Met Ala Tyr Tyr Asp Ala Arg Gln Ile Leu
1255            1260            1265 ctc tgg gag atc cct gat gtg ttg aat tca ctg gcg gta gct tgg       3945
Leu Trp Glu Ile Pro Asp Val Leu Asn Ser Leu Ala Val Ala Trp
    1270            1275            1280 atg ata ctg aga gcc ata aca ttc aca acg aca tca aac gtg gtt       3990
Met Ile Leu Arg Ala Ile Thr Phe Thr Thr Thr Ser Asn Val Val
1285            1290            1295 gtt ccg ctg cta gcc ctg cta aca ccc ggg ctg aga tgc ttg aat       4035
Val Pro Leu Leu Ala Leu Leu Thr Pro Gly Leu Arg Cys Leu Asn
    1300            1305            1310 ctg gat gtg tac agg ata ctg ctg ttg atg gtc gga ata ggc agc       4080
Leu Asp Val Tyr Arg Ile Leu Leu Leu Met Val Gly Ile Gly Ser
1315            1320            1325 ttg atc agg gag aag agg agt gca gct gca aaa aag aaa gga gca       4125
Leu Ile Arg Glu Lys Arg Ser Ala Ala Ala Lys Lys Lys Gly Ala
    1330            1335            1340 agt ctg cta tgc ttg gct cta gcc tca aca gga ctt ttc aac ccc       4170
Ser Leu Leu Cys Leu Ala Leu Ala Ser Thr Gly Leu Phe Asn Pro
```

-continued

```
                  1345                1350                1355
atg atc ctt gct gct gga ctg att gca tgt gat ccc aac cgt aaa        4215
Met Ile Leu Ala Ala Gly Leu Ile Ala Cys Asp Pro Asn Arg Lys
    1360                1365                1370 cgc gga tgg ccc gca act gaa gtg atg aca gct gtc ggc cta atg        4260
Arg Gly Trp Pro Ala Thr Glu Val Met Thr Ala Val Gly Leu Met
    1375                1380                1385 ttt gcc atc gtc gga ggg ctg gca gag ctt gac att gac tcc atg        4305
Phe Ala Ile Val Gly Gly Leu Ala Glu Leu Asp Ile Asp Ser Met
    1390                1395                1400 gcc att cca atg act atc gcg ggg ctc atg ttt gct gct ttc gtg        4350
Ala Ile Pro Met Thr Ile Ala Gly Leu Met Phe Ala Ala Phe Val
    1405                1410                1415 att tct ggg aaa tca aca gat atg tgg att gag aga acg gcg gac        4395
Ile Ser Gly Lys Ser Thr Asp Met Trp Ile Glu Arg Thr Ala Asp
    1420                1425                1430 att tcc tgg gaa agt gat gca gaa att aca ggc tcg agc gaa aga        4440
Ile Ser Trp Glu Ser Asp Ala Glu Ile Thr Gly Ser Ser Glu Arg
    1435                1440                1445 gtt gat gtg cgg ctt gat gat gat gga aac ttc cag ctc atg aat        4485
Val Asp Val Arg Leu Asp Asp Asp Gly Asn Phe Gln Leu Met Asn
    1450                1455                1460 gat cca gga gca cct tgg aag ata tgg atg ctc aga atg gtc tgt        4530
Asp Pro Gly Ala Pro Trp Lys Ile Trp Met Leu Arg Met Val Cys
    1465                1470                1475 ctc gcg att agt gcg tac acc ccc tgg gca atc ttg ccc tca gta        4575
Leu Ala Ile Ser Ala Tyr Thr Pro Trp Ala Ile Leu Pro Ser Val
    1480                1485                1490 gtt gga ttt tgg ata act ctc caa tac aca aag aga gga ggc gtg        4620
Val Gly Phe Trp Ile Thr Leu Gln Tyr Thr Lys Arg Gly Gly Val
    1495                1500                1505 ttg tgg gac act ccc tca cca aag gag tac aaa aag ggg gac acg        4665
Leu Trp Asp Thr Pro Ser Pro Lys Glu Tyr Lys Lys Gly Asp Thr
    1510                1515                1520 acc acc ggc gtc tac agg atc atg act cgt ggg ctg ctc ggc agt        4710
Thr Thr Gly Val Tyr Arg Ile Met Thr Arg Gly Leu Leu Gly Ser
    1525                1530                1535 tat caa gca gga gcg ggc gtg atg gtt gaa ggt gtt ttc cac acc        4755
Tyr Gln Ala Gly Ala Gly Val Met Val Glu Gly Val Phe His Thr
    1540                1545                1550 ctt tgg cat aca aca aaa gga gcc gct ttg atg agc gga gag ggc        4800
Leu Trp His Thr Thr Lys Gly Ala Ala Leu Met Ser Gly Glu Gly
    1555                1560                1565 cgc ctg gac cca tac tgg ggc agt gtc aag gag gat cga ctt tgt        4845
Arg Leu Asp Pro Tyr Trp Gly Ser Val Lys Glu Asp Arg Leu Cys
    1570                1575                1580 tac gga gga ccc tgg aaa ttg cag cac aag tgg aac ggg cag gat        4890
Tyr Gly Gly Pro Trp Lys Leu Gln His Lys Trp Asn Gly Gln Asp
    1585                1590                1595 gag gtg cag atg att gtg gtg gaa cct ggc agg aac gtt aag aac        4935
Glu Val Gln Met Ile Val Val Glu Pro Gly Arg Asn Val Lys Asn
    1600                1605                1610 gtc cag acg aaa cca ggg gtg ttc aaa aca cct gaa gga gaa atc        4980
Val Gln Thr Lys Pro Gly Val Phe Lys Thr Pro Glu Gly Glu Ile
    1615                1620                1625 ggg gcc gtg act ttg gac ttc ccc act gga aca tca ggc tca cca        5025
Gly Ala Val Thr Leu Asp Phe Pro Thr Gly Thr Ser Gly Ser Pro
    1630                1635                1640 ata gtg gac aaa aac ggt gat gtg att ggg ctt tat ggc aat gga        5070
```

```
                                                                     -continued Ile Val Asp Lys Asn Gly Asp Val Ile Gly Leu Tyr Gly Asn Gly
    1645            1650                1655 gtc ata atg ccc aac ggc tca tac ata agc gcg ata gtg cag ggt       5115
Val Ile Met Pro Asn Gly Ser Tyr Ile Ser Ala Ile Val Gln Gly
    1660            1665                1670 gaa agg atg gat gag cca atc cca gcc gga ttc gaa cct gag atg       5160
Glu Arg Met Asp Glu Pro Ile Pro Ala Gly Phe Glu Pro Glu Met
    1675            1680                1685 ctg agg aaa aaa cag atc act gta ctg gat ctc cat ccc ggc gcc       5205
Leu Arg Lys Lys Gln Ile Thr Val Leu Asp Leu His Pro Gly Ala
    1690            1695                1700 ggt aaa aca agg agg att ctg cca cag atc atc aaa gag gcc ata       5250
Gly Lys Thr Arg Arg Ile Leu Pro Gln Ile Ile Lys Glu Ala Ile
    1705            1710                1715 aac aga aga ctg aga aca gcc gtg cta gca cca acc agg gtt gtg       5295
Asn Arg Arg Leu Arg Thr Ala Val Leu Ala Pro Thr Arg Val Val
    1720            1725                1730 gct gct gag atg gct gaa gca ctg aga gga ctg ccc atc cgg tac       5340
Ala Ala Glu Met Ala Glu Ala Leu Arg Gly Leu Pro Ile Arg Tyr
    1735            1740                1745 cag aca tcc gca gtg ccc aga gaa cat aat gga aat gag att gtt       5385
Gln Thr Ser Ala Val Pro Arg Glu His Asn Gly Asn Glu Ile Val
    1750            1755                1760 gat gtc atg tgt cat gct acc ctc acc cac agg ctg atg tct cct       5430
Asp Val Met Cys His Ala Thr Leu Thr His Arg Leu Met Ser Pro
    1765            1770                1775 cac agg gtg ccg aac tac aac ctg ttc gtg atg gat gag gct cat       5475
His Arg Val Pro Asn Tyr Asn Leu Phe Val Met Asp Glu Ala His
    1780            1785                1790 ttc acc gac cca gct agc att gca gca aga ggt tac att tcc aca       5520
Phe Thr Asp Pro Ala Ser Ile Ala Ala Arg Gly Tyr Ile Ser Thr
    1795            1800                1805 aag gtc gag cta ggg gag gcg gcg gca ata ttc atg aca gcc acc       5565
Lys Val Glu Leu Gly Glu Ala Ala Ala Ile Phe Met Thr Ala Thr
    1810            1815                1820 cca cca ggc act tca gat cca ttc cca gag tcc aat tca cca att       5610
Pro Pro Gly Thr Ser Asp Pro Phe Pro Glu Ser Asn Ser Pro Ile
    1825            1830                1835 tcc gac tta cag act gag atc ccg gat cga gct tgg aac tct gga       5655
Ser Asp Leu Gln Thr Glu Ile Pro Asp Arg Ala Trp Asn Ser Gly
    1840            1845                1850 tac gaa tgg atc aca gaa tac acc ggg aag acg gtt tgg ttt gtg       5700
Tyr Glu Trp Ile Thr Glu Tyr Thr Gly Lys Thr Val Trp Phe Val
    1855            1860                1865 cct agt gtc aag atg ggg aat gag att gcc ctt tgc cta caa cgt       5745
Pro Ser Val Lys Met Gly Asn Glu Ile Ala Leu Cys Leu Gln Arg
    1870            1875                1880 gct gga aag aaa gta gtc caa ttg aac aga aag tcg tac gag acg       5790
Ala Gly Lys Lys Val Val Gln Leu Asn Arg Lys Ser Tyr Glu Thr
    1885            1890                1895 gag tac cca aaa tgt aag aac gat gat tgg gac ttt gtt atc aca       5835
Glu Tyr Pro Lys Cys Lys Asn Asp Asp Trp Asp Phe Val Ile Thr
    1900            1905                1910 aca gac ata tct gaa atg ggg gct aac ttc aag gcg agc agg gtg       5880
Thr Asp Ile Ser Glu Met Gly Ala Asn Phe Lys Ala Ser Arg Val
    1915            1920                1925 att gac agc cgg aag agt gtg aaa cca acc atc ata aca gaa gga       5925
Ile Asp Ser Arg Lys Ser Val Lys Pro Thr Ile Ile Thr Glu Gly
    1930            1935                1940
```

-continued

| | | | | | | | | | | | |
|---|---|---|---|---|---|---|---|---|---|---|---|
| gaa | ggg | aga | gtg | atc | ctg | gga | gaa | cca | tct | gca | gtg | aca | gca | gct | 5970 |
| Glu | Gly | Arg | Val | Ile | Leu | Gly | Glu | Pro | Ser | Ala | Val | Thr | Ala | Ala | |
| | 1945 | | | | 1950 | | | | | 1955 | | | | | |
| agt | gcc | gcc | cag | aga | cgt | gga | cgt | atc | ggt | aga | aat | ccg | tcg | caa | 6015 |
| Ser | Ala | Ala | Gln | Arg | Arg | Gly | Arg | Ile | Gly | Arg | Asn | Pro | Ser | Gln | |
| | 1960 | | | | 1965 | | | | | 1970 | | | | | |
| gtt | ggt | gat | gag | tac | tgt | tat | ggg | ggg | cac | acg | aat | gaa | gac | gac | 6060 |
| Val | Gly | Asp | Glu | Tyr | Cys | Tyr | Gly | Gly | His | Thr | Asn | Glu | Asp | Asp | |
| | 1975 | | | | 1980 | | | | | 1985 | | | | | |
| tcg | aac | ttc | gcc | cat | tgg | act | gag | gca | cga | atc | atg | ctg | gac | aac | 6105 |
| Ser | Asn | Phe | Ala | His | Trp | Thr | Glu | Ala | Arg | Ile | Met | Leu | Asp | Asn | |
| | 1990 | | | | 1995 | | | | | 2000 | | | | | |
| atc | aac | atg | cca | aac | gga | ctg | atc | gct | caa | ttc | tac | caa | cca | gag | 6150 |
| Ile | Asn | Met | Pro | Asn | Gly | Leu | Ile | Ala | Gln | Phe | Tyr | Gln | Pro | Glu | |
| | 2005 | | | | 2010 | | | | | 2015 | | | | | |
| cgt | gag | aag | gta | tat | acc | atg | gat | ggg | gaa | tac | cgg | ctc | aga | gga | 6195 |
| Arg | Glu | Lys | Val | Tyr | Thr | Met | Asp | Gly | Glu | Tyr | Arg | Leu | Arg | Gly | |
| | 2020 | | | | 2025 | | | | | 2030 | | | | | |
| gaa | gag | aga | aaa | aac | ttt | ctg | gaa | ctg | ttg | agg | act | gca | gat | ctg | 6240 |
| Glu | Glu | Arg | Lys | Asn | Phe | Leu | Glu | Leu | Leu | Arg | Thr | Ala | Asp | Leu | |
| | 2035 | | | | 2040 | | | | | 2045 | | | | | |
| cca | gtt | tgg | ctg | gct | tac | aag | gtt | gca | gcg | gct | gga | gtg | tca | tac | 6285 |
| Pro | Val | Trp | Leu | Ala | Tyr | Lys | Val | Ala | Ala | Ala | Gly | Val | Ser | Tyr | |
| | 2050 | | | | 2055 | | | | | 2060 | | | | | |
| cac | gac | cgg | agg | tgg | tgc | ttt | gat | ggt | cct | agg | aca | aac | aca | att | 6330 |
| His | Asp | Arg | Arg | Trp | Cys | Phe | Asp | Gly | Pro | Arg | Thr | Asn | Thr | Ile | |
| | 2065 | | | | 2070 | | | | | 2075 | | | | | |
| tta | gaa | gac | aac | aac | gaa | gtg | gaa | gtc | atc | acg | aag | ctt | ggt | gaa | 6375 |
| Leu | Glu | Asp | Asn | Asn | Glu | Val | Glu | Val | Ile | Thr | Lys | Leu | Gly | Glu | |
| | 2080 | | | | 2085 | | | | | 2090 | | | | | |
| agg | aag | att | ctg | agg | ccg | cgc | tgg | att | gac | gcc | agg | gtg | tac | tcg | 6420 |
| Arg | Lys | Ile | Leu | Arg | Pro | Arg | Trp | Ile | Asp | Ala | Arg | Val | Tyr | Ser | |
| | 2095 | | | | 2100 | | | | | 2105 | | | | | |
| gat | cac | cag | gca | cta | aag | gcg | ttc | aag | gac | ttc | gcc | tcg | gga | aaa | 6465 |
| Asp | His | Gln | Ala | Leu | Lys | Ala | Phe | Lys | Asp | Phe | Ala | Ser | Gly | Lys | |
| | 2110 | | | | 2115 | | | | | 2120 | | | | | |
| cgt | tct | cag | ata | ggg | ctc | att | gag | gtt | ctg | gga | aag | atg | cct | gag | 6510 |
| Arg | Ser | Gln | Ile | Gly | Leu | Ile | Glu | Val | Leu | Gly | Lys | Met | Pro | Glu | |
| | 2125 | | | | 2130 | | | | | 2135 | | | | | |
| cac | ttc | atg | ggg | aag | aca | tgg | gaa | gca | ctt | gac | acc | atg | tac | gtt | 6555 |
| His | Phe | Met | Gly | Lys | Thr | Trp | Glu | Ala | Leu | Asp | Thr | Met | Tyr | Val | |
| | 2140 | | | | 2145 | | | | | 2150 | | | | | |
| gtg | gcc | act | gca | gag | aaa | gga | gga | aga | gct | cac | aga | atg | gcc | ctg | 6600 |
| Val | Ala | Thr | Ala | Glu | Lys | Gly | Gly | Arg | Ala | His | Arg | Met | Ala | Leu | |
| | 2155 | | | | 2160 | | | | | 2165 | | | | | |
| gag | gaa | ctg | cca | gat | gct | ctt | cag | aca | att | gcc | ttg | att | gcc | tta | 6645 |
| Glu | Glu | Leu | Pro | Asp | Ala | Leu | Gln | Thr | Ile | Ala | Leu | Ile | Ala | Leu | |
| | 2170 | | | | 2175 | | | | | 2180 | | | | | |
| ttg | agt | gtg | atg | acc | atg | gga | gta | ttc | ttc | ctc | ctc | atg | cag | cgg | 6690 |
| Leu | Ser | Val | Met | Thr | Met | Gly | Val | Phe | Phe | Leu | Leu | Met | Gln | Arg | |
| | 2185 | | | | 2190 | | | | | 2195 | | | | | |
| aag | ggc | att | gga | aag | ata | ggt | ttg | gga | ggc | gct | gtc | ttg | gga | gtc | 6735 |
| Lys | Gly | Ile | Gly | Lys | Ile | Gly | Leu | Gly | Gly | Ala | Val | Leu | Gly | Val | |
| | 2200 | | | | 2205 | | | | | 2210 | | | | | |
| gcg | acc | ttt | ttc | tgt | tgg | atg | gct | gaa | gtt | cca | gga | acg | aag | atc | 6780 |
| Ala | Thr | Phe | Phe | Cys | Trp | Met | Ala | Glu | Val | Pro | Gly | Thr | Lys | Ile | |
| | 2215 | | | | 2220 | | | | | 2225 | | | | | |
| gcc | gga | atg | ttg | ctg | ctc | tcc | ctt | ctc | ttg | atg | att | gtg | cta | att | 6825 |
| Ala | Gly | Met | Leu | Leu | Leu | Ser | Leu | Leu | Leu | Met | Ile | Val | Leu | Ile | |
| | 2230 | | | | 2235 | | | | | 2240 | | | | | |

-continued

| | | | | | | | | | | |
|---|---|---|---|---|---|---|---|---|---|---|
| cct<br>Pro | gag<br>Glu<br>2245 | cca<br>Pro | gag<br>Glu | aag<br>Lys | caa<br>Gln<br>2250 | cgt<br>Arg | tcg<br>Ser | cag<br>Gln | aca<br>Thr<br>2255 | gac<br>Asp | aac<br>Asn | cag<br>Gln | cta<br>Leu | gcc<br>Ala | 6870 |
| gtg<br>Val | ttc<br>Phe<br>2260 | ctg<br>Leu | att<br>Ile | tgt<br>Cys | gtc<br>Val<br>2265 | atg<br>Met | acc<br>Thr | ctt<br>Leu | gtg<br>Val<br>2270 | agc<br>Ser | gca<br>Ala | gtg<br>Val | gca<br>Ala | gcc<br>Ala | 6915 |
| aac<br>Asn | gag<br>Glu<br>2275 | atg<br>Met | ggt<br>Gly | tgg<br>Trp | cta<br>Leu<br>2280 | gat<br>Asp | aag<br>Lys | acc<br>Thr | aag<br>Lys<br>2285 | agt<br>Ser | gac<br>Asp | ata<br>Ile | agc<br>Ser | agt<br>Ser | 6960 |
| ttg<br>Leu | ttt<br>Phe<br>2290 | ggg<br>Gly | caa<br>Gln | aga<br>Arg | att<br>Ile<br>2295 | gag<br>Glu | gtc<br>Val | aag<br>Lys | gag<br>Glu<br>2300 | aat<br>Asn | ttc<br>Phe | agc<br>Ser | atg<br>Met | gga<br>Gly | 7005 |
| gag<br>Glu | ttt<br>Phe<br>2305 | ctt<br>Leu | ttg<br>Leu | gac<br>Asp | ttg<br>Leu<br>2310 | agg<br>Arg | cct<br>Pro | gca<br>Ala | aca<br>Thr<br>2315 | gcc<br>Ala | tgg<br>Trp | tca<br>Ser | ctg<br>Leu | tac<br>Tyr | 7050 |
| gct<br>Ala | gtg<br>Val<br>2320 | aca<br>Thr | aca<br>Thr | gcg<br>Ala | gtc<br>Val<br>2325 | ctc<br>Leu | act<br>Thr | gcc<br>Ala | ctg<br>Leu<br>2330 | cta<br>Leu | aag<br>Lys | cat<br>His | ttg<br>Leu | atc<br>Ile | 7095 |
| acg<br>Thr | tca<br>Ser<br>2335 | gat<br>Asp | tac<br>Tyr | atc<br>Ile | aac<br>Asn<br>2340 | acc<br>Thr | tca<br>Ser | ttg<br>Leu | acc<br>Thr<br>2345 | tca<br>Ser | ata<br>Ile | aac<br>Asn | gtt<br>Val | cag<br>Gln | 7140 |
| gca<br>Ala | agt<br>Ser<br>2350 | gca<br>Ala | cta<br>Leu | ttc<br>Phe | aca<br>Thr<br>2355 | ctc<br>Leu | gcg<br>Ala | cga<br>Arg | ggc<br>Gly<br>2360 | ttc<br>Phe | ccc<br>Pro | ttc<br>Phe | gtc<br>Val | gat<br>Asp | 7185 |
| gtt<br>Val | gga<br>Gly<br>2365 | gtg<br>Val | tcg<br>Ser | gct<br>Ala | ctc<br>Leu<br>2370 | ctg<br>Leu | cta<br>Leu | gca<br>Ala | gcc<br>Ala<br>2375 | gga<br>Gly | tgc<br>Cys | tgg<br>Trp | gga<br>Gly | caa<br>Gln | 7230 |
| gtc<br>Val | acc<br>Thr<br>2380 | ctc<br>Leu | acc<br>Thr | gtt<br>Val | acg<br>Thr<br>2385 | gta<br>Val | aca<br>Thr | gcg<br>Ala | gca<br>Ala<br>2390 | aca<br>Thr | ctc<br>Leu | ctt<br>Leu | ttt<br>Phe | tgc<br>Cys | 7275 |
| cac<br>His | tat<br>Tyr<br>2395 | gcc<br>Ala | tac<br>Tyr | atg<br>Met | gtt<br>Val<br>2400 | ccc<br>Pro | ggt<br>Gly | tgg<br>Trp | caa<br>Gln<br>2405 | gct<br>Ala | gag<br>Glu | gca<br>Ala | atg<br>Met | cgc<br>Arg | 7320 |
| tca<br>Ser | gcc<br>Ala<br>2410 | cag<br>Gln | cgg<br>Arg | cgg<br>Arg | aca<br>Thr<br>2415 | gcg<br>Ala | gcc<br>Ala | gga<br>Gly | atc<br>Ile<br>2420 | atg<br>Met | aag<br>Lys | aac<br>Asn | gct<br>Ala | gta<br>Val | 7365 |
| gtg<br>Val | gat<br>Asp<br>2425 | ggc<br>Gly | atc<br>Ile | gtg<br>Val | gcc<br>Ala<br>2430 | acg<br>Thr | gac<br>Asp | gtc<br>Val | cca<br>Pro<br>2435 | gaa<br>Glu | tta<br>Leu | gag<br>Glu | cgc<br>Arg | acc<br>Thr | 7410 |
| aca<br>Thr | ccc<br>Pro<br>2440 | atc<br>Ile | atg<br>Met | cag<br>Gln | aag<br>Lys<br>2445 | aaa<br>Lys | gtt<br>Val | gga<br>Gly | cag<br>Gln<br>2450 | atc<br>Ile | atg<br>Met | ctg<br>Leu | atc<br>Ile | ttg<br>Leu | 7455 |
| gtg<br>Val | tct<br>Ser<br>2455 | cta<br>Leu | gct<br>Ala | gca<br>Ala | gta<br>Val<br>2460 | gta<br>Val | gtg<br>Val | aac<br>Asn | ccg<br>Pro<br>2465 | tct<br>Ser | gtg<br>Val | aag<br>Lys | aca<br>Thr | gta<br>Val | 7500 |
| cga<br>Arg | gaa<br>Glu<br>2470 | gcc<br>Ala | gga<br>Gly | att<br>Ile | ttg<br>Leu<br>2475 | atc<br>Ile | acg<br>Thr | gcc<br>Ala | gca<br>Ala<br>2480 | gcg<br>Ala | gtg<br>Val | acg<br>Thr | ctt<br>Leu | tgg<br>Trp | 7545 |
| gag<br>Glu | aat<br>Asn<br>2485 | gga<br>Gly | gca<br>Ala | agc<br>Ser | tct<br>Ser<br>2490 | gtt<br>Val | tgg<br>Trp | aac<br>Asn | gca<br>Ala<br>2495 | aca<br>Thr | act<br>Thr | gcc<br>Ala | atc<br>Ile | gga<br>Gly | 7590 |
| ctc<br>Leu | tgc<br>Cys<br>2500 | cac<br>His | atc<br>Ile | atg<br>Met | cgt<br>Arg<br>2505 | ggg<br>Gly | ggt<br>Gly | tgg<br>Trp | ttg<br>Leu<br>2510 | tca<br>Ser | tgt<br>Cys | cta<br>Leu | tcc<br>Ser | ata<br>Ile | 7635 |
| aca<br>Thr | tgg<br>Trp<br>2515 | aca<br>Thr | ctc<br>Leu | ata<br>Ile | aag<br>Lys<br>2520 | aac<br>Asn | atg<br>Met | gaa<br>Glu | aaa<br>Lys<br>2525 | cca<br>Pro | gga<br>Gly | cta<br>Leu | aaa<br>Lys | aga<br>Arg | 7680 |
| ggt<br>Gly | ggg<br>Gly | gca<br>Ala | aaa<br>Lys | gga<br>Gly | cgc<br>Arg | acc<br>Thr | ttg<br>Leu | gga<br>Gly | gag<br>Glu | gtt<br>Val | tgg<br>Trp | aaa<br>Lys | gaa<br>Glu | aga<br>Arg | 7725 |

-continued

|  |  |  |  |
|---|---|---|---|
| | 2530 | 2535 | 2540 | |
| ctc aac cag atg aca aaa gaa gag ttc act agg tac cgc aaa gag<br>Leu Asn Gln Met Thr Lys Glu Glu Phe Thr Arg Tyr Arg Lys Glu<br>2545                                 2550                              2555 | 7770 |

```
                    2530                    2535                    2540 ctc aac cag atg aca aaa gaa gag ttc act agg tac cgc aaa gag       7770
Leu Asn Gln Met Thr Lys Glu Glu Phe Thr Arg Tyr Arg Lys Glu
2545                    2550                    2555 gcc atc atc gaa gtc gat cgc tca gcg gca aaa cac gcc agg aaa       7815
Ala Ile Ile Glu Val Asp Arg Ser Ala Ala Lys His Ala Arg Lys
2560                    2565                    2570 gaa ggc aat gtc act gga ggg cat cca gtc tct agg ggc aca gca       7860
Glu Gly Asn Val Thr Gly Gly His Pro Val Ser Arg Gly Thr Ala
2575                    2580                    2585 aaa ctg aga tgg ctg gtc gaa cgg agg ttt ctc gaa ccg gtc gga       7905
Lys Leu Arg Trp Leu Val Glu Arg Arg Phe Leu Glu Pro Val Gly
2590                    2595                    2600 aaa gtg att gac ctt gga tgt gga aga ggc ggt tgg tgt tac tat       7950
Lys Val Ile Asp Leu Gly Cys Gly Arg Gly Gly Trp Cys Tyr Tyr
2605                    2610                    2615 atg gca acc caa aaa aga gtc caa gaa gtc aga ggg tac aca aag       7995
Met Ala Thr Gln Lys Arg Val Gln Glu Val Arg Gly Tyr Thr Lys
2620                    2625                    2630 ggc ggt ccc gga cat gaa gag ccc caa cta gtg caa agt tat gga       8040
Gly Gly Pro Gly His Glu Glu Pro Gln Leu Val Gln Ser Tyr Gly
2635                    2640                    2645 tgg aac att gtc acc atg aag agt gga gtg gat gtg ttc tac aga       8085
Trp Asn Ile Val Thr Met Lys Ser Gly Val Asp Val Phe Tyr Arg
2650                    2655                    2660 cct tct gag tgt tgt gac acc ctc ctt tgt gac atc gga gag tcc       8130
Pro Ser Glu Cys Cys Asp Thr Leu Leu Cys Asp Ile Gly Glu Ser
2665                    2670                    2675 tcg tca agt gct gag gtt gaa gag cat agg acg att cgg gtc ctt       8175
Ser Ser Ser Ala Glu Val Glu Glu His Arg Thr Ile Arg Val Leu
2680                    2685                    2690 gaa atg gtt gag gac tgg ctg cac cga ggg cca agg gaa ttt tgc       8220
Glu Met Val Glu Asp Trp Leu His Arg Gly Pro Arg Glu Phe Cys
2695                    2700                    2705 gtg aag gtg ctc tgc ccc tac atg ccg aaa gtc ata gag aag atg       8265
Val Lys Val Leu Cys Pro Tyr Met Pro Lys Val Ile Glu Lys Met
2710                    2715                    2720 gag ctg ctc caa cgc cgg tat ggg ggg gga ctg gtc aga aac cca       8310
Glu Leu Leu Gln Arg Arg Tyr Gly Gly Gly Leu Val Arg Asn Pro
2725                    2730                    2735 ctc tca cgg aat tcc acg cac gag atg tat tgg gtg agt cga gct       8355
Leu Ser Arg Asn Ser Thr His Glu Met Tyr Trp Val Ser Arg Ala
2740                    2745                    2750 tca ggc aat gtg gta cat tca gtg aat atg acc agc cag gtg ctc       8400
Ser Gly Asn Val Val His Ser Val Asn Met Thr Ser Gln Val Leu
2755                    2760                    2765 cta gga aga atg gaa aaa agg acc tgg aag gga ccc caa tac gag       8445
Leu Gly Arg Met Glu Lys Arg Thr Trp Lys Gly Pro Gln Tyr Glu
2770                    2775                    2780 gaa gat gta aac ttg gga agt gga acc agg gcg gtg gga aaa ccc       8490
Glu Asp Val Asn Leu Gly Ser Gly Thr Arg Ala Val Gly Lys Pro
2785                    2790                    2795 ctg ctc aac tca gac acc agt aaa atc aag aac agg att gaa cga       8535
Leu Leu Asn Ser Asp Thr Ser Lys Ile Lys Asn Arg Ile Glu Arg
2800                    2805                    2810 ctc agg cgt gag tac agt tcg acg tgg cac cac gat gag aac cac       8580
Leu Arg Arg Glu Tyr Ser Ser Thr Trp His His Asp Glu Asn His
2815                    2820                    2825 cca tat aga acc tgg aac tat cac ggc agt tat gat gtg aag ccc       8625
```

-continued

| | | | | | | | | | | | | | |
|---|---|---|---|---|---|---|---|---|---|---|---|---|---|
| Pro | Tyr | Arg | Thr | Trp | Asn | Tyr | His | Gly | Ser | Tyr | Asp | Val | Lys Pro |
| | 2830 | | | | 2835 | | | | 2840 | | | | |

| aca | ggc | tcc | gcc | agt | tcg | ctg | gtc | aat | gga | gtg | gtc | agg | ctc | ctc | 8670 |
|---|---|---|---|---|---|---|---|---|---|---|---|---|---|---|---|
| Thr | Gly | Ser | Ala | Ser | Ser | Leu | Val | Asn | Gly | Val | Val | Arg | Leu | Leu | |
| 2845 | | | | | 2850 | | | | | 2855 | | | | | |

| tca | aaa | cca | tgg | gac | acc | atc | acg | aat | gtt | acc | acc | atg | gcc | atg | 8715 |
|---|---|---|---|---|---|---|---|---|---|---|---|---|---|---|---|
| Ser | Lys | Pro | Trp | Asp | Thr | Ile | Thr | Asn | Val | Thr | Thr | Met | Ala | Met | |
| 2860 | | | | | 2865 | | | | | 2870 | | | | | |

| act | gac | act | act | ccc | ttc | ggg | cag | cag | cga | gtg | ttc | aaa | gag | aag | 8760 |
|---|---|---|---|---|---|---|---|---|---|---|---|---|---|---|---|
| Thr | Asp | Thr | Thr | Pro | Phe | Gly | Gln | Gln | Arg | Val | Phe | Lys | Glu | Lys | |
| 2875 | | | | | 2880 | | | | | 2885 | | | | | |

| gtg | gac | acg | aaa | gct | cct | gaa | ccg | cca | gaa | gga | gtg | aag | tac | gtg | 8805 |
|---|---|---|---|---|---|---|---|---|---|---|---|---|---|---|---|
| Val | Asp | Thr | Lys | Ala | Pro | Glu | Pro | Pro | Glu | Gly | Val | Lys | Tyr | Val | |
| 2890 | | | | | 2895 | | | | | 2900 | | | | | |

| ctc | aac | gag | acc | acc | aac | tgg | ttg | tgg | gcg | ttt | ttg | gcc | aga | gaa | 8850 |
|---|---|---|---|---|---|---|---|---|---|---|---|---|---|---|---|
| Leu | Asn | Glu | Thr | Thr | Asn | Trp | Leu | Trp | Ala | Phe | Leu | Ala | Arg | Glu | |
| 2905 | | | | | 2910 | | | | | 2915 | | | | | |

| aaa | cgt | ccc | aga | atg | tgc | tct | cga | gag | gaa | ttc | ata | aga | aag | gtc | 8895 |
|---|---|---|---|---|---|---|---|---|---|---|---|---|---|---|---|
| Lys | Arg | Pro | Arg | Met | Cys | Ser | Arg | Glu | Glu | Phe | Ile | Arg | Lys | Val | |
| 2920 | | | | | 2925 | | | | | 2930 | | | | | |

| aac | agc | aat | gca | gct | ttg | ggt | gcc | atg | ttt | gaa | gag | cag | aat | caa | 8940 |
|---|---|---|---|---|---|---|---|---|---|---|---|---|---|---|---|
| Asn | Ser | Asn | Ala | Ala | Leu | Gly | Ala | Met | Phe | Glu | Glu | Gln | Asn | Gln | |
| 2935 | | | | | 2940 | | | | | 2945 | | | | | |

| tgg | agg | agc | gcc | aga | gaa | gca | gtt | gaa | gat | cca | aaa | ttt | tgg | gag | 8985 |
|---|---|---|---|---|---|---|---|---|---|---|---|---|---|---|---|
| Trp | Arg | Ser | Ala | Arg | Glu | Ala | Val | Glu | Asp | Pro | Lys | Phe | Trp | Glu | |
| 2950 | | | | | 2955 | | | | | 2960 | | | | | |

| atg | gtg | gat | gag | gag | cgc | gag | gca | cat | ctg | cgg | ggg | gaa | tgt | cac | 9030 |
|---|---|---|---|---|---|---|---|---|---|---|---|---|---|---|---|
| Met | Val | Asp | Glu | Glu | Arg | Glu | Ala | His | Leu | Arg | Gly | Glu | Cys | His | |
| 2965 | | | | | 2970 | | | | | 2975 | | | | | |

| act | tgc | att | tac | aac | atg | atg | gga | aag | aga | gag | aaa | aaa | ccc | gga | 9075 |
|---|---|---|---|---|---|---|---|---|---|---|---|---|---|---|---|
| Thr | Cys | Ile | Tyr | Asn | Met | Met | Gly | Lys | Arg | Glu | Lys | Lys | Pro | Gly | |
| 2980 | | | | | 2985 | | | | | 2990 | | | | | |

| gag | ttc | gga | aag | gcc | aag | gga | agc | aga | gcc | att | tgg | ttc | atg | tgg | 9120 |
|---|---|---|---|---|---|---|---|---|---|---|---|---|---|---|---|
| Glu | Phe | Gly | Lys | Ala | Lys | Gly | Ser | Arg | Ala | Ile | Trp | Phe | Met | Trp | |
| 2995 | | | | | 3000 | | | | | 3005 | | | | | |

| ctc | gga | gct | cgc | ttt | ctg | gag | ttc | gag | gct | ctg | ggt | ttt | ctc | aat | 9165 |
|---|---|---|---|---|---|---|---|---|---|---|---|---|---|---|---|
| Leu | Gly | Ala | Arg | Phe | Leu | Glu | Phe | Glu | Ala | Leu | Gly | Phe | Leu | Asn | |
| 3010 | | | | | 3015 | | | | | 3020 | | | | | |

| gaa | gac | cac | tgg | ctt | gga | aga | aag | aac | tca | gga | gga | ggt | gtc | gag | 9210 |
|---|---|---|---|---|---|---|---|---|---|---|---|---|---|---|---|
| Glu | Asp | His | Trp | Leu | Gly | Arg | Lys | Asn | Ser | Gly | Gly | Gly | Val | Glu | |
| 3025 | | | | | 3030 | | | | | 3035 | | | | | |

| ggc | ttg | ggc | ctc | caa | aaa | ctg | ggt | tac | atc | ctg | cgt | gaa | gtt | ggc | 9255 |
|---|---|---|---|---|---|---|---|---|---|---|---|---|---|---|---|
| Gly | Leu | Gly | Leu | Gln | Lys | Leu | Gly | Tyr | Ile | Leu | Arg | Glu | Val | Gly | |
| 3040 | | | | | 3045 | | | | | 3050 | | | | | |

| acc | cgg | cct | ggg | ggc | aag | atc | tat | gct | gat | gac | aca | gct | ggc | tgg | 9300 |
|---|---|---|---|---|---|---|---|---|---|---|---|---|---|---|---|
| Thr | Arg | Pro | Gly | Gly | Lys | Ile | Tyr | Ala | Asp | Asp | Thr | Ala | Gly | Trp | |
| 3055 | | | | | 3060 | | | | | 3065 | | | | | |

| gac | acc | cgc | atc | acg | aga | gct | gac | ttg | gaa | aat | gaa | gct | aag | gtg | 9345 |
|---|---|---|---|---|---|---|---|---|---|---|---|---|---|---|---|
| Asp | Thr | Arg | Ile | Thr | Arg | Ala | Asp | Leu | Glu | Asn | Glu | Ala | Lys | Val | |
| 3070 | | | | | 3075 | | | | | 3080 | | | | | |

| ctt | gag | ctg | ctt | gat | ggg | gaa | cat | cgg | cgt | ctt | gcc | agg | gcc | atc | 9390 |
|---|---|---|---|---|---|---|---|---|---|---|---|---|---|---|---|
| Leu | Glu | Leu | Leu | Asp | Gly | Glu | His | Arg | Arg | Leu | Ala | Arg | Ala | Ile | |
| 3085 | | | | | 3090 | | | | | 3095 | | | | | |

| att | gag | ctc | acc | tat | cgt | cac | aaa | gtt | gtg | aaa | gtg | atg | cgc | ccg | 9435 |
|---|---|---|---|---|---|---|---|---|---|---|---|---|---|---|---|
| Ile | Glu | Leu | Thr | Tyr | Arg | His | Lys | Val | Val | Lys | Val | Met | Arg | Pro | |
| 3100 | | | | | 3105 | | | | | 3110 | | | | | |

| gct | gct | gat | gga | aga | acc | gtc | atg | gat | gtt | atc | tcc | aga | gaa | gat | 9480 |
|---|---|---|---|---|---|---|---|---|---|---|---|---|---|---|---|
| Ala | Ala | Asp | Gly | Arg | Thr | Val | Met | Asp | Val | Ile | Ser | Arg | Glu | Asp | |
| 3115 | | | | | 3120 | | | | | 3125 | | | | | |

```
cag agg ggg agt gga caa gtt gtc acc tac gcc cta aac act ttc      9525
Gln Arg Gly Ser Gly Gln Val Val Thr Tyr Ala Leu Asn Thr Phe
    3130                3135                3140 acc aac ctg gcc gtc cag ctg gtg agg atg atg gaa ggg gaa gga      9570
Thr Asn Leu Ala Val Gln Leu Val Arg Met Met Glu Gly Glu Gly
    3145                3150                3155 gtg att ggc cca gat gat gtg gag aaa ctc aca aaa ggg aaa gga      9615
Val Ile Gly Pro Asp Asp Val Glu Lys Leu Thr Lys Gly Lys Gly
    3160                3165                3170 ccc aaa gtc agg acc tgg ctg ttt gag aat ggg gaa gaa aga ctc      9660
Pro Lys Val Arg Thr Trp Leu Phe Glu Asn Gly Glu Glu Arg Leu
    3175                3180                3185 agc cgc atg gct gtc agt gga gat gac tgt gtg gta aag ccc ctg      9705
Ser Arg Met Ala Val Ser Gly Asp Asp Cys Val Val Lys Pro Leu
    3190                3195                3200 gac gat cgc ttt gcc acc tcg ctc cac ttc ctc aat gct atg tca      9750
Asp Asp Arg Phe Ala Thr Ser Leu His Phe Leu Asn Ala Met Ser
    3205                3210                3215 aag gtt cgc aaa gac atc caa gag tgg aaa ccg tca act gga tgg      9795
Lys Val Arg Lys Asp Ile Gln Glu Trp Lys Pro Ser Thr Gly Trp
    3220                3225                3230 tat gat tgg cag cag gtt cca ttt tgc tca aac cat ttc act gaa      9840
Tyr Asp Trp Gln Gln Val Pro Phe Cys Ser Asn His Phe Thr Glu
    3235                3240                3245 ttg atc atg aaa gat gga aga aca ctg gtg gtt cca tgc cga gga      9885
Leu Ile Met Lys Asp Gly Arg Thr Leu Val Val Pro Cys Arg Gly
    3250                3255                3260 cag gat gaa ttg gta ggc aga gct cgc ata tct cca ggg gcc gga      9930
Gln Asp Glu Leu Val Gly Arg Ala Arg Ile Ser Pro Gly Ala Gly
    3265                3270                3275 tgg aac gtc cgc gac act gct tgt ctg gct aag tct tat gcc cag      9975
Trp Asn Val Arg Asp Thr Ala Cys Leu Ala Lys Ser Tyr Ala Gln
    3280                3285                3290 atg tgg ctg ctt ctg tac ttc cac aga aga gac ctg cgg ctc atg     10020
Met Trp Leu Leu Leu Tyr Phe His Arg Arg Asp Leu Arg Leu Met
    3295                3300                3305 gcc aac gcc att tgc tcc gct gtc cct gtg aat tgg gtc cct acc     10065
Ala Asn Ala Ile Cys Ser Ala Val Pro Val Asn Trp Val Pro Thr
    3310                3315                3320 gga aga acc acg tgg tcc atc cat gca gga gga gag tgg atg aca     10110
Gly Arg Thr Thr Trp Ser Ile His Ala Gly Gly Glu Trp Met Thr
    3325                3330                3335 aca gag gac atg ttg gag gtc tgg aac cgt gtt tgg ata gag gag     10155
Thr Glu Asp Met Leu Glu Val Trp Asn Arg Val Trp Ile Glu Glu
    3340                3345                3350 aat gaa tgg atg gaa gac aaa acc cca gtg gag aaa tgg agt gac     10200
Asn Glu Trp Met Glu Asp Lys Thr Pro Val Glu Lys Trp Ser Asp
    3355                3360                3365 gtc cca tat tca gga aaa cga gag gac atc tgg tgt ggc agc ctg     10245
Val Pro Tyr Ser Gly Lys Arg Glu Asp Ile Trp Cys Gly Ser Leu
    3370                3375                3380 att ggc aca aga gcc cga gcc acg tgg gca gaa aac atc cag gtg     10290
Ile Gly Thr Arg Ala Arg Ala Thr Trp Ala Glu Asn Ile Gln Val
    3385                3390                3395 gct atc aac caa gtc aga gca atc atc gga gat gag aag tat gtg     10335
Ala Ile Asn Gln Val Arg Ala Ile Ile Gly Asp Glu Lys Tyr Val
    3400                3405                3410 gat tac atg agt tca cta aag aga tat gaa gac aca act ttg gtt     10380
Asp Tyr Met Ser Ser Leu Lys Arg Tyr Glu Asp Thr Thr Leu Val
    3415                3420                3425
```

-continued

```
gag gac  aca gta ctg tag atatttaatc aattgtaaat agacaatata    10428
Glu Asp  Thr Val Leu
     3430 agtatgcata aaagtgtagt tttatagtag tatttagtgg tgttagtgta aatagttaag    10488 aaaattttga ggagaaagtc aggccgggaa gttcccgcca ccggaagttg agtagacggt    10548 gctgcctgcg actcaacccc aggaggactg ggtgaacaaa gccgcgaagt gatccatgta    10608 agccctcaga accgtctcgg aaggaggacc ccacatgttg taacttcaaa gcccaatgtc    10668 agaccacgct acggcgtgct actctgcgga gagtgcagtc tgcgatagtg ccccaggagg    10728 actgggttaa caaggcaaa ccaacgcccc acgcggccct agccccggta atggtgttaa    10788 ccagggcgaa aggactagag gttagaggag accccgcggt ttaaagtgca cggcccagcc    10848 tggctgaagc tgtaggtcag gggaaggact agaggttagt ggagaccccg tgccacaaaa    10908 caccacaaca aaacagcata ttgacacctg ggatagacta ggagatcttc tgctctgcac    10968 aaccagccac acggcacagt gcgccgacaa tggtggctgg tggtgcgaga acacaggatc    11028 t                                                                    11029
```

<210> SEQ ID NO 4
<211> LENGTH: 3433
<212> TYPE: PRT
<213> ORGANISM: West Nile virus

<400> SEQUENCE: 4

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala Val Thr Leu Ser Asn
        115                 120                 125

Phe Gln Gly Lys Val Met Met Thr Val Asn Ala Thr Asp Val Thr Asp
    130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
            180                 185                 190

Thr Lys Ser Ala Val Tyr Val Arg Tyr Gly Arg Cys Thr Lys Thr Arg
        195                 200                 205

His Ser Arg Arg Ser Arg Arg Ser Leu Thr Val Gln Thr His Gly Glu
    210                 215                 220

Ser Thr Leu Ala Asn Lys Lys Gly Ala Trp Met Asp Ser Thr Lys Ala
225                 230                 235                 240
```

```
Thr Arg Tyr Leu Val Lys Thr Glu Ser Trp Ile Leu Arg Asn Pro Gly
            245                 250                 255

Tyr Ala Leu Val Ala Ala Val Ile Gly Trp Met Leu Gly Ser Asn Thr
            260                 265                 270

Met Gln Arg Val Val Phe Val Val Leu Leu Leu Val Ala Pro Ala
            275                 280                 285

Tyr Ser Phe Asn Cys Leu Gly Met Ser Asn Arg Asp Phe Leu Glu Gly
            290                 295                 300

Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                    325                 330                 335

Asn Met Glu Ala Ala Asn Leu Ala Glu Val Arg Ser Tyr Cys Tyr Leu
            340                 345                 350

Ala Thr Val Ser Asp Leu Ser Thr Lys Ala Ala Cys Pro Thr Met Gly
            355                 360                 365

Glu Ala His Asn Asp Lys Arg Ala Asp Pro Ala Phe Val Cys Arg Gln
            370                 375                 380

Gly Val Val Asp Arg Gly Trp Gly Asn Gly Cys Gly Leu Phe Gly Lys
385                 390                 395                 400

Gly Ser Ile Asp Thr Cys Ala Lys Phe Ala Cys Ser Thr Lys Ala Ile
                    405                 410                 415

Gly Arg Thr Ile Leu Lys Glu Asn Ile Lys Tyr Glu Val Ala Ile Phe
                    420                 425                 430

Val His Gly Pro Thr Thr Val Glu Ser His Gly Asn Tyr Ser Thr Gln
            435                 440                 445

Val Gly Ala Thr Gln Ala Gly Arg Phe Ser Ile Thr Pro Ala Ala Pro
            450                 455                 460

Ser Tyr Thr Leu Lys Leu Gly Glu Tyr Gly Glu Val Thr Val Asp Cys
465                 470                 475                 480

Glu Pro Arg Ser Gly Ile Asp Thr Asn Ala Tyr Tyr Val Met Thr Val
                    485                 490                 495

Gly Thr Lys Thr Phe Leu Val His Arg Glu Trp Phe Met Asp Leu Asn
                    500                 505                 510

Leu Pro Trp Ser Ser Ala Gly Ser Thr Val Trp Arg Asn Arg Glu Thr
            515                 520                 525

Leu Met Glu Phe Glu Glu Pro His Ala Thr Lys Gln Ser Val Ile Ala
            530                 535                 540

Leu Gly Ser Gln Glu Gly Ala Leu His Gln Ala Leu Ala Gly Ala Ile
545                 550                 555                 560

Pro Val Glu Phe Ser Ser Asn Thr Val Lys Leu Thr Ser Gly His Leu
                    565                 570                 575

Lys Cys Arg Val Lys Met Glu Lys Leu Gln Leu Lys Gly Thr Thr Tyr
                    580                 585                 590

Gly Val Cys Ser Lys Ala Phe Lys Phe Leu Gly Thr Pro Ala Asp Thr
                    595                 600                 605

Gly His Gly Thr Val Val Leu Glu Leu Gln Tyr Thr Gly Thr Asp Gly
            610                 615                 620

Pro Cys Lys Val Pro Ile Ser Ser Val Ala Ser Leu Asn Asp Leu Thr
625                 630                 635                 640

Pro Val Gly Arg Leu Val Thr Val Asn Pro Phe Val Ser Val Ala Thr
                    645                 650                 655
```

```
Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
        675                 680                 685

Lys Ser Gly Ser Ser Ile Gly Lys Ala Phe Thr Thr Thr Leu Lys Gly
    690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                725                 730                 735

Gly Gly Ala Phe Arg Ser Leu Phe Gly Gly Met Ser Trp Ile Thr Gln
            740                 745                 750

Gly Leu Leu Gly Ala Leu Leu Leu Trp Met Gly Ile Asn Ala Arg Asp
        755                 760                 765

Arg Ser Ile Ala Leu Thr Phe Leu Ala Val Gly Gly Val Leu Leu Phe
    770                 775                 780

Leu Ser Val Asn Val His Ala Asp Thr Gly Cys Ala Ile Asp Ile Ser
785                 790                 795                 800

Arg Gln Glu Leu Arg Cys Gly Ser Gly Val Phe Ile His Asn Asp Val
                805                 810                 815

Glu Ala Trp Met Asp Arg Tyr Lys Tyr Tyr Pro Glu Thr Pro Gln Gly
            820                 825                 830

Leu Ala Lys Ile Ile Gln Lys Ala His Lys Glu Gly Val Cys Gly Leu
        835                 840                 845

Arg Ser Val Ser Arg Leu Glu His Gln Met Trp Glu Ala Val Lys Asp
    850                 855                 860

Glu Leu Asn Thr Leu Leu Lys Glu Asn Gly Val Asp Leu Ser Val Val
865                 870                 875                 880

Val Glu Lys Gln Glu Gly Met Tyr Lys Ser Ala Pro Lys Arg Leu Thr
                885                 890                 895

Ala Thr Thr Glu Lys Leu Glu Ile Gly Trp Lys Ala Trp Gly Lys Ser
            900                 905                 910

Ile Leu Phe Ala Pro Glu Leu Ala Asn Asn Thr Phe Val Val Asp Gly
        915                 920                 925

Pro Glu Thr Lys Glu Cys Pro Thr Gln Asn Arg Ala Trp Asn Ser Leu
    930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
                965                 970                 975

Thr Ala Val Lys Asn Asn Leu Ala Ile His Ser Asp Leu Ser Tyr Trp
            980                 985                 990

Ile Glu Ser Arg Leu Asn Asp Thr Trp Lys Leu Glu Arg Ala Val Leu
        995                 1000                1005

Gly Glu Val Lys Ser Cys Thr Trp Pro Glu Thr His Thr Leu Trp
        1010                1015                1020

Gly Asp Gly Ile Leu Glu Ser Asp Leu Ile Ile Pro Val Thr Leu
        1025                1030                1035

Ala Gly Pro Arg Ser Asn His Asn Arg Arg Pro Gly Tyr Lys Thr
        1040                1045                1050

Gln Asn Gln Gly Pro Trp Asp Glu Gly Arg Val Glu Ile Asp Phe
        1055                1060                1065

Asp Tyr Cys Pro Gly Thr Thr Val Thr Leu Ser Glu Ser Cys Gly
```

```
              1070                1075                1080
His Arg Gly Pro Ala Thr Arg Thr Thr Thr Glu Ser Gly Lys Leu
              1085                1090                1095
Ile Thr Asp Trp Cys Cys Arg Ser Cys Thr Leu Pro Pro Leu Arg
              1100                1105                1110
Tyr Gln Thr Asp Ser Gly Cys Trp Tyr Gly Met Glu Ile Arg Pro
              1115                1120                1125
Gln Arg His Asp Glu Lys Thr Leu Val Gln Ser Gln Val Asn Ala
              1130                1135                1140
Tyr Asn Ala Asp Met Ile Asp Pro Phe Gln Leu Gly Leu Leu Val
              1145                1150                1155
Val Phe Leu Ala Thr Gln Glu Val Leu Arg Lys Arg Trp Thr Ala
              1160                1165                1170
Lys Ile Ser Met Pro Ala Ile Leu Ile Ala Leu Leu Val Leu Val
              1175                1180                1185
Phe Gly Gly Ile Thr Tyr Thr Asp Val Leu Arg Tyr Val Ile Leu
              1190                1195                1200
Val Gly Ala Ala Phe Ala Glu Ser Asn Ser Gly Gly Asp Val Val
              1205                1210                1215
His Leu Ala Leu Met Ala Thr Phe Lys Ile Gln Pro Val Phe Met
              1220                1225                1230
Val Ala Ser Phe Leu Lys Ala Arg Trp Thr Asn Gln Glu Asn Ile
              1235                1240                1245
Leu Leu Met Leu Ala Ala Val Phe Phe Gln Met Ala Tyr Tyr Asp
              1250                1255                1260
Ala Arg Gln Ile Leu Leu Trp Glu Ile Pro Asp Val Leu Asn Ser
              1265                1270                1275
Leu Ala Val Ala Trp Met Ile Leu Arg Ala Ile Thr Phe Thr Thr
              1280                1285                1290
Thr Ser Asn Val Val Val Pro Leu Leu Ala Leu Leu Thr Pro Gly
              1295                1300                1305
Leu Arg Cys Leu Asn Leu Asp Val Tyr Arg Ile Leu Leu Leu Met
              1310                1315                1320
Val Gly Ile Gly Ser Leu Ile Arg Glu Lys Arg Ser Ala Ala Ala
              1325                1330                1335
Lys Lys Lys Gly Ala Ser Leu Leu Cys Leu Ala Leu Ala Ser Thr
              1340                1345                1350
Gly Leu Phe Asn Pro Met Ile Leu Ala Ala Gly Leu Ile Ala Cys
              1355                1360                1365
Asp Pro Asn Arg Lys Arg Gly Trp Pro Ala Thr Glu Val Met Thr
              1370                1375                1380
Ala Val Gly Leu Met Phe Ala Ile Val Gly Gly Leu Ala Glu Leu
              1385                1390                1395
Asp Ile Asp Ser Met Ala Ile Pro Met Thr Ile Ala Gly Leu Met
              1400                1405                1410
Phe Ala Ala Phe Val Ile Ser Gly Lys Ser Thr Asp Met Trp Ile
              1415                1420                1425
Glu Arg Thr Ala Asp Ile Ser Trp Glu Ser Asp Ala Glu Ile Thr
              1430                1435                1440
Gly Ser Ser Glu Arg Val Asp Val Arg Leu Asp Asp Gly Asn
              1445                1450                1455
Phe Gln Leu Met Asn Asp Pro Gly Ala Pro Trp Lys Ile Trp Met
              1460                1465                1470
```

```
Leu Arg Met Val Cys Leu Ala Ile Ser Ala Tyr Thr Pro Trp Ala
    1475                1480                1485
Ile Leu Pro Ser Val Val Gly Phe Trp Ile Thr Leu Gln Tyr Thr
    1490                1495                1500
Lys Arg Gly Gly Val Leu Trp Asp Thr Pro Ser Pro Lys Glu Tyr
    1505                1510                1515
Lys Lys Gly Asp Thr Thr Thr Gly Val Tyr Arg Ile Met Thr Arg
    1520                1525                1530
Gly Leu Leu Gly Ser Tyr Gln Ala Gly Ala Gly Val Met Val Glu
    1535                1540                1545
Gly Val Phe His Thr Leu Trp His Thr Thr Lys Gly Ala Ala Leu
    1550                1555                1560
Met Ser Gly Glu Gly Arg Leu Asp Pro Tyr Trp Gly Ser Val Lys
    1565                1570                1575
Glu Asp Arg Leu Cys Tyr Gly Gly Pro Trp Lys Leu Gln His Lys
    1580                1585                1590
Trp Asn Gly Gln Asp Glu Val Gln Met Ile Val Val Glu Pro Gly
    1595                1600                1605
Arg Asn Val Lys Asn Val Gln Thr Lys Pro Gly Val Phe Lys Thr
    1610                1615                1620
Pro Glu Gly Glu Ile Gly Ala Val Thr Leu Asp Phe Pro Thr Gly
    1625                1630                1635
Thr Ser Gly Ser Pro Ile Val Asp Lys Asn Gly Asp Val Ile Gly
    1640                1645                1650
Leu Tyr Gly Asn Gly Val Ile Met Pro Asn Gly Ser Tyr Ile Ser
    1655                1660                1665
Ala Ile Val Gln Gly Glu Arg Met Asp Glu Pro Ile Pro Ala Gly
    1670                1675                1680
Phe Glu Pro Glu Met Leu Arg Lys Lys Gln Ile Thr Val Leu Asp
    1685                1690                1695
Leu His Pro Gly Ala Gly Lys Thr Arg Arg Ile Leu Pro Gln Ile
    1700                1705                1710
Ile Lys Glu Ala Ile Asn Arg Arg Leu Arg Thr Ala Val Leu Ala
    1715                1720                1725
Pro Thr Arg Val Val Ala Ala Glu Met Ala Glu Ala Leu Arg Gly
    1730                1735                1740
Leu Pro Ile Arg Tyr Gln Thr Ser Ala Val Pro Arg Glu His Asn
    1745                1750                1755
Gly Asn Glu Ile Val Asp Val Met Cys His Ala Thr Leu Thr His
    1760                1765                1770
Arg Leu Met Ser Pro His Arg Val Pro Asn Tyr Asn Leu Phe Val
    1775                1780                1785
Met Asp Glu Ala His Phe Thr Asp Pro Ala Ser Ile Ala Ala Arg
    1790                1795                1800
Gly Tyr Ile Ser Thr Lys Val Glu Leu Gly Glu Ala Ala Ala Ile
    1805                1810                1815
Phe Met Thr Ala Thr Pro Pro Gly Thr Ser Asp Pro Phe Pro Glu
    1820                1825                1830
Ser Asn Ser Pro Ile Ser Asp Leu Gln Thr Glu Ile Pro Asp Arg
    1835                1840                1845
Ala Trp Asn Ser Gly Tyr Glu Trp Ile Thr Glu Tyr Thr Gly Lys
    1850                1855                1860
```

```
Thr Val Trp Phe Val Pro Ser Val Lys Met Gly Asn Glu Ile Ala
1865                1870                1875

Leu Cys Leu Gln Arg Ala Gly Lys Lys Val Val Gln Leu Asn Arg
1880                1885                1890

Lys Ser Tyr Glu Thr Glu Tyr Pro Lys Cys Lys Asn Asp Asp Trp
1895                1900                1905

Asp Phe Val Ile Thr Thr Asp Ile Ser Glu Met Gly Ala Asn Phe
1910                1915                1920

Lys Ala Ser Arg Val Ile Asp Ser Arg Lys Ser Val Lys Pro Thr
1925                1930                1935

Ile Ile Thr Glu Gly Glu Gly Arg Val Ile Leu Gly Glu Pro Ser
1940                1945                1950

Ala Val Thr Ala Ala Ser Ala Ala Gln Arg Arg Gly Arg Ile Gly
1955                1960                1965

Arg Asn Pro Ser Gln Val Gly Asp Glu Tyr Cys Tyr Gly Gly His
1970                1975                1980

Thr Asn Glu Asp Asp Ser Asn Phe Ala His Trp Thr Glu Ala Arg
1985                1990                1995

Ile Met Leu Asp Asn Ile Asn Met Pro Asn Gly Leu Ile Ala Gln
2000                2005                2010

Phe Tyr Gln Pro Glu Arg Glu Lys Val Tyr Thr Met Asp Gly Glu
2015                2020                2025

Tyr Arg Leu Arg Gly Glu Glu Arg Lys Asn Phe Leu Glu Leu Leu
2030                2035                2040

Arg Thr Ala Asp Leu Pro Val Trp Leu Ala Tyr Lys Val Ala Ala
2045                2050                2055

Ala Gly Val Ser Tyr His Asp Arg Arg Trp Cys Phe Asp Gly Pro
2060                2065                2070

Arg Thr Asn Thr Ile Leu Glu Asp Asn Asn Glu Val Glu Val Ile
2075                2080                2085

Thr Lys Leu Gly Glu Arg Lys Ile Leu Arg Pro Arg Trp Ile Asp
2090                2095                2100

Ala Arg Val Tyr Ser Asp His Gln Ala Leu Lys Ala Phe Lys Asp
2105                2110                2115

Phe Ala Ser Gly Lys Arg Ser Gln Ile Gly Leu Ile Glu Val Leu
2120                2125                2130

Gly Lys Met Pro Glu His Phe Met Gly Lys Thr Trp Glu Ala Leu
2135                2140                2145

Asp Thr Met Tyr Val Val Ala Thr Ala Glu Lys Gly Gly Arg Ala
2150                2155                2160

His Arg Met Ala Leu Glu Glu Leu Pro Asp Ala Leu Gln Thr Ile
2165                2170                2175

Ala Leu Ile Ala Leu Leu Ser Val Met Thr Met Gly Val Phe Phe
2180                2185                2190

Leu Leu Met Gln Arg Lys Gly Ile Gly Lys Ile Gly Leu Gly Gly
2195                2200                2205

Ala Val Leu Gly Val Ala Thr Phe Phe Cys Trp Met Ala Glu Val
2210                2215                2220

Pro Gly Thr Lys Ile Ala Gly Met Leu Leu Leu Ser Leu Leu Leu
2225                2230                2235

Met Ile Val Leu Ile Pro Glu Pro Glu Lys Gln Arg Ser Gln Thr
2240                2245                2250

Asp Asn Gln Leu Ala Val Phe Leu Ile Cys Val Met Thr Leu Val
```

-continued

Ser Ala Val Ala Ala Asn Glu Met Gly Trp Leu Asp Lys Thr Lys
2270            2275                2280

Ser Asp Ile Ser Ser Leu Phe Gly Gln Arg Ile Glu Val Lys Glu
2285            2290                2295

Asn Phe Ser Met Gly Glu Phe Leu Leu Asp Leu Arg Pro Ala Thr
2300            2305                2310

Ala Trp Ser Leu Tyr Ala Val Thr Thr Ala Val Leu Thr Ala Leu
2315            2320                2325

Leu Lys His Leu Ile Thr Ser Asp Tyr Ile Asn Thr Ser Leu Thr
2330            2335                2340

Ser Ile Asn Val Gln Ala Ser Ala Leu Phe Thr Leu Ala Arg Gly
2345            2350                2355

Phe Pro Phe Val Asp Val Gly Val Ser Ala Leu Leu Leu Ala Ala
2360            2365                2370

Gly Cys Trp Gly Gln Val Thr Leu Thr Val Thr Val Thr Ala Ala
2375            2380                2385

Thr Leu Leu Phe Cys His Tyr Ala Tyr Met Val Pro Gly Trp Gln
2390            2395                2400

Ala Glu Ala Met Arg Ser Ala Gln Arg Arg Thr Ala Ala Gly Ile
2405            2410                2415

Met Lys Asn Ala Val Val Asp Gly Ile Val Ala Thr Asp Val Pro
2420            2425                2430

Glu Leu Glu Arg Thr Thr Pro Ile Met Gln Lys Lys Val Gly Gln
2435            2440                2445

Ile Met Leu Ile Leu Val Ser Leu Ala Ala Val Val Val Asn Pro
2450            2455                2460

Ser Val Lys Thr Val Arg Glu Ala Gly Ile Leu Ile Thr Ala Ala
2465            2470                2475

Ala Val Thr Leu Trp Glu Asn Gly Ala Ser Ser Val Trp Asn Ala
2480            2485                2490

Thr Thr Ala Ile Gly Leu Cys His Ile Met Arg Gly Gly Trp Leu
2495            2500                2505

Ser Cys Leu Ser Ile Thr Trp Thr Leu Ile Lys Asn Met Glu Lys
2510            2515                2520

Pro Gly Leu Lys Arg Gly Gly Ala Lys Gly Arg Thr Leu Gly Glu
2525            2530                2535

Val Trp Lys Glu Arg Leu Asn Gln Met Thr Lys Glu Glu Phe Thr
2540            2545                2550

Arg Tyr Arg Lys Glu Ala Ile Ile Glu Val Asp Arg Ser Ala Ala
2555            2560                2565

Lys His Ala Arg Lys Glu Gly Asn Val Thr Gly Gly His Pro Val
2570            2575                2580

Ser Arg Gly Thr Ala Lys Leu Arg Trp Leu Val Glu Arg Arg Phe
2585            2590                2595

Leu Glu Pro Val Gly Lys Val Ile Asp Leu Gly Cys Gly Arg Gly
2600            2605                2610

Gly Trp Cys Tyr Tyr Met Ala Thr Gln Lys Arg Val Gln Glu Val
2615            2620                2625

Arg Gly Tyr Thr Lys Gly Gly Pro Gly His Glu Glu Pro Gln Leu
2630            2635                2640

Val Gln Ser Tyr Gly Trp Asn Ile Val Thr Met Lys Ser Gly Val
2645            2650                2655

-continued

```
Asp Val Phe Tyr Arg Pro Ser Glu Cys Cys Asp Thr Leu Leu Cys
    2660                2665                2670

Asp Ile Gly Glu Ser Ser Ser Ala Glu Val Glu Glu His Arg
    2675                2680                2685

Thr Ile Arg Val Leu Glu Met Val Glu Asp Trp Leu His Arg Gly
    2690                2695                2700

Pro Arg Glu Phe Cys Val Lys Val Leu Cys Pro Tyr Met Pro Lys
    2705                2710                2715

Val Ile Glu Lys Met Glu Leu Leu Gln Arg Arg Tyr Gly Gly Gly
    2720                2725                2730

Leu Val Arg Asn Pro Leu Ser Arg Asn Ser Thr His Glu Met Tyr
    2735                2740                2745

Trp Val Ser Arg Ala Ser Gly Asn Val Val His Ser Val Asn Met
    2750                2755                2760

Thr Ser Gln Val Leu Leu Gly Arg Met Glu Lys Arg Thr Trp Lys
    2765                2770                2775

Gly Pro Gln Tyr Glu Glu Asp Val Asn Leu Gly Ser Gly Thr Arg
    2780                2785                2790

Ala Val Gly Lys Pro Leu Leu Asn Ser Asp Thr Ser Lys Ile Lys
    2795                2800                2805

Asn Arg Ile Glu Arg Leu Arg Arg Glu Tyr Ser Ser Thr Trp His
    2810                2815                2820

His Asp Glu Asn His Pro Tyr Arg Thr Trp Asn Tyr His Gly Ser
    2825                2830                2835

Tyr Asp Val Lys Pro Thr Gly Ser Ala Ser Ser Leu Val Asn Gly
    2840                2845                2850

Val Val Arg Leu Leu Ser Lys Pro Trp Asp Thr Ile Thr Asn Val
    2855                2860                2865

Thr Thr Met Ala Met Thr Asp Thr Thr Pro Phe Gly Gln Gln Arg
    2870                2875                2880

Val Phe Lys Glu Lys Val Asp Thr Lys Ala Pro Glu Pro Pro Glu
    2885                2890                2895

Gly Val Lys Tyr Val Leu Asn Glu Thr Thr Asn Trp Leu Trp Ala
    2900                2905                2910

Phe Leu Ala Arg Glu Lys Arg Pro Arg Met Cys Ser Arg Glu Glu
    2915                2920                2925

Phe Ile Arg Lys Val Asn Ser Asn Ala Ala Leu Gly Ala Met Phe
    2930                2935                2940

Glu Glu Gln Asn Gln Trp Arg Ser Ala Arg Glu Ala Val Glu Asp
    2945                2950                2955

Pro Lys Phe Trp Glu Met Val Asp Glu Glu Arg Glu Ala His Leu
    2960                2965                2970

Arg Gly Glu Cys His Thr Cys Ile Tyr Asn Met Met Gly Lys Arg
    2975                2980                2985

Glu Lys Lys Pro Gly Glu Phe Gly Lys Ala Lys Gly Ser Arg Ala
    2990                2995                3000

Ile Trp Phe Met Trp Leu Gly Ala Arg Phe Leu Glu Phe Glu Ala
    3005                3010                3015

Leu Gly Phe Leu Asn Glu Asp His Trp Leu Gly Arg Lys Asn Ser
    3020                3025                3030

Gly Gly Gly Val Glu Gly Leu Gly Leu Gln Lys Leu Gly Tyr Ile
    3035                3040                3045
```

-continued

```
Leu Arg Glu Val Gly Thr Arg Pro Gly Gly Lys Ile Tyr Ala Asp
    3050                3055                3060

Asp Thr Ala Gly Trp Asp Thr Arg Ile Thr Arg Ala Asp Leu Glu
    3065                3070                3075

Asn Glu Ala Lys Val Leu Glu Leu Leu Asp Gly Glu His Arg Arg
    3080                3085                3090

Leu Ala Arg Ala Ile Ile Glu Leu Thr Tyr Arg His Lys Val Val
    3095                3100                3105

Lys Val Met Arg Pro Ala Ala Asp Gly Arg Thr Val Met Asp Val
    3110                3115                3120

Ile Ser Arg Glu Asp Gln Arg Gly Ser Gly Gln Val Val Thr Tyr
    3125                3130                3135

Ala Leu Asn Thr Phe Thr Asn Leu Ala Val Gln Leu Val Arg Met
    3140                3145                3150

Met Glu Gly Glu Gly Val Ile Gly Pro Asp Asp Val Glu Lys Leu
    3155                3160                3165

Thr Lys Gly Lys Gly Pro Lys Val Arg Thr Trp Leu Phe Glu Asn
    3170                3175                3180

Gly Glu Glu Arg Leu Ser Arg Met Ala Val Ser Gly Asp Asp Cys
    3185                3190                3195

Val Val Lys Pro Leu Asp Asp Arg Phe Ala Thr Ser Leu His Phe
    3200                3205                3210

Leu Asn Ala Met Ser Lys Val Arg Lys Asp Ile Gln Glu Trp Lys
    3215                3220                3225

Pro Ser Thr Gly Trp Tyr Asp Trp Gln Gln Val Pro Phe Cys Ser
    3230                3235                3240

Asn His Phe Thr Glu Leu Ile Met Lys Asp Gly Arg Thr Leu Val
    3245                3250                3255

Val Pro Cys Arg Gly Gln Asp Glu Leu Val Gly Arg Ala Arg Ile
    3260                3265                3270

Ser Pro Gly Ala Gly Trp Asn Val Arg Asp Thr Ala Cys Leu Ala
    3275                3280                3285

Lys Ser Tyr Ala Gln Met Trp Leu Leu Leu Tyr Phe His Arg Arg
    3290                3295                3300

Asp Leu Arg Leu Met Ala Asn Ala Ile Cys Ser Ala Val Pro Val
    3305                3310                3315

Asn Trp Val Pro Thr Gly Arg Thr Thr Trp Ser Ile His Ala Gly
    3320                3325                3330

Gly Glu Trp Met Thr Thr Glu Asp Met Leu Glu Val Trp Asn Arg
    3335                3340                3345

Val Trp Ile Glu Glu Asn Glu Trp Met Glu Asp Lys Thr Pro Val
    3350                3355                3360

Glu Lys Trp Ser Asp Val Pro Tyr Ser Gly Lys Arg Glu Asp Ile
    3365                3370                3375

Trp Cys Gly Ser Leu Ile Gly Thr Arg Ala Arg Ala Thr Trp Ala
    3380                3385                3390

Glu Asn Ile Gln Val Ala Ile Asn Gln Val Arg Ala Ile Ile Gly
    3395                3400                3405

Asp Glu Lys Tyr Val Asp Tyr Met Ser Ser Leu Lys Arg Tyr Glu
    3410                3415                3420

Asp Thr Thr Leu Val Glu Asp Thr Val Leu
    3425                3430
```

-continued

```
<210> SEQ ID NO 5
<211> LENGTH: 11029
<212> TYPE: DNA
<213> ORGANISM: West Nile virus
<220> FEATURE:
<221> NAME/KEY: CDS
<222> LOCATION: (97)..(10398)

<400> SEQUENCE: 5
agtagttcgc ctgtgtgagc tgacaaactt agtagtgttt gtgaggatta acaacaatta      60
acacagtgcg agctgtttct tagcacgaag atctcg atg tct aag aaa cca gga       114
                                       Met Ser Lys Lys Pro Gly
                                        1               5 ggg ccc ggc aag agc cgg gct gtc aat atg cta aaa cgc gga atg ccc       162
Gly Pro Gly Lys Ser Arg Ala Val Asn Met Leu Lys Arg Gly Met Pro
         10                  15                  20 cgc gtg ttg tcc ttg att gga ctg aag agg gct atg ttg agc ctg atc       210
Arg Val Leu Ser Leu Ile Gly Leu Lys Arg Ala Met Leu Ser Leu Ile
 25                  30                  35 gac ggc aag ggg cca ata cga ttt gtg ttg gct ctc ttg gcg ttc ttc       258
Asp Gly Lys Gly Pro Ile Arg Phe Val Leu Ala Leu Leu Ala Phe Phe
         40                  45                  50 agg ttc aca gca att gct ccg acc cga gca gtg ctg gat cga tgg aga       306
Arg Phe Thr Ala Ile Ala Pro Thr Arg Ala Val Leu Asp Arg Trp Arg
 55                  60                  65                  70 ggt gtg aac aaa caa aca gcg atg aaa cac ctt ctg agt ttt aag aag       354
Gly Val Asn Lys Gln Thr Ala Met Lys His Leu Leu Ser Phe Lys Lys
                 75                  80                  85 gaa cta ggg acc ttg acc agt gct atc aat cgg cgg agc tca aaa caa       402
Glu Leu Gly Thr Leu Thr Ser Ala Ile Asn Arg Arg Ser Ser Lys Gln
             90                  95                 100 aag aaa aga gga gga aag acc gga att gca gtc atg att ggc ctg atc       450
Lys Lys Arg Gly Gly Lys Thr Gly Ile Ala Val Met Ile Gly Leu Ile
        105                 110                 115 gcc agc gta gga gca gtt acc ctc tct aac ttc caa ggg aag gtg atg       498
Ala Ser Val Gly Ala Val Thr Leu Ser Asn Phe Gln Gly Lys Val Met
120                 125                 130 atg acg gta aat gct act gac gtc aca gat gtc atc acg att cca aca       546
Met Thr Val Asn Ala Thr Asp Val Thr Asp Val Ile Thr Ile Pro Thr
135                 140                 145                 150 gct gct gga aag aac cta tgc att gtc aga gca atg gat gtg gga tac       594
Ala Ala Gly Lys Asn Leu Cys Ile Val Arg Ala Met Asp Val Gly Tyr
                155                 160                 165 atg tgc gat gat act atc act tat gaa tgc cca gtg ctg tcg gct ggt       642
Met Cys Asp Asp Thr Ile Thr Tyr Glu Cys Pro Val Leu Ser Ala Gly
            170                 175                 180 aat gat cca gaa gac atc gac tgt tgg tgc aca aag tca gca gtc tac       690
Asn Asp Pro Glu Asp Ile Asp Cys Trp Cys Thr Lys Ser Ala Val Tyr
        185                 190                 195 gtc agg tat gga aga tgc acc aag aca cgc cac tca aga cgc agt cgg       738
Val Arg Tyr Gly Arg Cys Thr Lys Thr Arg His Ser Arg Arg Ser Arg
200                 205                 210 agg tca ctg aca gtg cag aca cac gga gaa agc act cta gcg aac aag       786
Arg Ser Leu Thr Val Gln Thr His Gly Glu Ser Thr Leu Ala Asn Lys
215                 220                 225                 230 aag ggg gct tgg atg gac agc acc aag gcc aca agg tat ttg gta aaa       834
Lys Gly Ala Trp Met Asp Ser Thr Lys Ala Thr Arg Tyr Leu Val Lys
                235                 240                 245 aca gaa tca tgg atc ttg agg aac cct gga tat gcc ctg gtg gca gcc       882
Thr Glu Ser Trp Ile Leu Arg Asn Pro Gly Tyr Ala Leu Val Ala Ala
            250                 255                 260
```

| | | |
|---|---|---|
| gtc att ggt tgg atg ctt ggg agc aac acc atg cag aga gtt gtg ttt<br>Val Ile Gly Trp Met Leu Gly Ser Asn Thr Met Gln Arg Val Val Phe<br>265                      270                     275 | 930 | |
| gtc gtg cta ttg ctt ttg gtg gcc cca gct tac agc ttc aac tgc ctt<br>Val Val Leu Leu Leu Leu Val Ala Pro Ala Tyr Ser Phe Asn Cys Leu<br>280                      285                     290 | 978 | |
| gga atg agc aac aga gac ttc ttg gaa gga gtg tct gga gca aca tgg<br>Gly Met Ser Asn Arg Asp Phe Leu Glu Gly Val Ser Gly Ala Thr Trp<br>295                      300                     305               310 | 1026 | |
| gtg gat ttg gtt ctc gaa ggc gac agc tgc gtg act atc atg tct aag<br>Val Asp Leu Val Leu Glu Gly Asp Ser Cys Val Thr Ile Met Ser Lys<br>                     315                     320                     325 | 1074 | |
| gac aag cct acc atc gat gtg aag atg atg aat atg gag gcg gcc aac<br>Asp Lys Pro Thr Ile Asp Val Lys Met Met Asn Met Glu Ala Ala Asn<br>            330                     335                     340 | 1122 | |
| ctg gca gag gtc cgc agt tat tgc tat ttg gct acc gtc agc gat ctc<br>Leu Ala Glu Val Arg Ser Tyr Cys Tyr Leu Ala Thr Val Ser Asp Leu<br>               345                     350                     355 | 1170 | |
| tcc acc aaa gct gcg tgc ccg acc atg gga gaa gct cac aat gac aaa<br>Ser Thr Lys Ala Ala Cys Pro Thr Met Gly Glu Ala His Asn Asp Lys<br>360                     365                     370 | 1218 | |
| cgt gct gac cca gct ttt gtg tgc aga caa gga gtg gtg gac agg ggc<br>Arg Ala Asp Pro Ala Phe Val Cys Arg Gln Gly Val Val Asp Arg Gly<br>375                     380                     385               390 | 1266 | |
| tgg ggc aac ggc tgc gga cta ttt ggc aaa gga agc att gac aca tgc<br>Trp Gly Asn Gly Cys Gly Leu Phe Gly Lys Gly Ser Ile Asp Thr Cys<br>                   395                     400                    405 | 1314 | |
| gcc aaa ttt gcc tgc tct acc aag gca ata gga aga acc atc ttg aaa<br>Ala Lys Phe Ala Cys Ser Thr Lys Ala Ile Gly Arg Thr Ile Leu Lys<br>            410                     415                     420 | 1362 | |
| gag aat atc aag tac gaa gtg gcc att ttt gtc cat gga cca act act<br>Glu Asn Ile Lys Tyr Glu Val Ala Ile Phe Val His Gly Pro Thr Thr<br>               425                     430                     435 | 1410 | |
| gtg gag tcg cac gga aat tac tcc aca cag gtt gga gcc act cag gca<br>Val Glu Ser His Gly Asn Tyr Ser Thr Gln Val Gly Ala Thr Gln Ala<br>440                     445                     450 | 1458 | |
| ggg aga ttc agc atc act cct gcg gcg cct tca tac aca cta aag ctt<br>Gly Arg Phe Ser Ile Thr Pro Ala Ala Pro Ser Tyr Thr Leu Lys Leu<br>455                     460                     465                   470 | 1506 | |
| gga gaa tat gga gag gtg aca gtg gac tgt gaa cca cgg tca ggg att<br>Gly Glu Tyr Gly Glu Val Thr Val Asp Cys Glu Pro Arg Ser Gly Ile<br>                   475                     480                    485 | 1554 | |
| gac acc aat gca tac tac gtg atg act gtt gga aca aag acg ttc ttg<br>Asp Thr Asn Ala Tyr Tyr Val Met Thr Val Gly Thr Lys Thr Phe Leu<br>            490                     495                     500 | 1602 | |
| gtc cat cgt gag tgg ttc atg gac ctc aac ctc cct tgg agc agt gct<br>Val His Arg Glu Trp Phe Met Asp Leu Asn Leu Pro Trp Ser Ser Ala<br>               505                     510                     515 | 1650 | |
| gga agt act gtg tgg agg aac aga gag acg tta atg gag ttt gag gaa<br>Gly Ser Thr Val Trp Arg Asn Arg Glu Thr Leu Met Glu Phe Glu Glu<br>520                     525                     530 | 1698 | |
| cca cac gcc acg aag cag tct gtg ata gca ttg ggc tca caa gag gga<br>Pro His Ala Thr Lys Gln Ser Val Ile Ala Leu Gly Ser Gln Glu Gly<br>535                     540                     545                    550 | 1746 | |
| gct ctg cat caa gct ttg gct gga gcc att cct gtg gaa ttt tca agc<br>Ala Leu His Gln Ala Leu Ala Gly Ala Ile Pro Val Glu Phe Ser Ser<br>               555                     560                     565 | 1794 | |
| aac act gtc aag ttg acg tcg ggt cat ttg aag tgt aga gtg aag atg<br>Asn Thr Val Lys Leu Thr Ser Gly His Leu Lys Cys Arg Val Lys Met | 1842 | |

```
                  570                 575                 580
gaa aaa ttg cag ctg aag gga aca acc tat ggc gtc tgt tca aag gct    1890
Glu Lys Leu Gln Leu Lys Gly Thr Thr Tyr Gly Val Cys Ser Lys Ala
            585                 590                 595 ttc aag ttt ctt ggg act ccc gca gac aca ggt cac ggc act gtg gtg    1938
Phe Lys Phe Leu Gly Thr Pro Ala Asp Thr Gly His Gly Thr Val Val
        600                 605                 610 ttg gaa ttg cag tac act ggc acg gat gga cct tgc aaa gtt cct atc    1986
Leu Glu Leu Gln Tyr Thr Gly Thr Asp Gly Pro Cys Lys Val Pro Ile
615                 620                 625                 630 tcg tca gtg gct tca ttg aac gac cta acg cca gtg ggc aga ttg gtc    2034
Ser Ser Val Ala Ser Leu Asn Asp Leu Thr Pro Val Gly Arg Leu Val
                635                 640                 645 act gtc aac cct ttt gtt tca gtg gcc acg gcc aac gct aag gtc ctg    2082
Thr Val Asn Pro Phe Val Ser Val Ala Thr Ala Asn Ala Lys Val Leu
            650                 655                 660 att gaa ttg gaa cca ccc ttt gga gac tca tac ata gtg gtg ggc aga    2130
Ile Glu Leu Glu Pro Pro Phe Gly Asp Ser Tyr Ile Val Val Gly Arg
        665                 670                 675 gga gaa caa cag atc aat cac cat tgg cac aag tct gga agc agc att    2178
Gly Glu Gln Gln Ile Asn His His Trp His Lys Ser Gly Ser Ser Ile
680                 685                 690 ggc aaa gcc ttt aca acc acc ctc aaa gga gcg cag aga cta gcc gct    2226
Gly Lys Ala Phe Thr Thr Thr Leu Lys Gly Ala Gln Arg Leu Ala Ala
695                 700                 705                 710 cta gga gac aca gct tgg gac ttt gga tca gtt gga ggg gtg ttc acc    2274
Leu Gly Asp Thr Ala Trp Asp Phe Gly Ser Val Gly Gly Val Phe Thr
                715                 720                 725 tca gtt ggg aag gct gtc cat caa gtg ttc gga gga gca ttc cgc tca    2322
Ser Val Gly Lys Ala Val His Gln Val Phe Gly Gly Ala Phe Arg Ser
            730                 735                 740 ctg ttc gga ggc atg tcc tgg ata acg caa gga ttg ctg ggg gct ctc    2370
Leu Phe Gly Gly Met Ser Trp Ile Thr Gln Gly Leu Leu Gly Ala Leu
        745                 750                 755 ctg ttg tgg atg ggc atc aat gct cgt gat agg tcc ata gct ctc acg    2418
Leu Leu Trp Met Gly Ile Asn Ala Arg Asp Arg Ser Ile Ala Leu Thr
760                 765                 770 ttt ctc gca gtt gga gga gtt ctg ctc ttc ctc tcc gtg aac gtg cac    2466
Phe Leu Ala Val Gly Gly Val Leu Leu Phe Leu Ser Val Asn Val His
775                 780                 785                 790 gct gac act ggg tgt gcc ata gac atc agc cgg caa gag ctg aga tgt    2514
Ala Asp Thr Gly Cys Ala Ile Asp Ile Ser Arg Gln Glu Leu Arg Cys
                795                 800                 805 gga agt gga gtg ttc ata cac aat gat gtg gag gct tgg atg gac cgg    2562
Gly Ser Gly Val Phe Ile His Asn Asp Val Glu Ala Trp Met Asp Arg
            810                 815                 820 tac aag tat tac cct gaa acg cca caa ggc cta gcc aag atc att cag    2610
Tyr Lys Tyr Tyr Pro Glu Thr Pro Gln Gly Leu Ala Lys Ile Ile Gln
        825                 830                 835 aaa gct cat aag gaa gga gtg tgc ggt cta cga tca gtt tcc aga ctg    2658
Lys Ala His Lys Glu Gly Val Cys Gly Leu Arg Ser Val Ser Arg Leu
840                 845                 850 gag cat caa atg tgg gaa gca gtg aag gac gag ctg aac act ctt ttg    2706
Glu His Gln Met Trp Glu Ala Val Lys Asp Glu Leu Asn Thr Leu Leu
855                 860                 865                 870 aag gag aat ggt gtg gac ctt agt gtc gtg gtt gag aaa cag gag gga    2754
Lys Glu Asn Gly Val Asp Leu Ser Val Val Val Glu Lys Gln Glu Gly
                875                 880                 885 atg tac aag tca gca cct aaa cgc ctc acc gcc acc acg gaa aaa ttg    2802
```

```
                Met Tyr Lys Ser Ala Pro Lys Arg Leu Thr Ala Thr Thr Glu Lys Leu
                            890                 895                 900 gaa att ggc tgg aag gcc tgg gga aag agt att tta ttt gca cca gaa         2850
Glu Ile Gly Trp Lys Ala Trp Gly Lys Ser Ile Leu Phe Ala Pro Glu
        905                 910                 915 ctc gcc aac aac acc ttt gtg gtt gat ggt ccg gag acc aag gaa tgt         2898
Leu Ala Asn Asn Thr Phe Val Val Asp Gly Pro Glu Thr Lys Glu Cys
920                 925                 930 ccg act cag aat cgc gct tgg aat agc tta gaa gtg gag gat ttt gga         2946
Pro Thr Gln Asn Arg Ala Trp Asn Ser Leu Glu Val Glu Asp Phe Gly
935                 940                 945                 950 ttt ggt ctc acc agc act cgg atg ttc ctg aag gtc aga gag agc aac         2994
Phe Gly Leu Thr Ser Thr Arg Met Phe Leu Lys Val Arg Glu Ser Asn
            955                 960                 965 aca act gaa tgt gac tcg aag atc att gga acg gct gtc aag aac aac         3042
Thr Thr Glu Cys Asp Ser Lys Ile Ile Gly Thr Ala Val Lys Asn Asn
                970                 975                 980 ttg gcg atc cac agt gac ctg tcc tat tgg att gaa agc agg ctc aat         3090
Leu Ala Ile His Ser Asp Leu Ser Tyr Trp Ile Glu Ser Arg Leu Asn
            985                 990                 995 gat acg tgg aag ctt gaa agg gca gtt ctg ggt gaa    gtc aaa tca         3135
Asp Thr Trp Lys Leu Glu Arg Ala Val Leu Gly Glu    Val Lys Ser
1000                1005                1010 tgt acg tgg cct gag acg cat acc ttg tgg ggc gat    gga atc ctt         3180
Cys Thr Trp Pro Glu Thr His Thr Leu Trp Gly Asp    Gly Ile Leu
    1015                1020                1025 gag agt gac ttg ata ata cca gtc aca ctg gcg gga    cca cga agc         3225
Glu Ser Asp Leu Ile Ile Pro Val Thr Leu Ala Gly    Pro Arg Ser
1030                1035                1040 aat cac aat cgg aga cct ggg tac aag aca caa aac    cag ggc cca         3270
Asn His Asn Arg Arg Pro Gly Tyr Lys Thr Gln Asn    Gln Gly Pro
1045                1050                1055 tgg gac gaa ggc cgg gta gag att gac ttc gat tac    tgc cca gga         3315
Trp Asp Glu Gly Arg Val Glu Ile Asp Phe Asp Tyr    Cys Pro Gly
    1060                1065                1070 act acg gtc acc ctg agt gag agc tgc gga cac cgt    gga cct gcc         3360
Thr Thr Val Thr Leu Ser Glu Ser Cys Gly His Arg    Gly Pro Ala
    1075                1080                1085 act cgc acc acc aca gag agc gga aag ttg ata aca    gat tgg tgc         3405
Thr Arg Thr Thr Thr Glu Ser Gly Lys Leu Ile Thr    Asp Trp Cys
1090                1095                1100 tgc agg agc tgc acc tta cca cca ctg cgc tac caa    act gac agc         3450
Cys Arg Ser Cys Thr Leu Pro Pro Leu Arg Tyr Gln    Thr Asp Ser
1105                1110                1115 ggc tgt tgg tat ggt atg gag atc aga cca cag aga    cat gat gaa         3495
Gly Cys Trp Tyr Gly Met Glu Ile Arg Pro Gln Arg    His Asp Glu
    1120                1125                1130 aag acc ctc gtg cag tca caa gtg aat gct tat aat    gct gat atg         3540
Lys Thr Leu Val Gln Ser Gln Val Asn Ala Tyr Asn    Ala Asp Met
1135                1140                1145 att gac cct ttt cag ttg ggc ctt ctg gtc gtg ttc    ttg gcc acc         3585
Ile Asp Pro Phe Gln Leu Gly Leu Leu Val Val Phe    Leu Ala Thr
    1150                1155                1160 cag gag gtc ctt cgc aag agg tgg aca gcc aag atc    agc atg cca         3630
Gln Glu Val Leu Arg Lys Arg Trp Thr Ala Lys Ile    Ser Met Pro
1165                1170                1175 gct ata ctg att gct ctg cta gtc ctg gtg ttt ggg    ggc att act         3675
Ala Ile Leu Ile Ala Leu Leu Val Leu Val Phe Gly    Gly Ile Thr
1180                1185                1190
```

```
tac act gat gtg tta cgc tat gtc atc ttg gtg ggg gca gct ttc         3720
Tyr Thr Asp Val Leu Arg Tyr Val Ile Leu Val Gly Ala Ala Phe
    1195                1200                1205 gca gaa tct aat tcg gga gga gac gtg gta cac ttg gcg ctc atg         3765
Ala Glu Ser Asn Ser Gly Gly Asp Val Val His Leu Ala Leu Met
1210                1215                1220 gcg acc ttc aag ata caa cca gtg ttt atg gtg gca tcg ttt ctc         3810
Ala Thr Phe Lys Ile Gln Pro Val Phe Met Val Ala Ser Phe Leu
    1225                1230                1235 aaa gcg aga tgg acc aac cag gag aac att ttg ttg atg ttg gcg         3855
Lys Ala Arg Trp Thr Asn Gln Glu Asn Ile Leu Leu Met Leu Ala
1240                1245                1250 gct gtt ttc ttt caa atg gct tat tac gat gcc cgc caa att ctg         3900
Ala Val Phe Phe Gln Met Ala Tyr Tyr Asp Ala Arg Gln Ile Leu
    1255                1260                1265 ctc tgg gag atc cct gat gtg ttg aat tca ctg gcg gta gct tgg         3945
Leu Trp Glu Ile Pro Asp Val Leu Asn Ser Leu Ala Val Ala Trp
1270                1275                1280 atg ata ctg aga gcc ata aca ttc aca acg aca tca aac gtg gtt         3990
Met Ile Leu Arg Ala Ile Thr Phe Thr Thr Thr Ser Asn Val Val
    1285                1290                1295 gtt ccg ctg cta gcc ctg cta aca ccc ggg ctg aga tgc ttg aat         4035
Val Pro Leu Leu Ala Leu Leu Thr Pro Gly Leu Arg Cys Leu Asn
1300                1305                1310 ctg gat gtg tac agg ata ctg ctg ttg atg gtc gga ata ggc agc         4080
Leu Asp Val Tyr Arg Ile Leu Leu Leu Met Val Gly Ile Gly Ser
    1315                1320                1325 ttg atc agg gag aag agg agt gca gct gca aaa aag aaa gga gca         4125
Leu Ile Arg Glu Lys Arg Ser Ala Ala Ala Lys Lys Lys Gly Ala
1330                1335                1340 agt ctg cta tgc ttg gct cta gcc tca aca gga ctt ttc aac ccc         4170
Ser Leu Leu Cys Leu Ala Leu Ala Ser Thr Gly Leu Phe Asn Pro
    1345                1350                1355 atg atc ctt gct gct gga ctg att gca tgt gat ccc aac cgt aaa         4215
Met Ile Leu Ala Ala Gly Leu Ile Ala Cys Asp Pro Asn Arg Lys
1360                1365                1370 cgc gga tgg ccc gca act gaa gtg atg aca gct gtc ggc cta atg         4260
Arg Gly Trp Pro Ala Thr Glu Val Met Thr Ala Val Gly Leu Met
    1375                1380                1385 ttt gcc atc gtc gga ggg ctg gca gag ctt gac att gac tcc atg         4305
Phe Ala Ile Val Gly Gly Leu Ala Glu Leu Asp Ile Asp Ser Met
1390                1395                1400 gcc att cca atg act atc gcg ggg ctc atg ttt gct gct ttc gtg         4350
Ala Ile Pro Met Thr Ile Ala Gly Leu Met Phe Ala Ala Phe Val
    1405                1410                1415 att tct ggg aaa tca aca gat atg tgg att gag aga acg gcg gac         4395
Ile Ser Gly Lys Ser Thr Asp Met Trp Ile Glu Arg Thr Ala Asp
1420                1425                1430 att tcc tgg gaa agt gat gca gaa att aca ggc tcg agc gaa aga         4440
Ile Ser Trp Glu Ser Asp Ala Glu Ile Thr Gly Ser Ser Glu Arg
    1435                1440                1445 gtt gat gtg cgg ctt gat gat gat gga aac ttc cag ctc atg aat         4485
Val Asp Val Arg Leu Asp Asp Asp Gly Asn Phe Gln Leu Met Asn
1450                1455                1460 gat cca gga gca cct tgg aag ata tgg atg ctc aga atg gtc tgt         4530
Asp Pro Gly Ala Pro Trp Lys Ile Trp Met Leu Arg Met Val Cys
    1465                1470                1475 ctc gcg att agt gcg tac acc ccc tgg gca atc ttg ccc tca gta         4575
Leu Ala Ile Ser Ala Tyr Thr Pro Trp Ala Ile Leu Pro Ser Val
1480                1485                1490
```

| | | | | | | | | | | |
|---|---|---|---|---|---|---|---|---|---|---|
| gtt | gga | ttt | tgg | ata | act | ctc | caa | tac | aca | aag | aga | gga | ggc | gtg | 4620 |
| Val | Gly | Phe | Trp | Ile | Thr | Leu | Gln | Tyr | Thr | Lys | Arg | Gly | Gly | Val | |
| | 1495 | | | | 1500 | | | | | 1505 | | | | | |
| ttg | tgg | gac | act | ccc | tca | cca | aag | gag | tac | aaa | aag | ggg | gac | acg | 4665 |
| Leu | Trp | Asp | Thr | Pro | Ser | Pro | Lys | Glu | Tyr | Lys | Lys | Gly | Asp | Thr | |
| 1510 | | | | | 1515 | | | | | 1520 | | | | | |
| acc | acc | ggc | gtc | tac | agg | atc | atg | act | cgt | ggg | ctg | ctc | ggc | agt | 4710 |
| Thr | Thr | Gly | Val | Tyr | Arg | Ile | Met | Thr | Arg | Gly | Leu | Leu | Gly | Ser | |
| 1525 | | | | | 1530 | | | | | 1535 | | | | | |
| tat | caa | gca | gga | gcg | ggc | gtg | atg | gtt | gaa | ggt | gtt | ttc | cac | acc | 4755 |
| Tyr | Gln | Ala | Gly | Ala | Gly | Val | Met | Val | Glu | Gly | Val | Phe | His | Thr | |
| | 1540 | | | | 1545 | | | | | 1550 | | | | | |
| ctt | tgg | cat | aca | aca | aaa | gga | gcc | gct | ttg | atg | agc | gga | gag | ggc | 4800 |
| Leu | Trp | His | Thr | Thr | Lys | Gly | Ala | Ala | Leu | Met | Ser | Gly | Glu | Gly | |
| 1555 | | | | | 1560 | | | | | 1565 | | | | | |
| cgc | ctg | gac | cca | tac | tgg | ggc | agt | gtc | aag | gag | gat | cga | ctt | tgt | 4845 |
| Arg | Leu | Asp | Pro | Tyr | Trp | Gly | Ser | Val | Lys | Glu | Asp | Arg | Leu | Cys | |
| 1570 | | | | | 1575 | | | | | 1580 | | | | | |
| tac | gga | gga | ccc | tgg | aaa | ttg | cag | cac | aag | tgg | aac | ggg | cag | gat | 4890 |
| Tyr | Gly | Gly | Pro | Trp | Lys | Leu | Gln | His | Lys | Trp | Asn | Gly | Gln | Asp | |
| | 1585 | | | | 1590 | | | | | 1595 | | | | | |
| gag | gtg | cag | atg | att | gtg | gtg | gaa | cct | ggc | agg | aac | gtt | aag | aac | 4935 |
| Glu | Val | Gln | Met | Ile | Val | Val | Glu | Pro | Gly | Arg | Asn | Val | Lys | Asn | |
| 1600 | | | | | 1605 | | | | | 1610 | | | | | |
| gtc | cag | acg | aaa | cca | ggg | gtg | ttc | aaa | aca | cct | gaa | gga | gaa | atc | 4980 |
| Val | Gln | Thr | Lys | Pro | Gly | Val | Phe | Lys | Thr | Pro | Glu | Gly | Glu | Ile | |
| 1615 | | | | | 1620 | | | | | 1625 | | | | | |
| ggg | gcc | gtg | act | ttg | gac | ttc | ccc | act | gga | aca | tca | ggc | tca | cca | 5025 |
| Gly | Ala | Val | Thr | Leu | Asp | Phe | Pro | Thr | Gly | Thr | Ser | Gly | Ser | Pro | |
| 1630 | | | | | 1635 | | | | | 1640 | | | | | |
| ata | gtg | gac | aaa | aac | ggt | gat | gtg | att | ggg | ctt | tat | ggc | aat | gga | 5070 |
| Ile | Val | Asp | Lys | Asn | Gly | Asp | Val | Ile | Gly | Leu | Tyr | Gly | Asn | Gly | |
| 1645 | | | | | 1650 | | | | | 1655 | | | | | |
| gtc | ata | atg | ccc | aac | ggc | tca | tac | ata | agc | gcg | ata | gtg | cag | ggt | 5115 |
| Val | Ile | Met | Pro | Asn | Gly | Ser | Tyr | Ile | Ser | Ala | Ile | Val | Gln | Gly | |
| 1660 | | | | | 1665 | | | | | 1670 | | | | | |
| gaa | agg | atg | gat | gag | cca | atc | cca | gcc | gga | ttc | gaa | cct | gag | atg | 5160 |
| Glu | Arg | Met | Asp | Glu | Pro | Ile | Pro | Ala | Gly | Phe | Glu | Pro | Glu | Met | |
| 1675 | | | | | 1680 | | | | | 1685 | | | | | |
| ctg | agg | aaa | aaa | cag | atc | act | gta | ctg | gat | ctc | cat | ccc | ggc | gcc | 5205 |
| Leu | Arg | Lys | Lys | Gln | Ile | Thr | Val | Leu | Asp | Leu | His | Pro | Gly | Ala | |
| 1690 | | | | | 1695 | | | | | 1700 | | | | | |
| ggt | aaa | aca | agg | agg | att | ctg | cca | cag | atc | atc | aaa | gag | gcc | ata | 5250 |
| Gly | Lys | Thr | Arg | Arg | Ile | Leu | Pro | Gln | Ile | Ile | Lys | Glu | Ala | Ile | |
| 1705 | | | | | 1710 | | | | | 1715 | | | | | |
| aac | aga | aga | ctg | aga | aca | gcc | gtg | cta | gca | cca | acc | agg | gtt | gtg | 5295 |
| Asn | Arg | Arg | Leu | Arg | Thr | Ala | Val | Leu | Ala | Pro | Thr | Arg | Val | Val | |
| 1720 | | | | | 1725 | | | | | 1730 | | | | | |
| gct | gct | gag | atg | gct | gaa | gca | ctg | aga | gga | ctg | ccc | atc | cgg | tac | 5340 |
| Ala | Ala | Glu | Met | Ala | Glu | Ala | Leu | Arg | Gly | Leu | Pro | Ile | Arg | Tyr | |
| 1735 | | | | | 1740 | | | | | 1745 | | | | | |
| cag | aca | tcc | gca | gtg | ccc | aga | gaa | cat | aat | gga | aat | gag | att | gtt | 5385 |
| Gln | Thr | Ser | Ala | Val | Pro | Arg | Glu | His | Asn | Gly | Asn | Glu | Ile | Val | |
| 1750 | | | | | 1755 | | | | | 1760 | | | | | |
| gat | gtc | atg | tgt | cat | gct | acc | ctc | acc | cac | agg | ctg | atg | tct | cct | 5430 |
| Asp | Val | Met | Cys | His | Ala | Thr | Leu | Thr | His | Arg | Leu | Met | Ser | Pro | |
| 1765 | | | | | 1770 | | | | | 1775 | | | | | |
| cac | agg | gtg | ccg | aac | tac | aac | ctg | ttc | gtg | atg | gat | gag | gct | cat | 5475 |
| His | Arg | Val | Pro | Asn | Tyr | Asn | Leu | Phe | Val | Met | Asp | Glu | Ala | His | |

```
                   1780                1785                1790
ttc  acc  gac  cca  gct  agc  att  gca  gca  aga  ggt  tac  att  tcc  aca      5520
Phe  Thr  Asp  Pro  Ala  Ser  Ile  Ala  Ala  Arg  Gly  Tyr  Ile  Ser  Thr
     1795                1800                1805 aag  gtc  gag  cta  ggg  gag  gcg  gcg  gca  ata  ttc  atg  aca  gcc  acc      5565
Lys  Val  Glu  Leu  Gly  Glu  Ala  Ala  Ala  Ile  Phe  Met  Thr  Ala  Thr
     1810                1815                1820 cca  cca  ggc  act  tca  gat  cca  ttc  cca  gag  tcc  aat  tca  cca  att      5610
Pro  Pro  Gly  Thr  Ser  Asp  Pro  Phe  Pro  Glu  Ser  Asn  Ser  Pro  Ile
     1825                1830                1835 tcc  gac  tta  cag  act  gag  atc  ccg  gat  cga  gct  tgg  aac  tct  gga      5655
Ser  Asp  Leu  Gln  Thr  Glu  Ile  Pro  Asp  Arg  Ala  Trp  Asn  Ser  Gly
     1840                1845                1850 tac  gaa  tgg  atc  aca  gaa  tac  acc  ggg  aag  acg  gtt  tgg  ttt  gtg      5700
Tyr  Glu  Trp  Ile  Thr  Glu  Tyr  Thr  Gly  Lys  Thr  Val  Trp  Phe  Val
     1855                1860                1865 cct  agt  gtc  aag  atg  ggg  aat  gag  att  gcc  ctt  tgc  cta  caa  cgt      5745
Pro  Ser  Val  Lys  Met  Gly  Asn  Glu  Ile  Ala  Leu  Cys  Leu  Gln  Arg
     1870                1875                1880 gct  gga  aag  aaa  gta  gtc  caa  ttg  aac  aga  aag  tcg  tac  gag  acg      5790
Ala  Gly  Lys  Lys  Val  Val  Gln  Leu  Asn  Arg  Lys  Ser  Tyr  Glu  Thr
     1885                1890                1895 gag  tac  cca  aaa  tgt  aag  aac  gat  gat  tgg  gac  ttt  gtt  atc  aca      5835
Glu  Tyr  Pro  Lys  Cys  Lys  Asn  Asp  Asp  Trp  Asp  Phe  Val  Ile  Thr
     1900                1905                1910 aca  gac  ata  tct  gaa  atg  ggg  gct  aac  ttc  aag  gcg  agc  agg  gtg      5880
Thr  Asp  Ile  Ser  Glu  Met  Gly  Ala  Asn  Phe  Lys  Ala  Ser  Arg  Val
     1915                1920                1925 att  gac  agc  cgg  aag  agt  gtg  aaa  cca  acc  atc  ata  aca  gaa  gga      5925
Ile  Asp  Ser  Arg  Lys  Ser  Val  Lys  Pro  Thr  Ile  Ile  Thr  Glu  Gly
     1930                1935                1940 gaa  ggg  aga  gtg  atc  ctg  gga  gaa  cca  tct  gca  gtg  aca  gca  gct      5970
Glu  Gly  Arg  Val  Ile  Leu  Gly  Glu  Pro  Ser  Ala  Val  Thr  Ala  Ala
     1945                1950                1955 agt  gcc  gcc  cag  aga  cgt  gga  cgt  atc  ggt  aga  aat  ccg  tcg  caa      6015
Ser  Ala  Ala  Gln  Arg  Arg  Gly  Arg  Ile  Gly  Arg  Asn  Pro  Ser  Gln
     1960                1965                1970 gtt  ggt  gat  gag  tac  tgt  tat  ggg  ggg  cac  acg  aat  gaa  gac  gac      6060
Val  Gly  Asp  Glu  Tyr  Cys  Tyr  Gly  Gly  His  Thr  Asn  Glu  Asp  Asp
     1975                1980                1985 tcg  aac  ttc  gcc  cat  tgg  act  gag  gca  cga  atc  atg  ctg  gac  aac      6105
Ser  Asn  Phe  Ala  His  Trp  Thr  Glu  Ala  Arg  Ile  Met  Leu  Asp  Asn
     1990                1995                2000 atc  aac  atg  cca  aac  gga  ctg  atc  gct  caa  ttc  tac  caa  cca  gag      6150
Ile  Asn  Met  Pro  Asn  Gly  Leu  Ile  Ala  Gln  Phe  Tyr  Gln  Pro  Glu
     2005                2010                2015 cgt  gag  aag  gta  tat  acc  atg  gat  ggg  gaa  tac  cgg  ctc  aga  gga      6195
Arg  Glu  Lys  Val  Tyr  Thr  Met  Asp  Gly  Glu  Tyr  Arg  Leu  Arg  Gly
     2020                2025                2030 gaa  gag  aga  aaa  aac  ttt  ctg  gaa  ctg  ttg  agg  act  gca  gat  ctg      6240
Glu  Glu  Arg  Lys  Asn  Phe  Leu  Glu  Leu  Leu  Arg  Thr  Ala  Asp  Leu
     2035                2040                2045 cca  gtt  tgg  ctg  gct  tac  aag  gtt  gca  gcg  gct  gga  gtg  tca  tac      6285
Pro  Val  Trp  Leu  Ala  Tyr  Lys  Val  Ala  Ala  Ala  Gly  Val  Ser  Tyr
     2050                2055                2060 cac  gac  cgg  agg  tgg  tgc  ttt  gat  ggt  cct  agg  aca  aac  aca  att      6330
His  Asp  Arg  Arg  Trp  Cys  Phe  Asp  Gly  Pro  Arg  Thr  Asn  Thr  Ile
     2065                2070                2075 tta  gaa  gac  aac  aac  gaa  gtg  gaa  gtc  atc  acg  aag  ctt  ggt  gaa      6375
```

-continued

| | | | | | | | | | | | | |
|---|---|---|---|---|---|---|---|---|---|---|---|---|
| Leu | Glu | Asp | Asn | Asn | Glu | Val | Glu | Val | Ile | Thr | Lys | Leu Gly Glu |
| | 2080 | | | | 2085 | | | | 2090 | | | |

```
agg aag att ctg agg ccg cgc tgg att gac gcc agg gtg tac tcg       6420
Arg Lys Ile Leu Arg Pro Arg Trp Ile Asp Ala Arg Val Tyr Ser
    2095                2100                2105 gat cac cag gca cta aag gcg ttc aag gac ttc gcc tcg gga aaa       6465
Asp His Gln Ala Leu Lys Ala Phe Lys Asp Phe Ala Ser Gly Lys
    2110                2115                2120 cgt tct cag ata ggg ctc att gag gtt ctg gga aag atg cct gag       6510
Arg Ser Gln Ile Gly Leu Ile Glu Val Leu Gly Lys Met Pro Glu
    2125                2130                2135 cac ttc atg ggg aag aca tgg gaa gca ctt gac acc atg tac gtt       6555
His Phe Met Gly Lys Thr Trp Glu Ala Leu Asp Thr Met Tyr Val
    2140                2145                2150 gtg gcc act gca gag aaa gga gga aga gct cac aga atg gcc ctg       6600
Val Ala Thr Ala Glu Lys Gly Gly Arg Ala His Arg Met Ala Leu
    2155                2160                2165 gag gaa ctg cca gat gct ctt cag aca att gcc ttg att gcc tta       6645
Glu Glu Leu Pro Asp Ala Leu Gln Thr Ile Ala Leu Ile Ala Leu
    2170                2175                2180 ttg agt gtg atg acc atg gga gta ttc ttc ctc ctc atg cag cgg       6690
Leu Ser Val Met Thr Met Gly Val Phe Phe Leu Leu Met Gln Arg
    2185                2190                2195 aag ggc att gga aag ata ggt ttg gga ggc gct gtc ttg gga gtc       6735
Lys Gly Ile Gly Lys Ile Gly Leu Gly Gly Ala Val Leu Gly Val
    2200                2205                2210 gcg acc ttt ttc tgt tgg atg gct gaa gtt cca gga acg aag atc       6780
Ala Thr Phe Phe Cys Trp Met Ala Glu Val Pro Gly Thr Lys Ile
    2215                2220                2225 gcc gga atg ttg ctg ctc tcc ctt ctc ttg atg att gtg cta att       6825
Ala Gly Met Leu Leu Leu Ser Leu Leu Leu Met Ile Val Leu Ile
    2230                2235                2240 cct gag cca gag aag caa cgt tcg cag aca gac aac cag cta gcc       6870
Pro Glu Pro Glu Lys Gln Arg Ser Gln Thr Asp Asn Gln Leu Ala
    2245                2250                2255 gtg ttc ctg att tgt gtc atg acc ctt gtg agc gca gtg gca gcc       6915
Val Phe Leu Ile Cys Val Met Thr Leu Val Ser Ala Val Ala Ala
    2260                2265                2270 aac gag atg ggt tgg cta gat aag acc aag agt gac ata agc agt       6960
Asn Glu Met Gly Trp Leu Asp Lys Thr Lys Ser Asp Ile Ser Ser
    2275                2280                2285 ttg ttt ggg caa aga att gag gtc aag gag aat ttc agc atg gga       7005
Leu Phe Gly Gln Arg Ile Glu Val Lys Glu Asn Phe Ser Met Gly
    2290                2295                2300 gag ttt ctt ttg gac ttg agg cct gca aca gcc tgg tca ctg tac       7050
Glu Phe Leu Leu Asp Leu Arg Pro Ala Thr Ala Trp Ser Leu Tyr
    2305                2310                2315 gct gtg aca aca gcg gtc ctc act gga ctg cta aag cat ttg atc       7095
Ala Val Thr Thr Ala Val Leu Thr Gly Leu Leu Lys His Leu Ile
    2320                2325                2330 acg tca gat tac atc aac acc tca ttg acc tca ata aac gtt cag       7140
Thr Ser Asp Tyr Ile Asn Thr Ser Leu Thr Ser Ile Asn Val Gln
    2335                2340                2345 gca agt gca cta ttc aca ctc gcg cga ggc ttc ccc ttc gtc gat       7185
Ala Ser Ala Leu Phe Thr Leu Ala Arg Gly Phe Pro Phe Val Asp
    2350                2355                2360 gtt gga gtg tcg gct ctc ctg cta gca gcc gga tgc tgg gga caa       7230
Val Gly Val Ser Ala Leu Leu Leu Ala Ala Gly Cys Trp Gly Gln
    2365                2370                2375
```

```
gtc acc ctc acc gtt acg gta aca gcg gca aca ctc ctt ttt tgc    7275
Val Thr Leu Thr Val Thr Val Thr Ala Ala Thr Leu Leu Phe Cys
    2380            2385                2390 cac tat gcc tac atg gtt ccc ggt tgg caa gct gag gca atg cgc    7320
His Tyr Ala Tyr Met Val Pro Gly Trp Gln Ala Glu Ala Met Arg
    2395            2400                2405 tca gcc cag cgg cgg aca gcg gcc gga atc atg aag aac gct gta    7365
Ser Ala Gln Arg Arg Thr Ala Ala Gly Ile Met Lys Asn Ala Val
    2410            2415                2420 gtg gat ggc atc gtg gcc acg gac gtc cca gaa tta gag cgc acc    7410
Val Asp Gly Ile Val Ala Thr Asp Val Pro Glu Leu Glu Arg Thr
    2425            2430                2435 aca ccc atc atg cag aag aaa gtt gga cag atc atg ctg atc ttg    7455
Thr Pro Ile Met Gln Lys Lys Val Gly Gln Ile Met Leu Ile Leu
    2440            2445                2450 gtg tct cta gct gca gta gta gtg aac ccg tct gtg aag aca gta    7500
Val Ser Leu Ala Ala Val Val Val Asn Pro Ser Val Lys Thr Val
    2455            2460                2465 cga gaa gcc gga att ttg atc acg gcc gca gcg gtg acg ctt tgg    7545
Arg Glu Ala Gly Ile Leu Ile Thr Ala Ala Ala Val Thr Leu Trp
    2470            2475                2480 gag aat gga gca agc tct gtt tgg aac gca aca act gcc atc gga    7590
Glu Asn Gly Ala Ser Ser Val Trp Asn Ala Thr Thr Ala Ile Gly
    2485            2490                2495 ctc tgc cac atc atg cgt ggg ggt tgg ttg tca tgt cta tcc ata    7635
Leu Cys His Ile Met Arg Gly Gly Trp Leu Ser Cys Leu Ser Ile
    2500            2505                2510 aca tgg aca ctc ata aag aac atg gaa aaa cca gga cta aaa aga    7680
Thr Trp Thr Leu Ile Lys Asn Met Glu Lys Pro Gly Leu Lys Arg
    2515            2520                2525 ggt ggg gca aaa gga cgc acc ttg gga gag gtt tgg aaa gaa aga    7725
Gly Gly Ala Lys Gly Arg Thr Leu Gly Glu Val Trp Lys Glu Arg
    2530            2535                2540 ctc aac cag atg aca aaa gaa gag ttc act agg tac cgc aaa gag    7770
Leu Asn Gln Met Thr Lys Glu Glu Phe Thr Arg Tyr Arg Lys Glu
    2545            2550                2555 gcc atc atc gaa gtc gat cgc tca gcg gca aaa cac gcc agg aaa    7815
Ala Ile Ile Glu Val Asp Arg Ser Ala Ala Lys His Ala Arg Lys
    2560            2565                2570 gaa ggc aat gtc act gga ggg cat cca gtc tct agg ggc aca gca    7860
Glu Gly Asn Val Thr Gly Gly His Pro Val Ser Arg Gly Thr Ala
    2575            2580                2585 aaa ctg aga tgg ctg gtc gaa cgg agg ttt ctc gaa ccg gtc gga    7905
Lys Leu Arg Trp Leu Val Glu Arg Arg Phe Leu Glu Pro Val Gly
    2590            2595                2600 aaa gtg att gac ctt gga tgt gga aga ggc ggt tgg tgt tac tat    7950
Lys Val Ile Asp Leu Gly Cys Gly Arg Gly Gly Trp Cys Tyr Tyr
    2605            2610                2615 atg gca acc caa aaa aga gtc caa gaa gtc aga ggg tac aca aag    7995
Met Ala Thr Gln Lys Arg Val Gln Glu Val Arg Gly Tyr Thr Lys
    2620            2625                2630 ggc ggt ccc gga cat gaa gag ccc caa cta gtg caa agt tat gga    8040
Gly Gly Pro Gly His Glu Glu Pro Gln Leu Val Gln Ser Tyr Gly
    2635            2640                2645 tgg aac att gtc acc atg aag agt gga gtg gat gtg ttc tac aga    8085
Trp Asn Ile Val Thr Met Lys Ser Gly Val Asp Val Phe Tyr Arg
    2650            2655                2660 cct tct gag tgt tgt gac acc ctc ctt tgt gac atc gga gag tcc    8130
Pro Ser Glu Cys Cys Asp Thr Leu Leu Cys Asp Ile Gly Glu Ser
    2665            2670                2675
```

| | | | | | | | | | | | | | | |
|---|---|---|---|---|---|---|---|---|---|---|---|---|---|---|
| tcg | tca | agt | gct | gag | gtt | gaa | gag | cat | agg | acg | att | cgg | gtc | ctt | 8175 |
| Ser | Ser | Ser | Ala | Glu | Val | Glu | Glu | His | Arg | Thr | Ile | Arg | Val | Leu | |
| | 2680 | | | | 2685 | | | | 2690 | | | | | | |
| gaa | atg | gtt | gag | gac | tgg | ctg | cac | cga | ggg | cca | agg | gaa | ttt | tgc | 8220 |
| Glu | Met | Val | Glu | Asp | Trp | Leu | His | Arg | Gly | Pro | Arg | Glu | Phe | Cys | |
| | 2695 | | | | 2700 | | | | 2705 | | | | | | |
| gtg | aag | gtg | ctc | tgc | ccc | tac | atg | ccg | aaa | gtc | ata | gag | aag | atg | 8265 |
| Val | Lys | Val | Leu | Cys | Pro | Tyr | Met | Pro | Lys | Val | Ile | Glu | Lys | Met | |
| | 2710 | | | | 2715 | | | | 2720 | | | | | | |
| gag | ctg | ctc | caa | cgc | cgg | tat | ggg | ggg | gga | ctg | gtc | aga | aac | cca | 8310 |
| Glu | Leu | Leu | Gln | Arg | Arg | Tyr | Gly | Gly | Gly | Leu | Val | Arg | Asn | Pro | |
| | 2725 | | | | 2730 | | | | 2735 | | | | | | |
| ctc | tca | cgg | aat | tcc | acg | cac | gag | atg | tat | tgg | gtg | agt | cga | gct | 8355 |
| Leu | Ser | Arg | Asn | Ser | Thr | His | Glu | Met | Tyr | Trp | Val | Ser | Arg | Ala | |
| | 2740 | | | | 2745 | | | | 2750 | | | | | | |
| tca | ggc | aat | gtg | gta | cat | tca | gtg | aat | atg | acc | agc | cag | gtg | ctc | 8400 |
| Ser | Gly | Asn | Val | Val | His | Ser | Val | Asn | Met | Thr | Ser | Gln | Val | Leu | |
| | 2755 | | | | 2760 | | | | 2765 | | | | | | |
| cta | gga | aga | atg | gaa | aaa | agg | acc | tgg | aag | gga | ccc | caa | tac | gag | 8445 |
| Leu | Gly | Arg | Met | Glu | Lys | Arg | Thr | Trp | Lys | Gly | Pro | Gln | Tyr | Glu | |
| | 2770 | | | | 2775 | | | | 2780 | | | | | | |
| gaa | gat | gta | aac | ttg | gga | agt | gga | acc | agg | gcg | gtg | gga | aaa | ccc | 8490 |
| Glu | Asp | Val | Asn | Leu | Gly | Ser | Gly | Thr | Arg | Ala | Val | Gly | Lys | Pro | |
| | 2785 | | | | 2790 | | | | 2795 | | | | | | |
| ctg | ctc | aac | tca | gac | acc | agt | aaa | atc | aag | aac | agg | att | gaa | cga | 8535 |
| Leu | Leu | Asn | Ser | Asp | Thr | Ser | Lys | Ile | Lys | Asn | Arg | Ile | Glu | Arg | |
| | 2800 | | | | 2805 | | | | 2810 | | | | | | |
| ctc | agg | cgt | gag | tac | agt | tcg | acg | tgg | cac | cac | gat | gag | aac | cac | 8580 |
| Leu | Arg | Arg | Glu | Tyr | Ser | Ser | Thr | Trp | His | His | Asp | Glu | Asn | His | |
| | 2815 | | | | 2820 | | | | 2825 | | | | | | |
| cca | tat | aga | acc | tgg | aac | tat | cac | ggc | agt | tat | gat | gtg | aag | ccc | 8625 |
| Pro | Tyr | Arg | Thr | Trp | Asn | Tyr | His | Gly | Ser | Tyr | Asp | Val | Lys | Pro | |
| | 2830 | | | | 2835 | | | | 2840 | | | | | | |
| aca | ggc | tcc | gcc | agt | tcg | ctg | gtc | aat | gga | gtg | gtc | agg | ctc | ctc | 8670 |
| Thr | Gly | Ser | Ala | Ser | Ser | Leu | Val | Asn | Gly | Val | Val | Arg | Leu | Leu | |
| | 2845 | | | | 2850 | | | | 2855 | | | | | | |
| tca | aaa | cca | tgg | gac | acc | atc | acg | aat | gtt | acc | acc | atg | gcc | atg | 8715 |
| Ser | Lys | Pro | Trp | Asp | Thr | Ile | Thr | Asn | Val | Thr | Thr | Met | Ala | Met | |
| | 2860 | | | | 2865 | | | | 2870 | | | | | | |
| act | gac | act | act | ccc | ttc | ggg | cag | cag | cga | gtg | ttc | aaa | gag | aag | 8760 |
| Thr | Asp | Thr | Thr | Pro | Phe | Gly | Gln | Gln | Arg | Val | Phe | Lys | Glu | Lys | |
| | 2875 | | | | 2880 | | | | 2885 | | | | | | |
| gtg | gac | acg | aaa | gct | cct | gaa | ccg | cca | gaa | gga | gtg | aag | tac | gtg | 8805 |
| Val | Asp | Thr | Lys | Ala | Pro | Glu | Pro | Pro | Glu | Gly | Val | Lys | Tyr | Val | |
| | 2890 | | | | 2895 | | | | 2900 | | | | | | |
| ctc | aac | gag | acc | acc | aac | tgg | ttg | tgg | gcg | ttt | ttg | gcc | aga | gaa | 8850 |
| Leu | Asn | Glu | Thr | Thr | Asn | Trp | Leu | Trp | Ala | Phe | Leu | Ala | Arg | Glu | |
| | 2905 | | | | 2910 | | | | 2915 | | | | | | |
| aaa | cgt | ccc | aga | atg | tgc | tct | cga | gag | gaa | ttc | ata | aga | aag | gtc | 8895 |
| Lys | Arg | Pro | Arg | Met | Cys | Ser | Arg | Glu | Glu | Phe | Ile | Arg | Lys | Val | |
| | 2920 | | | | 2925 | | | | 2930 | | | | | | |
| aac | agc | aat | gca | gct | ttg | ggt | gcc | atg | ttt | gaa | gag | cag | aat | caa | 8940 |
| Asn | Ser | Asn | Ala | Ala | Leu | Gly | Ala | Met | Phe | Glu | Glu | Gln | Asn | Gln | |
| | 2935 | | | | 2940 | | | | 2945 | | | | | | |
| tgg | agg | agc | gcc | aga | gaa | gca | gtt | gaa | gat | cca | aaa | ttt | tgg | gag | 8985 |
| Trp | Arg | Ser | Ala | Arg | Glu | Ala | Val | Glu | Asp | Pro | Lys | Phe | Trp | Glu | |
| | 2950 | | | | 2955 | | | | 2960 | | | | | | |
| atg | gtg | gat | gag | gag | cgc | gag | gca | cat | ctg | cgg | ggg | gaa | tgt | cac | 9030 |
| Met | Val | Asp | Glu | Glu | Arg | Glu | Ala | His | Leu | Arg | Gly | Glu | Cys | His | |

-continued

|  |  |  |  |  |  |  |  |  |  |  |  |  |
|--|--|--|--|--|--|--|--|--|--|--|--|--|
| | | 2965 | | | | 2970 | | | | 2975 | | |
| act | tgc | att | tac | aac | atg | atg | gga | aag | aga | gag | aaa | aaa ccc gga |
| Thr | Cys | Ile | Tyr | Asn | Met | Met | Gly | Lys | Arg | Glu | Lys | Lys Pro Gly |
| 2980 | | | | | 2985 | | | | | 2990 | | | 9075 |
| gag | ttc | gga | aag | gcc | aag | gga | agc | aga | gcc | att | tgg | ttc atg tgg |
| Glu | Phe | Gly | Lys | Ala | Lys | Gly | Ser | Arg | Ala | Ile | Trp | Phe Met Trp |
| 2995 | | | | | 3000 | | | | | 3005 | | | 9120 |
| ctc | gga | gct | cgc | ttt | ctg | gag | ttc | gag | gct | ctg | ggt | ttt ctc aat |
| Leu | Gly | Ala | Arg | Phe | Leu | Glu | Phe | Glu | Ala | Leu | Gly | Phe Leu Asn |
| 3010 | | | | | 3015 | | | | | 3020 | | | 9165 |
| gaa | gac | cac | tgg | ctt | gga | aga | aag | aac | tca | gga | ggt | gtc gag |
| Glu | Asp | His | Trp | Leu | Gly | Arg | Lys | Asn | Ser | Gly | Gly | Val Glu |
| 3025 | | | | | 3030 | | | | | 3035 | | | 9210 |
| ggc | ttg | ggc | ctc | caa | aaa | ctg | ggt | tac | atc | ctg | cgt | gaa gtt ggc |
| Gly | Leu | Gly | Leu | Gln | Lys | Leu | Gly | Tyr | Ile | Leu | Arg | Glu Val Gly |
| 3040 | | | | | 3045 | | | | | 3050 | | | 9255 |
| acc | cgg | cct | ggg | ggc | aag | atc | tat | gct | gat | gac | aca | gct ggc tgg |
| Thr | Arg | Pro | Gly | Gly | Lys | Ile | Tyr | Ala | Asp | Asp | Thr | Ala Gly Trp |
| 3055 | | | | | 3060 | | | | | 3065 | | | 9300 |
| gac | acc | cgc | atc | acg | aga | gct | gac | ttg | gaa | aat | gaa | gct aag gtg |
| Asp | Thr | Arg | Ile | Thr | Arg | Ala | Asp | Leu | Glu | Asn | Glu | Ala Lys Val |
| 3070 | | | | | 3075 | | | | | 3080 | | | 9345 |
| ctt | gag | ctg | ctt | gat | ggg | gaa | cat | cgg | cgt | ctt | gcc | agg gcc atc |
| Leu | Glu | Leu | Leu | Asp | Gly | Glu | His | Arg | Arg | Leu | Ala | Arg Ala Ile |
| 3085 | | | | | 3090 | | | | | 3095 | | | 9390 |
| att | gag | ctc | acc | tat | cgt | cac | aaa | gtt | gtg | aaa | gtg | atg cgc ccg |
| Ile | Glu | Leu | Thr | Tyr | Arg | His | Lys | Val | Val | Lys | Val | Met Arg Pro |
| 3100 | | | | | 3105 | | | | | 3110 | | | 9435 |
| gct | gct | gat | gga | aga | acc | gtc | atg | gat | gtt | atc | tcc | aga gaa gat |
| Ala | Ala | Asp | Gly | Arg | Thr | Val | Met | Asp | Val | Ile | Ser | Arg Glu Asp |
| 3115 | | | | | 3120 | | | | | 3125 | | | 9480 |
| cag | agg | ggg | agt | gga | caa | gtt | gtc | acc | tac | gcc | cta | aac act ttc |
| Gln | Arg | Gly | Ser | Gly | Gln | Val | Val | Thr | Tyr | Ala | Leu | Asn Thr Phe |
| 3130 | | | | | 3135 | | | | | 3140 | | | 9525 |
| acc | aac | ctg | gcc | gtc | cag | ctg | gtg | agg | atg | atg | gaa | ggg gaa gga |
| Thr | Asn | Leu | Ala | Val | Gln | Leu | Val | Arg | Met | Met | Glu | Gly Glu Gly |
| 3145 | | | | | 3150 | | | | | 3155 | | | 9570 |
| gtg | att | ggc | cca | gat | gat | gtg | gag | aaa | ctc | aca | aaa | ggg aaa gga |
| Val | Ile | Gly | Pro | Asp | Asp | Val | Glu | Lys | Leu | Thr | Lys | Gly Lys Gly |
| 3160 | | | | | 3165 | | | | | 3170 | | | 9615 |
| ccc | aaa | gtc | agg | acc | tgg | ctg | ttt | gag | aat | ggg | gaa | gaa aga ctc |
| Pro | Lys | Val | Arg | Thr | Trp | Leu | Phe | Glu | Asn | Gly | Glu | Glu Arg Leu |
| 3175 | | | | | 3180 | | | | | 3185 | | | 9660 |
| agc | cgc | atg | gct | gtc | agt | gga | gat | gac | tgt | gtg | gta | aag ccc ctg |
| Ser | Arg | Met | Ala | Val | Ser | Gly | Asp | Asp | Cys | Val | Val | Lys Pro Leu |
| 3190 | | | | | 3195 | | | | | 3200 | | | 9705 |
| gac | gat | cgc | ttt | gcc | acc | tcg | ctc | cac | ttc | ctc | aat | gct atg tca |
| Asp | Asp | Arg | Phe | Ala | Thr | Ser | Leu | His | Phe | Leu | Asn | Ala Met Ser |
| 3205 | | | | | 3210 | | | | | 3215 | | | 9750 |
| aag | gtt | cgc | aaa | gac | atc | caa | gag | tgg | aaa | ccg | tca | act gga tgg |
| Lys | Val | Arg | Lys | Asp | Ile | Gln | Glu | Trp | Lys | Pro | Ser | Thr Gly Trp |
| 3220 | | | | | 3225 | | | | | 3230 | | | 9795 |
| tat | gat | tgg | cag | cag | gtt | cca | ttt | tgc | tca | aac | cat | ttc act gaa |
| Tyr | Asp | Trp | Gln | Gln | Val | Pro | Phe | Cys | Ser | Asn | His | Phe Thr Glu |
| 3235 | | | | | 3240 | | | | | 3245 | | | 9840 |
| ttg | atc | atg | aaa | gat | gga | aga | aca | ctg | gtg | gtt | cca | tgc cga gga |
| Leu | Ile | Met | Lys | Asp | Gly | Arg | Thr | Leu | Val | Val | Pro | Cys Arg Gly |
| 3250 | | | | | 3255 | | | | | 3260 | | | 9885 |
| cag | gat | gaa | ttg | gta | ggc | aga | gct | cgc | ata | tct | cca | ggg gcc gga |
| | | | | | | | | | | | | | 9930 |

| | | | | | | | | | | | | | |
|---|---|---|---|---|---|---|---|---|---|---|---|---|---|
| Gln | Asp | Glu | Leu | Val | Gly | Arg | Ala | Arg | Ile | Ser | Pro | Gly | Ala | Gly |
| | 3265 | | | | 3270 | | | | 3275 | | | | | |

```
tgg aac gtc cgc gac act gct tgt ctg gct aag tct tat gcc cag     9975
Trp Asn Val Arg Asp Thr Ala Cys Leu Ala Lys Ser Tyr Ala Gln
3280                 3285                 3290 atg tgg ctg ctt ctg tac ttc cac aga aga gac ctg cgg ctc atg    10020
Met Trp Leu Leu Leu Tyr Phe His Arg Arg Asp Leu Arg Leu Met
    3295                 3300                 3305 gcc aac gcc att tgc tcc gct gtc cct gtg aat tgg gtc cct acc    10065
Ala Asn Ala Ile Cys Ser Ala Val Pro Val Asn Trp Val Pro Thr
        3310                 3315                 3320 gga aga acc acg tgg tcc atc cat gca gga gga gag tgg atg aca    10110
Gly Arg Thr Thr Trp Ser Ile His Ala Gly Gly Glu Trp Met Thr
            3325                 3330                 3335 aca gag gac atg ttg gag gtc tgg aac cgt gtt tgg ata gag gag    10155
Thr Glu Asp Met Leu Glu Val Trp Asn Arg Val Trp Ile Glu Glu
                3340                 3345                 3350 aat gaa tgg atg gaa gac aaa acc cca gtg gag aaa tgg agt gac    10200
Asn Glu Trp Met Glu Asp Lys Thr Pro Val Glu Lys Trp Ser Asp
                    3355                 3360                 3365 gtc cca tat tca gga aaa cga gag gac atc tgg tgt ggc agc ctg    10245
Val Pro Tyr Ser Gly Lys Arg Glu Asp Ile Trp Cys Gly Ser Leu
                        3370                 3375                 3380 att ggc aca aga gcc cga gcc acg tgg gca gaa aac atc cag gtg    10290
Ile Gly Thr Arg Ala Arg Ala Thr Trp Ala Glu Asn Ile Gln Val
3385                 3390                 3395 gct atc aac caa gtc aga gca atc atc gga gat gag aag tat gtg    10335
Ala Ile Asn Gln Val Arg Ala Ile Ile Gly Asp Glu Lys Tyr Val
    3400                 3405                 3410 gat tac atg agt tca cta aag aga tat gaa gac aca act ttg gtt    10380
Asp Tyr Met Ser Ser Leu Lys Arg Tyr Glu Asp Thr Thr Leu Val
        3415                 3420                 3425 gag gac aca gta ctg tag atatttaatc aattgtaaat agacaatata       10428
Glu Asp Thr Val Leu
            3430 agtatgcata aaagtgtagt tttatagtag tatttagtgg tgttagtgta aatagttaag   10488 aaaattttga ggagaaagtc aggccgggaa gttcccgcca ccggaagttg agtagacggt   10548 gctgcctgcg actcaacccc aggaggactg ggtgaacaaa gccgcgaagt gatccatgta   10608 agccctcaga accgtctcgg aaggaggacc ccacatgttg taacttcaaa gcccaatgtc   10668 agaccacgct acggcgtgct actctgcgga gagtgcagtc tgcgatagtg ccccaggagg   10728 actgggttaa caaaggcaaa ccaacgcccc acgcggccct agccccggta atggtgttaa   10788 ccagggcgaa aggactagag gttagaggag accccgcggt ttaaagtgca cggcccagcc   10848 tggctgaagc tgtaggtcag gggaaggact agaggttagt ggagacccccg tgccacaaaa   10908 caccacaaca aaacagcata ttgacacctg ggatagacta ggagatcttc tgctctgcac   10968 aaccagccac acggcacagt gcgccgacaa tggtggctgg tggtgcgaga acacaggatc   11028 t                                                                  11029
```

<210> SEQ ID NO 6
<211> LENGTH: 3433
<212> TYPE: PRT
<213> ORGANISM: West Nile virus

<400> SEQUENCE: 6

```
Met Ser Lys Lys Pro Gly Gly Pro Gly Lys Ser Arg Ala Val Asn Met
1               5                   10                  15
```

```
Leu Lys Arg Gly Met Pro Arg Val Leu Ser Leu Ile Gly Leu Lys Arg
                20                  25                  30

Ala Met Leu Ser Leu Ile Asp Gly Lys Gly Pro Ile Arg Phe Val Leu
            35                  40                  45

Ala Leu Leu Ala Phe Phe Arg Phe Thr Ala Ile Ala Pro Thr Arg Ala
50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
                100                 105                 110

Val Met Ile Gly Leu Ile Ala Ser Val Gly Ala Val Thr Leu Ser Asn
            115                 120                 125

Phe Gln Gly Lys Val Met Met Thr Val Asn Ala Thr Asp Val Thr Asp
130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
            180                 185                 190

Thr Lys Ser Ala Val Tyr Val Arg Tyr Gly Arg Cys Thr Lys Thr Arg
            195                 200                 205

His Ser Arg Arg Ser Arg Arg Ser Leu Thr Val Gln Thr His Gly Glu
210                 215                 220

Ser Thr Leu Ala Asn Lys Lys Gly Ala Trp Met Asp Ser Thr Lys Ala
225                 230                 235                 240

Thr Arg Tyr Leu Val Lys Thr Glu Ser Trp Ile Leu Arg Asn Pro Gly
            245                 250                 255

Tyr Ala Leu Val Ala Ala Val Ile Gly Trp Met Leu Gly Ser Asn Thr
            260                 265                 270

Met Gln Arg Val Val Phe Val Val Leu Leu Leu Val Ala Pro Ala
            275                 280                 285

Tyr Ser Phe Asn Cys Leu Gly Met Ser Asn Arg Asp Phe Leu Glu Gly
290                 295                 300

Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                325                 330                 335

Asn Met Glu Ala Ala Asn Leu Ala Glu Val Arg Ser Tyr Cys Tyr Leu
            340                 345                 350

Ala Thr Val Ser Asp Leu Ser Thr Lys Ala Ala Cys Pro Thr Met Gly
            355                 360                 365

Glu Ala His Asn Asp Lys Arg Ala Asp Pro Ala Phe Val Cys Arg Gln
            370                 375                 380

Gly Val Val Asp Arg Gly Trp Gly Asn Gly Cys Gly Leu Phe Gly Lys
385                 390                 395                 400

Gly Ser Ile Asp Thr Cys Ala Lys Phe Ala Cys Ser Thr Lys Ala Ile
                405                 410                 415

Gly Arg Thr Ile Leu Lys Glu Asn Ile Lys Tyr Glu Val Ala Ile Phe
            420                 425                 430
```

```
Val His Gly Pro Thr Thr Val Glu Ser His Gly Asn Tyr Ser Thr Gln
        435                 440                 445
Val Gly Ala Thr Gln Ala Gly Arg Phe Ser Ile Thr Pro Ala Ala Pro
450                 455                 460
Ser Tyr Thr Leu Lys Leu Gly Glu Tyr Gly Glu Val Thr Val Asp Cys
465                 470                 475                 480
Glu Pro Arg Ser Gly Ile Asp Thr Asn Ala Tyr Tyr Val Met Thr Val
                485                 490                 495
Gly Thr Lys Thr Phe Leu Val His Arg Glu Trp Phe Met Asp Leu Asn
            500                 505                 510
Leu Pro Trp Ser Ser Ala Gly Ser Thr Val Trp Arg Asn Arg Glu Thr
        515                 520                 525
Leu Met Glu Phe Glu Glu Pro His Ala Thr Lys Gln Ser Val Ile Ala
530                 535                 540
Leu Gly Ser Gln Glu Gly Ala Leu His Gln Ala Leu Ala Gly Ala Ile
545                 550                 555                 560
Pro Val Glu Phe Ser Ser Asn Thr Val Lys Leu Thr Ser Gly His Leu
                565                 570                 575
Lys Cys Arg Val Lys Met Glu Lys Leu Gln Leu Lys Gly Thr Thr Tyr
            580                 585                 590
Gly Val Cys Ser Lys Ala Phe Lys Phe Leu Gly Thr Pro Ala Asp Thr
        595                 600                 605
Gly His Gly Thr Val Val Leu Glu Leu Gln Tyr Thr Gly Thr Asp Gly
610                 615                 620
Pro Cys Lys Val Pro Ile Ser Ser Val Ala Ser Leu Asn Asp Leu Thr
625                 630                 635                 640
Pro Val Gly Arg Leu Val Thr Val Asn Pro Phe Val Ser Val Ala Thr
                645                 650                 655
Ala Asn Ala Lys Val Leu Ile Glu Leu Glu Pro Pro Phe Gly Asp Ser
            660                 665                 670
Tyr Ile Val Val Gly Arg Gly Glu Gln Gln Ile Asn His His Trp His
        675                 680                 685
Lys Ser Gly Ser Ser Ile Gly Lys Ala Phe Thr Thr Thr Leu Lys Gly
690                 695                 700
Ala Gln Arg Leu Ala Ala Leu Gly Asp Thr Ala Trp Asp Phe Gly Ser
705                 710                 715                 720
Val Gly Gly Val Phe Thr Ser Val Gly Lys Ala Val His Gln Val Phe
                725                 730                 735
Gly Gly Ala Phe Arg Ser Leu Phe Gly Gly Met Ser Trp Ile Thr Gln
            740                 745                 750
Gly Leu Leu Gly Ala Leu Leu Leu Trp Met Gly Ile Asn Ala Arg Asp
        755                 760                 765
Arg Ser Ile Ala Leu Thr Phe Leu Ala Val Gly Gly Val Leu Leu Phe
770                 775                 780
Leu Ser Val Asn Val His Ala Asp Thr Gly Cys Ala Ile Asp Ile Ser
785                 790                 795                 800
Arg Gln Glu Leu Arg Cys Gly Ser Gly Val Phe Ile His Asn Asp Val
                805                 810                 815
Glu Ala Trp Met Asp Arg Tyr Lys Tyr Tyr Pro Glu Thr Pro Gln Gly
            820                 825                 830
Leu Ala Lys Ile Ile Gln Lys Ala His Lys Glu Gly Val Cys Gly Leu
        835                 840                 845
Arg Ser Val Ser Arg Leu Glu His Gln Met Trp Glu Ala Val Lys Asp
```

-continued

```
                850                 855                 860
Glu Leu Asn Thr Leu Leu Lys Glu Asn Gly Val Asp Leu Ser Val Val
865                 870                 875                 880

Val Glu Lys Gln Glu Gly Met Tyr Lys Ser Ala Pro Lys Arg Leu Thr
                885                 890                 895

Ala Thr Thr Glu Lys Leu Glu Ile Gly Trp Lys Ala Trp Gly Lys Ser
                900                 905                 910

Ile Leu Phe Ala Pro Glu Leu Ala Asn Asn Thr Phe Val Val Asp Gly
            915                 920                 925

Pro Glu Thr Lys Glu Cys Pro Thr Gln Asn Arg Ala Trp Asn Ser Leu
            930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
                965                 970                 975

Thr Ala Val Lys Asn Asn Leu Ala Ile His Ser Asp Leu Ser Tyr Trp
            980                 985                 990

Ile Glu Ser Arg Leu Asn Asp Thr Trp Lys Leu Glu Arg Ala Val Leu
            995                 1000                1005

Gly Glu Val Lys Ser Cys Thr Trp Pro Glu Thr His Thr Leu Trp
        1010                1015                1020

Gly Asp Gly Ile Leu Glu Ser Asp Leu Ile Ile Pro Val Thr Leu
        1025                1030                1035

Ala Gly Pro Arg Ser Asn His Asn Arg Arg Pro Gly Tyr Lys Thr
        1040                1045                1050

Gln Asn Gln Gly Pro Trp Asp Glu Gly Arg Val Glu Ile Asp Phe
        1055                1060                1065

Asp Tyr Cys Pro Gly Thr Thr Val Thr Leu Ser Glu Ser Cys Gly
        1070                1075                1080

His Arg Gly Pro Ala Thr Arg Thr Thr Thr Glu Ser Gly Lys Leu
        1085                1090                1095

Ile Thr Asp Trp Cys Cys Arg Ser Cys Thr Leu Pro Pro Leu Arg
        1100                1105                1110

Tyr Gln Thr Asp Ser Gly Cys Trp Tyr Gly Met Glu Ile Arg Pro
        1115                1120                1125

Gln Arg His Asp Glu Lys Thr Leu Val Gln Ser Gln Val Asn Ala
        1130                1135                1140

Tyr Asn Ala Asp Met Ile Asp Pro Phe Gln Leu Gly Leu Leu Val
        1145                1150                1155

Val Phe Leu Ala Thr Gln Glu Val Leu Arg Lys Arg Trp Thr Ala
        1160                1165                1170

Lys Ile Ser Met Pro Ala Ile Leu Ile Ala Leu Leu Val Leu Val
        1175                1180                1185

Phe Gly Gly Ile Thr Tyr Thr Asp Val Leu Arg Tyr Val Ile Leu
        1190                1195                1200

Val Gly Ala Ala Phe Ala Glu Ser Asn Ser Gly Gly Asp Val Val
        1205                1210                1215

His Leu Ala Leu Met Ala Thr Phe Lys Ile Gln Pro Val Phe Met
        1220                1225                1230

Val Ala Ser Phe Leu Lys Ala Arg Trp Thr Asn Gln Glu Asn Ile
        1235                1240                1245

Leu Leu Met Leu Ala Ala Val Phe Phe Gln Met Ala Tyr Tyr Asp
        1250                1255                1260
```

```
Ala Arg Gln Ile Leu Leu Trp Glu Ile Pro Asp Val Leu Asn Ser
    1265            1270            1275

Leu Ala Val Ala Trp Met Ile Leu Arg Ala Ile Thr Phe Thr Thr
    1280            1285            1290

Thr Ser Asn Val Val Val Pro Leu Leu Ala Leu Leu Thr Pro Gly
    1295            1300            1305

Leu Arg Cys Leu Asn Leu Asp Val Tyr Arg Ile Leu Leu Leu Met
    1310            1315            1320

Val Gly Ile Gly Ser Leu Ile Arg Glu Lys Arg Ser Ala Ala Ala
    1325            1330            1335

Lys Lys Lys Gly Ala Ser Leu Leu Cys Leu Ala Leu Ala Ser Thr
    1340            1345            1350

Gly Leu Phe Asn Pro Met Ile Leu Ala Ala Gly Leu Ile Ala Cys
    1355            1360            1365

Asp Pro Asn Arg Lys Arg Gly Trp Pro Ala Thr Glu Val Met Thr
    1370            1375            1380

Ala Val Gly Leu Met Phe Ala Ile Val Gly Gly Leu Ala Glu Leu
    1385            1390            1395

Asp Ile Asp Ser Met Ala Ile Pro Met Thr Ile Ala Gly Leu Met
    1400            1405            1410

Phe Ala Ala Phe Val Ile Ser Gly Lys Ser Thr Asp Met Trp Ile
    1415            1420            1425

Glu Arg Thr Ala Asp Ile Ser Trp Glu Ser Asp Ala Glu Ile Thr
    1430            1435            1440

Gly Ser Ser Glu Arg Val Asp Val Arg Leu Asp Asp Asp Gly Asn
    1445            1450            1455

Phe Gln Leu Met Asn Asp Pro Gly Ala Pro Trp Lys Ile Trp Met
    1460            1465            1470

Leu Arg Met Val Cys Leu Ala Ile Ser Ala Tyr Thr Pro Trp Ala
    1475            1480            1485

Ile Leu Pro Ser Val Val Gly Phe Trp Ile Thr Leu Gln Tyr Thr
    1490            1495            1500

Lys Arg Gly Gly Val Leu Trp Asp Thr Pro Ser Pro Lys Glu Tyr
    1505            1510            1515

Lys Lys Gly Asp Thr Thr Thr Gly Val Tyr Arg Ile Met Thr Arg
    1520            1525            1530

Gly Leu Leu Gly Ser Tyr Gln Ala Gly Ala Gly Val Met Val Glu
    1535            1540            1545

Gly Val Phe His Thr Leu Trp His Thr Thr Lys Gly Ala Ala Leu
    1550            1555            1560

Met Ser Gly Glu Gly Arg Leu Asp Pro Tyr Trp Gly Ser Val Lys
    1565            1570            1575

Glu Asp Arg Leu Cys Tyr Gly Gly Pro Trp Lys Leu Gln His Lys
    1580            1585            1590

Trp Asn Gly Gln Asp Glu Val Gln Met Ile Val Val Glu Pro Gly
    1595            1600            1605

Arg Asn Val Lys Asn Val Gln Thr Lys Pro Gly Val Phe Lys Thr
    1610            1615            1620

Pro Glu Gly Glu Ile Gly Ala Val Thr Leu Asp Phe Pro Thr Gly
    1625            1630            1635

Thr Ser Gly Ser Pro Ile Val Asp Lys Asn Gly Asp Val Ile Gly
    1640            1645            1650
```

```
Leu Tyr Gly Asn Gly Val Ile Met Pro Asn Gly Ser Tyr Ile Ser
1655                1660                1665

Ala Ile Val Gln Gly Glu Arg Met Asp Glu Pro Ile Pro Ala Gly
1670                1675                1680

Phe Glu Pro Glu Met Leu Arg Lys Lys Gln Ile Thr Val Leu Asp
1685                1690                1695

Leu His Pro Gly Ala Gly Lys Thr Arg Arg Ile Leu Pro Gln Ile
1700                1705                1710

Ile Lys Glu Ala Ile Asn Arg Arg Leu Arg Thr Ala Val Leu Ala
1715                1720                1725

Pro Thr Arg Val Val Ala Ala Glu Met Ala Glu Ala Leu Arg Gly
1730                1735                1740

Leu Pro Ile Arg Tyr Gln Thr Ser Ala Val Pro Arg Glu His Asn
1745                1750                1755

Gly Asn Glu Ile Val Asp Val Met Cys His Ala Thr Leu Thr His
1760                1765                1770

Arg Leu Met Ser Pro His Arg Val Pro Asn Tyr Asn Leu Phe Val
1775                1780                1785

Met Asp Glu Ala His Phe Thr Asp Pro Ala Ser Ile Ala Ala Arg
1790                1795                1800

Gly Tyr Ile Ser Thr Lys Val Glu Leu Gly Glu Ala Ala Ala Ile
1805                1810                1815

Phe Met Thr Ala Thr Pro Pro Gly Thr Ser Asp Pro Phe Pro Glu
1820                1825                1830

Ser Asn Ser Pro Ile Ser Asp Leu Gln Thr Glu Ile Pro Asp Arg
1835                1840                1845

Ala Trp Asn Ser Gly Tyr Glu Trp Ile Thr Glu Tyr Thr Gly Lys
1850                1855                1860

Thr Val Trp Phe Val Pro Ser Val Lys Met Gly Asn Glu Ile Ala
1865                1870                1875

Leu Cys Leu Gln Arg Ala Gly Lys Lys Val Val Gln Leu Asn Arg
1880                1885                1890

Lys Ser Tyr Glu Thr Glu Tyr Pro Lys Cys Lys Asn Asp Asp Trp
1895                1900                1905

Asp Phe Val Ile Thr Thr Asp Ile Ser Glu Met Gly Ala Asn Phe
1910                1915                1920

Lys Ala Ser Arg Val Ile Asp Ser Arg Lys Ser Val Lys Pro Thr
1925                1930                1935

Ile Ile Thr Glu Gly Glu Gly Arg Val Ile Leu Gly Glu Pro Ser
1940                1945                1950

Ala Val Thr Ala Ala Ser Ala Ala Gln Arg Arg Gly Arg Ile Gly
1955                1960                1965

Arg Asn Pro Ser Gln Val Gly Asp Glu Tyr Cys Tyr Gly Gly His
1970                1975                1980

Thr Asn Glu Asp Asp Ser Asn Phe Ala His Trp Thr Glu Ala Arg
1985                1990                1995

Ile Met Leu Asp Asn Ile Asn Met Pro Asn Gly Leu Ile Ala Gln
2000                2005                2010

Phe Tyr Gln Pro Glu Arg Glu Lys Val Tyr Thr Met Asp Gly Glu
2015                2020                2025

Tyr Arg Leu Arg Gly Glu Glu Arg Lys Asn Phe Leu Glu Leu Leu
2030                2035                2040

Arg Thr Ala Asp Leu Pro Val Trp Leu Ala Tyr Lys Val Ala Ala
```

-continued

```
            2045                2050                2055
Ala Gly Val Ser Tyr His Asp Arg Arg Trp Cys Phe Asp Gly Pro
        2060                2065                2070
Arg Thr Asn Thr Ile Leu Glu Asp Asn Glu Val Glu Val Ile
        2075                2080                2085
Thr Lys Leu Gly Glu Arg Lys Ile Leu Arg Pro Arg Trp Ile Asp
        2090                2095                2100
Ala Arg Val Tyr Ser Asp His Gln Ala Leu Lys Ala Phe Lys Asp
        2105                2110                2115
Phe Ala Ser Gly Lys Arg Ser Gln Ile Gly Leu Ile Glu Val Leu
        2120                2125                2130
Gly Lys Met Pro Glu His Phe Met Gly Lys Thr Trp Glu Ala Leu
        2135                2140                2145
Asp Thr Met Tyr Val Val Ala Thr Ala Glu Lys Gly Gly Arg Ala
        2150                2155                2160
His Arg Met Ala Leu Glu Glu Leu Pro Asp Ala Leu Gln Thr Ile
        2165                2170                2175
Ala Leu Ile Ala Leu Leu Ser Val Met Thr Met Gly Val Phe Phe
        2180                2185                2190
Leu Leu Met Gln Arg Lys Gly Ile Gly Lys Ile Gly Leu Gly Gly
        2195                2200                2205
Ala Val Leu Gly Val Ala Thr Phe Phe Cys Trp Met Ala Glu Val
        2210                2215                2220
Pro Gly Thr Lys Ile Ala Gly Met Leu Leu Leu Ser Leu Leu Leu
        2225                2230                2235
Met Ile Val Leu Ile Pro Glu Pro Glu Lys Gln Arg Ser Gln Thr
        2240                2245                2250
Asp Asn Gln Leu Ala Val Phe Leu Ile Cys Val Met Thr Leu Val
        2255                2260                2265
Ser Ala Val Ala Ala Asn Glu Met Gly Trp Leu Asp Lys Thr Lys
        2270                2275                2280
Ser Asp Ile Ser Ser Leu Phe Gly Gln Arg Ile Glu Val Lys Glu
        2285                2290                2295
Asn Phe Ser Met Gly Glu Phe Leu Leu Asp Leu Arg Pro Ala Thr
        2300                2305                2310
Ala Trp Ser Leu Tyr Ala Val Thr Thr Ala Val Leu Thr Gly Leu
        2315                2320                2325
Leu Lys His Leu Ile Thr Ser Asp Tyr Ile Asn Thr Ser Leu Thr
        2330                2335                2340
Ser Ile Asn Val Gln Ala Ser Ala Leu Phe Thr Leu Ala Arg Gly
        2345                2350                2355
Phe Pro Phe Val Asp Val Gly Val Ser Ala Leu Leu Leu Ala Ala
        2360                2365                2370
Gly Cys Trp Gly Gln Val Thr Leu Thr Val Thr Val Thr Ala Ala
        2375                2380                2385
Thr Leu Leu Phe Cys His Tyr Ala Tyr Met Val Pro Gly Trp Gln
        2390                2395                2400
Ala Glu Ala Met Arg Ser Ala Gln Arg Arg Thr Ala Ala Gly Ile
        2405                2410                2415
Met Lys Asn Ala Val Val Asp Gly Ile Val Ala Thr Asp Val Pro
        2420                2425                2430
Glu Leu Glu Arg Thr Thr Pro Ile Met Gln Lys Lys Val Gly Gln
        2435                2440                2445
```

-continued

Ile Met Leu Ile Leu Val Ser Leu Ala Ala Val Val Asn Pro
        2450                2455            2460

Ser Val Lys Thr Val Arg Glu Ala Gly Ile Leu Ile Thr Ala Ala
        2465                2470            2475

Ala Val Thr Leu Trp Glu Asn Gly Ala Ser Ser Val Trp Asn Ala
        2480                2485            2490

Thr Thr Ala Ile Gly Leu Cys His Ile Met Arg Gly Gly Trp Leu
        2495                2500            2505

Ser Cys Leu Ser Ile Thr Trp Thr Leu Ile Lys Asn Met Glu Lys
        2510                2515            2520

Pro Gly Leu Lys Arg Gly Gly Ala Lys Gly Arg Thr Leu Gly Glu
        2525                2530            2535

Val Trp Lys Glu Arg Leu Asn Gln Met Thr Lys Glu Glu Phe Thr
        2540                2545            2550

Arg Tyr Arg Lys Glu Ala Ile Ile Glu Val Asp Arg Ser Ala Ala
        2555                2560            2565

Lys His Ala Arg Lys Glu Gly Asn Val Thr Gly Gly His Pro Val
        2570                2575            2580

Ser Arg Gly Thr Ala Lys Leu Arg Trp Leu Val Glu Arg Arg Phe
        2585                2590            2595

Leu Glu Pro Val Gly Lys Val Ile Asp Leu Gly Cys Gly Arg Gly
        2600                2605            2610

Gly Trp Cys Tyr Tyr Met Ala Thr Gln Lys Arg Val Gln Glu Val
        2615                2620            2625

Arg Gly Tyr Thr Lys Gly Gly Pro Gly His Glu Glu Pro Gln Leu
        2630                2635            2640

Val Gln Ser Tyr Gly Trp Asn Ile Val Thr Met Lys Ser Gly Val
        2645                2650            2655

Asp Val Phe Tyr Arg Pro Ser Glu Cys Cys Asp Thr Leu Leu Cys
        2660                2665            2670

Asp Ile Gly Glu Ser Ser Ser Ser Ala Glu Val Glu Glu His Arg
        2675                2680            2685

Thr Ile Arg Val Leu Glu Met Val Glu Asp Trp Leu His Arg Gly
        2690                2695            2700

Pro Arg Glu Phe Cys Val Lys Val Leu Cys Pro Tyr Met Pro Lys
        2705                2710            2715

Val Ile Glu Lys Met Glu Leu Leu Gln Arg Arg Tyr Gly Gly Gly
        2720                2725            2730

Leu Val Arg Asn Pro Leu Ser Arg Asn Ser Thr His Glu Met Tyr
        2735                2740            2745

Trp Val Ser Arg Ala Ser Gly Asn Val Val His Ser Val Asn Met
        2750                2755            2760

Thr Ser Gln Val Leu Leu Gly Arg Met Glu Lys Arg Thr Trp Lys
        2765                2770            2775

Gly Pro Gln Tyr Glu Glu Asp Val Asn Leu Gly Ser Gly Thr Arg
        2780                2785            2790

Ala Val Gly Lys Pro Leu Leu Asn Ser Asp Thr Ser Lys Ile Lys
        2795                2800            2805

Asn Arg Ile Glu Arg Leu Arg Arg Glu Tyr Ser Ser Thr Trp His
        2810                2815            2820

His Asp Glu Asn His Pro Tyr Arg Thr Trp Asn Tyr His Gly Ser
        2825                2830            2835

```
Tyr Asp Val Lys Pro Thr Gly Ser Ala Ser Ser Leu Val Asn Gly
    2840            2845                2850

Val Val Arg Leu Leu Ser Lys Pro Trp Asp Thr Ile Thr Asn Val
    2855            2860                2865

Thr Thr Met Ala Met Thr Asp Thr Thr Pro Phe Gly Gln Gln Arg
    2870            2875                2880

Val Phe Lys Glu Lys Val Asp Thr Lys Ala Pro Glu Pro Pro Glu
    2885            2890                2895

Gly Val Lys Tyr Val Leu Asn Glu Thr Thr Asn Trp Leu Trp Ala
    2900            2905                2910

Phe Leu Ala Arg Glu Lys Arg Pro Arg Met Cys Ser Arg Glu Glu
    2915            2920                2925

Phe Ile Arg Lys Val Asn Ser Asn Ala Ala Leu Gly Ala Met Phe
    2930            2935                2940

Glu Glu Gln Asn Gln Trp Arg Ser Ala Arg Glu Ala Val Glu Asp
    2945            2950                2955

Pro Lys Phe Trp Glu Met Val Asp Glu Glu Arg Glu Ala His Leu
    2960            2965                2970

Arg Gly Glu Cys His Thr Cys Ile Tyr Asn Met Met Gly Lys Arg
    2975            2980                2985

Glu Lys Lys Pro Gly Glu Phe Gly Lys Ala Lys Gly Ser Arg Ala
    2990            2995                3000

Ile Trp Phe Met Trp Leu Gly Ala Arg Phe Leu Glu Phe Glu Ala
    3005            3010                3015

Leu Gly Phe Leu Asn Glu Asp His Trp Leu Gly Arg Lys Asn Ser
    3020            3025                3030

Gly Gly Gly Val Glu Gly Leu Gly Leu Gln Lys Leu Gly Tyr Ile
    3035            3040                3045

Leu Arg Glu Val Gly Thr Arg Pro Gly Gly Lys Ile Tyr Ala Asp
    3050            3055                3060

Asp Thr Ala Gly Trp Asp Thr Arg Ile Thr Arg Ala Asp Leu Glu
    3065            3070                3075

Asn Glu Ala Lys Val Leu Glu Leu Leu Asp Gly Glu His Arg Arg
    3080            3085                3090

Leu Ala Arg Ala Ile Ile Glu Leu Thr Tyr Arg His Lys Val Val
    3095            3100                3105

Lys Val Met Arg Pro Ala Ala Asp Gly Arg Thr Val Met Asp Val
    3110            3115                3120

Ile Ser Arg Glu Asp Gln Arg Gly Ser Gly Gln Val Val Thr Tyr
    3125            3130                3135

Ala Leu Asn Thr Phe Thr Asn Leu Ala Val Gln Leu Val Arg Met
    3140            3145                3150

Met Glu Gly Glu Gly Val Ile Gly Pro Asp Asp Val Glu Lys Leu
    3155            3160                3165

Thr Lys Gly Lys Gly Pro Lys Val Arg Thr Trp Leu Phe Glu Asn
    3170            3175                3180

Gly Glu Glu Arg Leu Ser Arg Met Ala Val Ser Gly Asp Asp Cys
    3185            3190                3195

Val Val Lys Pro Leu Asp Asp Arg Phe Ala Thr Ser Leu His Phe
    3200            3205                3210

Leu Asn Ala Met Ser Lys Val Arg Lys Asp Ile Gln Glu Trp Lys
    3215            3220                3225

Pro Ser Thr Gly Trp Tyr Asp Trp Gln Gln Val Pro Phe Cys Ser
```

```
              3230              3235              3240
Asn His Phe Thr Glu Leu Ile Met Lys Asp Gly Arg  Thr Leu Val
    3245                  3250                3255

Val Pro Cys Arg Gly Gln Asp Glu Leu Val Gly Arg Ala Arg Ile
    3260                  3265                3270

Ser Pro Gly Ala Gly Trp Asn Val Arg Asp Thr Ala Cys Leu Ala
    3275                  3280                3285

Lys Ser Tyr Ala Gln Met Trp Leu Leu Leu Tyr Phe His Arg Arg
    3290                  3295                3300

Asp Leu Arg Leu Met Ala Asn Ala Ile Cys Ser Ala Val Pro Val
    3305                  3310                3315

Asn Trp Val Pro Thr Gly Arg Thr Thr Trp Ser Ile His Ala Gly
    3320                  3325                3330

Gly Glu Trp Met Thr Thr Glu Asp Met Leu Glu Val Trp Asn Arg
    3335                  3340                3345

Val Trp Ile Glu Glu Asn Glu Trp Met Glu Asp Lys Thr Pro Val
    3350                  3355                3360

Glu Lys Trp Ser Asp Val Pro Tyr Ser Gly Lys Arg Glu Asp Ile
    3365                  3370                3375

Trp Cys Gly Ser Leu Ile Gly Thr Arg Ala Arg Ala Thr Trp Ala
    3380                  3385                3390

Glu Asn Ile Gln Val Ala Ile Asn Gln Val Arg Ala Ile Ile Gly
    3395                  3400                3405

Asp Glu Lys Tyr Val Asp Tyr Met Ser Ser Leu Lys Arg Tyr Glu
    3410                  3415                3420

Asp Thr Thr Leu Val Glu Asp Thr Val Leu
    3425                  3430

<210> SEQ ID NO 7
<211> LENGTH: 10862
<212> TYPE: DNA
<213> ORGANISM: Yellow fever virus
<220> FEATURE:
<221> NAME/KEY: CDS
<222> LOCATION: (119)..(10354)

<400> SEQUENCE: 7
agtaaatcct gtgtgctaat tgaggtgcat tggtctgcaa atcgagttgc taggcaataa      60
acacatttgg attaatttta atcgttcgtt gagcgattag cagagaactg accagaac       118 atg tct ggt cgt aaa gct cag gga aaa acc ctg ggc gtc aat atg gta      166
Met Ser Gly Arg Lys Ala Gln Gly Lys Thr Leu Gly Val Asn Met Val
1               5                  10                  15 cga cga gga gtt cgc tcc ttg tca aac aaa ata aaa caa aaa aca aaa    214
Arg Arg Gly Val Arg Ser Leu Ser Asn Lys Ile Lys Gln Lys Thr Lys
                20                  25                  30 caa att gga aac aga cct gga cct tca aga ggt gtt caa gga ttt atc    262
Gln Ile Gly Asn Arg Pro Gly Pro Ser Arg Gly Val Gln Gly Phe Ile
            35                  40                  45 ttt ttc ttt ttg ttc aac att ttg act gga aaa aag atc aca gcc cac    310
Phe Phe Phe Leu Phe Asn Ile Leu Thr Gly Lys Lys Ile Thr Ala His
        50                  55                  60 cta aag agg ttg tgg aaa atg ctg gac cca aga caa ggc ttg gct gtt    358
Leu Lys Arg Leu Trp Lys Met Leu Asp Pro Arg Gln Gly Leu Ala Val
65                  70                  75                  80 cta agg aaa gtc aag aga gtg gtg gcc agt ttg atg aga gga ttg tcc    406
Leu Arg Lys Val Lys Arg Val Val Ala Ser Leu Met Arg Gly Leu Ser
                85                  90                  95
```

-continued

```
tca agg aaa cgc cgt tcc cat gat gtt ctg act gtg caa ttc cta att     454
Ser Arg Lys Arg Arg Ser His Asp Val Leu Thr Val Gln Phe Leu Ile
        100                 105                 110 ttg gga atg ctg ttg atg acg ggt gga gtg acc ttg gtc cgg aaa aac     502
Leu Gly Met Leu Leu Met Thr Gly Gly Val Thr Leu Val Arg Lys Asn
    115                 120                 125 aga tgg ttg ctc cta aat gtg aca tct gag gac ctc ggg aaa aca ttc     550
Arg Trp Leu Leu Leu Asn Val Thr Ser Glu Asp Leu Gly Lys Thr Phe
130                 135                 140 tct gtg ggc aca ggc aac tgc aca aca aac att ttg gaa gcc aag tac     598
Ser Val Gly Thr Gly Asn Cys Thr Thr Asn Ile Leu Glu Ala Lys Tyr
145                 150                 155                 160 tgg tgc cca gac tca atg gaa tac aac tgt ccc aat ctc agt cca aga     646
Trp Cys Pro Asp Ser Met Glu Tyr Asn Cys Pro Asn Leu Ser Pro Arg
                165                 170                 175 gag gag cca gat gac att gat tgc tgg tgc tat ggg gtg gaa aac gtt     694
Glu Glu Pro Asp Asp Ile Asp Cys Trp Cys Tyr Gly Val Glu Asn Val
                180                 185                 190 aga gtc gca tat ggt aag tgt gac tca gca ggc agg tct agg agg tca     742
Arg Val Ala Tyr Gly Lys Cys Asp Ser Ala Gly Arg Ser Arg Arg Ser
            195                 200                 205 aga agg gcc att gac ttg cct acg cat gaa aac cat ggt ttg aag acc     790
Arg Arg Ala Ile Asp Leu Pro Thr His Glu Asn His Gly Leu Lys Thr
210                 215                 220 cgg caa gaa aaa tgg atg act gga aga atg ggt gaa agg caa ctc caa     838
Arg Gln Glu Lys Trp Met Thr Gly Arg Met Gly Glu Arg Gln Leu Gln
225                 230                 235                 240 aag att gag aga tgg ctc gtg agg aac ccc ttt ttt gca gtg aca gct     886
Lys Ile Glu Arg Trp Leu Val Arg Asn Pro Phe Phe Ala Val Thr Ala
                245                 250                 255 ctg acc att gcc tac ctt gtg gga agc aac atg acg caa cga gtc gtg     934
Leu Thr Ile Ala Tyr Leu Val Gly Ser Asn Met Thr Gln Arg Val Val
            260                 265                 270 att gcc cta ctg gtc ttg gct gtt ggt ccg gcc tac tca gct cac tgc     982
Ile Ala Leu Leu Val Leu Ala Val Gly Pro Ala Tyr Ser Ala His Cys
            275                 280                 285 att gga att act gac agg gat ttc att gag ggg gtg cat gga gga act    1030
Ile Gly Ile Thr Asp Arg Asp Phe Ile Glu Gly Val His Gly Gly Thr
        290                 295                 300 tgg gtt tca gct acc ctg gag caa gac aag tgt gtc act gtt atg gcc    1078
Trp Val Ser Ala Thr Leu Glu Gln Asp Lys Cys Val Thr Val Met Ala
305                 310                 315                 320 cct gac aag cct tca ttg gac atc tca cta gag aca gta gcc att gat    1126
Pro Asp Lys Pro Ser Leu Asp Ile Ser Leu Glu Thr Val Ala Ile Asp
                325                 330                 335 gga cct gct gag gcg agg aaa gtg tgt tac aat gca gtt ctc act cat    1174
Gly Pro Ala Glu Ala Arg Lys Val Cys Tyr Asn Ala Val Leu Thr His
            340                 345                 350 gtg aag att aat gac aag tgc ccc agc act gga gag gcc cac cta gct    1222
Val Lys Ile Asn Asp Lys Cys Pro Ser Thr Gly Glu Ala His Leu Ala
355                 360                 365 gaa gag aac gaa ggg gac aat gcg tgc aag cgc act tat tct gat aga    1270
Glu Glu Asn Glu Gly Asp Asn Ala Cys Lys Arg Thr Tyr Ser Asp Arg
370                 375                 380 ggc tgg ggc aat ggc tgt ggc cta ttt ggg aaa ggg agc att gtg gca    1318
Gly Trp Gly Asn Gly Cys Gly Leu Phe Gly Lys Gly Ser Ile Val Ala
385                 390                 395                 400 tgc gcc aaa ttc act tgt gcc aaa tcc atg agt ttg ttt gag gtt gat    1366
Cys Ala Lys Phe Thr Cys Ala Lys Ser Met Ser Leu Phe Glu Val Asp
```

```
                    405                 410                 415
cag acc aaa att cag tat gtc atc aga gca caa ttg cat gta ggg gcc    1414
Gln Thr Lys Ile Gln Tyr Val Ile Arg Ala Gln Leu His Val Gly Ala
            420                 425                 430 aag cag gaa aat tgg aat acc gac att aag act ctc aag ttt gat gcc    1462
Lys Gln Glu Asn Trp Asn Thr Asp Ile Lys Thr Leu Lys Phe Asp Ala
                435                 440                 445 ctg tca ggc tcc cag gaa gcc gag ttc act ggg tat gga aaa gct aca    1510
Leu Ser Gly Ser Gln Glu Ala Glu Phe Thr Gly Tyr Gly Lys Ala Thr
450                 455                 460 ctg gaa tgc cag gtg caa act gcg gtg gac ttt ggt aac agt tac atc    1558
Leu Glu Cys Gln Val Gln Thr Ala Val Asp Phe Gly Asn Ser Tyr Ile
465                 470                 475                 480 gct gag atg gaa aaa gag agc tgg ata gtg gac aga cag tgg gcc cag    1606
Ala Glu Met Glu Lys Glu Ser Trp Ile Val Asp Arg Gln Trp Ala Gln
            485                 490                 495 gac ttg acc ctg cca tgg cag agt gga agt ggc ggg gtg tgg aga gag    1654
Asp Leu Thr Leu Pro Trp Gln Ser Gly Ser Gly Gly Val Trp Arg Glu
                500                 505                 510 atg cat cat ctt gtc gaa ttt gaa cct ccg cat gcc gcc act atc aga    1702
Met His His Leu Val Glu Phe Glu Pro Pro His Ala Ala Thr Ile Arg
                    515                 520                 525 gta ctg gcc ctg gga aac cag gaa ggc tcc ttg aaa aca gct ctt acc    1750
Val Leu Ala Leu Gly Asn Gln Glu Gly Ser Leu Lys Thr Ala Leu Thr
530                 535                 540 ggc gca atg agg gtt aca aag gac aca aat gac aac aac ctt tac aaa    1798
Gly Ala Met Arg Val Thr Lys Asp Thr Asn Asp Asn Asn Leu Tyr Lys
545                 550                 555                 560 cta cat ggt gga cat gtt tcc tgc aga gtg aaa ttg tca gct ttg aca    1846
Leu His Gly Gly His Val Ser Cys Arg Val Lys Leu Ser Ala Leu Thr
            565                 570                 575 ctc aag ggg aca tcc tac aaa atg tgc act gac aaa atg tct ttt gtc    1894
Leu Lys Gly Thr Ser Tyr Lys Met Cys Thr Asp Lys Met Ser Phe Val
                580                 585                 590 aag aac cca act gac act ggc cat ggc act gtt gtg atg cag gtg aaa    1942
Lys Asn Pro Thr Asp Thr Gly His Gly Thr Val Val Met Gln Val Lys
                    595                 600                 605 gtg cca aaa gga gcc ccc tgc aag att cca gtg ata gta gct gat gat    1990
Val Pro Lys Gly Ala Pro Cys Lys Ile Pro Val Ile Val Ala Asp Asp
610                 615                 620 ctt aca gcg gca atc aat aaa ggc att ttg gtt aca gtt aac ccc atc    2038
Leu Thr Ala Ala Ile Asn Lys Gly Ile Leu Val Thr Val Asn Pro Ile
625                 630                 635                 640 gcc tca acc aat gat gat gaa gtg ctg att gag gtg aac cca cct ttt    2086
Ala Ser Thr Asn Asp Asp Glu Val Leu Ile Glu Val Asn Pro Pro Phe
            645                 650                 655 gga gac agc tac att atc gtt ggg aca gga gat tca cgt ctc act tac    2134
Gly Asp Ser Tyr Ile Ile Val Gly Thr Gly Asp Ser Arg Leu Thr Tyr
                660                 665                 670 cag tgg cac aaa gag gga agc tca ata gga aag ttg ttc act cag acc    2182
Gln Trp His Lys Glu Gly Ser Ser Ile Gly Lys Leu Phe Thr Gln Thr
                    675                 680                 685 atg aaa ggc gcg gaa cgc ctg gcc gtc atg gga gac gcc gcc tgg gat    2230
Met Lys Gly Ala Glu Arg Leu Ala Val Met Gly Asp Ala Ala Trp Asp
690                 695                 700 ttc agc tcc gct gga ggg ttc ttc act tcg gtt ggg aaa gga att cat    2278
Phe Ser Ser Ala Gly Gly Phe Phe Thr Ser Val Gly Lys Gly Ile His
705                 710                 715                 720 acg gtg ttt ggc tct gcc ttt cag ggg cta ttt ggc ggc ttg aac tgg    2326
```

```
Thr Val Phe Gly Ser Ala Phe Gln Gly Leu Phe Gly Gly Leu Asn Trp
                725                 730                 735 ata aca aag gtc atc atg ggg gcg gta ctc ata tgg gtt ggc atc aac      2374
Ile Thr Lys Val Ile Met Gly Ala Val Leu Ile Trp Val Gly Ile Asn
                740                 745                 750 aca aga aac atg aca atg tcc atg agc atg atc ttg gta gga gtg atc      2422
Thr Arg Asn Met Thr Met Ser Met Ser Met Ile Leu Val Gly Val Ile
                755                 760                 765 atg atg ttt ttg tct cta gga gtt ggg gcg gat caa gga tgc gcc atc      2470
Met Met Phe Leu Ser Leu Gly Val Gly Ala Asp Gln Gly Cys Ala Ile
                770                 775                 780 aac ttt ggc aag aga gag ctc aag tgc gga gat ggt atc ttc ata ttt      2518
Asn Phe Gly Lys Arg Glu Leu Lys Cys Gly Asp Gly Ile Phe Ile Phe
785                 790                 795                 800 aga gac tct gat gac tgg ctg aac aag tac tca tac tat cca gaa gat      2566
Arg Asp Ser Asp Asp Trp Leu Asn Lys Tyr Ser Tyr Tyr Pro Glu Asp
                805                 810                 815 cct gtg aag ctt gca tca ata gtg aaa gcc tct ttt gaa gaa ggg aag      2614
Pro Val Lys Leu Ala Ser Ile Val Lys Ala Ser Phe Glu Glu Gly Lys
                820                 825                 830 tgt ggc cta aat tca gtt gac tcc ctt gag cat gag atg tgg aga agc      2662
Cys Gly Leu Asn Ser Val Asp Ser Leu Glu His Glu Met Trp Arg Ser
                835                 840                 845 agg gca gat gag atc aat gcc att ctt gag gaa aac gag gtg gac att      2710
Arg Ala Asp Glu Ile Asn Ala Ile Leu Glu Glu Asn Glu Val Asp Ile
850                 855                 860 tct gtt gtc gtg cag gat cca aag aat gtt tac cag aga gga act cat      2758
Ser Val Val Val Gln Asp Pro Lys Asn Val Tyr Gln Arg Gly Thr His
865                 870                 875                 880 cca ttt tcc aga att cgg gat ggt ctg cag tat ggt tgg aag act tgg      2806
Pro Phe Ser Arg Ile Arg Asp Gly Leu Gln Tyr Gly Trp Lys Thr Trp
                885                 890                 895 ggt aag aac ctt gtg ttc tcc cca ggg agg aag aat gga agc ttc atc      2854
Gly Lys Asn Leu Val Phe Ser Pro Gly Arg Lys Asn Gly Ser Phe Ile
                900                 905                 910 ata gat gga aag tcc agg aaa gaa tgc ccg ttt tca aac cgg gtc tgg      2902
Ile Asp Gly Lys Ser Arg Lys Glu Cys Pro Phe Ser Asn Arg Val Trp
                915                 920                 925 aat tct ttc cag ata gag gag ttt ggg acg gga gtg ttc acc aca cgc      2950
Asn Ser Phe Gln Ile Glu Glu Phe Gly Thr Gly Val Phe Thr Thr Arg
                930                 935                 940 gtg tac atg gac gca gtc ttt gaa tac acc ata gac tgc gat gga tct      2998
Val Tyr Met Asp Ala Val Phe Glu Tyr Thr Ile Asp Cys Asp Gly Ser
945                 950                 955                 960 atc ttg ggt gca gcg gtg aac gga aaa aag agt gcc cat ggc tct cca      3046
Ile Leu Gly Ala Ala Val Asn Gly Lys Lys Ser Ala His Gly Ser Pro
                965                 970                 975 aca ttt tgg atg gga agt cat gaa gta aat ggg aca tgg atg atc cac      3094
Thr Phe Trp Met Gly Ser His Glu Val Asn Gly Thr Trp Met Ile His
                980                 985                 990 acc ttg gag gca tta gat tac aag  gag tgt gag tgg cca  ctg aca cat    3142
Thr Leu Glu Ala Leu Asp Tyr Lys  Glu Cys Glu Trp Pro  Leu Thr His
                995                 1000                1005 acg att  gga aca tca gtt gaa  gag agt gaa atg ttc  atg ccg aga        3187
Thr Ile  Gly Thr Ser Val Glu  Glu Ser Glu Met Phe  Met Pro Arg
         1010                 1015                 1020 tca atc  gga ggc cca gtt agc  tct cac aat cat atc  cct gga tac        3232
Ser Ile  Gly Gly Pro Val Ser  Ser His Asn His Ile  Pro Gly Tyr
         1025                 1030                 1035
```

-continued

| | | |
|---|---|---|
| aag gtt cag acg aac gga cct tgg atg cag gta cca cta gaa gtg<br>Lys Val Gln Thr Asn Gly Pro Trp Met Gln Val Pro Leu Glu Val<br>1040                       1045                         1050 | 3277 | |
| aag aga gaa gct tgc cca ggg act agc gtg atc att gat ggc aac<br>Lys Arg Glu Ala Cys Pro Gly Thr Ser Val Ile Ile Asp Gly Asn<br>1055                       1060                       1065 | 3322 | |
| tgt gat gga cgg gga aaa tca acc aga tcc acc acg gat agc ggg<br>Cys Asp Gly Arg Gly Lys Ser Thr Arg Ser Thr Thr Asp Ser Gly<br>1070                       1075                       1080 | 3367 | |
| aaa att att cct gaa tgg tgt tgc cgc tcc tgc aca atg ccg cct<br>Lys Ile Ile Pro Glu Trp Cys Cys Arg Ser Cys Thr Met Pro Pro<br>1085                       1090                       1095 | 3412 | |
| gtg agc ttc cat ggt agt gat ggg tgt tgg tat ccc atg gaa att<br>Val Ser Phe His Gly Ser Asp Gly Cys Trp Tyr Pro Met Glu Ile<br>1100                       1105                       1110 | 3457 | |
| agg cca agg aaa acg cat gaa agc cat ctg gtg cgc tcc tgg gtt<br>Arg Pro Arg Lys Thr His Glu Ser His Leu Val Arg Ser Trp Val<br>1115                       1120                       1125 | 3502 | |
| aca gct gga gaa ata cat gct gtc cct ttt ggt ttg gtg agc atg<br>Thr Ala Gly Glu Ile His Ala Val Pro Phe Gly Leu Val Ser Met<br>1130                       1135                       1140 | 3547 | |
| atg ata gca atg gaa gtg gtc cta agg aaa aga cag gga cca aag<br>Met Ile Ala Met Glu Val Val Leu Arg Lys Arg Gln Gly Pro Lys<br>1145                       1150                       1155 | 3592 | |
| caa atg ttg gtt gga gga gtg gtg ctc ttg gga gca atg ctg gtc<br>Gln Met Leu Val Gly Gly Val Val Leu Leu Gly Ala Met Leu Val<br>1160                       1165                       1170 | 3637 | |
| ggg caa gta act ctc ctt gat ttg ctg aaa ctc aca gtg gct gtg<br>Gly Gln Val Thr Leu Leu Asp Leu Leu Lys Leu Thr Val Ala Val<br>1175                       1180                       1185 | 3682 | |
| gga ttg cat ttc cat gag atg aac aat gga gga gac gcc atg tat<br>Gly Leu His Phe His Glu Met Asn Asn Gly Gly Asp Ala Met Tyr<br>1190                       1195                       1200 | 3727 | |
| atg gcg ttg att gct gcc ttt tca atc aga cca ggg ctg ctc atc<br>Met Ala Leu Ile Ala Ala Phe Ser Ile Arg Pro Gly Leu Leu Ile<br>1205                       1210                       1215 | 3772 | |
| ggc ttt ggg ctc agg acc cta tgg agc cct cgg gaa cgc ctt gta<br>Gly Phe Gly Leu Arg Thr Leu Trp Ser Pro Arg Glu Arg Leu Val<br>1220                       1225                       1230 | 3817 | |
| ctg acc cta gga gca gcc atg gtg gag att gcc ttg ggt ggc atg<br>Leu Thr Leu Gly Ala Ala Met Val Glu Ile Ala Leu Gly Gly Met<br>1235                       1240                       1245 | 3862 | |
| atg ggc ggc ctg tgg aag tat cta aat gca gtt tct ctc tgc atc<br>Met Gly Gly Leu Trp Lys Tyr Leu Asn Ala Val Ser Leu Cys Ile<br>1250                       1255                       1260 | 3907 | |
| ctg aca ata aat gct gta gct tct agg aaa gca tca aat acc atc<br>Leu Thr Ile Asn Ala Val Ala Ser Arg Lys Ala Ser Asn Thr Ile<br>1265                       1270                       1275 | 3952 | |
| ttg ccc ctc atg gct ctg ttg aca cct gtc act atg gct gag gtg<br>Leu Pro Leu Met Ala Leu Leu Thr Pro Val Thr Met Ala Glu Val<br>1280                       1285                       1290 | 3997 | |
| aga ctt gcc aca atg ctc ttt tgt acc gtg gtt atc ata ggg gtc<br>Arg Leu Ala Thr Met Leu Phe Cys Thr Val Val Ile Ile Gly Val<br>1295                       1300                       1305 | 4042 | |
| ctt cac cag aac tcc aag gac acc tcc atg cag aag act ata cct<br>Leu His Gln Asn Ser Lys Asp Thr Ser Met Gln Lys Thr Ile Pro<br>1310                       1315                       1320 | 4087 | |
| ctg gtg gcc ctc aca ctc aca tct tac ctg ggc ttg aca caa cct<br>Leu Val Ala Leu Thr Leu Thr Ser Tyr Leu Gly Leu Thr Gln Pro<br>1325                       1330                       1335 | 4132 | |

| | | | | | | | | | | | | |
|---|---|---|---|---|---|---|---|---|---|---|---|---|
| ttt | ttg | ggc | ctg | tgt | gca | ttt | ctg | gca | acc | cgc | ata | ttt | ggg | cga | 4177 |
| Phe | Leu | Gly | Leu | Cys | Ala | Phe | Leu | Ala | Thr | Arg | Ile | Phe | Gly | Arg | |
| | 1340 | | | | 1345 | | | | | 1350 | | | | | |

| agg | agt | atc | cca | gtg | aat | gag | gca | ctc | gca | gca | gct | ggt | cta | gtg | 4222 |
| Arg | Ser | Ile | Pro | Val | Asn | Glu | Ala | Leu | Ala | Ala | Ala | Gly | Leu | Val | |
| | 1355 | | | | 1360 | | | | | 1365 | | | | | |

| gga | gtg | ctg | gca | gga | ctg | gct | ttt | cag | gag | atg | gag | aac | ttc | ctt | 4267 |
| Gly | Val | Leu | Ala | Gly | Leu | Ala | Phe | Gln | Glu | Met | Glu | Asn | Phe | Leu | |
| | 1370 | | | | 1375 | | | | | 1380 | | | | | |

| ggt | ccg | att | gca | gtt | gga | gga | atc | ctg | atg | atg | ctg | gtt | agc | gtg | 4312 |
| Gly | Pro | Ile | Ala | Val | Gly | Gly | Ile | Leu | Met | Met | Leu | Val | Ser | Val | |
| | 1385 | | | | 1390 | | | | | 1395 | | | | | |

| gct | ggg | agg | gtg | gat | ggg | cta | gag | ctc | aag | aag | ctt | ggt | gaa | gtt | 4357 |
| Ala | Gly | Arg | Val | Asp | Gly | Leu | Glu | Leu | Lys | Lys | Leu | Gly | Glu | Val | |
| | 1400 | | | | 1405 | | | | | 1410 | | | | | |

| tca | tgg | gaa | gag | gag | gcg | gag | atc | agc | gga | agt | tcc | gcc | cgc | tat | 4402 |
| Ser | Trp | Glu | Glu | Glu | Ala | Glu | Ile | Ser | Gly | Ser | Ser | Ala | Arg | Tyr | |
| | 1415 | | | | 1420 | | | | | 1425 | | | | | |

| gat | gtg | gca | ctc | agt | gaa | caa | ggg | gag | ttc | aag | ctg | ctt | tct | gaa | 4447 |
| Asp | Val | Ala | Leu | Ser | Glu | Gln | Gly | Glu | Phe | Lys | Leu | Leu | Ser | Glu | |
| | 1430 | | | | 1435 | | | | | 1440 | | | | | |

| gag | aaa | gtg | cca | tgg | gac | cag | gtt | gtg | atg | acc | tcg | ctg | gcc | ttg | 4492 |
| Glu | Lys | Val | Pro | Trp | Asp | Gln | Val | Val | Met | Thr | Ser | Leu | Ala | Leu | |
| | 1445 | | | | 1450 | | | | | 1455 | | | | | |

| gtt | ggg | gct | gcc | att | cat | cca | ttt | gct | ctt | ctg | gtc | ctt | gct | 4537 |
| Val | Gly | Ala | Ala | Ile | His | Pro | Phe | Ala | Leu | Leu | Val | Leu | Ala | |
| | 1460 | | | | 1465 | | | | | 1470 | | | | | |

| ggg | tgg | ctg | ttt | cat | gtc | agg | gga | gct | agg | aga | agt | ggg | gat | gtc | 4582 |
| Gly | Trp | Leu | Phe | His | Val | Arg | Gly | Ala | Arg | Arg | Ser | Gly | Asp | Val | |
| | 1475 | | | | 1480 | | | | | 1485 | | | | | |

| ttg | tgg | gat | att | ccc | act | cct | aag | atc | att | gag | gaa | tgt | gaa | cat | 4627 |
| Leu | Trp | Asp | Ile | Pro | Thr | Pro | Lys | Ile | Ile | Glu | Glu | Cys | Glu | His | |
| | 1490 | | | | 1495 | | | | | 1500 | | | | | |

| ctg | gag | gat | ggg | att | tat | ggc | ata | ttc | cag | tca | acc | ttc | ttg | ggg | 4672 |
| Leu | Glu | Asp | Gly | Ile | Tyr | Gly | Ile | Phe | Gln | Ser | Thr | Phe | Leu | Gly | |
| | 1505 | | | | 1510 | | | | | 1515 | | | | | |

| gcc | tcc | cag | cga | gga | gtg | gga | gtg | gca | cag | gga | ggg | gtg | ttc | cac | 4717 |
| Ala | Ser | Gln | Arg | Gly | Val | Gly | Val | Ala | Gln | Gly | Gly | Val | Phe | His | |
| | 1520 | | | | 1525 | | | | | 1530 | | | | | |

| aca | atg | tgg | cat | gtc | aca | aga | gga | gct | ttc | ctt | gtc | agg | aat | ggc | 4762 |
| Thr | Met | Trp | His | Val | Thr | Arg | Gly | Ala | Phe | Leu | Val | Arg | Asn | Gly | |
| | 1535 | | | | 1540 | | | | | 1545 | | | | | |

| aag | aag | ttg | att | cca | tct | tgg | gct | tca | gta | aag | gaa | gac | ctt | gtc | 4807 |
| Lys | Lys | Leu | Ile | Pro | Ser | Trp | Ala | Ser | Val | Lys | Glu | Asp | Leu | Val | |
| | 1550 | | | | 1555 | | | | | 1560 | | | | | |

| gcc | tat | ggt | ggc | tca | tgg | aag | ttg | gaa | ggc | aga | tgg | gat | gga | gag | 4852 |
| Ala | Tyr | Gly | Gly | Ser | Trp | Lys | Leu | Glu | Gly | Arg | Trp | Asp | Gly | Glu | |
| | 1565 | | | | 1570 | | | | | 1575 | | | | | |

| gaa | gag | gtc | caa | ttg | atc | gct | gct | gtt | cca | gga | aag | aac | gtg | gtc | 4897 |
| Glu | Glu | Val | Gln | Leu | Ile | Ala | Ala | Val | Pro | Gly | Lys | Asn | Val | Val | |
| | 1580 | | | | 1585 | | | | | 1590 | | | | | |

| aac | gtc | cag | aca | aaa | ccg | agc | ttg | ttc | aaa | gtg | agg | aat | ggg | gga | 4942 |
| Asn | Val | Gln | Thr | Lys | Pro | Ser | Leu | Phe | Lys | Val | Arg | Asn | Gly | Gly | |
| | 1595 | | | | 1600 | | | | | 1605 | | | | | |

| gaa | atc | ggg | gct | gtc | gct | ctt | gac | tat | ccg | agt | ggc | act | tca | gga | 4987 |
| Glu | Ile | Gly | Ala | Val | Ala | Leu | Asp | Tyr | Pro | Ser | Gly | Thr | Ser | Gly | |
| | 1610 | | | | 1615 | | | | | 1620 | | | | | |

| tct | cct | att | gtt | aac | agg | aac | gga | gag | gtg | att | ggg | ctg | tac | ggc | 5032 |
| Ser | Pro | Ile | Val | Asn | Arg | Asn | Gly | Glu | Val | Ile | Gly | Leu | Tyr | Gly | |

-continued

```
            1625                1630                1635 aat  ggc  atc  ctt  gtc  ggt  gac  aac  tcc  ttc  gtg  tcc  gcc  ata  tcc     5077
Asn  Gly  Ile  Leu  Val  Gly  Asp  Asn  Ser  Phe  Val  Ser  Ala  Ile  Ser
     1640                1645                1650 cag  act  gag  gtg  aag  gaa  gaa  gga  aag  gag  gag  ctc  caa  gag  atc     5122
Gln  Thr  Glu  Val  Lys  Glu  Glu  Gly  Lys  Glu  Glu  Leu  Gln  Glu  Ile
     1655                1660                1665 ccg  aca  atg  cta  aag  aaa  gga  atg  aca  act  atc  ctt  gat  ttt  cat     5167
Pro  Thr  Met  Leu  Lys  Lys  Gly  Met  Thr  Thr  Ile  Leu  Asp  Phe  His
     1670                1675                1680 cct  gga  gct  ggg  aag  aca  aga  cgt  ttt  ctc  cca  cag  atc  ttg  gcc     5212
Pro  Gly  Ala  Gly  Lys  Thr  Arg  Arg  Phe  Leu  Pro  Gln  Ile  Leu  Ala
     1685                1690                1695 gag  tgc  gca  cgg  aga  cgc  ttg  cgc  act  ctt  gtg  ttg  gcc  ccc  acc     5257
Glu  Cys  Ala  Arg  Arg  Arg  Leu  Arg  Thr  Leu  Val  Leu  Ala  Pro  Thr
     1700                1705                1710 agg  gtt  gtt  ctt  tct  gaa  atg  aag  gag  gct  ttt  cac  ggc  ctg  gac     5302
Arg  Val  Val  Leu  Ser  Glu  Met  Lys  Glu  Ala  Phe  His  Gly  Leu  Asp
     1715                1720                1725 gtg  aaa  ttc  cac  aca  cag  gct  ttt  tcc  gct  cac  ggc  agc  ggg  aga     5347
Val  Lys  Phe  His  Thr  Gln  Ala  Phe  Ser  Ala  His  Gly  Ser  Gly  Arg
     1730                1735                1740 gaa  gtc  att  gat  gcc  atg  tgc  cat  gcc  acc  cta  act  tac  agg  atg     5392
Glu  Val  Ile  Asp  Ala  Met  Cys  His  Ala  Thr  Leu  Thr  Tyr  Arg  Met
     1745                1750                1755 ttg  gaa  cca  act  agg  gtt  gtt  aac  tgg  gaa  gtg  atc  atc  atg  gat     5437
Leu  Glu  Pro  Thr  Arg  Val  Val  Asn  Trp  Glu  Val  Ile  Ile  Met  Asp
     1760                1765                1770 gaa  gcc  cat  ttt  ttg  gat  cca  gct  agc  ata  gcc  gcc  aga  ggt  tgg     5482
Glu  Ala  His  Phe  Leu  Asp  Pro  Ala  Ser  Ile  Ala  Ala  Arg  Gly  Trp
     1775                1780                1785 gca  gcg  cac  aga  gct  agg  gca  aat  gaa  agt  gca  aca  atc  ttg  atg     5527
Ala  Ala  His  Arg  Ala  Arg  Ala  Asn  Glu  Ser  Ala  Thr  Ile  Leu  Met
     1790                1795                1800 aca  gcc  aca  ccg  cct  ggg  act  agt  gat  gaa  ttt  cca  cat  tca  aat     5572
Thr  Ala  Thr  Pro  Pro  Gly  Thr  Ser  Asp  Glu  Phe  Pro  His  Ser  Asn
     1805                1810                1815 ggt  gaa  ata  gaa  gat  gtt  caa  acg  gac  ata  ccc  agt  gag  ccc  tgg     5617
Gly  Glu  Ile  Glu  Asp  Val  Gln  Thr  Asp  Ile  Pro  Ser  Glu  Pro  Trp
     1820                1825                1830 aac  aca  ggg  cat  gac  tgg  atc  ctg  gct  gac  aaa  agg  ccc  acg  gca     5662
Asn  Thr  Gly  His  Asp  Trp  Ile  Leu  Ala  Asp  Lys  Arg  Pro  Thr  Ala
     1835                1840                1845 tgg  ttc  ctt  cca  tcc  atc  aga  gct  gca  aat  gtc  atg  gct  gcc  tct     5707
Trp  Phe  Leu  Pro  Ser  Ile  Arg  Ala  Ala  Asn  Val  Met  Ala  Ala  Ser
     1850                1855                1860 ttg  cgt  aag  gct  gga  aag  agt  gtg  gtg  gtc  ctg  aac  agg  aaa  acc     5752
Leu  Arg  Lys  Ala  Gly  Lys  Ser  Val  Val  Val  Leu  Asn  Arg  Lys  Thr
     1865                1870                1875 ttt  gag  aga  gaa  tac  ccc  acg  ata  aag  cag  aag  aaa  cct  gac  ttt     5797
Phe  Glu  Arg  Glu  Tyr  Pro  Thr  Ile  Lys  Gln  Lys  Lys  Pro  Asp  Phe
     1880                1885                1890 ata  ttg  gcc  act  gac  ata  gct  gaa  atg  gga  gcc  aac  ctt  tgc  gtg     5842
Ile  Leu  Ala  Thr  Asp  Ile  Ala  Glu  Met  Gly  Ala  Asn  Leu  Cys  Val
     1895                1900                1905 gag  cga  gtg  ctg  gat  tgc  agg  acg  gct  ttt  aag  cct  gtg  ctt  gtg     5887
Glu  Arg  Val  Leu  Asp  Cys  Arg  Thr  Ala  Phe  Lys  Pro  Val  Leu  Val
     1910                1915                1920 gat  gaa  ggg  agg  aag  gtg  gca  ata  aaa  ggg  cca  ctt  cgc  atc  tcc     5932
```

```
                                                            -continued

Asp Glu Gly Arg Lys Val Ala Ile Lys Gly Pro Leu Arg Ile Ser
    1925                1930                1935 gca tcc tct gct gct caa agg agg ggg cgc att ggg aga aat ccc      5977
Ala Ser Ser Ala Ala Gln Arg Arg Gly Arg Ile Gly Arg Asn Pro
    1940                1945                1950 aac aga gat gga gac tca tac tac tat tct gag cct aca agt gaa      6022
Asn Arg Asp Gly Asp Ser Tyr Tyr Tyr Ser Glu Pro Thr Ser Glu
    1955                1960                1965 gat aat gcc cac cac gtc tgc tgg ttg gag gcc tca atg ctc ttg      6067
Asp Asn Ala His His Val Cys Trp Leu Glu Ala Ser Met Leu Leu
    1970                1975                1980 gac aac atg gag gtg agg ggt gga atg gtc gcc cca ctc tat ggc      6112
Asp Asn Met Glu Val Arg Gly Gly Met Val Ala Pro Leu Tyr Gly
    1985                1990                1995 gtt gaa gga act aaa aca cca gtt tcc cct ggt gaa atg aga ctg      6157
Val Glu Gly Thr Lys Thr Pro Val Ser Pro Gly Glu Met Arg Leu
    2000                2005                2010 agg gat gac cag agg aaa gtc ttc aga gaa cta gtg agg aat tgt      6202
Arg Asp Asp Gln Arg Lys Val Phe Arg Glu Leu Val Arg Asn Cys
    2015                2020                2025 gac ctg ccc gtt tgg ctt tcg tgg caa gtg gcc aag gct ggt ttg      6247
Asp Leu Pro Val Trp Leu Ser Trp Gln Val Ala Lys Ala Gly Leu
    2030                2035                2040 aag acg aat gat cgt aag tgg tgt ttt gaa ggc cct gag gaa cat      6292
Lys Thr Asn Asp Arg Lys Trp Cys Phe Glu Gly Pro Glu Glu His
    2045                2050                2055 gag atc ttg aat gac agc ggt gaa aca gtg aag tgc agg gct cct      6337
Glu Ile Leu Asn Asp Ser Gly Glu Thr Val Lys Cys Arg Ala Pro
    2060                2065                2070 gga gga gca aag aag cct ctg cgc cca agg tgg tgt gat gaa agg      6382
Gly Gly Ala Lys Lys Pro Leu Arg Pro Arg Trp Cys Asp Glu Arg
    2075                2080                2085 gtg tca tct gac cag agt gcg ctg tct gaa ttt att aag ttt gct      6427
Val Ser Ser Asp Gln Ser Ala Leu Ser Glu Phe Ile Lys Phe Ala
    2090                2095                2100 gaa ggt agg agg gga gct gcg gaa gtg cta gtt gtg ctg agt gaa      6472
Glu Gly Arg Arg Gly Ala Ala Glu Val Leu Val Val Leu Ser Glu
    2105                2110                2115 ctc cct gat ttc ctg gct aaa aaa ggt gga gag gca atg gat acc      6517
Leu Pro Asp Phe Leu Ala Lys Lys Gly Gly Glu Ala Met Asp Thr
    2120                2125                2130 atc agt gtg ttt ctc cac tct gag gaa ggc tct agg gct tac cgc      6562
Ile Ser Val Phe Leu His Ser Glu Glu Gly Ser Arg Ala Tyr Arg
    2135                2140                2145 aat gca cta tca atg atg cct gag gca atg aca ata gtc atg ctg      6607
Asn Ala Leu Ser Met Met Pro Glu Ala Met Thr Ile Val Met Leu
    2150                2155                2160 ttt ata ctg gct gga cta ctg aca tcg gga atg gtc atc ttt ttc      6652
Phe Ile Leu Ala Gly Leu Leu Thr Ser Gly Met Val Ile Phe Phe
    2165                2170                2175 atg tct ccc aaa ggc atc agt aga atg tct atg gcg atg ggc aca      6697
Met Ser Pro Lys Gly Ile Ser Arg Met Ser Met Ala Met Gly Thr
    2180                2185                2190 atg gcc ggc tgt gga tat ctc atg ttc ctt gga ggc gtc aaa ccc      6742
Met Ala Gly Cys Gly Tyr Leu Met Phe Leu Gly Gly Val Lys Pro
    2195                2200                2205 act cac atc tcc tat atc atg ctc ata ttc ttt gtc ctg atg gtg      6787
Thr His Ile Ser Tyr Ile Met Leu Ile Phe Phe Val Leu Met Val
    2210                2215                2220
```

```
gtt gtg atc ccc gag cca ggg caa caa agg tcc atc caa gac aac    6832
Val Val Ile Pro Glu Pro Gly Gln Gln Arg Ser Ile Gln Asp Asn
    2225            2230                2235 caa gtg gca tac ctc att att ggc atc ctg acg ctg gtt tca gtg    6877
Gln Val Ala Tyr Leu Ile Ile Gly Ile Leu Thr Leu Val Ser Val
    2240            2245                2250 gtg gca gcc aac gag cta ggc atg ctg gag aaa acc aaa gag gac    6922
Val Ala Ala Asn Glu Leu Gly Met Leu Glu Lys Thr Lys Glu Asp
    2255            2260                2265 ctc ttt ggg aag aag aac tta att cca tct agt gct tca ccc tgg    6967
Leu Phe Gly Lys Lys Asn Leu Ile Pro Ser Ser Ala Ser Pro Trp
    2270            2275                2280 agt tgg ccg gat ctt gac ctg aag cca gga gct gcc tgg aca gtg    7012
Ser Trp Pro Asp Leu Asp Leu Lys Pro Gly Ala Ala Trp Thr Val
    2285            2290                2295 tac gtt ggc att gtt aca atg ctc tct gga atg ttg cac cac tgg    7057
Tyr Val Gly Ile Val Thr Met Leu Ser Gly Met Leu His His Trp
    2300            2305                2310 atc aaa gtc gaa tat ggc aac ctg tct ctg tct gga ata gcc cag    7102
Ile Lys Val Glu Tyr Gly Asn Leu Ser Leu Ser Gly Ile Ala Gln
    2315            2320                2325 tca gcc tca gtc ctt tct ttc atg gac aag ggg ata cca ttc atg    7147
Ser Ala Ser Val Leu Ser Phe Met Asp Lys Gly Ile Pro Phe Met
    2330            2335                2340 aag atg aat atc tcg gtc ata ata ctg ctg gtc agt ggc tgg aat    7192
Lys Met Asn Ile Ser Val Ile Ile Leu Leu Val Ser Gly Trp Asn
    2345            2350                2355 tca ata aca gtg atg cct ctg ctc tgt ggc ata ggg tgc gcc atg    7237
Ser Ile Thr Val Met Pro Leu Leu Cys Gly Ile Gly Cys Ala Met
    2360            2365                2370 ctc cac tgg tct ctc att tta cct gga atc aaa gcg cag cag tca    7282
Leu His Trp Ser Leu Ile Leu Pro Gly Ile Lys Ala Gln Gln Ser
    2375            2380                2385 aag ctt gca cag aga agg gtg ttc cat ggc gtt gcc aag aac cct    7327
Lys Leu Ala Gln Arg Arg Val Phe His Gly Val Ala Lys Asn Pro
    2390            2395                2400 gtg gtt gat ggg aat cca aca gtt gac att gag gaa gct cct gaa    7372
Val Val Asp Gly Asn Pro Thr Val Asp Ile Glu Glu Ala Pro Glu
    2405            2410                2415 atg cct gcc ctt tat gag aag aaa ctg gct cta tat ctc ctt ctt    7417
Met Pro Ala Leu Tyr Glu Lys Lys Leu Ala Leu Tyr Leu Leu Leu
    2420            2425                2430 gct ctc agc cta gct tct gtt gcc atg tgc aga acg ccc ttt tca    7462
Ala Leu Ser Leu Ala Ser Val Ala Met Cys Arg Thr Pro Phe Ser
    2435            2440                2445 ttg gct gaa ggc att gtc cta gca tca gct gcc tta ggg ccg ctc    7507
Leu Ala Glu Gly Ile Val Leu Ala Ser Ala Ala Leu Gly Pro Leu
    2450            2455                2460 ata gag gga aac acc agc ctt ctt tgg aat gga ccc atg gct gtc    7552
Ile Glu Gly Asn Thr Ser Leu Leu Trp Asn Gly Pro Met Ala Val
    2465            2470                2475 tcc atg aca gga gtc atg cgg ggg aat tac tat gct ttt gtg gga    7597
Ser Met Thr Gly Val Met Arg Gly Asn Tyr Tyr Ala Phe Val Gly
    2480            2485                2490 gtc atg tac aat cta tgg aag atg aaa act gga cgc cgg ggg agt    7642
Val Met Tyr Asn Leu Trp Lys Met Lys Thr Gly Arg Arg Gly Ser
    2495            2500                2505 gcg aat gga aaa act ttg ggt gaa gtc tgg aag agg gaa ctg aat    7687
Ala Asn Gly Lys Thr Leu Gly Glu Val Trp Lys Arg Glu Leu Asn
    2510            2515                2520
```

```
ctg ttg gac aag caa cag ttt gag ttg tat aaa agg acc gac att    7732
Leu Leu Asp Lys Gln Gln Phe Glu Leu Tyr Lys Arg Thr Asp Ile
    2525                2530                2535 gtg gag gtg gat cgt gat acg gca cgc agg cat ttg gcc gaa ggg    7777
Val Glu Val Asp Arg Asp Thr Ala Arg Arg His Leu Ala Glu Gly
2540                2545                2550 aag gtg gac acc ggg gtg gcg gtc tcc agg ggg acc gca aag tta    7822
Lys Val Asp Thr Gly Val Ala Val Ser Arg Gly Thr Ala Lys Leu
    2555                2560                2565 agg tgg ttc cat gag cgt ggc tat gtc aag ctg gaa ggt agg gtg    7867
Arg Trp Phe His Glu Arg Gly Tyr Val Lys Leu Glu Gly Arg Val
2570                2575                2580 att gac ctg ggg tgt ggc cgc gga ggc tgg tgt tac tac gct gct    7912
Ile Asp Leu Gly Cys Gly Arg Gly Gly Trp Cys Tyr Tyr Ala Ala
    2585                2590                2595 gcg caa aag gaa gtg agt ggg gtc aaa gga ttc act ctt gga aga    7957
Ala Gln Lys Glu Val Ser Gly Val Lys Gly Phe Thr Leu Gly Arg
2600                2605                2610 gac ggc cat gag aaa ccc atg aat gtg caa agt ctg gga tgg aac    8002
Asp Gly His Glu Lys Pro Met Asn Val Gln Ser Leu Gly Trp Asn
    2615                2620                2625 atc att acc ttc aag gac aaa act gat atc cac cgc cta gaa cca    8047
Ile Ile Thr Phe Lys Asp Lys Thr Asp Ile His Arg Leu Glu Pro
2630                2635                2640 gtg aaa tgt gac acc ctt ttg tgt gac att gga gag tca tca tcg    8092
Val Lys Cys Asp Thr Leu Leu Cys Asp Ile Gly Glu Ser Ser Ser
    2645                2650                2655 tca tcg gtc aca gag ggg gaa agg acc gtg aga gtt ctt gat act    8137
Ser Ser Val Thr Glu Gly Glu Arg Thr Val Arg Val Leu Asp Thr
2660                2665                2670 gta gaa aaa tgg ctg gct tgt ggg gtt gac aac ttc tgt gtg aag    8182
Val Glu Lys Trp Leu Ala Cys Gly Val Asp Asn Phe Cys Val Lys
    2675                2680                2685 gtg tta gct cca tac atg cca gat gtt ctc gag aaa ctg gaa ttg    8227
Val Leu Ala Pro Tyr Met Pro Asp Val Leu Glu Lys Leu Glu Leu
2690                2695                2700 ctc caa agg agg ttt ggc gga aca gtg atc agg aac cct ctc tcc    8272
Leu Gln Arg Arg Phe Gly Gly Thr Val Ile Arg Asn Pro Leu Ser
    2705                2710                2715 agg aat tcc act cat gaa atg tac tac gtg tct gga gcc cgc agc    8317
Arg Asn Ser Thr His Glu Met Tyr Tyr Val Ser Gly Ala Arg Ser
2720                2725                2730 aat gtc aca ttt act gtg aac caa aca tcc cgc ctc ctg atg agg    8362
Asn Val Thr Phe Thr Val Asn Gln Thr Ser Arg Leu Leu Met Arg
    2735                2740                2745 aga atg agg cgt cca act gga aaa gtg acc ctg gag gct gac gtc    8407
Arg Met Arg Arg Pro Thr Gly Lys Val Thr Leu Glu Ala Asp Val
2750                2755                2760 atc ctc cca att ggg aca cgc agt gtt gag aca gac aag gga ccc    8452
Ile Leu Pro Ile Gly Thr Arg Ser Val Glu Thr Asp Lys Gly Pro
    2765                2770                2775 ctg gac aaa gag gcc ata gaa gaa agg gtt gag agg ata aaa tct    8497
Leu Asp Lys Glu Ala Ile Glu Glu Arg Val Glu Arg Ile Lys Ser
2780                2785                2790 gag tac atg acc tct tgg ttt tat gac aat gac aac ccc tac agg    8542
Glu Tyr Met Thr Ser Trp Phe Tyr Asp Asn Asp Asn Pro Tyr Arg
    2795                2800                2805 acc tgg cac tac tgt ggc tcc tat gtc aca aaa acc tca gga agt    8587
Thr Trp His Tyr Cys Gly Ser Tyr Val Thr Lys Thr Ser Gly Ser
```

| | | | | | | | | | | | |
|---|---|---|---|---|---|---|---|---|---|---|---|
| | | 2810 | | | 2815 | | | 2820 | | | |
| gcg | gcg | agc | atg | gta | aat | ggt | gtt | att | aaa | att | ctg | aca | tac | cca | 8632 |
| Ala | Ala | Ser | Met | Val | Asn | Gly | Val | Ile | Lys | Ile | Leu | Thr | Tyr | Pro | |
| | 2825 | | | | 2830 | | | | 2835 | | | |

```
gcg gcg agc atg gta aat ggt gtt att aaa att ctg aca tac cca     8632
Ala Ala Ser Met Val Asn Gly Val Ile Lys Ile Leu Thr Tyr Pro
    2825              2830              2835 tgg gac agg ata gag gag gtc aca aga atg gca atg act gac aca     8677
Trp Asp Arg Ile Glu Glu Val Thr Arg Met Ala Met Thr Asp Thr
    2840              2845              2850 acc cct ttt gga cag caa aga gtg ttt aaa gaa aaa gtt gac acc     8722
Thr Pro Phe Gly Gln Gln Arg Val Phe Lys Glu Lys Val Asp Thr
    2855              2860              2865 aga gca aag gat cca cca gcg gga act agg aag atc atg aaa gtt     8767
Arg Ala Lys Asp Pro Pro Ala Gly Thr Arg Lys Ile Met Lys Val
    2870              2875              2880 gtc aac agg tgg ctg ttc cgc cac ctg gcc aga gaa aag aac ccc     8812
Val Asn Arg Trp Leu Phe Arg His Leu Ala Arg Glu Lys Asn Pro
    2885              2890              2895 aga ctg tgc aca aag gaa gaa ttt att gca aaa gtc cga agt cat     8857
Arg Leu Cys Thr Lys Glu Glu Phe Ile Ala Lys Val Arg Ser His
    2900              2905              2910 gca gcc att gga gct tac ctg gaa gaa caa gaa cag tgg aag act     8902
Ala Ala Ile Gly Ala Tyr Leu Glu Glu Gln Glu Gln Trp Lys Thr
    2915              2920              2925 gcc aat gag gct gtc caa gac cca aag ttc tgg gaa ctg gtg gat     8947
Ala Asn Glu Ala Val Gln Asp Pro Lys Phe Trp Glu Leu Val Asp
    2930              2935              2940 gaa gaa agg aag ctg cac caa caa ggc agg tgt cgg act tgt gtg     8992
Glu Glu Arg Lys Leu His Gln Gln Gly Arg Cys Arg Thr Cys Val
    2945              2950              2955 tac aac atg atg ggg aaa aga gag aag aag ctg tca gag ttt ggg     9037
Tyr Asn Met Met Gly Lys Arg Glu Lys Lys Leu Ser Glu Phe Gly
    2960              2965              2970 aaa gca aag gga agc cgt gcc ata tgg tat atg tgg ctg gga gcg     9082
Lys Ala Lys Gly Ser Arg Ala Ile Trp Tyr Met Trp Leu Gly Ala
    2975              2980              2985 cgg tat ctt gag ttt gag gcc ctg gga ttc ctg aat gag gac cat     9127
Arg Tyr Leu Glu Phe Glu Ala Leu Gly Phe Leu Asn Glu Asp His
    2990              2995              3000 tgg gct tcc agg gaa aac tca gga gga gga gtg gaa ggc att ggc     9172
Trp Ala Ser Arg Glu Asn Ser Gly Gly Gly Val Glu Gly Ile Gly
    3005              3010              3015 tta caa tac cta gga tat gtg atc aga gac ctg gct gca atg gat     9217
Leu Gln Tyr Leu Gly Tyr Val Ile Arg Asp Leu Ala Ala Met Asp
    3020              3025              3030 ggt ggt gga ttc tac gcg gat gac acc gct gga tgg gac acg cgc     9262
Gly Gly Gly Phe Tyr Ala Asp Asp Thr Ala Gly Trp Asp Thr Arg
    3035              3040              3045 atc aca gag gca gac ctt gat gat gaa cag gag atc ttg aac tac     9307
Ile Thr Glu Ala Asp Leu Asp Asp Glu Gln Glu Ile Leu Asn Tyr
    3050              3055              3060 atg agc cca cat cac aaa aaa ctg gca caa gca gtg atg gaa atg     9352
Met Ser Pro His His Lys Lys Leu Ala Gln Ala Val Met Glu Met
    3065              3070              3075 aca tac aag aac aaa gtg gtg aaa gtg ttg aga cca gcc cca gga     9397
Thr Tyr Lys Asn Lys Val Val Lys Val Leu Arg Pro Ala Pro Gly
    3080              3085              3090 ggg aaa gcc tac atg gat gtc ata agt cga cga gac cag aga gga     9442
Gly Lys Ala Tyr Met Asp Val Ile Ser Arg Arg Asp Gln Arg Gly
    3095              3100              3105 tcc ggg cag gta gtg act tat gct ctg aac acc atc acc aac ttg     9487
```

```
Ser Gly Gln Val Val Thr Tyr Ala Leu Asn Thr Ile Thr Asn Leu
    3110            3115            3120 aaa gtc caa ttg atc aga atg gca gaa gca gag atg gtg ata cat    9532
Lys Val Gln Leu Ile Arg Met Ala Glu Ala Glu Met Val Ile His
3125            3130            3135 cac caa cat gtt caa gat tgt gat gaa tca gtt ctg acc agg ctg    9577
His Gln His Val Gln Asp Cys Asp Glu Ser Val Leu Thr Arg Leu
3140            3145            3150 gag gca tgg ctc act gag cac gga tgt aac aga ctg aag agg atg    9622
Glu Ala Trp Leu Thr Glu His Gly Cys Asn Arg Leu Lys Arg Met
3155            3160            3165 gcg gtg agt gga gac gac tgt gtg gtc cgg ccc atc gat gac agg    9667
Ala Val Ser Gly Asp Asp Cys Val Val Arg Pro Ile Asp Asp Arg
3170            3175            3180 ttc ggc ctg gcc ctg tcc cat ctc aac gcc atg tcc aag gtt aga    9712
Phe Gly Leu Ala Leu Ser His Leu Asn Ala Met Ser Lys Val Arg
3185            3190            3195 aag gac ata tct gaa tgg cag cca tca aaa ggg tgg aat gat tgg    9757
Lys Asp Ile Ser Glu Trp Gln Pro Ser Lys Gly Trp Asn Asp Trp
3200            3205            3210 gag aat gtg ccc ttc tgt tcc cac cac ttc cat gaa cta cag ctg    9802
Glu Asn Val Pro Phe Cys Ser His His Phe His Glu Leu Gln Leu
3215            3220            3225 aag gat ggc agg agg att gtg gtg cct tgc cga gaa cag gac gag    9847
Lys Asp Gly Arg Arg Ile Val Val Pro Cys Arg Glu Gln Asp Glu
3230            3235            3240 ctc att ggg aga gga agg gtg tct cca gga aac ggc tgg atg atc    9892
Leu Ile Gly Arg Gly Arg Val Ser Pro Gly Asn Gly Trp Met Ile
3245            3250            3255 aag gaa aca gct tgc ctc agc aaa gcc tat gcc aac atg tgg tca    9937
Lys Glu Thr Ala Cys Leu Ser Lys Ala Tyr Ala Asn Met Trp Ser
3260            3265            3270 ctg atg tat ttt cac aaa agg gac atg agg cta ctg tca ttg gct    9982
Leu Met Tyr Phe His Lys Arg Asp Met Arg Leu Leu Ser Leu Ala
3275            3280            3285 gtt tcc tca gct gtt ccc acc tca tgg gtt cca caa gga cgc aca    10027
Val Ser Ser Ala Val Pro Thr Ser Trp Val Pro Gln Gly Arg Thr
3290            3295            3300 aca tgg tcg att cat ggg aaa ggg gag tgg atg acc acg gaa gac    10072
Thr Trp Ser Ile His Gly Lys Gly Glu Trp Met Thr Thr Glu Asp
3305            3310            3315 atg ctt gag gtg tgg aac aga gta tgg ata acc aac aac cca cac    10117
Met Leu Glu Val Trp Asn Arg Val Trp Ile Thr Asn Asn Pro His
3320            3325            3330 atg cag gac aag aca atg gtg aaa gaa tgg aga gat gtc cct tat    10162
Met Gln Asp Lys Thr Met Val Lys Glu Trp Arg Asp Val Pro Tyr
3335            3340            3345 cta acc aag aga caa gac aag ctg tgc gga tca ctg att gga atg    10207
Leu Thr Lys Arg Gln Asp Lys Leu Cys Gly Ser Leu Ile Gly Met
3350            3355            3360 acc aat agg gcc acc tgg gcc tcc cac atc cat ttg gtc atc cat    10252
Thr Asn Arg Ala Thr Trp Ala Ser His Ile His Leu Val Ile His
3365            3370            3375 cgt atc cga acg ctg att gga cag gag aaa tat act gac tac cta    10297
Arg Ile Arg Thr Leu Ile Gly Gln Glu Lys Tyr Thr Asp Tyr Leu
3380            3385            3390 aca gtc atg gac aga tat tct gtg gat gct gac ctg caa ccg ggt    10342
Thr Val Met Asp Arg Tyr Ser Val Asp Ala Asp Leu Gln Pro Gly
3395            3400            3405
```

```
gag ctt atc tga aacaccatct aataggaata accgggatac aaaccacggg    10394
Glu Leu Ile
    3410 tggagaaccg gactccccac aacttgaaac cgggatataa accacggctg gagaaccgga    10454 ctccgcactt aaaatgaaac agaaaccggg ataaaaacta cggatggaga accggactcc    10514 acacattgag acagaagaag ttgtcagccc agaactccac acgagttttg ccactgctaa    10574 gctgtgaggc agtgcaggct gggacagccg acctccaggt tgcgaaaaac ctggtttctg    10634 ggacctccca ccccagagta aaagaacgg agcctccgct accaccctcc cacgtggtgg    10694 tagaaagacg gggtctagag gttagaggag accctccagg gaacaaatag tgggaccata    10754 ttgacgccag ggaagaccg gagtggttct ctgcttttcc tccagggtc tgtgagcaca    10814 gtttgctcaa gaataagcag acctttggat gaaaaacaca aaaccact              10862
```

<210> SEQ ID NO 8
<211> LENGTH: 3411
<212> TYPE: PRT
<213> ORGANISM: Yellow fever virus

<400> SEQUENCE: 8

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
                20                  25                  30

Gln Ile Gly Asn Arg Pro Gly Pro Ser Arg Gly Val Gln Gly Phe Ile
            35                  40                  45

Phe Phe Phe Leu Phe Asn Ile Leu Thr Gly Lys Lys Ile Thr Ala His
        50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
                100                 105                 110

Leu Gly Met Leu Leu Met Thr Gly Gly Val Thr Leu Val Arg Lys Asn
            115                 120                 125

Arg Trp Leu Leu Leu Asn Val Thr Ser Glu Asp Leu Gly Lys Thr Phe
        130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
            180                 185                 190

Arg Val Ala Tyr Gly Lys Cys Asp Ser Ala Gly Arg Ser Arg Arg Ser
        195                 200                 205

Arg Arg Ala Ile Asp Leu Pro Thr His Glu Asn His Gly Leu Lys Thr
    210                 215                 220

Arg Gln Glu Lys Trp Met Thr Gly Arg Met Gly Glu Arg Gln Leu Gln
225                 230                 235                 240

Lys Ile Glu Arg Trp Leu Val Arg Asn Pro Phe Phe Ala Val Thr Ala
                245                 250                 255

Leu Thr Ile Ala Tyr Leu Val Gly Ser Asn Met Thr Gln Arg Val Val
            260                 265                 270
```

```
Ile Ala Leu Leu Val Leu Ala Val Gly Pro Ala Tyr Ser Ala His Cys
            275                 280                 285

Ile Gly Ile Thr Asp Arg Asp Phe Ile Glu Gly Val His Gly Gly Thr
        290                 295                 300

Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
                325                 330                 335

Gly Pro Ala Glu Ala Arg Lys Val Cys Tyr Asn Ala Val Leu Thr His
            340                 345                 350

Val Lys Ile Asn Asp Lys Cys Pro Ser Thr Gly Glu Ala His Leu Ala
        355                 360                 365

Glu Glu Asn Glu Gly Asp Asn Ala Cys Lys Arg Thr Tyr Ser Asp Arg
370                 375                 380

Gly Trp Gly Asn Gly Cys Gly Leu Phe Gly Lys Gly Ser Ile Val Ala
385                 390                 395                 400

Cys Ala Lys Phe Thr Cys Ala Lys Ser Met Ser Leu Phe Glu Val Asp
                405                 410                 415

Gln Thr Lys Ile Gln Tyr Val Ile Arg Ala Gln Leu His Val Gly Ala
            420                 425                 430

Lys Gln Glu Asn Trp Asn Thr Asp Ile Lys Thr Leu Lys Phe Asp Ala
        435                 440                 445

Leu Ser Gly Ser Gln Glu Ala Glu Phe Thr Gly Tyr Gly Lys Ala Thr
            450                 455                 460

Leu Glu Cys Gln Val Gln Thr Ala Val Asp Phe Gly Asn Ser Tyr Ile
465                 470                 475                 480

Ala Glu Met Glu Lys Glu Ser Trp Ile Val Asp Arg Gln Trp Ala Gln
                485                 490                 495

Asp Leu Thr Leu Pro Trp Gln Ser Gly Ser Gly Val Trp Arg Glu
            500                 505                 510

Met His His Leu Val Glu Phe Glu Pro Pro His Ala Ala Thr Ile Arg
            515                 520                 525

Val Leu Ala Leu Gly Asn Gln Glu Gly Ser Leu Lys Thr Ala Leu Thr
        530                 535                 540

Gly Ala Met Arg Val Thr Lys Asp Thr Asn Asp Asn Leu Tyr Lys
545                 550                 555                 560

Leu His Gly Gly His Val Ser Cys Arg Val Lys Leu Ser Ala Leu Thr
                565                 570                 575

Leu Lys Gly Thr Ser Tyr Lys Met Cys Thr Asp Lys Met Ser Phe Val
            580                 585                 590

Lys Asn Pro Thr Asp Thr Gly His Gly Thr Val Val Met Gln Val Lys
        595                 600                 605

Val Pro Lys Gly Ala Pro Cys Lys Ile Pro Val Ile Val Ala Asp Asp
        610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
                645                 650                 655

Gly Asp Ser Tyr Ile Ile Val Gly Thr Gly Asp Ser Arg Leu Thr Tyr
            660                 665                 670

Gln Trp His Lys Glu Gly Ser Ser Ile Gly Lys Leu Phe Thr Gln Thr
        675                 680                 685

Met Lys Gly Ala Glu Arg Leu Ala Val Met Gly Asp Ala Ala Trp Asp
```

690             695             700
Phe Ser Ser Ala Gly Gly Phe Thr Ser Val Gly Lys Gly Ile His
705             710             715             720

Thr Val Phe Gly Ser Ala Phe Gln Gly Leu Phe Gly Gly Leu Asn Trp
                725             730             735

Ile Thr Lys Val Ile Met Gly Ala Val Leu Ile Trp Val Gly Ile Asn
                740             745             750

Thr Arg Asn Met Thr Met Ser Met Ser Met Ile Leu Val Gly Val Ile
                755             760             765

Met Met Phe Leu Ser Leu Gly Val Gly Ala Asp Gln Gly Cys Ala Ile
                770             775             780

Asn Phe Gly Lys Arg Glu Leu Lys Cys Gly Asp Gly Ile Phe Ile Phe
785             790             795             800

Arg Asp Ser Asp Asp Trp Leu Asn Lys Tyr Ser Tyr Tyr Pro Glu Asp
                805             810             815

Pro Val Lys Leu Ala Ser Ile Val Lys Ala Ser Phe Glu Glu Gly Lys
                820             825             830

Cys Gly Leu Asn Ser Val Asp Ser Leu Glu His Glu Met Trp Arg Ser
                835             840             845

Arg Ala Asp Glu Ile Asn Ala Ile Leu Glu Glu Asn Glu Val Asp Ile
850             855             860

Ser Val Val Val Gln Asp Pro Lys Asn Val Tyr Gln Arg Gly Thr His
865             870             875             880

Pro Phe Ser Arg Ile Arg Asp Gly Leu Gln Tyr Gly Trp Lys Thr Trp
                885             890             895

Gly Lys Asn Leu Val Phe Ser Pro Gly Arg Lys Asn Gly Ser Phe Ile
                900             905             910

Ile Asp Gly Lys Ser Arg Lys Glu Cys Pro Phe Ser Asn Arg Val Trp
                915             920             925

Asn Ser Phe Gln Ile Glu Glu Phe Gly Thr Gly Val Phe Thr Thr Arg
930             935             940

Val Tyr Met Asp Ala Val Phe Glu Tyr Thr Ile Asp Cys Asp Gly Ser
945             950             955             960

Ile Leu Gly Ala Ala Val Asn Gly Lys Lys Ser Ala His Gly Ser Pro
                965             970             975

Thr Phe Trp Met Gly Ser His Glu Val Asn Gly Thr Trp Met Ile His
                980             985             990

Thr Leu Glu Ala Leu Asp Tyr Lys Glu Cys Glu Trp Pro Leu Thr His
                995             1000            1005

Thr Ile Gly Thr Ser Val Glu Glu Ser Glu Met Phe Met Pro Arg
    1010            1015            1020

Ser Ile Gly Gly Pro Val Ser Ser His Asn His Ile Pro Gly Tyr
    1025            1030            1035

Lys Val Gln Thr Asn Gly Pro Trp Met Gln Val Pro Leu Glu Val
    1040            1045            1050

Lys Arg Glu Ala Cys Pro Gly Thr Ser Val Ile Ile Asp Gly Asn
    1055            1060            1065

Cys Asp Gly Arg Gly Lys Ser Thr Arg Ser Thr Thr Asp Ser Gly
    1070            1075            1080

Lys Ile Ile Pro Glu Trp Cys Cys Arg Ser Cys Thr Met Pro Pro
    1085            1090            1095

Val Ser Phe His Gly Ser Asp Gly Cys Trp Tyr Pro Met Glu Ile
    1100            1105            1110

Arg Pro Arg Lys Thr His Glu Ser His Leu Val Arg Ser Trp Val
1115                1120                1125

Thr Ala Gly Glu Ile His Ala Val Pro Phe Gly Leu Val Ser Met
1130                1135                1140

Met Ile Ala Met Glu Val Val Leu Arg Lys Arg Gln Gly Pro Lys
1145                1150                1155

Gln Met Leu Val Gly Gly Val Val Leu Leu Gly Ala Met Leu Val
1160                1165                1170

Gly Gln Val Thr Leu Leu Asp Leu Leu Lys Leu Thr Val Ala Val
1175                1180                1185

Gly Leu His Phe His Glu Met Asn Asn Gly Gly Asp Ala Met Tyr
1190                1195                1200

Met Ala Leu Ile Ala Ala Phe Ser Ile Arg Pro Gly Leu Leu Ile
1205                1210                1215

Gly Phe Gly Leu Arg Thr Leu Trp Ser Pro Arg Glu Arg Leu Val
1220                1225                1230

Leu Thr Leu Gly Ala Ala Met Val Glu Ile Ala Leu Gly Gly Met
1235                1240                1245

Met Gly Gly Leu Trp Lys Tyr Leu Asn Ala Val Ser Leu Cys Ile
1250                1255                1260

Leu Thr Ile Asn Ala Val Ala Ser Arg Lys Ala Ser Asn Thr Ile
1265                1270                1275

Leu Pro Leu Met Ala Leu Leu Thr Pro Val Thr Met Ala Glu Val
1280                1285                1290

Arg Leu Ala Thr Met Leu Phe Cys Thr Val Val Ile Ile Gly Val
1295                1300                1305

Leu His Gln Asn Ser Lys Asp Thr Ser Met Gln Lys Thr Ile Pro
1310                1315                1320

Leu Val Ala Leu Thr Leu Thr Ser Tyr Leu Gly Leu Thr Gln Pro
1325                1330                1335

Phe Leu Gly Leu Cys Ala Phe Leu Ala Thr Arg Ile Phe Gly Arg
1340                1345                1350

Arg Ser Ile Pro Val Asn Glu Ala Leu Ala Ala Ala Gly Leu Val
1355                1360                1365

Gly Val Leu Ala Gly Leu Ala Phe Gln Glu Met Glu Asn Phe Leu
1370                1375                1380

Gly Pro Ile Ala Val Gly Gly Ile Leu Met Met Leu Val Ser Val
1385                1390                1395

Ala Gly Arg Val Asp Gly Leu Glu Leu Lys Lys Leu Gly Glu Val
1400                1405                1410

Ser Trp Glu Glu Glu Ala Glu Ile Ser Gly Ser Ser Ala Arg Tyr
1415                1420                1425

Asp Val Ala Leu Ser Glu Gln Gly Glu Phe Lys Leu Leu Ser Glu
1430                1435                1440

Glu Lys Val Pro Trp Asp Gln Val Val Met Thr Ser Leu Ala Leu
1445                1450                1455

Val Gly Ala Ala Ile His Pro Phe Ala Leu Leu Leu Val Leu Ala
1460                1465                1470

Gly Trp Leu Phe His Val Arg Gly Ala Arg Arg Ser Gly Asp Val
1475                1480                1485

Leu Trp Asp Ile Pro Thr Pro Lys Ile Ile Glu Glu Cys Glu His
1490                1495                1500

```
Leu Glu Asp Gly Ile Tyr Gly Ile Phe Gln Ser Thr Phe Leu Gly
1505                1510                1515

Ala Ser Gln Arg Gly Val Gly Val Ala Gln Gly Gly Val Phe His
1520                1525                1530

Thr Met Trp His Val Thr Arg Gly Ala Phe Leu Val Arg Asn Gly
1535                1540                1545

Lys Lys Leu Ile Pro Ser Trp Ala Ser Val Lys Glu Asp Leu Val
1550                1555                1560

Ala Tyr Gly Gly Ser Trp Lys Leu Glu Gly Arg Trp Asp Gly Glu
1565                1570                1575

Glu Glu Val Gln Leu Ile Ala Ala Val Pro Gly Lys Asn Val Val
1580                1585                1590

Asn Val Gln Thr Lys Pro Ser Leu Phe Lys Val Arg Asn Gly Gly
1595                1600                1605

Glu Ile Gly Ala Val Ala Leu Asp Tyr Pro Ser Gly Thr Ser Gly
1610                1615                1620

Ser Pro Ile Val Asn Arg Asn Gly Glu Val Ile Gly Leu Tyr Gly
1625                1630                1635

Asn Gly Ile Leu Val Gly Asp Asn Ser Phe Val Ser Ala Ile Ser
1640                1645                1650

Gln Thr Glu Val Lys Glu Glu Gly Lys Glu Glu Leu Gln Glu Ile
1655                1660                1665

Pro Thr Met Leu Lys Lys Gly Met Thr Thr Ile Leu Asp Phe His
1670                1675                1680

Pro Gly Ala Gly Lys Thr Arg Arg Phe Leu Pro Gln Ile Leu Ala
1685                1690                1695

Glu Cys Ala Arg Arg Arg Leu Arg Thr Leu Val Leu Ala Pro Thr
1700                1705                1710

Arg Val Val Leu Ser Glu Met Lys Glu Ala Phe His Gly Leu Asp
1715                1720                1725

Val Lys Phe His Thr Gln Ala Phe Ser Ala His Gly Ser Gly Arg
1730                1735                1740

Glu Val Ile Asp Ala Met Cys His Ala Thr Leu Thr Tyr Arg Met
1745                1750                1755

Leu Glu Pro Thr Arg Val Val Asn Trp Glu Val Ile Ile Met Asp
1760                1765                1770

Glu Ala His Phe Leu Asp Pro Ala Ser Ile Ala Ala Arg Gly Trp
1775                1780                1785

Ala Ala His Arg Ala Arg Ala Asn Glu Ser Ala Thr Ile Leu Met
1790                1795                1800

Thr Ala Thr Pro Pro Gly Thr Ser Asp Glu Phe Pro His Ser Asn
1805                1810                1815

Gly Glu Ile Glu Asp Val Gln Thr Asp Ile Pro Ser Glu Pro Trp
1820                1825                1830

Asn Thr Gly His Asp Trp Ile Leu Ala Asp Lys Arg Pro Thr Ala
1835                1840                1845

Trp Phe Leu Pro Ser Ile Arg Ala Ala Asn Val Met Ala Ala Ser
1850                1855                1860

Leu Arg Lys Ala Gly Lys Ser Val Val Val Leu Asn Arg Lys Thr
1865                1870                1875

Phe Glu Arg Glu Tyr Pro Thr Ile Lys Gln Lys Lys Pro Asp Phe
1880                1885                1890

Ile Leu Ala Thr Asp Ile Ala Glu Met Gly Ala Asn Leu Cys Val
```

```
            1895                1900                1905
Glu Arg Val Leu Asp Cys Arg Thr Ala Phe Lys Pro Val Leu Val
            1910                1915                1920

Asp Glu Gly Arg Lys Val Ala Ile Lys Gly Pro Leu Arg Ile Ser
            1925                1930                1935

Ala Ser Ser Ala Ala Gln Arg Arg Gly Arg Ile Gly Arg Asn Pro
            1940                1945                1950

Asn Arg Asp Gly Asp Ser Tyr Tyr Tyr Ser Glu Pro Thr Ser Glu
            1955                1960                1965

Asp Asn Ala His His Val Cys Trp Leu Glu Ala Ser Met Leu Leu
            1970                1975                1980

Asp Asn Met Glu Val Arg Gly Gly Met Val Ala Pro Leu Tyr Gly
            1985                1990                1995

Val Glu Gly Thr Lys Thr Pro Val Ser Pro Gly Glu Met Arg Leu
            2000                2005                2010

Arg Asp Asp Gln Arg Lys Val Phe Arg Glu Leu Val Arg Asn Cys
            2015                2020                2025

Asp Leu Pro Val Trp Leu Ser Trp Gln Val Ala Lys Ala Gly Leu
            2030                2035                2040

Lys Thr Asn Asp Arg Lys Trp Cys Phe Glu Gly Pro Glu Glu His
            2045                2050                2055

Glu Ile Leu Asn Asp Ser Gly Glu Thr Val Lys Cys Arg Ala Pro
            2060                2065                2070

Gly Gly Ala Lys Lys Pro Leu Arg Pro Arg Trp Cys Asp Glu Arg
            2075                2080                2085

Val Ser Ser Asp Gln Ser Ala Leu Ser Glu Phe Ile Lys Phe Ala
            2090                2095                2100

Glu Gly Arg Arg Gly Ala Ala Glu Val Leu Val Val Leu Ser Glu
            2105                2110                2115

Leu Pro Asp Phe Leu Ala Lys Lys Gly Gly Glu Ala Met Asp Thr
            2120                2125                2130

Ile Ser Val Phe Leu His Ser Glu Glu Gly Ser Arg Ala Tyr Arg
            2135                2140                2145

Asn Ala Leu Ser Met Met Pro Glu Ala Met Thr Ile Val Met Leu
            2150                2155                2160

Phe Ile Leu Ala Gly Leu Leu Thr Ser Gly Met Val Ile Phe Phe
            2165                2170                2175

Met Ser Pro Lys Gly Ile Ser Arg Met Ser Met Ala Met Gly Thr
            2180                2185                2190

Met Ala Gly Cys Gly Tyr Leu Met Phe Leu Gly Gly Val Lys Pro
            2195                2200                2205

Thr His Ile Ser Tyr Ile Met Leu Ile Phe Phe Val Leu Met Val
            2210                2215                2220

Val Val Ile Pro Glu Pro Gly Gln Gln Arg Ser Ile Gln Asp Asn
            2225                2230                2235

Gln Val Ala Tyr Leu Ile Ile Gly Ile Leu Thr Leu Val Ser Val
            2240                2245                2250

Val Ala Ala Asn Glu Leu Gly Met Leu Glu Lys Thr Lys Glu Asp
            2255                2260                2265

Leu Phe Gly Lys Lys Asn Leu Ile Pro Ser Ser Ala Ser Pro Trp
            2270                2275                2280

Ser Trp Pro Asp Leu Asp Leu Lys Pro Gly Ala Ala Trp Thr Val
            2285                2290                2295
```

```
Tyr Val Gly Ile Val Thr Met Leu Ser Gly Met Leu His His Trp
         2300                2305            2310

Ile Lys Val Glu Tyr Gly Asn Leu Ser Leu Ser Gly Ile Ala Gln
         2315                2320            2325

Ser Ala Ser Val Leu Ser Phe Met Asp Lys Gly Ile Pro Phe Met
         2330                2335            2340

Lys Met Asn Ile Ser Val Ile Ile Leu Leu Val Ser Gly Trp Asn
         2345                2350            2355

Ser Ile Thr Val Met Pro Leu Leu Cys Gly Ile Gly Cys Ala Met
         2360                2365            2370

Leu His Trp Ser Leu Ile Leu Pro Gly Ile Lys Ala Gln Gln Ser
         2375                2380            2385

Lys Leu Ala Gln Arg Arg Val Phe His Gly Val Ala Lys Asn Pro
         2390                2395            2400

Val Val Asp Gly Asn Pro Thr Val Asp Ile Glu Glu Ala Pro Glu
         2405                2410            2415

Met Pro Ala Leu Tyr Glu Lys Lys Leu Ala Leu Tyr Leu Leu Leu
         2420                2425            2430

Ala Leu Ser Leu Ala Ser Val Ala Met Cys Arg Thr Pro Phe Ser
         2435                2440            2445

Leu Ala Glu Gly Ile Val Leu Ala Ser Ala Ala Leu Gly Pro Leu
         2450                2455            2460

Ile Glu Gly Asn Thr Ser Leu Leu Trp Asn Gly Pro Met Ala Val
         2465                2470            2475

Ser Met Thr Gly Val Met Arg Gly Asn Tyr Tyr Ala Phe Val Gly
         2480                2485            2490

Val Met Tyr Asn Leu Trp Lys Met Lys Thr Gly Arg Arg Gly Ser
         2495                2500            2505

Ala Asn Gly Lys Thr Leu Gly Glu Val Trp Lys Arg Glu Leu Asn
         2510                2515            2520

Leu Leu Asp Lys Gln Gln Phe Glu Leu Tyr Lys Arg Thr Asp Ile
         2525                2530            2535

Val Glu Val Asp Arg Asp Thr Ala Arg Arg His Leu Ala Glu Gly
         2540                2545            2550

Lys Val Asp Thr Gly Val Ala Val Ser Arg Gly Thr Ala Lys Leu
         2555                2560            2565

Arg Trp Phe His Glu Arg Gly Tyr Val Lys Leu Glu Gly Arg Val
         2570                2575            2580

Ile Asp Leu Gly Cys Gly Arg Gly Gly Trp Cys Tyr Tyr Ala Ala
         2585                2590            2595

Ala Gln Lys Glu Val Ser Gly Val Lys Gly Phe Thr Leu Gly Arg
         2600                2605            2610

Asp Gly His Glu Lys Pro Met Asn Val Gln Ser Leu Gly Trp Asn
         2615                2620            2625

Ile Ile Thr Phe Lys Asp Lys Thr Asp Ile His Arg Leu Glu Pro
         2630                2635            2640

Val Lys Cys Asp Thr Leu Leu Cys Asp Ile Gly Glu Ser Ser Ser
         2645                2650            2655

Ser Ser Val Thr Glu Gly Glu Arg Thr Val Arg Val Leu Asp Thr
         2660                2665            2670

Val Glu Lys Trp Leu Ala Cys Gly Val Asp Asn Phe Cys Val Lys
         2675                2680            2685
```

-continued

| | | | | | | | | | | | |
|---|---|---|---|---|---|---|---|---|---|---|---|
| Val | Leu | Ala | Pro | Tyr | Met | Pro | Asp | Val | Leu | Glu | Lys | Leu | Glu | Leu |
| 2690 | | | | | 2695 | | | | | 2700 | | | | |

Val Leu Ala Pro Tyr Met Pro Asp Val Leu Glu Lys Leu Glu Leu
2690                     2695                2700

Leu Gln Arg Arg Phe Gly Gly Thr Val Ile Arg Asn Pro Leu Ser
2705                     2710                2715

Arg Asn Ser Thr His Glu Met Tyr Tyr Val Ser Gly Ala Arg Ser
2720                     2725                2730

Asn Val Thr Phe Thr Val Asn Gln Thr Ser Arg Leu Leu Met Arg
2735                     2740                2745

Arg Met Arg Arg Pro Thr Gly Lys Val Thr Leu Glu Ala Asp Val
2750                     2755                2760

Ile Leu Pro Ile Gly Thr Arg Ser Val Glu Thr Asp Lys Gly Pro
2765                     2770                2775

Leu Asp Lys Glu Ala Ile Glu Glu Arg Val Glu Arg Ile Lys Ser
2780                     2785                2790

Glu Tyr Met Thr Ser Trp Phe Tyr Asp Asn Asp Asn Pro Tyr Arg
2795                     2800                2805

Thr Trp His Tyr Cys Gly Ser Tyr Val Thr Lys Thr Ser Gly Ser
2810                     2815                2820

Ala Ala Ser Met Val Asn Gly Val Ile Lys Ile Leu Thr Tyr Pro
2825                     2830                2835

Trp Asp Arg Ile Glu Glu Val Thr Arg Met Ala Met Thr Asp Thr
2840                     2845                2850

Thr Pro Phe Gly Gln Gln Arg Val Phe Lys Glu Lys Val Asp Thr
2855                     2860                2865

Arg Ala Lys Asp Pro Pro Ala Gly Thr Arg Lys Ile Met Lys Val
2870                     2875                2880

Val Asn Arg Trp Leu Phe Arg His Leu Ala Arg Glu Lys Asn Pro
2885                     2890                2895

Arg Leu Cys Thr Lys Glu Glu Phe Ile Ala Lys Val Arg Ser His
2900                     2905                2910

Ala Ala Ile Gly Ala Tyr Leu Glu Glu Gln Glu Gln Trp Lys Thr
2915                     2920                2925

Ala Asn Glu Ala Val Gln Asp Pro Lys Phe Trp Glu Leu Val Asp
2930                     2935                2940

Glu Glu Arg Lys Leu His Gln Gln Gly Arg Cys Arg Thr Cys Val
2945                     2950                2955

Tyr Asn Met Met Gly Lys Arg Glu Lys Lys Leu Ser Glu Phe Gly
2960                     2965                2970

Lys Ala Lys Gly Ser Arg Ala Ile Trp Tyr Met Trp Leu Gly Ala
2975                     2980                2985

Arg Tyr Leu Glu Phe Glu Ala Leu Gly Phe Leu Asn Glu Asp His
2990                     2995                3000

Trp Ala Ser Arg Glu Asn Ser Gly Gly Gly Val Glu Gly Ile Gly
3005                     3010                3015

Leu Gln Tyr Leu Gly Tyr Val Ile Arg Asp Leu Ala Ala Met Asp
3020                     3025                3030

Gly Gly Gly Phe Tyr Ala Asp Asp Thr Ala Gly Trp Asp Thr Arg
3035                     3040                3045

Ile Thr Glu Ala Asp Leu Asp Asp Glu Gln Glu Ile Leu Asn Tyr
3050                     3055                3060

Met Ser Pro His His Lys Lys Leu Ala Gln Ala Val Met Glu Met
3065                     3070                3075

Thr Tyr Lys Asn Lys Val Val Lys Val Leu Arg Pro Ala Pro Gly

```
             3080                3085                3090
Gly Lys Ala Tyr Met Asp Val Ile Ser Arg Arg Asp Gln Arg Gly
     3095                3100                3105
Ser Gly Gln Val Val Thr Tyr Ala Leu Asn Thr Ile Thr Asn Leu
     3110                3115                3120
Lys Val Gln Leu Ile Arg Met Ala Glu Ala Glu Met Val Ile His
     3125                3130                3135
His Gln His Val Gln Asp Cys Asp Glu Ser Val Leu Thr Arg Leu
     3140                3145                3150
Glu Ala Trp Leu Thr Glu His Gly Cys Asn Arg Leu Lys Arg Met
     3155                3160                3165
Ala Val Ser Gly Asp Asp Cys Val Val Arg Pro Ile Asp Asp Arg
     3170                3175                3180
Phe Gly Leu Ala Leu Ser His Leu Asn Ala Met Ser Lys Val Arg
     3185                3190                3195
Lys Asp Ile Ser Glu Trp Gln Pro Ser Lys Gly Trp Asn Asp Trp
     3200                3205                3210
Glu Asn Val Pro Phe Cys Ser His His Phe His Glu Leu Gln Leu
     3215                3220                3225
Lys Asp Gly Arg Arg Ile Val Val Pro Cys Arg Glu Gln Asp Glu
     3230                3235                3240
Leu Ile Gly Arg Gly Arg Val Ser Pro Gly Asn Gly Trp Met Ile
     3245                3250                3255
Lys Glu Thr Ala Cys Leu Ser Lys Ala Tyr Ala Asn Met Trp Ser
     3260                3265                3270
Leu Met Tyr Phe His Lys Arg Asp Met Arg Leu Leu Ser Leu Ala
     3275                3280                3285
Val Ser Ser Ala Val Pro Thr Ser Trp Val Pro Gln Gly Arg Thr
     3290                3295                3300
Thr Trp Ser Ile His Gly Lys Gly Glu Trp Met Thr Thr Glu Asp
     3305                3310                3315
Met Leu Glu Val Trp Asn Arg Val Trp Ile Thr Asn Asn Pro His
     3320                3325                3330
Met Gln Asp Lys Thr Met Val Lys Glu Trp Arg Asp Val Pro Tyr
     3335                3340                3345
Leu Thr Lys Arg Gln Asp Lys Leu Cys Gly Ser Leu Ile Gly Met
     3350                3355                3360
Thr Asn Arg Ala Thr Trp Ala Ser His Ile His Leu Val Ile His
     3365                3370                3375
Arg Ile Arg Thr Leu Ile Gly Gln Glu Lys Tyr Thr Asp Tyr Leu
     3380                3385                3390
Thr Val Met Asp Arg Tyr Ser Val Asp Ala Asp Leu Gln Pro Gly
     3395                3400                3405
Glu Leu Ile
     3410

<210> SEQ ID NO 9
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 9
acaacagcgg tcctcactgc cctgctaaag catttgatc                              39
```

<210> SEQ ID NO 10
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 10
gatcaaatgc tttagcaggg cagtgaggac cgctgttgt                                39

<210> SEQ ID NO 11
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 11
tgctttagca gtccagtgag gaccgctgtt gtcaca                                   36

<210> SEQ ID NO 12
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 12
tgtgacaaca gcggtcctca ctggactgct aaagca                                   36

<210> SEQ ID NO 13
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 13
gacgtgatca aatgctttgc cagtggagtg aggaccgc                                 38

<210> SEQ ID NO 14
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 14
gcggtcctca ctccactggc aaagcatttg atcacgtc                                 38

<210> SEQ ID NO 15
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 15
gctagcagcc ggatgctatg gacaagtcac cctc                                     34

<210> SEQ ID NO 16
<211> LENGTH: 34
<212> TYPE: DNA
<213> ORGANISM: Artificial Sequence
<220> FEATURE:

<223> OTHER INFORMATION: Synthetic oligonucleotide

<400> SEQUENCE: 16
gagggtgact tgtccatagc atccggctgc tagc    34

<210> SEQ ID NO 17
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 17
gatccagtgg tgcaacattc cagagagcat tgtaacaatg    40

<210> SEQ ID NO 18
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 18
cattgttaca atgctctctg gaatgttgca ccactggatc    40

<210> SEQ ID NO 19
<211> LENGTH: 246
<212> TYPE: PRT
<213> ORGANISM: West Nile virus

<400> SEQUENCE: 19

Asn Glu Met Gly Trp Leu Asp Lys Thr Lys Ser Asp Ile Ser Ser Leu
1               5                   10                  15

Phe Gly Gln Arg Ile Glu Val Lys Glu Asn Phe Ser Met Gly Glu Phe
            20                  25                  30

Leu Leu Asp Leu Arg Pro Ala Thr Ala Trp Ser Leu Tyr Ala Val Thr
        35                  40                  45

Thr Ala Val Leu Thr Pro Leu Leu Lys His Leu Ile Thr Ser Asp Tyr
    50                  55                  60

Ile Asn Thr Ser Leu Thr Ser Ile Asn Val Gln Ala Ser Ala Leu Phe
65                  70                  75                  80

Thr Leu Ala Arg Gly Phe Pro Phe Val Asp Val Gly Val Ser Ala Leu
                85                  90                  95

Leu Leu Ala Ala Gly Cys Trp Gly Gln Val Thr Leu Thr Val Thr Val
            100                 105                 110

Thr Ala Ala Thr Leu Leu Phe Cys His Tyr Ala Tyr Met Val Pro Gly
        115                 120                 125

Trp Gln Ala Glu Ala Met Arg Ser Ala Gln Arg Thr Ala Ala Gly
    130                 135                 140

Ile Met Lys Asn Ala Val Val Asp Gly Ile Val Ala Thr Asp Val Pro
145                 150                 155                 160

Glu Leu Glu Arg Thr Thr Pro Ile Met Gln Lys Lys Val Gly Gln Ile
                165                 170                 175

Met Leu Ile Leu Val Ser Leu Ala Ala Val Val Val Asn Pro Ser Val
            180                 185                 190

Lys Thr Val Arg Glu Ala Gly Ile Leu Ile Thr Ala Ala Val Thr
        195                 200                 205

Leu Trp Glu Asn Gly Ala Ser Ser Val Trp Asn Ala Thr Thr Ala Ile
    210                 215                 220

```
Gly Leu Cys His Ile Met Arg Gly Gly Trp Leu Ser Cys Leu Ser Ile
225                 230                 235                 240

Thr Trp Thr Leu Ile Lys
                245
```

<210> SEQ ID NO 20
<211> LENGTH: 58
<212> TYPE: PRT
<213> ORGANISM: west nile virus

<400> SEQUENCE: 20

```
Asn Glu Met Gly Trp Leu Asp Lys Thr Lys Ser Asp Ile Ser Ser Leu
1               5                   10                  15

Phe Gly Gln Arg Ile Glu Val Lys Glu Asn Phe Ser Met Gly Glu Phe
            20                  25                  30

Leu Leu Asp Leu Arg Pro Ala Thr Ala Trp Ser Leu Tyr Ala Val Thr
        35                  40                  45

Thr Ala Val Leu Thr Pro Leu Leu Lys His
    50                  55
```

<210> SEQ ID NO 21
<211> LENGTH: 58
<212> TYPE: PRT
<213> ORGANISM: kunjin virus

<400> SEQUENCE: 21

```
Asn Glu Met Gly Trp Leu Asp Lys Thr Lys Ser Asp Ile Ser Gly Leu
1               5                   10                  15

Phe Gly Gln Arg Ile Glu Thr Lys Glu Asn Phe Ser Ile Gly Glu Phe
            20                  25                  30

Leu Leu Asp Leu Arg Pro Ala Thr Ala Trp Ser Leu Tyr Ala Val Thr
        35                  40                  45

Thr Ala Val Leu Thr Pro Leu Leu Lys His
    50                  55
```

<210> SEQ ID NO 22
<211> LENGTH: 58
<212> TYPE: PRT
<213> ORGANISM: japanese encephalitis virus

<400> SEQUENCE: 22

```
Asn Glu Tyr Gly Met Leu Glu Lys Thr Lys Ala Asp Leu Lys Ser Met
1               5                   10                  15

Phe Gly Gly Lys Thr Gln Ala Ser Gly Leu Thr Gly Leu Pro Ser Met
            20                  25                  30

Ala Leu Asp Leu Arg Pro Ala Thr Ala Trp Ala Leu Tyr Gly Gly Ser
        35                  40                  45

Thr Val Val Leu Thr Pro Leu Leu Lys His
    50                  55
```

<210> SEQ ID NO 23
<211> LENGTH: 60
<212> TYPE: PRT
<213> ORGANISM: Saint Louis encephalitis virus

<400> SEQUENCE: 23

```
Asn Glu Met Gly Leu Leu Glu Lys Thr Lys Ser Asp Ile Ala Lys Leu
1               5                   10                  15

Phe Gly Ser Gln Pro Gly Pro Met Gly Phe Val Arg Thr Thr Pro Trp
```

```
                20                  25                  30

Asp Ile Ser Leu Asp Ile Lys Pro Ala Thr Ala Trp Ala Leu Tyr Ala
        35                  40                  45

Ala Ala Thr Met Val Met Thr Pro Leu Ile Lys His
    50                  55                  60

<210> SEQ ID NO 24
<211> LENGTH: 56
<212> TYPE: PRT
<213> ORGANISM: zika virus

<400> SEQUENCE: 24

Asn Glu Leu Gly Trp Leu Glu Arg Thr Lys Ser Asp Ile Ala His Leu
1               5                   10                  15

Met Gly Arg Lys Glu Glu Gly Thr Thr Met Gly Phe Ser Met Asp Ile
            20                  25                  30

Asp Leu Arg Pro Ala Ser Ala Trp Ala Ile Tyr Ala Ala Leu Thr Thr
        35                  40                  45

Leu Ile Thr Pro Ala Val Gln His
    50                  55

<210> SEQ ID NO 25
<211> LENGTH: 56
<212> TYPE: PRT
<213> ORGANISM: dengue virus 1

<400> SEQUENCE: 25

Asn Glu Met Gly Leu Leu Glu Thr Thr Lys Lys Asp Leu Gly Ile
1               5                   10                  15

Gly His Val Ala Val Glu Asn His His His Ala Thr Met Leu Asp Val
            20                  25                  30

Asp Leu Arg Pro Ala Ser Ala Trp Thr Leu Tyr Ala Val Ala Thr Thr
        35                  40                  45

Ile Ile Thr Pro Met Met Arg His
    50                  55

<210> SEQ ID NO 26
<211> LENGTH: 54
<212> TYPE: PRT
<213> ORGANISM: dengue virus 2

<400> SEQUENCE: 26

Asn Glu Met Gly Phe Leu Glu Lys Thr Lys Lys Asp Leu Gly Leu Gly
1               5                   10                  15

Ser Ile Thr Thr Gln Gln Pro Glu Ser Asn Ile Leu Asp Ile Asp Leu
            20                  25                  30

Arg Pro Ala Ser Ala Trp Thr Leu Tyr Ala Val Ala Thr Thr Phe Val
        35                  40                  45

Thr Pro Met Leu Arg His
    50

<210> SEQ ID NO 27
<211> LENGTH: 54
<212> TYPE: PRT
<213> ORGANISM: dengue virus 3

<400> SEQUENCE: 27

Asn Glu Met Gly Leu Leu Glu Thr Thr Lys Arg Asp Leu Gly Met Ser
1               5                   10                  15
```

Lys Glu Pro Gly Val Val Ser Ser Thr Ser Tyr Leu Asp Val Asp Leu
            20                  25                  30

His Pro Ala Ser Ala Trp Thr Leu Tyr Ala Val Ala Thr Thr Val Ile
                35                  40                  45

Thr Pro Met Leu Arg His
    50

<210> SEQ ID NO 28
<211> LENGTH: 51
<212> TYPE: PRT
<213> ORGANISM: dengue virus 4

<400> SEQUENCE: 28

Asn Glu Met Gly Leu Ile Glu Lys Thr Lys Thr Asp Phe Gly Phe Tyr
1               5                   10                  15

Gln Val Lys Thr Glu Thr Thr Ile Leu Asp Val Asp Leu Arg Pro Ala
            20                  25                  30

Ser Ala Trp Thr Leu Tyr Ala Val Ala Thr Thr Ile Leu Thr Pro Met
                35                  40                  45

Leu Arg His
    50

<210> SEQ ID NO 29
<211> LENGTH: 56
<212> TYPE: PRT
<213> ORGANISM: yellow fever virus

<400> SEQUENCE: 29

Asn Glu Leu Gly Met Leu Glu Lys Thr Lys Glu Asp Leu Phe Gly Lys
1               5                   10                  15

Lys Asn Leu Ile Pro Ser Ser Ala Ser Pro Trp Ser Trp Pro Asp Leu
            20                  25                  30

Asp Leu Lys Pro Gly Ala Ala Trp Thr Val Tyr Val Gly Ile Val Thr
                35                  40                  45

Met Leu Ser Pro Met Leu His His
    50                  55

<210> SEQ ID NO 30
<211> LENGTH: 58
<212> TYPE: PRT
<213> ORGANISM: powassan virus

<400> SEQUENCE: 30

Asn Glu Leu Gly Gly Tyr Leu Glu Gln Thr Lys Thr Asp Ile Ser Gly
1               5                   10                  15

Leu Phe Arg Arg Glu Asp Gln Gly Gly Met Val Trp Asp Ala Trp Thr
            20                  25                  30

Asn Ile Asp Ile Gln Pro Ala Arg Ser Trp Gly Thr Tyr Val Leu Ile
                35                  40                  45

Val Ser Leu Phe Thr Pro Tyr Met Leu His
    50                  55

<210> SEQ ID NO 31
<211> LENGTH: 57
<212> TYPE: PRT
<213> ORGANISM: tick-borne encephalitis virus

<400> SEQUENCE: 31

Asn Glu Met Gly Phe Leu Glu Lys Thr Lys Ala Asp Leu Ser Thr Ala
1               5                   10                  15

-continued

```
Leu Trp Ser Glu Arg Glu Glu Pro Arg Pro Trp Ser Glu Trp Thr Asn
                20                  25                  30

Val Asp Ile Gln Pro Ala Arg Ser Trp Gly Thr Tyr Val Leu Val Val
            35                  40                  45

Ser Leu Phe Thr Pro Tyr Ile Ile His
        50                  55

<210> SEQ ID NO 32
<211> LENGTH: 57
<212> TYPE: PRT
<213> ORGANISM: langat virus

<400> SEQUENCE: 32

Asn Glu Met Gly Leu Leu Glu Lys Thr Lys Ala Asp Leu Ala Ala Leu
1               5                   10                  15

Phe Ala Arg Asp Gln Gly Glu Thr Val Arg Trp Gly Glu Trp Thr Asn
                20                  25                  30

Leu Asp Ile Gln Pro Ala Arg Ser Trp Gly Thr Tyr Val Leu Val Val
            35                  40                  45

Ser Leu Phe Thr Pro Tyr Met Leu His
        50                  55

<210> SEQ ID NO 33
<211> LENGTH: 57
<212> TYPE: PRT
<213> ORGANISM: Omsk hemorrhagic fever virus

<400> SEQUENCE: 33

Asn Glu Met Gly Phe Leu Glu Lys Thr Lys Ala Asp Leu Ser Ala Val
1               5                   10                  15

Leu Trp Ser Glu Arg Glu Glu Pro Arg Val Trp Ser Glu Trp Thr Asn
                20                  25                  30

Ile Asp Ile Gln Pro Ala Lys Ser Trp Gly Thr Tyr Val Leu Val Val
            35                  40                  45

Ser Leu Phe Thr Pro Tyr Ile Ile His
        50                  55
```

ATTENUATING VIRAL MUTATIONS IN PROTEIN GENES

RELATED APPLICATIONS

This application is a U.S. Utility application claiming priority to U.S. Provisional Application 63/186,160 filed May 9, 2021, which is incorporated herein by reference in its entirety.

STATEMENT REGARDING FEDERALLY FUNDED RESEARCH

This invention was made with government support under T32 AI007526, R01 AI099123, and AI127744 awarded by the National Institutes of Health. The government has certain rights in the invention.

SEQUENCE LISTING

A sequence listing required by 37 CFR 1.821-1.825 is being submitted electronically with this application. The sequence listing is incorporated herein by reference. The sequence listing that is contained in the file named "UTMBP0400US" which is 91 KB (as measured in Microsoft Windows®) and was created on Mar. 28, 2021 and modified on Mar. 21, 2024.

FIELD OF THE INVENTION

The invention relates to compositions that elicit an immunological response against flavivirus infections and the clinical manifestations thereof, useful for the prevention and/or treatment of flavivirus infections in human and animal subjects.

BACKGROUND

West Nile virus (WNV) is a mosquito-borne flavivirus that is endemic in many parts of the world [1]. WNV was introduced into the United States (US) in 1999 and shortly thereafter spread throughout all of North America [1,2]. WNV cases are asymptomatic or manifest as WNV fever with symptoms such as fatigue, myalgia, arthralgia, or rash [3]. While most people recover completely from WNV fever, WNV is also capable of causing neurological disease, which may result in meningitis, encephalitis, acute flaccid paralysis, or other long-lasting neurological sequelae [3]. Approximately one of every 150 WNV neuroinvasive disease (WNND) cases are fatal [3]. Between 2002-2019, annual WNND reports to the US CDC ranged between 486-2946 with 43-284 deaths annually [4]. Since flaviviruses, such as WNV and yellow fever virus (YFV), are arthropod-borne and cannot be eradicated, there is a need for methods and compositions to protect humans from flaviviruses, for example, WNV and YFV.

SUMMARY

Aspects of the present disclosure address needs in the art by providing methods and compositions for treating and preventing flavivirus infection in subjects, human and animal. Certain embodiments are directed to methods for inducing an immune response in a subject comprising administering an effective amount of an immunogenic composition comprising an attenuated flavivirus and a pharmaceutically acceptable carrier or diluent to the subject. Also provided herein, in some aspects, are methods of immunizing a subject against a flavivirus infection comprising administering an effective amount of a vaccine composition comprising an attenuated flavivirus and a pharmaceutically acceptable carrier or diluent. In some embodiments, the disclosed methods comprise providing the immunogenic composition or vaccine composition to a subject who does not have, but is at risk of developing, infection by a flavivirus. In certain aspects a subject is at risk of infection by flavivirus by being in a geographic area in which a flavivirus is present. In some embodiments, the disclosed methods comprise providing the immunogenic composition to a subject who is infected by a flavivirus, i.e., therapeutically administering the immunogenic composition.

Embodiments include compositions comprising an attenuated flavivirus. In certain aspects, an attenuated flavivirus comprises one or more mutations in a nucleic acid construct encoding the attenuated flavivirus. Embodiments also include nucleic acid molecules encoding for all or part of the genome of an attenuated flavivirus. Embodiments include recombinant, transformed, or modified cells, vectors, and/or expression cassettes comprising such nucleic acid molecules. In certain aspects the flavivirus is West Nile Virus, Yellow Fever Virus, or Dengue virus (e.g., Dengue virus-4, accession MW793460.1, the nucleotide sequence and encoded protein sequence is incorporated herein by reference as of the filing date of this application).

In some embodiments, the compositions contemplated herein can comprise 1, 2, 3, 4, 5, or more of the following components: an attenuated flavivirus, a nucleic acid, a vector, a cell, a polypeptide, an oligonucleotide, a capsid (C) protein, a membrane (M) protein, an envelope (E) protein, or one or more non-structural (NS) proteins (NS1, NS2A, NS2B, NS3, NS4A, NS4B, and NS5). Any one or more of these components may be excluded from the disclosed compositions.

Embodiments of the disclosure include methods and compositions for treating or preventing a flavivirus infection in a subject, methods for diagnosing a flavivirus infection in a subject, methods for prognosing a flavivirus infection in a subject, and methods for identifying a subject having or at risk of having a flavivirus infection as a candidate for an attenuated flavivirus prophylactic or therapy. Methods of the disclosure can include 1, 2, 3, 4, 5, 6, or more of the following steps: providing an attenuated flavivirus prophylactic or therapy to a subject, providing a second antiviral therapy to a subject, providing both an attenuated flavivirus prophylactic or therapy and a second antiviral to a subject, providing an alternative therapy to a subject, determining a subject to have a flavivirus infection, providing two or more types of antiviral therapy to a subject, and identifying a subject as being a candidate for an attenuated flavivirus prophylactic or therapy. Certain embodiments of the disclosure may exclude one or more of the preceding elements and/or steps.

Embodiments also include, inter alia, methods of generating an attenuated flavivirus prophylactic or therapy, methods of producing an attenuated flavivirus prophylactic or therapy, methods of expressing an attenuated flavivirus, methods of detecting flavivirus infection, methods of treating one or more conditions, methods of purifying an attenuated flavivirus, and methods of treating flavivirus infection. The steps and embodiments discussed in this disclosure are contemplated as part of any of these methods. In some embodiments, the methods contemplated herein can comprise or exclude 1, 2, 3, 4, 5, or more of the following steps: providing an attenuated flavivirus, providing a nucleic acid to a cell, subjecting a cell to conditions sufficient to express a nucleic acid, providing an additional therapeutic, expressing a vector in a cell, and providing a pharmaceutical composition to a subject. Any one or more of these steps may be excluded from the disclosed methods.

Embodiments of the present disclosure include an attenuated flavivirus as represented by a West Nile Virus (WNV) wherein a nucleic acid construct encoding the genome of the attenuated flavivirus comprises one or more mutations corresponding to a mutation in the transmembrane domain of non-structural protein 4B (NS4B) of the flavivirus, wherein the one or more mutations result in a substitution of wild-type amino acid 54 present in a transmembrane domain of NS4B. NS4B protein is encoded, for example, by nucleotides 6916 to 7680 of SEQ ID NO:1. NS4B protein can also be identified as amino acid 2274 to 2519 of the polyprotein sequence of SEQ ID NO:2. NS4B region and NS4B protein can be readily identified in other flavivirus by nucleic acid and protein alignment. SEQ ID NO:19 provides the amino acid sequence of wild-type or non-attenuated WNV NS4B protein. In particular aspects, an attenuated flavivirus comprises a mutation in NS4B protein that corresponds to proline 54 of SEQ ID NO:19. In some embodiments, the substitution of wild-type amino acid 54 comprises a substitution of a proline residue with a nonpolar amino acid. In some embodiments, the nonpolar amino acid comprises alanine residue (P54A) or glycine residue (P54G).

In some embodiments, the nucleic acid construct encoding the genome of the attenuated WNV further comprises one or more mutations corresponding to one or more glycosylation sites of non-structural protein 1 (NS1) of the flavivirus. In some embodiments, the one or more mutations corresponding to one or more glycosylation sites of NS1 of the flavivirus result in a substitution of wild-type amino acids 130-132 of NS1. In some embodiments, the substitution of wild-type amino acids 130 and 131 comprises a substitution of an asparagine residue with a polar amino acid. In some embodiments, the polar amino acid comprises a glutamine residue. In some embodiments, the substitution of amino acid 132 comprises a substitution of a threonine residue with a nonpolar amino acid. In some embodiments, the nonpolar amino acid comprises an alanine residue. In some embodiments, the one or more mutations corresponding to one or more glycosylation sites of NS1 of the flavivirus further comprise a substitution of wild-type amino acid 175 of NS1. In some embodiments, the one or more mutations corresponding to one or more glycosylation sites of NS1 of the flavivirus further comprise a substitution of wild-type amino acid 207 of NS1. In some embodiments, the substitution of wild-type amino acid 175 or wild-type amino acid 207 comprises a substitution of an asparagine residue with a nonpolar amino acid. In some embodiments, the nonpolar amino acid comprises an alanine residue.

Embodiments of the present disclosure also include, inter alia, an attenuated flavivirus comprising a flavivirus wherein a nucleic acid construct encoding the genome of the attenuated flavivirus comprises one or more mutations corresponding to a transmembrane domain of non-structural protein 4B (NS4B) of the flavivirus, wherein the one or more mutations comprise a substitution of a wild-type amino acid homologous to wild-type amino acid 54 present in a transmembrane domain of WNV NS4B. In some embodiments, the flavivirus is selected from the group consisting of WNV, Japanese encephalitis virus, St. Louis encephalitis virus, tickborne encephalitis virus, dengue fever virus, Zika virus, and yellow fever virus (YFV) because a proline is found at the equivalent residue in all mosquito- and tick-borne flaviviruses sequenced to date where WNV is residue 54. For example, in some embodiments, the flavivirus is YFV. In some embodiments, the YFV wild-type amino acid homologous to wild-type amino acid 54 of the transmembrane domain of WNV NS4B is amino acid 52, and wherein substitution of amino acid 52 comprises a substitution of a proline residue with a nonpolar amino acid. In some embodiments, the nonpolar amino acid comprises alanine residue or glycine residue. In some embodiments, the nucleic acid construct encoding the genome of the attenuated flavivirus further comprises one or more mutations corresponding to one or more glycosylation sites of non-structural protein 1 (NS1) of the flavivirus.

In some embodiments, the one or more mutations of the attenuated flaviviruses decrease the neurotropism of the flavivirus, relative to a corresponding flavivirus lacking the mutation. In some embodiments, the one or more mutations decrease the viscerotropism of the flavivirus, relative to a corresponding flavivirus lacking the mutation. In some embodiments, the one or more mutations decrease cytokine response to the flavivirus, relative to a corresponding flavivirus lacking the mutation. In some embodiments, reversion of the one or more mutations to the wild-type amino acid is inhibited when the virus is grown in a host. In some embodiments, the virus induces an immune response when administered to or infecting a human or an animal host.

In some aspects, the disclosure relates to an immunogenic composition comprising an attenuated flavivirus described herein and a pharmaceutically acceptable carrier or diluent. In some embodiments, the immunogenic composition induces an immune response in a subject that is equivalent to an immune response induced by a corresponding wild type virus.

In some aspects, the disclosure relates to a method of decreasing viscerotropism of a flavivirus in a subject comprising administering an effective amount of the immunogenic composition to the subject. In some aspects, the disclosure relates to a method of decreasing neurotropism of a flavivirus in a subject comprising administering an effective amount of the immunogenic composition to the subject. In some aspects, the disclosure relates to a method of inducing an immune response in a subject comprising administering an effective amount of the immunogenic composition to the subject. In some embodiments, the subject does not have, but is at risk of developing, infection by a flavivirus. In some embodiments, the subject is infected by a flavivirus.

In some embodiments, the flavivirus is selected from the group of mosquito-borne and tick-borne flaviviruses. In certain aspects, the flavivirus is selected from the group consisting of WNV, Japanese encephalitis virus, St. Louis encephalitis virus, tickborne encephalitis virus, dengue fever virus, and YFV. In some embodiments, the flavivirus is WNV. In some embodiments, the flavivirus is YFV. In some embodiments, an immune response to at least one of WNV, Japanese encephalitis virus, St. Louis encephalitis virus, tickborne encephalitis virus, dengue fever virus, and YFV is induced in the subject. In some embodiments, the immune response induced in the subject is to WNV. In some embodiments, the immune response induced in the subject is to YFV.

In some aspects, the disclosure relates to a vaccine composition comprising an attenuated flavivirus described herein and a pharmaceutically acceptable carrier or diluent. In some aspects, the disclosure relates to a method of immunizing a subject against a flavivirus infection comprising administering an effective amount of the vaccine composition to the subject. In some embodiments, the subject does not have, but is at risk of developing, infection by a flavivirus. In some embodiments, the flavivirus is selected from the group of mosquito-borne and tick-borne flaviviruses. In certain aspects, the flavivirus is selected from the group consisting of WNV, Japanese encephalitis virus, St. Louis encephalitis virus, tickborne encephalitis virus, dengue fever virus, and YFV. In some embodiments, the flavivirus is WNV. In some embodiments, the flavivirus is YFV.

In some embodiments, the subjects disclosed herein are non-human primates, humans, horses, or birds. In some embodiments, the compositions are administered to the subject subcutaneously, intramuscularly, intranasally, orally, topically, transdermally, parenterally, gastrointestinally, transbronchially or transalveolarly. In some embodiments, the compositions are administered to the subject as a single dose or in multiple doses. In some embodiments, the compositions are administered to the subject as a single composition followed by a boost of the same or different composition.

In some aspects, the disclosure relates to a method of producing a vaccine against an attenuated flavivirus comprising WNV, the method comprising introducing into a nucleic acid construct encoding the genome of the attenuated WNV one or more mutations corresponding to a transmembrane domain of NS4B of the flavivirus, wherein the one or more mutations attenuates the flavivirus, relative to a corresponding flavivirus lacking the mutation, and further wherein the one or more mutations result in a substitution of wild-type amino acid 54 of the transmembrane domain of NS4B. In some embodiments, the substitution of wild-type amino acid 54 comprises a substitution of a proline residue with a nonpolar amino acid. In some embodiments, the nonpolar amino acid comprises alanine residue or glycine residue. In some embodiments, the method further comprises introducing into the nucleic acid construct encoding the genome of the attenuated WNV one or more additional mutations corresponding to one or more glycosylation sites of non-structural protein 1 (NS1) of the flavivirus. In some embodiments, the one or more mutations corresponding to one or more glycosylation sites of NS1 of the flavivirus result in a substitution of wild-type amino acids 130-132 of NS1. In some embodiments, the substitution of wild-type amino acids 130 and 131 comprises a substitution of an asparagine residue with a polar amino acid. In some embodiments, the polar amino acid comprises a glutamine residue. In some embodiments, the substitution of amino acid 132 comprises a substitution of a threonine residue with a nonpolar amino acid. In some embodiments, the nonpolar amino acid comprises an alanine residue.

In some aspects, the disclosure relates to a method of producing a vaccine against a flavivirus, the method comprising introducing into a nucleic acid construct encoding the genome of the attenuated flavivirus one or more mutations corresponding to a transmembrane domain of NS4B of the flavivirus, wherein the one or more mutations attenuates the flavivirus, relative to a corresponding flavivirus lacking the mutation, and further wherein the one or more mutations comprise a substitution of a wild-type amino acid homologous to wild-type amino acid 54 of the transmembrane domain of WNV NS4B. In some embodiments, the flavivirus is selected from the group consisting of WNV, Japanese encephalitis virus, St. Louis encephalitis virus, tickborne encephalitis virus, dengue fever virus, and YFV. In some embodiments, the flavivirus is YFV. In some embodiments, the YFV wild-type amino acid homologous to wild-type amino acid 54 of the transmembrane domain of WNV NS4B comprises amino acid 52, and wherein substitution of amino acid 52 comprises a substitution of a proline residue with a nonpolar amino acid. In some embodiments, the method further comprises introducing into the nucleic acid construct encoding the genome of the attenuated flavivirus one or more additional mutations corresponding to one or more glycosylation sites of non-structural protein 1 (NS1) of the flavivirus.

In some aspects, the disclosure relates to a method of manufacturing an attenuated flavivirus disclosed herein, the method comprising introducing a nucleic acid construct encoding the genome of the attenuated flavivirus into cells and isolating flavivirus produced in the cells from the cells or the supernatant thereof. In some embodiments, the cells are Vero cells. In some embodiments, the cells are cultured in serum free medium.

Other embodiments of the disclosure are discussed throughout this application. Any embodiment discussed with respect to one aspect of the disclosure applies to other aspects of the disclosure as well and vice versa. Each embodiment described herein is understood to be embodiments of the disclosure that are applicable to all aspects of the disclosure. It is contemplated that any embodiment discussed herein can be implemented with respect to any method or composition of the disclosure, and vice versa. Furthermore, compositions and kits of the disclosure can be used to achieve methods of the disclosure.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the disclosure. The term "consisting essentially of" occupies a middle ground between "comprising" and "consisting of".

Any method in the context of a therapeutic, diagnostic, or physiologic purpose or effect may also be described in "use" claim language such as "Use of" any compound, composition, or agent discussed herein for achieving or implementing a described therapeutic, diagnostic, or physiologic purpose or effect.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

DESCRIPTION OF THE DRAWINGS

The following drawings form part of the present specification and are included to further demonstrate certain aspects of the present disclosure. The disclosure may be better understood by reference to one or more of these drawings in combination with the detailed description of the specification embodiments presented herein.

FIG. 1. NS4B residue P54 is conserved amongst multiple flaviviruses. The highlighted residue is the specific amino acid characterized by mutagenesis and correspond to WNV NS4B residue P54. The alignment was generated using Clustal Omega and virus abbreviations and Genbank accession numbers are as follows: WNV: West Nile virus (AAF20092.2)(SEQ ID NO:20); KUNV: Kunjin virus (BAA00176.1)(SEQ ID NO:21); JEV: Japanese encephalitis virus (ABQ52691.1)(SEQ ID NO:22); SLEV: Saint Louis encephalitis virus (ACT31738.1)(SEQ ID NO:23); ZIKV: zika virus (AMR39836.1)(SEQ ID NO:24); DENV-1: dengue virus 1 (AIU47321.1)(SEQ ID NO:25); DENV-2: dengue virus 2 (AAC59275.1)(SEQ ID NO:26); DENV-3: dengue virus 3 (ALS05358.1)(SEQ ID NO:27); DENV-4: dengue virus 4 (ALB78116.1)(SEQ ID NO:28); YFV: YFV (AHB63685.1)(SEQ ID NO:29); POWV: powassan virus (NP_620099.1)(SEQ ID NO:30); TBEV: tick-borne encephalitis virus (AAA86870.1)(SEQ ID NO:31); LGTV: langat virus (ACH42698.1)(SEQ ID NO:32); OFFV: Omsk hemorrhagic fever virus (NP_878909.1)(SEQ ID NO:33).

FIG. 5. Each NS4B-P54 mutant has a unique SNV profile. For Vero cell P1 virus stocks, the frequency of each SNV is indicated by an (x), and the grey bars in the background display the total number of SNVs detected.

DESCRIPTION

Figure 2:
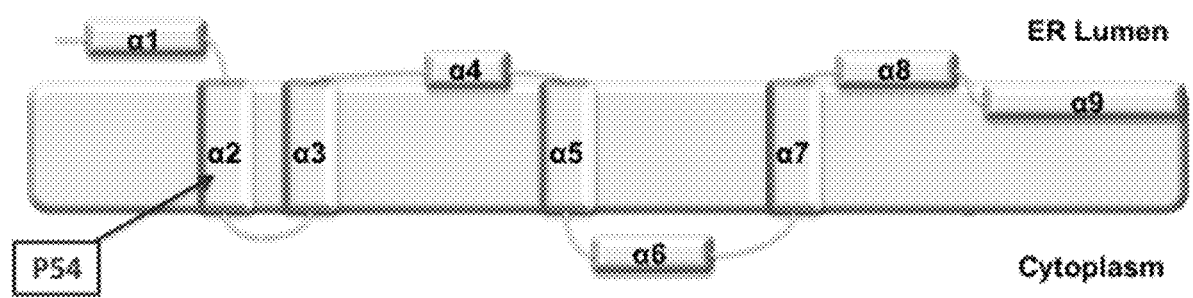
FIG. 2. Location of P54 amino acid residue within the predicted structure of NS4B. Each alpha helix is labeled as $\alpha 1$-$\alpha 9$ and locations are based on NMR studies of DENV NS4B. Residue P54 was investigated in the present disclosure. Residue P54 is predicted to be within $\alpha 2$, which is the first transmembrane domain.

The present disclosure is based, at least in part, on the discovery that flavivirus infections can be associated with neuroinvasion, neurotropism, and/or viscerotropism, and administration of an immunogenic or vaccine composition comprising an attenuated flavivirus disclosed herein has been surprising and unexpectedly found to prevent or decrease neuroinvasion. Further, administering an immunogenic or vaccine composition comprising an attenuated flavivirus disclosed herein can surprisingly prevent or decrease cytokine induction in infected cells.

The attenuated flaviviruses disclosed herein provide live, attenuated viruses useful as immunogens or vaccines. Live vaccines confer the most potent and durable, protective immune responses against disease caused by viral infections. In the case of flaviviruses, the development of a successful vaccine requires that the virulence properties are modified, for example, by mutation, so that the immunogenic composition or vaccine virus has reduced neurotropism and viscerotropism for humans or animals.

As disclosed herein, administration of a therapeutically effective amount of an immunogenic composition or vaccine comprising an attenuated flavivirus can prevent or decrease neuroinvasion, neurotropism, and/or viscerotropism. Accordingly, in some embodiments, disclosed are methods and compositions for treating or preventing flavivirus infection in a subject or inhibiting or decreasing neuroinvasion, neurotropism, and/or viscerotropism comprising administering a therapeutically effective amount of an immunogenic or vaccine composition comprising an attenuated flavivirus. In some embodiments, the flavivirus is selected from the group consisting of WNV, Japanese encephalitis virus, St. Louis encephalitis virus, tickborne encephalitis virus, dengue fever virus, and YFV. In some embodiments, the flavivirus is WNV. In some embodiments, the flavivirus is YFV. In some embodiments, the subject does not have, but is at risk of developing, infection by a flavivirus. In some embodiments, the subject has symptoms of a flavivirus infection. In some embodiments, the subject is infected by a flavivirus.

The following discussion is directed to various embodiments of the invention. The term “invention” is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment. All publications mentioned herein are incorporated by reference for the purpose of describing and disclosing methodologies and materials that might be used in connection with the present disclosure.

I. FLAVIVIRUSES

Flaviviruses are small, enveloped, positive-strand RNA viruses that are generally transmitted by infected arthropods, such as mosquitoes and ticks. The Flavivirus genus of the Flaviviridae family includes approximately 70 viruses, mostly arboviruses, many of which, such as West Nile virus (WNV), yellow fever virus (YFV), dengue (DEN), Japanese encephalitis (JE), and tick-borne encephalitis (TBE) viruses, are major human pathogens (reviewed in Burke and Monath, Fields Virology, 4th Ed.: 1043-1126, 2001). For example, Japanese encephalitis is the leading cause of viral encephalitis in Asia, where 30,000 to 50,000 new cases are reported each year. As another example, since the first cases were diagnosed in the New York area in 1999, WNV has continued to spread rapidly across North America. The risks of this virus migrating into South America, as well as an epidemic in underdeveloped countries, are extremely high. Effective methods for preventing infection by these viruses are needed, with vaccination being the most cost-effective measure. In certain embodiments insect-specific flaviviruses (i.e., those that multiply in insects only and not vertebrate cells) can be specifically excluded.

A. West Nile Virus

WNV is a member of the Japanese encephalitis virus (JE) serocomplex of mosquito-borne flaviviruses that includes St. Louis encephalitis, JE, and Murray Valley encephalitis viruses (Calisher et al. 1989 *J Gen Virol* 70:27-43; Burke and Monath, 2001 in: Fields Virology, eds. Knipe and Howley, Lippincott Williams and Wilkins, Philadelphia, 4-th ed., pp. 1043-1125). Like other members of the JE antigenic complex, WNV is maintained in a natural cycle that involves mosquito vectors and birds, while humans and equines are usually incidental hosts. For many years WNV has been recognized as one of the most widely distributed flaviviruses with a geographic range including Africa, Australia, Europe, the Middle East and West Asia (Burke and Monath, 2001 in: Fields Virology, eds. Knipe, D. M. & Howley, P. M. Lippincott Williams and Wilkins, Philadelphia, 4-th ed., pp. 1043-1125; Hayes, 1989 in: The Arboviruses: Epidemiology and Ecology, ed. Monath Boca Raton, Fla. CRC Press, Volume V, pp. 59-88). During 1999 WNV first established itself in the USA in the Northeast and Mid-Atlantic States and more recently this virus extended its range to include the Southeastern and Western States (Anderson, J. F. et al. 1999 Science 286:2331-2333; Lanciotti, R. S. et al. 1999 Science 286:2333-2337; Campbell, G. L. et al. 2002 Lancet 2:519-529). The natural hosts for WNV are birds and mosquitoes. Over 300 different species of bird have been shown to be infected with the virus.

WNV has been demonstrated in a large number of mosquito species, but the most significant for viral transmission are *Culex* species that feed on birds, including *C. pipiens, C. restuans, C. salinarius, C. quinquefasciatus, C. nigripalpus, C. erraticus* and *C. tarsalis*. Experimental infection has also been demonstrated with soft tick vectors.

WNV has a broad host range, and is also known to be able to infect at least 30 mammalian species, including humans, some non-human primates, horses, dogs and cats. Some infected humans and horses experience disease but dogs and cats rarely show symptoms. Reptiles and amphibians can also be infected, including some species of crocodiles, alligators, snakes, lizards, and frogs. Mammals are considered incidental or dead-end hosts for the virus: they do not usually develop a high enough level of virus in the blood (viremia) to infect another mosquito feeding on them and carry on the transmission cycle.

According to the Center for Disease Control, infection with WNV is seasonal in temperate zones. Climates that are temperate, such as those in the United States and Europe, see peak season from July to October. Peak season changes depending on geographic region and warmer and humid climates can see longer peak seasons. All ages are equally likely to be infected but there is a higher amount of death and neuroinvasive WNV in people 60-89 years old. People of older age are more likely to have adverse effects of being infected.

In humans, WNV can cause a disease known as West Nile fever. According to the U.S. Centers for Disease Control and Prevention, approximately 80% of infected people have few or no symptoms, around 20% of people develop mild symptoms (such as fever, headache, vomiting, or a rash), and less than 1% of people develop severe symptoms (such as encephalitis, meningitis, or acute flaccid paralysis). WNV meningitis is clinically indistinguishable from viral meningitis due to other etiologies and typically presents with fever, headache, and nuchal rigidity. WNV encephalitis is a more severe clinical syndrome that usually manifests with fever and altered mental status, seizures, focal neurologic deficits, or movement disorders such as tremor or parkinsonism. WNV acute flaccid paralysis is usually clinically and pathologically identical to poliovirus-associated poliomyelitis, with damage of anterior horn cells, and may progress to respiratory paralysis requiring mechanical ventilation. WNV poliomyelitis often presents as isolated limb paresis or paralysis and can occur without fever or apparent viral prodrome. WNV-associated Guillain-Barre syndrome and radiculopathy have also been reported and can be distinguished from WNV poliomyelitis by clinical manifestations and electrophysiologic testing. Rarely, cardiac dysrhythmias, myocarditis, rhabdomyolysis, optic neuritis, uveitis, chorioretinitis, orchitis, pancreatitis, and hepatitis have been described in subjects with WNV disease.

In endemic regions, most human WNV infections are asymptomatic or cause mild illness with symptoms of low-grade fever, headache, body aches, rash, myalgia, and polyarthropathy. However, human epidemics with severe disease have been reported in Israel, France, Romania, and Russia. In acute severe illness, the virus can cause hepatitis, meningitis and encephalitis leading to paralysis, and coma resulting in death. The neuropathologic lesions are similar to those of JE, with diffuse CNS inflammation and neuronal degeneration. Virus is also found in the spleen, liver, lymph nodes, and lungs of infected individuals. During the 1999 outbreak of WNV in the USA, more than 60 people became ill and 7 died, while during 2002, morbidity was 3873 cases and there were 246 deaths (CDC Report: West Nile Update Current case Count, Jan. 2, 2003). Because of the recent and unexpected spread of WNV from the Northeast to the Southeast and the West of the USA, this virus is considered a significant emerging disease threat that has embedded itself over a considerable region of the country.

Laboratory diagnosis is generally accomplished by testing of serum or cerebrospinal fluid (CSF) to detect WNV-specific IgM antibodies. Immunoassays for WNV-specific IgM are available commercially and through state public health laboratories. WNV-specific IgM antibodies are usually detectable 3 to 8 days after onset of illness and persist for 30 to 90 days, but longer persistence has been documented. Therefore, positive IgM antibodies occasionally may reflect a past infection. If serum is collected within 8 days of illness onset, the absence of detectable virus-specific IgM does not rule out the diagnosis of WNV infection, and the test may need to be repeated on a later sample. The presence of WNV-specific IgM in blood or CSF provides good evidence of recent infection but may also result from cross-reactive antibodies after infection with other flaviviruses or from non-specific reactivity. According to product inserts for commercially available WNV IgM assays, all positive results obtained with these assays should be confirmed by neutralizing antibody testing of acute- and convalescent-phase serum specimens at a state public health laboratory or CDC. WNV IgG antibodies generally are detected shortly after IgM antibodies and persist for many years following a symptomatic or asymptomatic infection. Therefore, the presence of IgG antibodies alone is only evidence of previous infection and clinically compatible cases with the presence of IgG, but not IgM, should be evaluated for other etiologic agents. Plaque-reduction neutralization tests (PRNTs) performed in reference laboratories, including some state public health laboratories and CDC, can help determine the specific infecting flavivirus. PRNTs can also confirm acute infection by demonstrating a fourfold or greater change in WNV-specific neutralizing antibody titer between acute- and convalescent-phase serum samples collected 2 to 3 weeks apart. Viral cultures and tests to detect viral RNA (e.g., reverse transcriptase-polymerase chain reaction [RT-PCR]) can be performed on serum, CSF, and tissue specimens that are collected early in the course of illness and, if results are positive, can confirm an infection. Immunohistochemistry (IHC) can detect WNV antigen in formalin-fixed tissue. Negative results of these tests do not rule out WNV infection. Viral culture, RT-PCR, and IHC can be requested through state public health laboratories or CDC.

There is no specific treatment for WNV disease; clinical management is supportive. Subjects with severe meningeal symptoms often require pain control for headaches and antiemetic therapy and rehydration for associated nausea and vomiting. Subjects with encephalitis require close monitoring for the development of elevated intracranial pressure and seizures. Subjects with encephalitis or poliomyelitis should be monitored for inability to protect their airway. Acute neuromuscular respiratory failure may develop rapidly and prolonged ventilatory support may be required. Currently, no WNV vaccines are licensed for use in humans. In the absence of a vaccine, prevention of WNV disease depends on community-level mosquito control programs to reduce vector densities, personal protective measures to decrease exposure to infected mosquitoes, and screening of blood and organ donors. Personal protective measures include use of mosquito repellents, wearing long-sleeved shirts and long pants, and limiting outdoor exposure from dusk to dawn. Using air conditioning, installing window and door screens, and reducing peridomestic mosquito breeding sites, can further decrease the risk for WNV exposure.

B. Yellow Fever Virus (YFV)

Yellow fever is caused by YFV and is spread by the bite of an infected female mosquito. It infects only humans, other primates, and several types of mosquitoes. Yellow fever begins after an incubation period of three to six days. Most cases only cause a mild infection with fever, headache, chills, back pain, fatigue, loss of appetite, muscle pain, nausea, and vomiting. In these cases, the infection lasts only three to four days. In 15% of cases, people enter a second, toxic phase of the disease with recurring fever, this time accompanied by jaundice due to liver damage, as well as abdominal pain. Bleeding in the mouth, nose, the eyes, and the gastrointestinal tract cause vomit containing blood, hence the Spanish name for yellow fever, vómito negro ("black vomit"). There may also be kidney failure, hiccups, and delirium. Among those who develop jaundice, the fatality rate is 20 to 50%, while the overall fatality rate is about 3 to 7.5%. Severe cases may have a mortality greater than 50%.

Yellow fever belongs to the group of hemorrhagic fevers. After transmission from a mosquito, the viruses replicate in the lymph nodes and infect cells. The viruses infect, amongst others, monocytes, macrophages, Schwann cells, and dendritic cells. From there, they reach the liver and infect hepatocytes (probably indirectly via Kupffer cells), which leads to eosinophilic degradation of these cells and to the release of cytokines. Apoptotic masses known as Councilman bodies appear in the cytoplasm of hepatocytes. Fatality may occur when cytokine storm, shock, and multiple organ failure follow.

The viruses attach to the cell surfaces via specific receptors and are taken up by an endosomal vesicle. Receptor binding, as well as membrane fusion, are catalyzed by the protein E, which changes its conformation at low pH, causing a rearrangement of the 90 homodimers to 60 homotrimers. Inside the endosome, the decreased pH induces the fusion of the endosomal membrane with the virus envelope. The capsid enters the cytosol, decays, and releases the genome. After entering the host cell, the viral genome is replicated in the rough endoplasmic reticulum (ER) and in the so-called vesicle packets. At first, an immature form of the virus particle is produced inside the ER, whose M-protein is not yet cleaved to its mature form, so is denoted as precursor M (prM) and forms a complex with protein E. The immature particles are processed in the Golgi apparatus by the host protein furin, which cleaves prM to M. This releases E from the complex, which can now take its place in the mature, infectious virion.

Yellow fever virus is mainly transmitted through the bite of different *Aedes* species of mosquitoes in Africa and *Hemagoggus* and *Sabethes* species in South America. When YFV is found in urban areas, *Aedes aegypti* can be the mosquito vector. Like other arboviruses, which are transmitted by mosquitoes, YFV is taken up by a female mosquito when it ingests the blood of an infected human or another primate. Viruses reach the stomach of the mosquito, and if the virus concentration is high enough, the virions can infect epithelial cells and replicate there. From there, they reach the haemocoel (the blood system of mosquitoes) and from there the salivary glands. When the mosquito next sucks blood, it injects its saliva into the wound, and the virus reaches the bloodstream of the bitten person.

Three epidemiologically different infectious cycles occur in which the virus is transmitted from mosquitoes to humans or other primates. In the "urban cycle", only the YFV mosquito *Ae. aegypti* is involved. It is well adapted to urban areas, and can also transmit other diseases, including Zika fever, dengue fever, and chikungunya. Besides the urban cycle, both in Africa and South America, a sylvatic cycle (forest or jungle cycle) is present, where *Aedes africanus* (in Africa) or mosquitoes of the genus *Haemagogus* and *Sabethes* (in South America) serve as vectors. In the jungle, the mosquitoes infect mainly nonhuman primates; the disease is mostly asymptomatic in African primates. People who become infected in the jungle can carry the virus to urban areas, where *Ae. aegypti* acts as a vector. Because of this sylvatic cycle, YFV cannot be eradicated except by eradicating the mosquitoes that serve as vectors. In Africa, a third infectious cycle known as "savannah cycle" or intermediate cycle, occurs between the jungle and urban cycles. Different mosquitoes of the genus *Aedes* are involved. Concern exists about YFV spreading to southeast Asia, where its vector *A. aegypti* already occurs.

Yellow fever virus has been the cause of epidemics in certain jungle locations of sub-Saharan Africa, as well as in some parts of South America. Although many YFV infections are mild, the disease can also cause severe, life-threatening illness. The initial or acute phase of the disease state is normally characterized by high fever, chills, headache, backache, muscle ache, loss of appetite, nausea, and vomiting. After three to four days, these symptoms disappear. In some subjects, symptoms then reappear, as the disease enters its so-called toxic phase. During this phase, high fever reappears and can lead to shock, bleeding (e.g., bleeding from the mouth, nose, eyes, and/or stomach), kidney failure, and liver failure. Indeed, liver failure causes jaundice, which is yellowing of the skin and the whites of the eyes, and thus gives "YFV" its name. About half of the subjects who enter the toxic phase die within 10 to 14 days. However, persons that recover from YFV have lifelong immunity against reinfection. The number of people infected with YFV over the last two decades has been increasing, with there now being about 200,000 YFV cases, and about 30,000 associated deaths, each year. The re-emergence of YFV thus presents a serious public health concern.

Yellow fever is most frequently a clinical diagnosis, based on symptomatology and travel history. Mild cases of the disease can only be confirmed virologically. Since mild cases of YFV can also contribute significantly to regional outbreaks, every suspected case of YFV (involving symptoms of fever, pain, nausea, and vomiting 6-10 days after leaving the affected area) is treated seriously. If YFV is suspected, the virus cannot be confirmed until 6-10 days following the illness. In a differential diagnosis, infections with YFV must be distinguished from other feverish illnesses such as malaria. Other viral hemorrhagic fevers, such as Ebola virus, Lassa virus, Marburg virus, and Junin virus, must be excluded as the cause.

As with other Flavivirus infections, no cure is known for YFV. Hospitalization is advisable and intensive care may be necessary because of rapid deterioration in some cases. Certain acute treatment methods lack efficacy: passive immunization after the emergence of symptoms is probably without effect; ribavirin and other antiviral drugs, as well as treatment with interferons, are ineffective in YFV subjects. Symptomatic treatment includes rehydration and pain relief with drugs such as paracetamol (acetaminophen).

Vaccination is recommended for those traveling to affected areas, because non-native people tend to develop more severe illness when infected. Protection begins by the 10th day after vaccine administration in 95% of people, and had been reported to last for at least 10 years. The World Health Organization (WHO) now states that a single dose of vaccine is sufficient to confer lifelong immunity against YFV disease. The attenuated live vaccine stem 17D was developed in 1937 by Max Theiler.

II. FLAVIVIRUS BIOLOGY

Flaviviruses share several common aspects: common size (40-65 nm), symmetry (enveloped, icosahedral nucleocapsid), nucleic acid (positive-sense, single-stranded RNA around 10,000-11,000 bases), and appearance in the electron microscope.

Most of these viruses are primarily transmitted by the bite from an infected arthropod (mosquito or tick), and hence are classified as arboviruses. Human infections with most of these arboviruses are incidental, as humans are unable to replicate the virus to high enough titers to reinfect the arthropods needed to continue the virus lifecycle—humans are then a dead end host. The exceptions to this are the YFV, dengue, and zika viruses. These three viruses still require mosquito vectors, but are well-enough adapted to humans as to not necessarily depend upon animal hosts (although they continue to have important animal transmission routes, as well). Other virus transmission routes for arboviruses include handling infected animal carcasses, blood transfusion, sex, child birth and consumption of unpasteurized milk products. Transmission from nonhuman vertebrates to humans without an intermediate vector arthropod however mostly occurs with low probability.

Entry into the host cell is achieved by attachment of the viral envelope protein E to host receptors, which mediates clathrin-mediated endocytosis. Replication follows the positive stranded RNA virus replication model. Flaviviruses have a (+) sense RNA genome and replicate in the cytoplasm of the host cells. The genome mimics the cellular mRNA molecule in all aspects except for the absence of the polyadenylated (poly-A) tail. This feature allows the virus to exploit cellular apparatus to synthesize both structural and non-structural proteins, during replication. The cellular ribosome is crucial to the replication of the flavivirus, as it translates the RNA, in a similar fashion to cellular mRNA, resulting in the synthesis of a single polyprotein.

In general, the genome encodes a 5' untranslated region (5' UTR); a coding region encoding the three viral structural proteins; seven non-structural proteins, designated NS1, NS2A, NS2B, NS3, NS4A, NS4B, NS5; and a 3' untranslated region (3' UTR). The viral structural proteins include the capsid (C), premembrane/membrane (prM) and envelope (E) proteins.

The flavivirus particle contains a nucleocapsid composed of viral RNA and capsid protein C. The nucleocapsid is surrounded by an envelope containing the envelope glycoprotein E (50-60 kDa) and a small membrane protein M (7-8 kDa). Translation of the genomic RNA results in a single polyprotein precursor that is cleaved by cellular and viral proteases into viral proteins, in the order: C, prM/M, E, NS 1, NS2A, NS2B, NS3, NS4A, 2K, NS4B, and NS5, where C through E are the structural components of the virion and NS 1 through NS5 are non-structural proteins required for replication (Lindenbach and Rice, Fields Virology, 4th Ed.: 991-1041, 2001). The prM protein (~25 kDa) is the intracellular precursor for M. Immature virions containing prM are produced by budding into the lumen of the endoplasmic reticulum (ER) and are transported to the cell surface through the exocytosis pathway. Cleavage of prM occurs shortly prior to particle release in post-Golgi vesicles. Mature extracellular virus contains predominantly M protein, although a small fraction of uncleaved prM can also be present.

Once translated, cleavage of the polyprotein by a combination of viral and host proteases releases mature polypeptide products. Nevertheless, cellular post-translational modification is dependent on the presence of a poly-A tail; therefore this process is not host-dependent. Instead, the polyprotein contains an autocatalytic feature which automatically releases the first peptide, a virus specific enzyme. This enzyme is then able to cleave the remaining polyprotein into the individual products. One of the products cleaved is a polymerase, responsible for the synthesis of a (−) sense RNA molecule. Consequently, this molecule acts as the template for the synthesis of the genomic progeny RNA.

The genomic RNA is modified at the 5' end of positive-strand genomic RNA with a cap-1 structure (me7-GpppA-me2). Cellular RNA cap structures are formed via the action of an RNA triphosphatase, with guanylyltransferase, N7-methyltransferase and 2'-O methyltransferase. The virus encodes these activities in its non-structural proteins.

Most of the non-structural proteins associate to form the replicase complex, which catalyzes RNA accumulation in close association with modified cytoplasmic membranes. NS3 and its cofactor NS2B is the main viral protease. NS2B contributes to the structure of NS3, anchors the enzyme to the membrane, is required for the majority of NS3-mediated processing events, and can modulate its helicase activity. NS3, together with the NS2B cofactor, mediates cleavage of the flavivirus C protein from its membrane anchor, and is therefore essential for maturation of a major virion component. Processing of C on the cytosolic side of the ER membrane by the flaviviral protease is essential for subsequent cleavage of C from the envelope protein, prM, by the host enzyme signal peptidase in the ER lumen. This regulated sequence of cleavages ensures that processing of prM from the polyprotein is delayed, and budding is stalled, until genomic RNA substrates accumulate through replication; the secretion of the flavivirus glycoproteins, E and prM, as immunogenic subviral particles is thereby minimized. NS3 also has helicase and nucleoside triphosphatase (NTPase) activities, which are essential for replication. The NS3 protein encodes a RNA triphosphatase within its helicase domain. It uses the helicase ATP hydrolysis site to remove the γ-phosphate from the 5' end of the RNA. The N-terminal domain of the non-structural protein 5 (NS5) has both the N7-methyltransferase and guanylyltransferase activities necessary for forming mature RNA cap structures. RNA binding affinity is reduced by the presence of ATP or GTP and enhanced by S-adenosyl methionine. This protein also encodes a 2'-O methyltransferase.

NS2A is also an essential component of the replicase; it colocalizes with replication complexes and has an essential role in the process of RNA accumulation. Purified NS2A binds RNA, leading to the hypothesis that this integral membrane protein might shuttle genomic substrates out of membrane bound replication complexes to the sites of packaging. NS5 constitutes the viral RNA-dependent RNA polymerases and methyltransferase activities, which are important for RNA synthesis and genome capping respectively. NS1, a secreted protein unique to flaviviruses, plays a role early in replication. It is an essential gene that generates a highly conserved ca. 48 kDa glycoprotein that is localized to the lumen of the ER by a signal sequence located at the C-terminus of the structural envelope protein E. NS1 is a highly conserved protein consisting of 352 amino acids with an approximate molecular weight of 40 to 50 kDa, depending on its glycosylation status. The majority of the Flavivirus genus members have two N-linked glycosylation sites at asparagine 130 and asparagine 207, including all four DEN serotypes, JE, and ZIK viruses; YF has glycosylation sites at positions 130 and 208. A few members, such as WN, St. Louis encephalitis, and Murray Valley encephalitis (MVE) viruses, have a third glycosylation site found at amino acid position 175. Interestingly, Entebbe bat virus (ENTV) has four potential N-linked glycosylation sites in NS1, including the two commonly found in all flaviviruses as well as at residues 106 and 326. TBEV appears to have three putative N-linked glycosylation sites at residues 85, 207, and 223. The amino acids at each glycosylation motif are characterized by N-X-T/S.

Flavivirus NS4A and NS4B proteins also have essential roles in RNA accumulation. The flavivirus NS4B is a predominantly hydrophobic transmembrane protein that localizes in the perinuclear region of virus-infected cells and traverses the ER membrane [7]. Detailed nuclear magnetic resonance (NMR) studies of dengue virus 2 (DENV-2) and DENV-3 NS4B structures indicate that this protein has five transmembrane domains as well as several regions that reside within the ER lumen and a series of amino acids that reside in the cytoplasm [8,9]. Although structural studies have not been reported for WNV NS4B, it is predicted that the structure is conserved amongst members of the flavivirus genus. NS4B is known to exist as both a monomer and dimer [10], and it interacts with other viral proteins including NS1, NS2B, NS3, and NS4A at various times during the replication cycle [11-14]. During replication, NS4B is found closely associated to all NS proteins and to double-stranded RNA (dsRNA), indicating it plays a role in the replication complex [15]. Along with a function in viral replication, several roles of NS4B in host innate immune antagonism have been identified. For instance, DENV, YFV (YFV), and WNV NS4B are able to antagonize type-1 interferon signaling by inhibiting STAT1 and STAT2 phosphorylation and thus inhibiting downstream induction of interferon-stimulated genes (ISGs) [16,17]. Studies of the four serotypes of DENV have found that NS4B can inhibit host RNA interference (RNAi) by inhibiting Dicer activity [18], but it is not yet known if WNV NS4B functions similarly.

NS4B has proven to be capable of harboring a number of amino acids whose mutation can have varying impacts on virus viability, virulence, and attenuation. Specifically, there have been reports of NS4B mutations that confer an attenuated phenotype identified in DENV-2 and DENV-4 NS4B [19-21], as well as YFV [22]. Additionally, the YFV 17D and the Japanese encephalitis virus (JEV) SA14-14-2 live, attenuated vaccines have two and one NS4B mutation(s), respectively, that may be important to vaccine attenuation [23,24]. In terms of WNV, the inventors have previously identified several NS4B mutations that confer attenuation in mice including P38G, C102S, and E249G, although compensatory mutations typically appear to contribute to the attenuated phenotype [25-27].

The 5' UTR of flaviviruses are highly structured, has a length of approximately 100 nucleotides and harbors two conserved RNA secondary structures which are vital for the viral life cycle. The first structural element is termed 5'SLA and comprises three stems (S1, S2, S3) folded as Y-shaped-like stem structure, and a side structure domain (SSD). Its overall length is around 70 nucleotides. Disruption experiments of S1 and S2 led to a stop of viral replication. Further, SLA is the promoter for RNA synthesis and interacts with the viral protein NS5 during circularization of the viral genome. After recruitment of NS5, the two loop regions of S3 (TL) and SSD (SSL) are considered to interact with NS5 to promote polymerase activity. Despite the diversity of SSD, its stable structure is essential for infectivity. The second element is termed 5'SLB and contains the translation initiation codon at the top region of the stem loop. It further contains the 5'UAR (upstream AUG region), which is essential for the circularization of the genome. The 5'UAR interacts with the 3'UAR, which is located at the 3' UTR of the genome to form a long-range RNA-RNA interaction. During replication, the 5' UTR interacts with the 3' UTR of the genome to initiate synthesis of new viral replicates and viral protein translation. In direct adjacency to the 5' UTR lies the capsid-coding hairpin region (cHP) structure, which is essential for the viral replication. The cHP actually lies in the ORF of the viral genome and is followed by the 5'CS (conserved sequence), which forms another long-range RNA-RNA interaction with the 3' UTR (3'CS). The cHP aids in the start codon recognition and viral replication. Studies show that the function of cHP is sequence-independent but structure-dependent.

The 3' UTR ranges between 400 and 700 nucleotides in length. Its RNA secondary structure is known to be necessary for the viral replication during infection. The 3' UTR of flavivirus—and sometimes even a small part of the 3' end of the coding region—is also called subgenomic flavivirus RNA (sfRNA). SfRNA is produced by incomplete degradation of the viral genome by the host cell (via XRN1). Local RNA secondary structures (xrRNA elements) in the 3' UTR and long-range RNA-RNA interactions between 5' UTR and 3' UTR of flaviviruses stall XRN1 and cause the undigested fragment of the genome, which has been shown to play a role in pathways comprising both host defense and viral infection.

In contrast to the structurally conserved 5' UTR of flaviviruses, individual structural elements differ between different viruses, which is associated with the host-adaptation. Flaviviruses are therefore classified into four different groups: Mosquito-borne flaviviruses (MBFV), tick-borne flaviviruses (TBFV), insect-specific flaviviruses (ISFV) and those with no known vector (NKV). Across all groups, three RNA secondary structure elements are conserved within the 3' UTR: the dumbbell element (DB), cis-acting replication element (CRE) and the exoribonuclease-resistant RNA elements (xrRNA). Further, unique elements have been observed for specific groups as well.

Dumbbell (DB) elements are important for viral RNA synthesis. These two conserved secondary structures are also known as pseudo-repeat elements. They were originally identified within the genome of Dengue virus and are found adjacent to each other within the 3'UTR. These DB elements have a secondary structure consisting of three helices and they play a role in ensuring efficient translation. Via the formation of additional pseudoknots, the loop regions of DB pairs with a complementary motif further downstream of the respective DB element. The DB elements also expose conserved sequences (CS) and repeated conserved sequences (RCS). Deletion of DB1 has a small but significant reduction in translation but deletion of DB2 has little effect. Deleting both DB1 and DB2 reduced translation efficiency of the viral genome to 25%. Further, the DB elements also play a role in viral translation, as deletion of both elements reduced viral translation levels.

The cis-acting replication element (CRE) structure is structurally conserved among known flaviviruses. It consists of a small hairpin (sHP) and a larger structural element (3'SL). Mutations of sHP are shown to be lethal for Dengue virus in mosquito cells. CRE is highly involved in the 5'-3' UTR interaction of flaviviruses. Regions of sHP are interacting with the SLB element and the cHP in the 5' UTR, whereas the 3'SL harbors a sequence that can interact with SLB, to further stabilize this long-range RNA-RNA interaction.

The exoribonuclease-resistant RNA elements (xrRNA) are described throughout all groups of flaviviruses. Usually, each virus harbors two xrRNAs, xrRNA1 and xrRNA2, in the beginning of the 3' UTR. The formation of these stem-loops, especially xrRNA1, is vital to ensure resistance against XRN1 activity. The Y-shaped stem-loop is also termed SL II and SL IV, respectively. In order to function as xrRNA, the sequence downstream is needed as well, since the upper loop region forms a pseudoknot (PK) with the single-stranded region directly downstream to its respective hairpin. In some species, the region downstream also forms a small hairpin. In such cases, the PK interactions takes place between the two loop regions. Conserved formation of these structures were observed in mammalian cells but not in mosquito cells, suggesting this region has varying functions in different hosts. In plant-viruses, xrRNA elements have been observed as well, showing some similarities to flaviviral xrRNAs. However, plant-virus xrRNA and flaviviral xrRNA are distinguishable by their underlying three-dimensional folds.

The E protein is the main functional and antigenic surface component of the virion. The molecular structure of the ectodomain of E, which forms a homodimer on the surface of mature viral particles at neutral pH, has been resolved by cryoelectron microscopy (Rey et al., Nature 375:291-298, 1995) and fitted into the electron density map of viral particles (Kuhn et al., Cell 108:717-725, 2002). During infection, the E protein functions as a class II fusion protein (Modis et al., Nature 427:313-319, 2004). Following virus binding to a cellular receptor and internalization, the acidic pH in the resulting endosomes triggers dissociation of the dimers such that the previously hidden hydrophobic fusion loop of each monomer is exposed outwardly. Concurrently, the loops insert into the cell (endosome) membrane and monomers rearrange into elongated trimers. Further refolding of the trimers brings the cell and viral membranes into close proximity and forces them to fuse, releasing the contents of the viral particle into the cytoplasm. Previous studies showed that some substitutions in the E protein of DEN and JE, which are selected during serial passages in mouse brain and in cultured monkey kidney and mosquito cells, have been localized in particular regions of the 3D structure of the protein, and were reported to be associated with changes in the fusion function of the viruses. The studies showed that the fusion pH threshold for some attenuated vaccines decreased by 0.6 to 1 pH unit by comparison with the corresponding parental virus isolate. Some changes in six residues in the DEN3 protein E (residues 54, 191, 202, 266, 268, and 277) map to the region in domain II. This region is proposed as a focus for the low-pH mediated conformational change required for the surface exposure of the conserved hydrophobic cd fusion loop (Lee et al., Virology 232:281-290, 1997).

There is no evidence that the small (mature) M protein plays a role in the events leading to virus internalization from the endosome or has any other appreciable function, while its intracellular precursor, prM, is known to be important for morphogenesis and transport of progeny viral particles. The prM protein also facilitates proper folding of E (Lorenz et al., J. Virol. 76:5480-5491, 2002) and functions to protect the E protein dimer from premature conformational rearrangement during passage of new particles towards the cell surface through acidic secretory compartments (Guirakhoo et al., J. Gen. Virol. 72:1323-1329, 1991; Guirakhoo et al., Virology 191:921-931, 1992).

Flavivirus genomic RNA replication occurs on rough endoplasmic reticulum membranes in membranous compartments. New viral particles are subsequently assembled. This occurs during the budding process which is also responsible for the accumulation of the envelope and cell lysis.

Flaviviruses, including YFV and WNV, have two principal biological properties responsible for their induction of disease states in humans and animals. The first of these two properties is neurotropism, which is the propensity of the virus to invade and infect nervous tissue of the host. Neurotropic flavivirus infection can result in inflammation of and injury to the brain and spinal cord (i.e., encephalitis), impaired consciousness, paralysis, and convulsions. The second of these biological properties of flaviviruses is viscerotropism, which is the propensity of the virus to invade and infect vital visceral organs, including the liver, kidney, and heart.

Neurotropic flavivirus infection begins with neuroinvasion, which is the ability of viruses to enter nervous tissue and cause neurological alterations. Once inoculated in the dermis, these viruses spread to infect target cells such as dendritic cells or monocytes/macrophages or enter directly into the lymph nodes, muscles, liver, spleen or nervous system via nerve endings (Chambers & Diamond, 2003; McMinn, 1997). In some cases during infection with these viruses, the blood-brain barrier (BBB) is disturbed as a result of cytokines and chemokines, such as such as tumour necrosis factor-alpha (TNF-alpha), or enzymes, such as matrix metalloproteinase (MMP), that favor the entry of WNV and JEV into nervous tissue by increasing permeability of the endothelium and permitting the entry of viruses into the cerebral parenchyma (Chambers & Diamond 2003; Chaturvedi et al., 1991). Additionally during infection, endothelial cells are activated and overexpress cellular adhesion molecules that favour the transmigration of immune cells into the cerebral parenchyma, such as E-selectin, VCAM-1 and ICAM-1 (Shen et al., 1997; Verna et al., 2009).

The ability of some viruses to infect and replicate in neurons is called neurotropism and is determined by viral and cellular factors. Mostly virus determinants are associated with envelope glycoprotein gene mutations that favor interactions between the virus and molecules on the neuron surface. These interactions promote the fusion of the virus with the plasma membrane and can also trigger endocytosis or transcytosis of the virus. In flaviviruses, the envelope protein (E) is the principal component of the virion surface. It participates in the recognition and subsequent binding to the receptor and the fusion of the virus with the cell membranes (Lindenbach et al., 2007). This protein is formed by three beta-barrel domains known as domains I, II and III, and these last two are responsible for interacting with putative receptor molecules (Pastorino et al., 2010). The molecules that have been reported as possible receptors for flavivirus in different cell populations include ICAM-3 (Jindadamrongwech & Smith, 2004), CD209 (DC-SIGN) (Tassaneetrithep et al., 2003), DC-SIGNR (Davis et al., 2006), integrins (Chu & Ng, 2004), the mannose receptor (Miller et al., 2008), HSP70 and HSP90 (Das et al., 2009; Reyes del Valle et al., 2005), the laminin receptor (Tio et al., 2005) and heparin sulphate (HS) (Germi et al., 2002) among others (Barba-Spaeth et al., 2005; Upanan et al., 2008).

Flaviviruses also have some propensity to infect visceral organs. Viscerotropic flavivirus infection can result in inflammation and injury of the liver (hepatitis), kidney (nephritis), and cardiac muscle (myocarditis), leading to failure or dysfunction of these organs.

Neurotropism and viscerotropism appear to be distinct and separate properties of flaviviruses. Some flaviviruses are primarily neurotropic (such as WNV), others are primarily viscerotropic (e.g., YFV and dengue virus), and still others exhibit both properties (such as Kyasanur Forest disease virus). However, both neurotropism and viscerotropism are present to some degree in all flaviviruses. Within a host, an interaction between viscerotropism and neurotropism is likely to occur, because infection of viscera occurs before invasion of the central nervous system. Thus, neurotropism depends on the ability of the virus to replicate in extraneural organs (viscera). This extraneural replication produces viremia, which in turn is responsible for invasion of the brain and spinal cord. Therefore, while the viscerotropism of these viruses may not necessarily cause dysfunction of vital visceral organs, replication of virus in these organs can cause viremia and thus contribute to invasion of the central nervous system. Thus, in addition to decreasing risk of damage to visceral organs, decreasing the viscerotropism of these viruses by mutagenesis can reduce their abilities to invade the brain and cause encephalitis and other conditions.

III. RECOMBINANT FLAVIVIRUSES

The present disclosure provides recombinant attenuated flaviviruses that can be used in therapeutic methods, such as methods of inducing an immune response and vaccination methods. Central to the flaviviruses of the disclosure are the presence of attenuating mutations in the genomes of the viruses. These mutations can attenuate the viruses by, for example, decreasing the viscerotropism and/or neurotropism of the viruses. The mutations can be present in regions of the flavivirus genome including the 3' untranslated region (3' UTR), capsid sequences, envelope sequences, and/or non-structural sequences. Thus, in some embodiments, mutagenesis can be used to produce attenuated flavivirus that can reduce disease in a subject. Each of these types of mutations, which can be combined with each other and/or other attenuating mutations, are described herein.

Considering that small changes to NS4B can have a substantial impact on the phenotype of flaviviruses, mutation of NS4B may be important for live, attenuated flavivirus vaccine development. In some embodiments, the attenuated flavivirus comprises a flavivirus wherein a nucleic acid construct encoding the genome of the attenuated flavivirus comprises one or more mutations corresponding to a transmembrane domain of non-structural protein 4B (NS4B) of the flavivirus.

The NMR structure of DENV NS4B [8,9] can be used to determine the putative location of amino acid residues of interest, which allows for mutations in different domains of NS4B to be evaluated. Several novel amino acid mutations in NS4B can be made for their ability to alter the phenotype of flaviviruses. Proline 54 occupies the first transmembrane domain of NS4B in WNV and is a candidate for attenuating mutations to reduce neuroinvasion. Thus, in some embodiments, the one or more mutations comprise a substitution of wild-type amino acid proline 54 of the transmembrane domain of NS4B in WNV. In some embodiments, the substitution of wild-type amino acid 54 comprises a substitution of a proline residue with a nonpolar amino acid. In some embodiments, the nonpolar amino acid comprises alanine residue or glycine residue. In some embodiments, the substitution of wild-type amino acid 54 comprises a substitution of a proline residue with a glycine residue. In some embodiments, reversion of the P54G mutation to the wild-type amino acid is inhibited when the virus is grown in a host. Thus, in some embodiments, P54G is a stable mutation. Two nucleotide changes are required to revert glycine to proline, which may reduce reversion to the wild-type amino acid.

P54 in WNV is homologous to P52 in YFV. Thus, in some embodiments, the one or more mutations comprise a substitution of a wild-type amino acid homologous to wild-type amino acid 54 of the transmembrane domain of WNV NS4B. In some embodiments, the YFV wild-type amino acid homologous to wild-type amino acid 54 of the transmembrane domain of WNV NS4B comprises amino acid 52, and wherein substitution of amino acid 52 comprises a substitution of a proline residue with a nonpolar amino acid. In some embodiments, the nonpolar amino acid comprises alanine residue or glycine residue. In some embodiments, the substitution of wild-type amino acid 52 comprises a substitution of a proline residue with a glycine residue. In some embodiments, reversion of the P52G mutation to the wild-type amino acid is inhibited when the virus is grown in a host. Thus, in some embodiments, P52G is a stable mutation.

Since proline residues can be key to protein structure, specifically in alpha helices [9,39,40], it is possible that mutation of P54 or P52 alters the structure and thus the function of NS4B. For example, immunostaining of virus-infected cells demonstrated that cells infected with a P54G mutant do not accumulate NS4B as rapidly as NY99ic-infected cells even though NS1 staining was comparable. Furthermore, a reduction in colocalization of NS1 and NS4B in cells infected with the P54G mutant could indicate that there is less interaction between these two viral proteins, which may inhibit the function of the replication complex. Another consideration is that mutation in NS4B could alter dimer formation. The regions involved in NS4B dimerization include amino acids 129-165 in the cytoplasmic loop and amino acids 166-248 in the C-terminal region, whereas the region including residue 54 has very little impact on dimerization [10].

In some embodiments, the substitution of wild-type amino acid 54 in WNV or amino acid 52 in YFV of the transmembrane domain of NS4B results in reduced induction of cytokines and chemokines as compared to mock-infected cells. In some embodiments, the substitution of wild-type amino acid 54 in WNV or amino acid 52 in YFV of the transmembrane domain of NS4B results in reduced induction of IFN-β as compared to mock-infected cells. In many viral infections, cytokine storm is associated with severe pathology, thus, low cytokine induction by P54 WNV mutants or P52 YFV mutants could reduce disease severity. Previous studies demonstrated that a P38G (+NS3-N480H/NS4B-T116I) WNV mutant induced stronger pro-inflammatory cytokines than NY99 in dendritic cells, THP-1 cells, THP macrophages, and C57Bl/6 mice [35,36], indicating that induction of a robust immune response may contribute to the mechanism of attenuation for the WNV P38G mutant. Thus, the mechanism of attenuation and protection of a P38G as compared to a P54 WNV or P52 YFV mutant is likely to be different.

The mutations of the present disclosure can also be used to complement or improve the attenuation of flavivirus strains that already include one or more other attenuating mutations. For example, the mutations described herein may be combined with an attenuated virus strain developed by the ablation of the glycosylation sites in the envelope (E) and non-structural 1 (NS1) proteins. West Nile virus (WNV), like all members of the Japanese encephalitis (JE) serogroup except JE virus, contains three N-linked glycosylation (N-X-S/T) sites in the NS1 protein at asparagine residues NS1(130), NS1(175) and NS1(207). This E(154S)/NS1(130A/175A/207A) strain showed modest reduction in multiplication kinetics in cell culture and small plaque phenotype compared to the parental NY99 strain yet displayed greater than a 200,000-fold attenuation for mouse neuroinvasiveness compared to the parental strain. Mice infected with 1000PFU of E(154S)/NS1(130A/175A/207A) showed undetectable viremia at either two or three days post infection; nonetheless, high titer neutralizing antibodies were detected in mice inoculated with low doses of this virus and protected against lethal challenge with a 50% protective dose of 50PFU. See Whiteman et al., Vaccine. 2010, 28(4): 1075-83.

Further attenuation may be achieved by mutating the asparagine to serine or glutamine in addition to mutating other residues in the NS1(130-132) glycosylation motif and combining these mutations with those described herein to decrease neuroinvasiveness and neurovirulence. NS1(130-132QQA/175A/207A), the most attenuated mutant virus, showed modest changes in infectivity titers versus the parental strain, was not temperature sensitive, and did not show reversion in mice. Mutant virus was completely attenuated for neuroinvasiveness after intraperitoneal inoculation with >1,000,000 PFU, and mice were protected against lethal challenge. Overall, changing the asparagine of the NS1(130) glycosylation motif to a serine or glutamine attenuated WNV further than the asparagine to alanine substitution. Further, mutating all three of the amino acids of the NS1(130-132) glycosylation motif (NTT-QQA) along with NS1(175) and NS1(207) asparagine to alanine mutations gave the most stable and attenuated strain. See Whiteman et al., *Vaccine.* 2011, 29(52):9702-10.

Thus, in some embodiments, the nucleic acid construct encoding the genome of the attenuated flaviviruses disclosed herein further comprises one or more mutations corresponding to one or more glycosylation sites of non-structural protein 1 (NS1) of the flavivirus. In some embodiments, the one or more mutations corresponding to one or more glycosylation sites of NS1 of the flavivirus comprise a substitution of wild-type amino acids 130-132 of WNV NS1. In some embodiments, the substitution of wild-type amino acids 130 and 131 comprises a substitution of an asparagine residue with a polar amino acid. In some embodiments, the polar amino acid comprises a glutamine residue. In some embodiments, the substitution of amino acid 132 comprises a substitution of a threonine residue with a nonpolar amino acid. In some embodiments, the nonpolar amino acid comprises an alanine residue. In some embodiments, the one or more mutations corresponding to one or more glycosylation sites of NS1 of the flavivirus further comprise a substitution of wild-type amino acid 175 of WNV NS1. In some embodiments, the one or more mutations corresponding to one or more glycosylation sites of NS1 of the flavivirus further comprise a substitution of wild-type amino acid 207 of WNV NS1. In some embodiments, the substitution of wild-type amino acid 175 or wild-type amino acid 207 comprises a substitution of an asparagine residue with a nonpolar amino acid. In some embodiments, the nonpolar amino acid comprises an alanine residue. Homologous mutations to one or more glycosylation sites of YFV NS1 are also contemplated.

Other mutations which may be combined with the mutations disclosed herein include NS4B-P38G, NS4B-C102S, and/or E249G in WNV and homologous mutations in YFV. These mutations are described in detail in Wicker et al., *Virology.* 2006, 349(2):245-53; Wicker et al., *Virology.* 2012, 426(1): 22-33; and Davis et al., *Virology.* 2004, 330(1):342-50.

It is also possible to combine mutations or deletions specified in NS4B with one or more mutations or deletions in the 3'UTR, the capsid gene, in the prM gene, or in the E gene at sites known to attenuate flaviviruses. Thus, optionally, in some embodiments, the mutations of NS4B can be included in a strain with one or more additional attenuating mutations, such as 3'UTR mutations, attenuating mutations in the hinge region of the envelope protein of the virus, amino acids in the membrane protein (for example, the membrane helix portion of the membrane protein), or any of the capsid or envelope protein mutations described herein.

For example, 3'UTR mutations may comprise short, attenuating deletions of for example, less than 30 nucleotides (e.g., 1, 2, 3, etc., and up to 29 (e.g., 2-25, 3-20, 4-15, 5-10, or 6-8 nucleotides in length)) or substitutions in the 3'UTR. In some examples, the short 3'UTR deletions or substitutions are designed to destabilize the secondary structure of one or more predicted stem structures in the 3'UTR.

Capsid mutations may comprise short deletions (e.g., deletions of 1, 2, 3, or 4 amino acids) in the capsid protein. Examples of such mutations include viable deletions affecting Helix I of the protein. Other short mutations in this region can be tested for viability and attenuation, and are also included. Capsid protein sequences of other flaviviruses have been published, e.g., for TBE, WNV, Kunjin, JE, and dengue viruses (e.g., Pletnev et al., *Virology* 174:250-263, 1990).

Membrane mutations may comprise, for example, mutations in the membrane helix portion of the membrane protein (e.g., in any one or more amino acids corresponding to amino acids 40-75 of WNV, for example, amino acid 66). As a specific example, in the case of a WNV membrane protein, the membrane protein amino acid 66 (leucine in wild type WNV) can be replaced with another amino acid, such as proline. In addition to proline, other hydrophobic amino acids, such as isoleucine, methionine, or valine, or small amino acids, such as alanine or glycine, can substitute the wildtype amino acid at position 66 of the membrane protein. As other examples, amino acids at positions 60, 61, 62, 63, and/or 64 of WNV (or corresponding positions in other flaviviruses) can be substituted, alone or in combination with each other, a mutation at position 66, and/or another mutation(s). Examples of substitutions at these positions include: arginine to glycine at position 60, Valine to alanine at position 61, Valine to glutamic acid or methionine at position 62, phenylalanine to serine at position 63, and Valine to isoleucine at position 64.

Envelope mutations may comprise hinge region mutations (e.g., substitutions at positions corresponding to amino acids 48-61, 127, 131, 170, 173, 200, 299, 305, 380, and 196-283 of YFV and substitutions in residues lining the hydrophobic pocket of the domain II (Hurrelbrink et al., *Adv. Virus Res.* 60:1-42, 2003: Modis et al., *PNAS* 100:6986-91, 2003) including residues 52 and 200 in the case of YFV, amino acid 279 of Japanese encephalitis, and amino acids 204, 252, 253, 257, 258, and 261 of dengue 1 virus (see, e.g., WO 03/103571)), as well as substitutions in amino acids 107, 138, 176, 177, 244, 264, 280, 316, and 440 of the WNV. The envelope (E) gene contains functional domains within which amino acid changes may affect function and thereby reduce virulence, as described by Hurrelbrink and McMinn (*Adv. Virus Dis.* 60:1-42, 2003). The polypeptide chain of the envelope protein folds into three distinct domains: a central domain (domain I), a dimerization domain (domain II), and an immunoglobulin-like module domain (domain III). The hinge region is present between domains I and II and, upon exposure to acidic pH, undergoes a conformational change (hence the designation "hinge") that results in the formation of envelope protein trimers that are involved in the fusion of viral and endosomal membranes, after virus uptake by receptor-mediated endocytosis. Prior to the conformational change, the proteins are present in the form of dimers. The functional regions of the E protein in which mutations may be inserted that, together with NS4B deletions/mutations, may result in an appropriately attenuated vaccine include: (a) the putative receptor binding region on the external Surface of domain III, (b) the molecular hinge region between domains I and II, which determines the acid-dependent conformational changes of the E protein in the endosome and reduce the efficiency of virus internalization; (c) the interface of prM/M and E proteins, a region of the E protein that interfaces with prM/M following the rearrangement from dimer to trimer after exposure to low pH in the endosome; (d) the tip of the fusion domain of domain II, which is involved in fusion to the membrane of the endosome during internalization events; and (e) the stem-anchor region, which is also functionally is involved in conformational changes of the E protein during acid-induced fusion events.

Further, the viruses of the invention can also include any other mutations that may or may not be attenuating, but are otherwise beneficial for the vaccine (e.g., for vaccine manufacturing), for example, nucleotide changes in the UTRS or amino acid changes in structure or non-structural proteins that can spontaneously accumulate during virus propagation and be desirable.

Flaviviruses that can be subject to the mutations of the invention include mosquito-borne flaviviruses, such as West Nile (New York 1999 strain); YFV (the wildtype Asibi strain; the YF17D vaccine strain (Smithbum et al., World Health Org., p. 238, 1956; Freestone, in Plotkin et al. (eds.), Vaccines, 2nd edition, W. B. Saunders, Philadelphia, 1995); YF17DD (GenBank Accession No. U 17066); YF17D-213 (GenBank Accession No. U17067) (dos Santos et al., Virus Res. 35:35-41, 1995); YF17D-204 France (X15067, X15062); YF17D-204, 234 US (Rice et al., Science 229: 726-733, 1985; Rice et al., New Biologist 1:285-296, 1989; C 03700, K 02749); and YFV strains described by Galler et al., Vaccine 16 (9/10):1024-28, 1998); Japanese encephalitis (e.g., SA14-14-2), dengue (serotypes 1-4), Murray Valley encephalitis, St. Louis encephalitis, Kunjin, Rocio encephalitis, and Ilheus viruses; tick-borne flaviviruses, such as Central European encephalitis, Siberian encephalitis, Russian Spring-Summer encephalitis, Kyasanur Forest Disease, Alkhurma, Omsk Hemorrhagic fever, Louping ill, Powassan, Negishi, Absettarov, Hansalova, Apoi, and Hypr viruses; as well as viruses from the Hepacivirus genus (e.g., Hepatitis C virus).

A. Polypeptides

In that the compositions of the present disclosure are particularly suitable for use in treating or preventing flavivirus infection, preferred proteins are contemplated. Preferred proteins include flaviviral proteins, for example, the polyprotein precursor that is cleaved by cellular and viral proteases into viral proteins, in the order: C, prM/M, E, NS 1, NS2A, NS2B, NS3, NS4A, 2K, NS4B, and NS5, where C through E are the structural components of the virion and NS1 through NS5 are non-structural proteins required for replication.

As used herein, a "protein", "peptide", or "polypeptide" refers to a molecule comprising at least three amino acid residues. As used herein, the term "wild-type" refers to the endogenous version of a molecule that occurs naturally in an organism. In some embodiments, wild-type versions of a protein or peptide are employed, however, in many embodiments of the disclosure, a modified protein or peptide is employed. The terms described above may be used interchangeably. A "modified protein" or "modified polypeptide" or a "variant" or a "mutant" refers to a protein or peptide whose chemical structure, particularly its amino acid sequence, is altered with respect to the wild-type protein or peptide. In some embodiments, a modified/variant/mutant protein or peptide has at least one modified activity or function (recognizing that proteins or polypeptides may have multiple activities or functions). It is specifically contemplated that a modified/variant protein or peptide may be altered with respect to one activity or function yet retain a wild-type activity or function in other respects.

Recombinant DNA technology may be employed wherein a nucleotide sequence that encodes a peptide or polypeptide is inserted into an expression vector, transformed or transfected into an appropriate host cell and cultivated under conditions suitable for expression. In particular embodiments, there are isolated nucleic acid segments and recombinant vectors incorporating nucleic acid sequences that encode a peptide. The term "recombinant" may be used in conjunction with a peptide or the name of a specific peptide, and this generally refers to a peptide produced from a nucleic acid molecule that has been manipulated in vitro or that is a replication product of such a molecule.

In certain embodiments a protein may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide, or peptide.

B. Polynucleotides

Some aspects are directed to a nucleic acid construct encoding the genome of an attenuated flavivirus disclosed herein, or a complement thereof. Some aspects are directed to a nucleic acid construct encoding for a polypeptide or fragment thereof that corresponds to an attenuated flavivirus. In certain embodiments, nucleic acid sequences can exist in a variety of instances such as: isolated segments and recombinant vectors of incorporated sequences or recombinant polynucleotides encoding the genome of an attenuated flavivirus, or a fragment, derivative, mutein, or variant thereof, polynucleotides sufficient for use as hybridization probes, polymerase chain reaction (PCR) primers or sequencing primers for identifying, analyzing, mutating or amplifying a polynucleotide encoding a polypeptide, antisense oligonucleotides for inhibiting expression of a polynucleotide, and complementary sequences of the foregoing described herein. The nucleic acids can be single-stranded or double-stranded and can comprise RNA and/or DNA nucleotides and artificial variants thereof (e.g., peptide nucleic acids).

The term "polynucleotide" refers to a nucleic acid molecule that either is recombinant or has been isolated from total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein (SEQ ID NO:1, 3, 5, and 7) using the methods described herein (e.g., BLAST analysis using standard parameters). In certain aspects, the isolated polynucleotide will comprise a nucleotide sequence encoding a polypeptide that has at least 80%, at least 85%, at least 90%, or at least 95%, or at least 99% and above, identity to an amino acid sequence described herein, over the entire length of the sequence; or a nucleotide sequence complementary to said isolated polynucleotide. In certain aspects, the polynucleotide will encode a flavivirus polyprotein with a NS4B having a substitution at proline 54.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. The nucleic acids can be any length. They can be, for example, 5, 10, 15, 20, 25, 30, 35, 40, 45, 50, 75, 100, 125, 175, 200, 250, 300, 350, 400, 450, 500, 750, 1000, 1500, 3000, 5000 or more nucleotides in length, and/or can comprise one or more additional sequences, for example, regulatory sequences, and/or be a part of a larger nucleic acid, for example, a vector. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

C. Modified Polynucleotides and Peptides

Mutations can be made in the viruses of the disclosure using standard methods, including, but not limited to, site-directed mutagenesis, direct synthesis, deletion, or other method using techniques known to those skilled in the art. It is understood by those skilled in the art that the virulence screening assays, as described herein and as are well known in the art, can be used to distinguish between virulent and avirulent structures. Nucleic acid sequences of any construct disclosed herein and/or nucleic acid molecules encoding the flavivirus proteins may be synthesized using any known nucleic acid synthesis techniques and inserted into an appropriate vector. Avirulent, immunogenic viruses of embodiments herein can therefore be produced using recombinant engineering techniques known to those skilled in the art.

Thus, in some aspects, the present disclosure is directed to a method of producing a recombinant attenuated flavivirus. In some embodiments, the method produces a recombinant attenuated flavivirus that can be used as a vaccine to treat or prevent flavivirus infection. In some embodiments, the method comprises introducing into a nucleic acid construct encoding the genome of the attenuated flavivirus one or more mutations corresponding to a transmembrane domain of non-structural protein 4B (NS4B) of the flavivirus. In some embodiments, the one or more mutations attenuates the flavivirus, relative to a corresponding flavivirus lacking the mutation, and further.

In some embodiments, the one or more mutations comprise a substitution of wild-type amino acid 54 of the transmembrane domain of WNV NS4B. In some embodiments, the one or more mutations comprise a substitution of wild-type amino acid 52 of the transmembrane domain of YFV NS4B. In some embodiments, the substitution of wild-type amino acid 54 of WNV or wild-type amino acid 52 of YFV comprises a substitution of a proline residue with a nonpolar amino acid. In some embodiments, the nonpolar amino acid comprises alanine residue or glycine residue. In some embodiments, the method further comprises introducing into the nucleic acid construct encoding the genome of the attenuated flavivirus one or more additional mutations corresponding to one or more glycosylation sites of non-structural protein 1 (NS1) of the flavivirus. In some embodiments, the one or more mutations corresponding to one or more glycosylation sites of NS1 of the flavivirus comprise a substitution of wild-type amino acids 130-132 of WNV NS1. In some embodiments, the substitution of wild-type amino acids 130 and 131 comprises a substitution of an asparagine residue with a polar amino acid. In some embodiments, the polar amino acid comprises a glutamine residue. In some embodiments, the substitution of amino acid 132 comprises a substitution of a threonine residue with a nonpolar amino acid. In some embodiments, the nonpolar amino acid comprises an alanine residue. In some embodiments, the one or more mutations corresponding to one or more glycosylation sites of NS1 of the flavivirus further comprise a substitution of wild-type amino acid 175 of NS1. In some embodiments, the one or more mutations corresponding to one or more glycosylation sites of NS1 of the flavivirus further comprise a substitution of wild-type amino acid 207 of NS1. In some embodiments, the substitution of wild-type amino acid 175 or wild-type amino acid 207 comprises a substitution of an asparagine residue with a nonpolar amino acid. In some embodiments, the nonpolar amino acid comprises an alanine residue. Homologous mutations to one or more glycosylation sites of YFV NS1 are also contemplated.

The mutations described above are deletions and substitutions, but other types of mutations, such as insertions, can be used in the invention as well. In addition, as is noted above, the mutations can be present singly or in the context of one or more additional mutations. Further, in addition to the specific amino acids noted above, the substitutions can be made with other amino acids, such as amino acids that would result in a conservative change from those noted above. Conservative substitutions typically include substitutions within the following groups: glycine, alanine, valine, isoleucine, and leucine; aspartic acid, glutamic acid, asparagine, and glutamine; serine and threonine; lysine and arginine; and phenylalanine and tyrosine. Further, both conservative and non-conservative changes can be selected for analysis of their attenuating effect(s) based on computer-predicted (using protein structure modeling software) changes they cause in the E protein X-ray structure.

As modifications and/or changes may be made in the structure of the polynucleotides and/or proteins according to the present disclosure, while obtaining attenuated flaviviruses and/or molecules having similar or improved characteristics, such biologically functional equivalents are also encompassed within the present invention.

The biological functional equivalent may comprise a polynucleotide that has been engineered to contain distinct sequences while at the same time retaining the capacity to encode the "wild-type" or standard protein or peptide or "variant" protein or peptide. This can be accomplished to the degeneracy of the genetic code, i.e., the presence of multiple codons, which encode for the same amino acids. The term "functionally equivalent codon" is used herein to refer to codons that encode the same amino acid, such as the six different codons for arginine. Also considered are "neutral substitutions" or "neutral mutations" which refers to a change in the codon or codons that encode biologically equivalent amino acids. In one example, one of skill in the art may wish to introduce a restriction enzyme recognition sequence into a polynucleotide while not disturbing the ability of that polynucleotide to encode a protein.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in selected amino acids (or codons) which may be substituted.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification and retain a biologically viable virus that is infectious to cells.

In one example, a polynucleotide may be (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. So-called "conservative" changes do not disrupt the biological activity of the protein, as the structural change is not one that impinges of the protein's ability to carry out its designed function. It is thus contemplated by the inventors that various changes may be made in the sequence of genes and proteins disclosed herein, while still fulfilling the goals of the present invention. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa. Non-conservative substitutions may involve the exchange of a member of one of the amino acid classes for a member from another class.

In other embodiments, alteration of the function of a polypeptide is intended by introducing one or more substitutions. For example, certain amino acids may be substituted for other amino acids in a protein structure without appreciable loss of interactive binding capacity. Structures such as, for example, an enzymatic catalytic domain or interaction components may have amino acid substituted to maintain such function. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

Deletion variants typically lack one or more residues of the native or wild type protein. Individual residues can be deleted or a number of contiguous amino acids can be deleted. A stop codon may be introduced (by substitution or insertion) into an encoding nucleic acid sequence to generate a truncated protein. For example, it is contemplated that peptides may be mutated by truncation, or deletion of a number of contiguous amino acids, rendering them shorter than their corresponding wild-type form.

Insertional mutants typically involve the addition of amino acid residues at a non-terminal point in the polypeptide. This may include the insertion of one or more amino acid residues. Terminal additions may also be generated and can include fusion proteins which are multimers or concatemers of one or more peptides or polypeptides described or referenced herein. For example, it is contemplated that peptides might be altered by fusing or conjugating a heterologous protein or polypeptide sequence with a particular function (e.g., for targeting or localization, for enhanced activity, for purification purposes, etc.).

Additionally, the polypeptides of the disclosure may be chemically modified. Glycosylation of the polypeptides can be altered, for example, by modifying one or more sites of glycosylation within the polypeptide sequence to increase the affinity of the polypeptide for antigen (U.S. Pat. Nos. 5,714,350 and 6,350,861).

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

Amino acid sequence variants of the disclosure can be substitutional, insertional, or deletion variants, for example. It is contemplated that a region or fragment of a polypeptide of the disclosure may have an amino acid sequence that has, has at least or has at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200 or more amino acid substitutions, contiguous amino acid additions, or contiguous amino acid deletions with respect to any of SEQ ID NOs:2, 4, 6, 8, or 19. Alternatively, a region or fragment of a polypeptide of the disclosure may have an amino acid sequence that comprises or consists of an amino acid sequence that is, is at least, or is at most 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% (or any range derivable therein) identical to any of SEQ ID NOs:2, 4, 6, 8, or 19. In certain aspects the amino acid sequence will include a mutation corresponding to a WNV NS4B protein having a substitution of proline 54.

Moreover, in some embodiments, a region or fragment comprises an amino acid region of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 or more contiguous amino acids starting at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 in any of SEQ ID NOs:2, 4, 6, or 8 (where position 1 is at the N-terminus of the SEQ ID NO). The polypeptides of the disclosure may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more variant amino acids or be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% similar, identical, or homologous with at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 600, or more contiguous amino acids, or any range derivable therein, of any of SEQ ID NOs:2, 4, 6, or 8.

The polypeptides of the disclosure may include at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 substitutions (or any range derivable therein).

The substitution may be at amino acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 of any of SEQ ID NOs:2, 4, 6, or 8 (or any derivable range therein).

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

In making such changes to produce biologically functional equivalents, the hydropathic index of amino acids may be considered. The hydropathy profile of a protein is calculated by assigning each amino acid a numerical value ("hydropathy index") and then repetitively averaging these values along the peptide chain. Each amino acid has been assigned a value based on its hydrophobicity and charge characteristics. They are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. It is also known that certain amino acids may be substituted for other amino acids having a similar hydropathy index or score, and still retain a similar biological activity. In making changes based upon the hydropathy index, in certain embodiments, the substitution of amino acids whose hydropathy indices are within ±2 is included. In some aspects of the disclosure, those that are within ±1 are included, and in other aspects of the disclosure, those within ±0.5 are included.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. In certain embodiments, the greatest local average hydrophilicity of a protein, as governed by the hydrophilicity of its adjacent amino acids, correlates with its immunogenicity and antigen binding, that is, as a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, in certain embodiments, the substitution of amino acids whose hydrophilicity values are within +2 are included, in other embodiments, those which are within +1 are included, and in still other embodiments, those within +0.5 are included. In some instances, one may also identify epitopes from primary amino acid sequences based on hydrophilicity. These regions are also referred to as "epitopic core regions." It is understood that an amino acid can be substituted for another having a similar hydrophilicity value and still produce a biologically equivalent and immunologically equivalent protein.

Additionally, one skilled in the art can review structure-function studies identifying residues in similar polypeptides or proteins that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar proteins or polypeptides. In view of such information, one skilled in the art may predict the alignment of amino acid residues of an antibody with respect to its three-dimensional structure. One skilled in the art may choose not to make changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using standard assays for binding and/or activity, thus yielding information gathered from such routine experiments, which may allow one skilled in the art to determine the amino acid positions where further substitutions should be avoided either alone or in combination with other mutations. Various tools available to determine secondary structure can be found on the World Wide Web at expasy.org/proteomics/protein_structure.

In some embodiments of the disclosure, amino acid substitutions are made that: (1) reduce susceptibility to proteolysis, (2) reduce susceptibility to oxidation, (3) alter binding affinity for forming protein complexes, (4) alter ligand or antigen binding affinities, and/or (5) confer or modify other physicochemical or functional properties on such polypeptides. For example, single or multiple amino acid substitutions (in certain embodiments, conservative amino acid substitutions) may be made in the naturally occurring sequence. Substitutions can be made in that portion of the antibody that lies outside the domain(s) forming intermolecular contacts. In such embodiments, conservative amino acid substitutions can be used that do not substantially change the structural characteristics of the protein or polypeptide (e.g., one or more replacement amino acids that do not disrupt the secondary structure that characterizes the native antibody).

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

D. Methods of Making Recombinant Flaviviruses

The viruses of the present invention can be made using standard methods in the art. For example, an RNA molecule corresponding to the genome of a virus can be introduced into primary cells, chick embryos, or diploid cell lines, from which (or the supernatants of which) progeny virus can then be purified. Another method that can be used to produce the viruses employs heteroploid cells, such as Vero cells (Yasumura et al., Nihon Rinsho 21, 1201-1215, 1963). In this method, a nucleic acid molecule (e.g., an RNA molecule) corresponding to the genome of a virus is introduced into the heteroploid cells, virus is harvested from the medium in which the cells have been cultured, harvested virus is treated with a nuclease (e.g., an endonuclease that degrades both DNA and RNA, such as Benzonase™; U.S. Pat. No. 5,173,418), the nuclease-treated virus is concentrated (e.g., by use of ultrafiltration using a filter having a molecular weight cut-off of, e.g., 500 kDa), and the concentrated virus is formulated for the purposes of vaccination. Details of this method are provided in WO 03/060088 A2, which is incorporated herein by reference.

In some embodiments, a method of manufacturing an attenuated flavivirus disclosed herein comprises introducing a nucleic acid construct encoding the genome of the attenuated flavivirus into cells and isolating flavivirus produced in the cells from the cells or the supernatant thereof. In some embodiments, the cells are Vero cells. In some embodiments, the cells are cultured in serum free medium.

IV. FLAVIVIRUS INFECTION PREVENTION AND TREATMENT

Aspects of the present disclosure are directed to compositions and methods of using such compositions to treat or prevent flavivirus infection in a subject. In some embodiments, the flavivirus is selected from the group consisting of WNV, Japanese encephalitis virus, St. Louis encephalitis virus, tickborne encephalitis virus, dengue fever virus, and YFV. In some embodiments, the flavivirus is WNV. In some embodiments, the flavivirus is YFV.

In some embodiments, the attenuated flaviviruses or polynucleotides that encode the genome of the attenuated flaviviruses comprise the nucleic acid sequence of SEQ ID NOs:1, 3, 5, or 7.

In some aspects, the disclosure is directed to an immunogenic composition for inducing an immune response in a subject comprising an attenuated flavivirus disclosed herein and a pharmaceutically acceptable carrier or diluent. In some embodiments, the attenuated flavivirus induces the same immune response in the subject as the corresponding wild type virus. In some aspects, the disclosure is directed to a method of inducing an immune response in a subject comprising administering an effective amount of an immunogenic composition for inducing an immune response in a subject comprising an attenuated flavivirus disclosed herein and a pharmaceutically acceptable carrier or diluent to the subject. In some embodiments, an immune response to at least one of WNV, Japanese encephalitis virus, St. Louis encephalitis virus, tickborne encephalitis virus, dengue fever virus, and YFV is induced in the subject. In some embodiments, the immune response induced in the subject is to WNV. In some embodiments, the immune response induced in the subject is to YFV.

In some aspects, the disclosure is directed to a vaccine composition comprising an attenuated flavivirus disclosed herein and a pharmaceutically acceptable carrier or diluent. In some aspects, the disclosure is directed to a method of immunizing a subject against a flavivirus infection comprising administering an effective amount of a vaccine composition comprising an attenuated flavivirus disclosed herein to the subject.

In certain embodiments, the disclosed methods further comprise treating a subject who does not have, but is at risk of developing, infection by a flavivirus. In certain embodiments, the disclosed methods comprise treating a subject who is infected by a flavivirus. In certain embodiments, the disclosed methods further comprise treating a subject who has been diagnosed as having symptoms of a flavivirus infection. In certain embodiments, the disclosed methods further comprise treating a subject who has been identified as being at risk of having a flavivirus infection. A subject may be diagnosed with or as having symptoms of or may be identified as being at risk of having a flavivirus infection using tests and diagnostic methods known in the art and described herein.

In some embodiments, the methods further comprise determining a subject is in need of treatment comprising a therapeutically effective amount of an immunogenic or vaccine composition comprising an attenuated flavivirus disclosed herein. In some embodiments, the methods further comprise providing to a subject a treatment comprising a therapeutically effective amount of an immunogenic or vaccine composition comprising an attenuated flavivirus disclosed herein when it is determined that the subject is in need thereof. In some embodiments, determining a subject is in need of a treatment comprising a therapeutically effective amount of an immunogenic or vaccine composition comprising an attenuated flavivirus disclosed herein comprises diagnosing the subject with a flavivirus infection. In some embodiments, determining a subject is in need of a treatment comprising a therapeutically effective amount of an immunogenic or vaccine composition comprising an attenuated flavivirus disclosed herein comprises diagnosing the subject as having symptoms of a flavivirus infection. In some embodiments, determining a subject is in need of a treatment comprising a therapeutically effective amount of an immunogenic or vaccine composition comprising an attenuated flavivirus disclosed herein comprises identifying the subject as being at risk of having a flavivirus infection.

In some embodiments, the disclosed methods comprise administering to a subject suffering from a flavivirus infection a therapeutically effective amount of an immunogenic or vaccine composition comprising an attenuated flavivirus disclosed herein. As disclosed herein, flavivirus infections can be associated with neuroinvasion, neurotropism, and/or viscerotropism, and administration of an immunogenic or vaccine composition comprising an attenuated flavivirus disclosed herein has been surprising and unexpectedly found to prevent or decease neuroinvasion. Further, administering an immunogenic or vaccine composition comprising an attenuated flavivirus disclosed herein can surprisingly prevent or decrease cytokine induction in infected cells. Thus, in some embodiments, the one or more mutations decrease cytokine response to the flavivirus, relative to a corresponding flavivirus lacking the mutation. Accordingly, some embodiments are directed to compositions and corresponding methods for treating a subject suffering from flavivirus infection with a therapeutically effective amount of an immunogenic or vaccine composition comprising an attenuated flavivirus disclosed herein. In some embodiments, the immunogenic or vaccine composition comprising an attenuated flavivirus induces an immune response in a host.

The attenuated flaviviruses disclosed herein also demonstrate surprising genetic stability. Thus, in some embodiments, one or more mutations in a nucleic acid construct encoding the genome of the attenuated flavivirus inhibits reversion of the one or more mutations to the wild-type amino acid is inhibited when the virus is grown in a host.

In further embodiments, disclosed is an attenuated flavivirus, wherein one or more mutations in a nucleic acid construct encoding the genome of the attenuated flavivirus decrease the viscerotropism of the flavivirus, relative to a corresponding flavivirus lacking the mutation. Also disclosed is a method for decreasing viscerotropism of the flavivirus in vivo, comprising contacting at least one cell of a host with a therapeutically effective amount of an immunogenic or vaccine composition comprising an attenuated flavivirus disclosed herein. In further embodiments, disclosed is an attenuated flavivirus, wherein one or more mutations in a nucleic acid construct encoding the genome of the attenuated flavivirus decrease the neurotropism of the flavivirus, relative to a corresponding flavivirus lacking the mutation. Also disclosed is a method for decreasing neurotropism of the flavivirus in vivo, comprising contacting at least one cell of a host with a therapeutically effective amount of an immunogenic or vaccine composition comprising an attenuated flavivirus disclosed herein. In some embodiments, the flavivirus infection is one which is characterized by neuroinvasion, neurotropism, and/or viscerotropism.

The subject may have a condition that has as a symptom and/or a neuroinvasion, neurotropism, and/or viscerotropism, for example. Embodiments of the disclosure include treatment or prevention of any medical condition in which modulation of neuroinvasion, neurotropism, and/or viscerotropism by flaviviruses would be beneficial. In specific embodiments, an individual is provided a therapeutically effective amount of an immunogenic or vaccine composition comprising an attenuated flavivirus for attenuation of neuroinvasion, neurotropism, and/or viscerotropism in an individual or a delay or reversal in neuroinvasion, neurotropism, and/or viscerotropism in an individual. In specific embodiments, the medical condition treated or prevented with an immunogenic or vaccine composition comprising an attenuated flavivirus comprises flavivirus infections which can lead to neuroinvasion, neurotropism, and/or viscerotropism. In particular embodiments, neuroinvasion, neurotropism, and/or viscerotropism is not treated with compositions the disclosure. In some cases, an immunogenic or vaccine composition comprising an attenuated flavivirus treats or prevents the medical condition in the individual by ameliorating, inhibiting, delaying, or reversing neuroinvasion, neurotropism, and/or viscerotropism, for example.

Although in some cases the immunogenic or vaccine composition comprising an attenuated flavivirus is provided as a sole therapy for the individual, in other cases the individual is provided one or more additional therapies for treating or preventing flavivirus infection, neuroinvasion, neurotropism, and/or viscerotropism. The one or more additional therapies may be of any kind, but in specific cases the one or more additional therapies are one or more additional anti-viral therapeutics, for example, anti-flaviviral medications. In some embodiments, the one or more additional therapies are one or more additional therapeutics to treat symptoms of flaviviral infection.

V. FLAVIVIRUS IMMUNOGENIC COMPOSITIONS AND VACCINES

The flaviviruses disclosed herein provide live, attenuated viruses useful as immunogens or vaccines. In one embodiment, the flaviviruses exhibit high immunogenicity while at the same time not producing dangerous pathogenic or lethal effects. As used herein, an immunogen or vaccine is said to prevent or attenuate a disease if administration of the immunogen or vaccine to an individual results either in the total or partial immunity of the individual to the disease, or in the total or partial attenuation (i.e., suppression) of symptoms or conditions associated with the disease. Accordingly, the invention relates to a method for raising a protective immune response in a human subject, the method comprising administering a therapeutically effective amount of an immunogenic composition or vaccine as described anywhere throughout the specification to the subject. Also provided herein is a method of providing immune protection in humans against flavivirus infection comprising administering an effective amount of the attenuated flavivirus compositions of the disclosure to the subject, thereby providing protection from flavivirus infection. The disclosure also relates to a method for raising a protective immune response in a subject, the method comprising administering a therapeutically effective amount of an immunogenic composition comprising an attenuated flavivirus. Other aspects of this invention also describe the use of a composition as described above or throughout the specification for the manufacture of a medicament for the treatment or prevention of flavivirus infection or disease caused thereby.

The viruses of this disclosure can comprise the structural and non-structural genes of a WNV or a YFV, for example. The strategy described herein of using a genetic background that contains the viral genomes, and, by mutation, the properties of attenuation, has led to the development of live, attenuated flavivirus vaccine candidates of desired immunogenicity. Thus, vaccine candidates for control of flavivirus pathogens, for example, WNV or YFV, can be designed.

Viruses described herein are typically grown using techniques known in the art. Virus plaque or focus forming unit (FFU) titrations are then performed and plaques or FFU are counted in order to assess the viability, titer and phenotypic characteristics of the virus grown in cell culture. Wild type viruses are mutagenized to derive attenuated candidate starting materials.

Immunogenic compositions or vaccines may either be prophylactic (to prevent infection) or therapeutic (to treat disease after infection). The viruses of the invention can be administered as primary prophylactic agents in those at risk of infection, or can be used as secondary agents for treating infected subjects. Because the viruses are attenuated, they are particularly well suited for administration to "at risk individuals" such as the elderly, children, or HIV infected persons. The immunogenic compositions or vaccines can also be used in veterinary contexts, e.g., in the vaccination of horses against WNV infection, or in the vaccination of birds (e.g., valuable, endangered, or domestic birds, such as flamingos, bald eagles, and geese, respectively). Further, the immunogenic compositions or vaccines can include a virus, such as a virus, including a particular mutation, in a mixture with viruses lacking such mutations.

Such immunogenic compositions or vaccines comprise antigen or antigens, usually in combination with "pharmaceutically acceptable carriers" or "acceptable carriers", as may be used interchangeably as will be clear from the context, which include any carrier that does not itself induce the production of antibodies harmful to the individual receiving the composition.

A. Formulation

Formulation of the viruses of the invention can be carried out using methods that are standard in the art. Embodiments provide for administration of compositions to subjects in a biologically compatible form suitable for pharmaceutical administration in vivo. By "biologically compatible form suitable for administration in vivo," it is meant a form of the active agent (e.g. pharmaceutical protein, peptide, or gene etc. of the embodiments) to be administered in which any toxic effects are outweighed by the therapeutic effects of the active agent. Numerous pharmaceutically acceptable solutions for use in vaccine preparation are well known and can readily be adapted for use in the present invention by those of skill in this art (see, e.g., Remington's Pharmaceutical Sciences (18th edition), ed. A. Gennaro, 1990, Mack Publishing Co., Easton, Pa.). In two specific examples, the viruses are formulated in Minimum Essential Medium Earle's Salt (MEME) containing 7.5% lactose and 2.5% human serum albumin or MEME containing 10% sorbitol. However, the viruses can simply be diluted in a physiologically acceptable solution, such as sterile saline or sterile buffered saline. In another example, the viruses can be administered and formulated, for example, in the same manner as the YFV 17D vaccine, e.g., as a clarified suspension of infected chicken embryo tissue, or a fluid harvested from cell cultures infected with a chimeric virus.

The viruses described herein are individually or jointly combined with a pharmaceutically acceptable carrier or vehicle for administration as an immunogen or vaccine to humans or animals. The terms "pharmaceutically acceptable carrier" or "pharmaceutically acceptable vehicle" are used herein to mean any composition or compound including, but not limited to, water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a toxoid, such as a toxoid from diphtheria, tetanus, cholera, *H. pylori*, etc. Adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L 121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorolipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc; and (6) other substances that act as immunostimulating agents to enhance the effectiveness of the composition. Alum and MF59 are preferred. As mentioned above, muramyl peptides include, but are not limited to, N-acetyl-muramyl-L-threonyl-D-isoglutamine (thr-MDP), N-acetyl-nornuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-huydroxyphos-phoryloxy)-ethylamine (MTPPE), etc.

The immunogenic compositions (e.g., the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles. Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers. Immunogenic compositions of the present disclosure elicit formation of antibodies with high binding specificity to a composition of a flavivirus.

Such immunogenic compositions used as vaccines comprise an immunologically effective amount of the antigenic polypeptides, as well as any other of the above-mentioned components, as needed. By "immunologically effective amount", or "therapeutically effective amount" as may be used interchangeably and as will be clear from the context, it is meant that the administration of that amount to an individual or host subject animal, either in a single dose or as part of a series, is effective for treatment or prevention or the amount effective at various dosages and for periods of time necessary to achieve the desired result. For example, the active ingredients of the compositions of the invention are present in a therapeutically effective amount if the administration of the composition to a subject results in a detectable change in the physiology of the recipient subject, such as the induction of a neutralizing antibody against the attenuated flavivirus. This amount varies depending upon the health and physical condition of the individual or host subject animal to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. For example, effective amounts of the compositions can vary from 0.01-500 g per product per dose, 1-100 g per product per dose, or 5-50 g per product per dose. Dosage regima may be adjusted to provide the optimum therapeutic response. It is expected that the amount will fall in a relatively broad range that can be determined through routine trials.

The immunogenic compositions are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

The immunogenic or vaccine formulations may be conveniently presented in viral plaque forming unit (PFU) unit or focus forming unit (FFU) dosage form and prepared by using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used. In all cases, the composition can be sterile and can be fluid to the extent that easy syringability exists. It might be stable under the conditions of manufacture and storage and may be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of microorganisms can be achieved by heating, exposing the agent to detergent, irradiation or adding various antibacterial or antifungal agents.

Sterile injectable solutions can be prepared by incorporating active compound in the required amount with one or a combination of ingredients enumerated above, as required. Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art.

In another embodiment, nasal solutions or sprays, aerosols or inhalants may be used to deliver the compound of interest. Additional formulations that are suitable for other modes of administration include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, for example, 1% 2%.

Upon formulation, solutions will be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed. These particular aqueous solutions are especially suitable for intravenous, intramuscular, subcutaneous and intraperitoneal administration.

The composition may be stored at temperatures of from about −100° C. to about 4° C. The composition may also be stored in a lyophilized state at different temperatures including room temperature. The composition may be sterilized through conventional means known to one of ordinary skill in the art. Such means include, but are not limited to, filtration. The composition may also be combined with bacteriostatic agents to inhibit bacterial growth.

B. Administration

The vaccines of the invention can be administered using methods that are well known in the art, and appropriate amounts of the vaccines to be administered can readily be determined by those of skill in the art. What is determined to be an appropriate amount of virus to administer can be determined by consideration of factors such as, e.g., the size and general health of the subject to whom the virus is to be administered. For example, the viruses of the invention can be formulated as sterile aqueous solutions containing between $10^2$ and $10^8$, e.g., $10^3$ to $10^7$, infectious units (e.g., plaque-forming units or tissue culture infectious doses) in a dose volume of 0.1 to 1.0 ml, to be administered. In addition, because flaviviruses may be capable of infecting the human host via mucosal routes, such as the oral route (Gresikova et al., "Tick-borne Encephalitis," In The Arboviruses, Ecology and Epidemiology, Monath (ed.), CRC Press, Boca Raton, Fla., 1988, Volume IV, 177-203), the viruses can be administered by mucosal routes as well. Preferred unit dosage formulations are those containing a dose or unit, or an appropriate fraction thereof, of the administered ingredient. It should be understood that in addition to the ingredients particularly mentioned above, the formulations of the present invention may include other agents commonly used by one of ordinary skill in the art.

The immunogenic or vaccine composition may be administered through different routes, such as oral or parenteral, including, but not limited to, buccal and sublingual, rectal, aerosol, nasal, intramuscular, subcutaneous, intradermal, and topical. The composition may be administered in different forms, including, but not limited to, solutions, emulsions and suspensions, microspheres, particles, microparticles, nanoparticles and liposomes.

Further, the vaccines of the invention can be administered in a single dose or, optionally, administration can involve the use of a priming dose followed by a booster dose that is administered, as determined to be appropriate by those of skill in the art. In some embodiments, if multiple immunizations are given, they are given one to two months apart. In some embodiments, a subject is immunized at 0, 1, and 2 months. In some embodiments, a subject is immunized at 0, 1, and 3 months. In some embodiments, a subject is immunized at 0, 1, and 6 months.

In some embodiments, 1 to about 6 doses may be required per immunization schedule. Initial doses may range from about 100 to about 100,000 PFU or FFU, about 500 to about 20,000 PFU or FFU, about 1000 to about 12,000 PFU or FFU and about 1000 to about 4000 PFU or FFU. Booster injections may range in dosage from about 100 to about 20,000 PFU or FFU, about 500 to about 15,000, about 500 to about 10,000 PFU or FFU, and about 1000 to about 5000 PFU or FFU. For example, the volume of administration will vary depending on the route of administration. Intramuscular injections may range in volume from about 0.1 ml to 1.0 ml. In certain embodiments, a dual dose on day 0 may be administered in single anatomical or multiple anatomical locations in order to induce an immune response with reduced interference or different lymph nodes.

Optionally, adjuvants that are known to those skilled in the art can be used in the administration of the viruses of the invention. Such adjuvants include, but are not limited to, the following: polymers, co-polymers such as polyoxyethylene-polyoxypropylene copolymers, including block co-polymers, polymer p 1005, Freund's complete adjuvant (for animals), Freund's incomplete adjuvant; sorbitan monooleate, squalene, CRL-8300 adjuvant, alum, QS 21, muramyl dipeptide, CpG oligonucleotide motifs and combinations of CpG oligonucleotide motifs, trehalose, bacterial extracts, including mycobacterial extracts, detoxified endotoxins, membrane lipids, or combinations thereof. Further adjuvants that can be used to enhance the immunogenicity of the viruses include, for example, liposomal formulations, synthetic adjuvants, such as (e.g., QS21), muramyl dipeptide, monophosphoryl lipid A, polyphosphazine, CpG oligonucleotides, or other molecules that appear to work by activating Toll-like Receptor (TLR) molecules on the surface of cells or on nuclear membranes within cells. Although these adjuvants are typically used to enhance immune responses to inactivated vaccines, they can also be used with live vaccines. Both agonists of TLRs or antagonists may be useful in the case of live vaccines. In the case of a virus delivered via a mucosal route, for example, orally, mucosal adjuvants such as the heat-labile toxin of *E. coli* (LT) or mutant derivations of LT can be used as adjuvants. In addition, genes encoding cytokines that have adjuvant activities can be inserted into the viruses. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses.

VI. KITS

Other embodiments concern kits of use with the methods (e.g. methods of application or administration of a vaccine or immunogenic composition) and compositions described herein. Some embodiments concern kits having vaccine or immunogenic compositions of use to prevent or treat subjects having, exposed or suspected of being exposed to one or more flaviviruses. In certain embodiments, a kit may contain one or more than one formulation of attenuated vaccines at predetermined ratios. Kits can be portable, for example, able to be transported and used in remote areas such as military installations or remote villages. Other kits may be of use in a health facility to treat a subject having been exposed to one or more flaviviruses or suspected of being at risk of exposure to flaviviruses.

Kits can also include a suitable container, for example, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the agent, composition and any other reagent containers in close confinement for commercial sale. Such containers may include injection or blow-molded plastic containers into which the desired vials are retained. Optionally, one or more additional agents such as immunogenic agents or other anti-viral agents, anti-fungal or anti-bacterial agents may be needed for compositions described, for example, for compositions of use as a vaccine against one or more additional microorganisms.

VII. EXAMPLES

The following examples as well as the figures are included to demonstrate preferred embodiments of the disclosure. It should be appreciated by those of skill in the art that the techniques disclosed in the examples or figures represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Rescue of New West Nile Virus (WNV) NS4B Mutants

Figure 1:
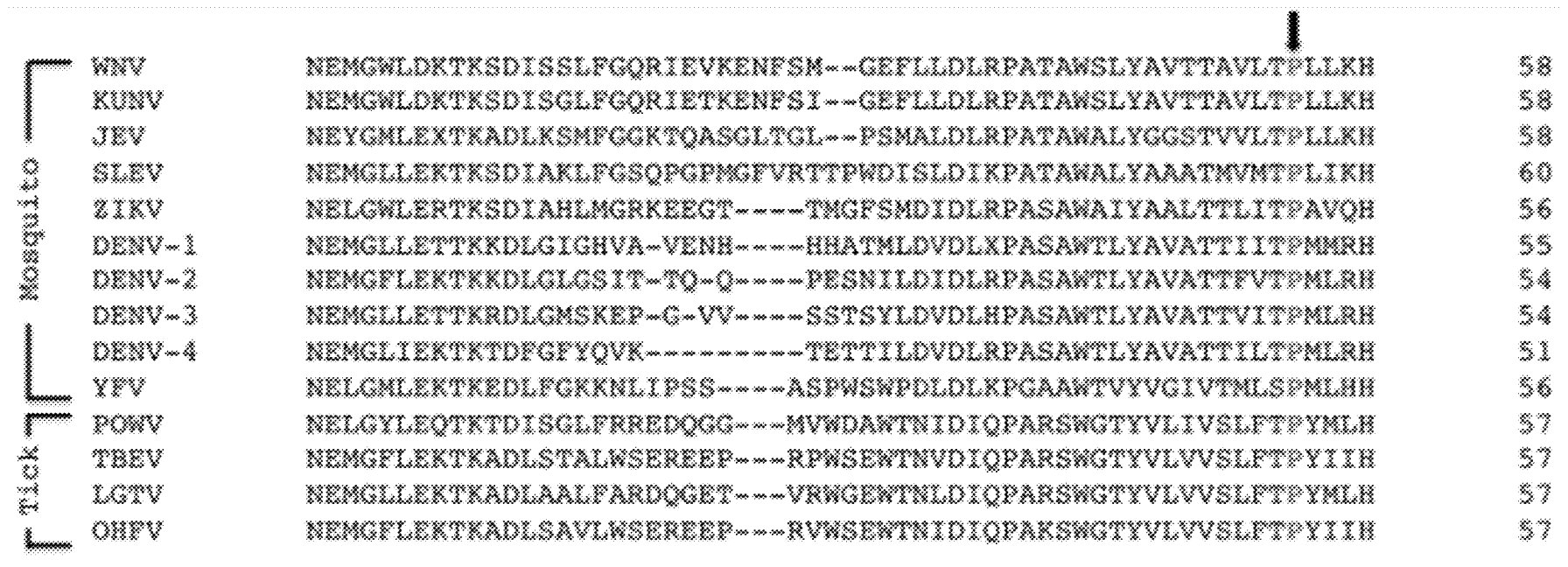

The inventors were interested in mutating residues that are shared between different mosquito-borne flaviviruses in order to correlate results obtained from WNV to other flaviviruses. Accordingly, residue P54 was targeted for mutation based on its homology in multiple flaviviruses (FIG. 1). Besides conservation in the flavivirus genus, the specified amino acid residue was selected due to its putative location in the NS4B protein, thus providing a means of investigation of a specific region of NS4B for attenuating mutations. Specifically, P54 is in the first transmembrane domain of NS4B (FIG. 2).

The genotypes of NS4B-P54 mutants are shown in Table 1. In total, two new NS4B mutants were generated including P54A and P54G. The genomic consensus sequence of each virus was verified using next-generation sequencing (NGS), and neither of the new mutants had any compensatory consensus mutations upon rescue. After a single passage in Vero cells, neither of the P54 mutants had additional consensus sequence mutations. All viruses had similar infectivity titers, with NY99ic producing large plaques while the NS4B-P54 mutants produced medium-sized plaques (Table 1).

All viruses were rescued from transfection and passaged once in Vero cells for subsequent studies. Infectivity titers are listed as log 10 PFU/mL. Temperature sensitivity significance was measured using a one-way ANOVA with Bonferroni's multiple comparisons. ***$p<0.001$.

TABLE 1

Consensus genotypes, plaque phenotypes, temperature sensitivity, and mouse attenuation of NS4B mutants

| NS4B mutant | Additional consensus mutations | Vero cell passage number | Plaque morphology | 37° C. titer | 41° C. titer | Δ titer 41° vs 37° C. | Survival 500 PFU i.p. (%) | Survived 10,000 PFU challenge | High dose (PFU/mouse) | High dose survival (%) |
|---|---|---|---|---|---|---|---|---|---|---|
| NY99ic | — | 1 | large | 8.2 | 8.1 | 0.1 | 0/10 (0) | n.d. | n.d. | n.d. |
| P54A | — | 1 | medium | 8.3 | 7.3 | ***1.0 | 5/5 (100) | 5/5 | $3.5 \times 10^5$ $5.4 \times 10^7$ | 5/5 (100) 5/5 (100) |
| P54G | — | 1 | medium | 8.2 | 8.0 | 0.2 | 5/5 (100) | 5/5 | $5.2 \times 10^5$ $1.5 \times 10^7$ | 5/5 (100) 5/10 (50) |

Infectivity titers are listed as $\log_{10}$ PFU/mL. Temperature sensivity significance was measured using a one-way ANOVA with Bonferroni's multiple comparisons.
Abbreviations:
n.d. = not done,
***$p < 0.001$.

Example 2—Multiplication Kinetics of WNV Mutants in Vero and A549 Cells

Figures 3A, 3B:
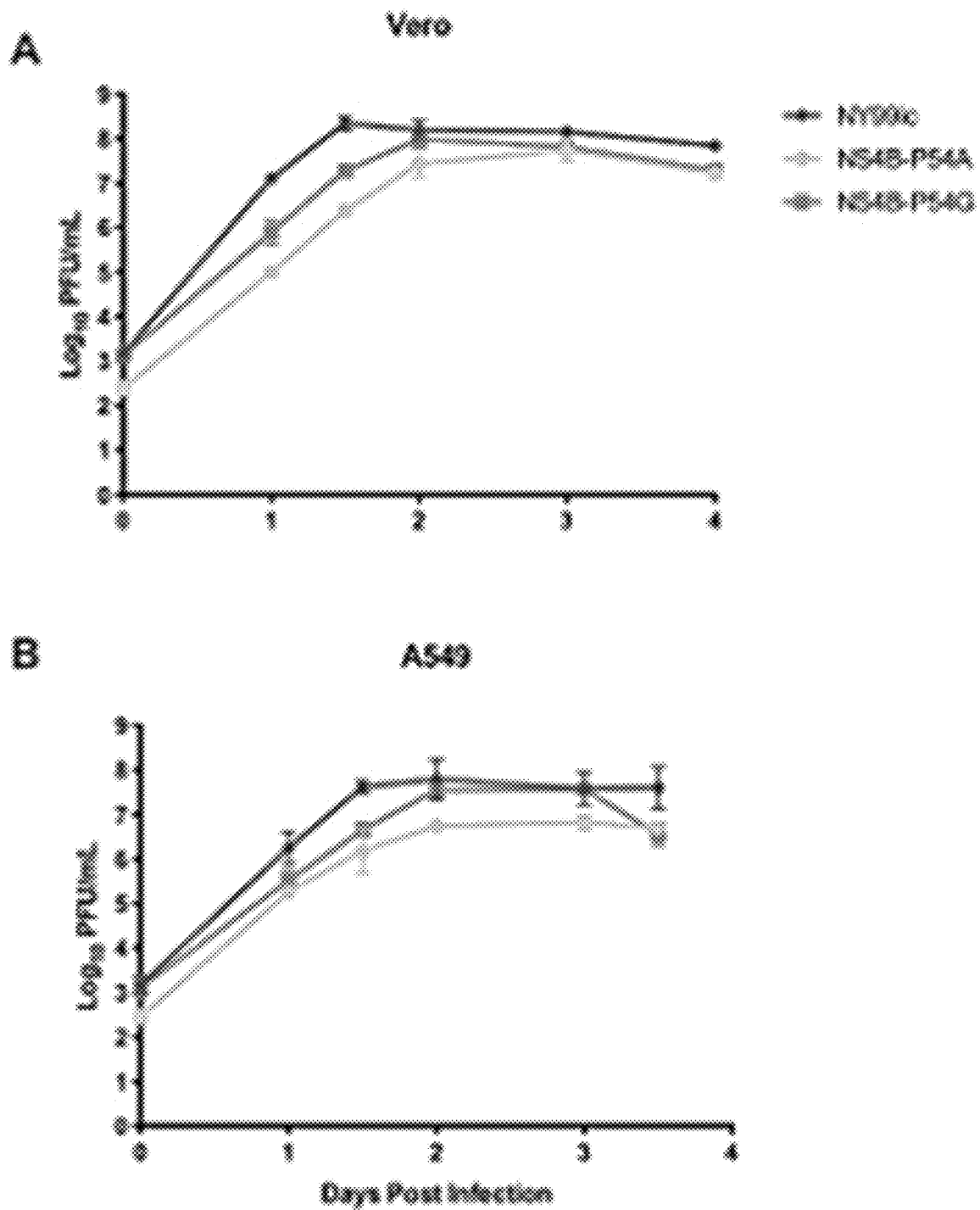
FIGS. 3A-3B. Multiplication kinetics are similar for NY99ic and WNV NS4B mutants. Vero cells (FIG. 3A) and A549 cells (FIG. 3B) were infected with a multiplicity of infection of 0.1 of each virus. Two biological replicates were infected and two samples from each flask were titrated at the time points indicated.
Figure 4A:
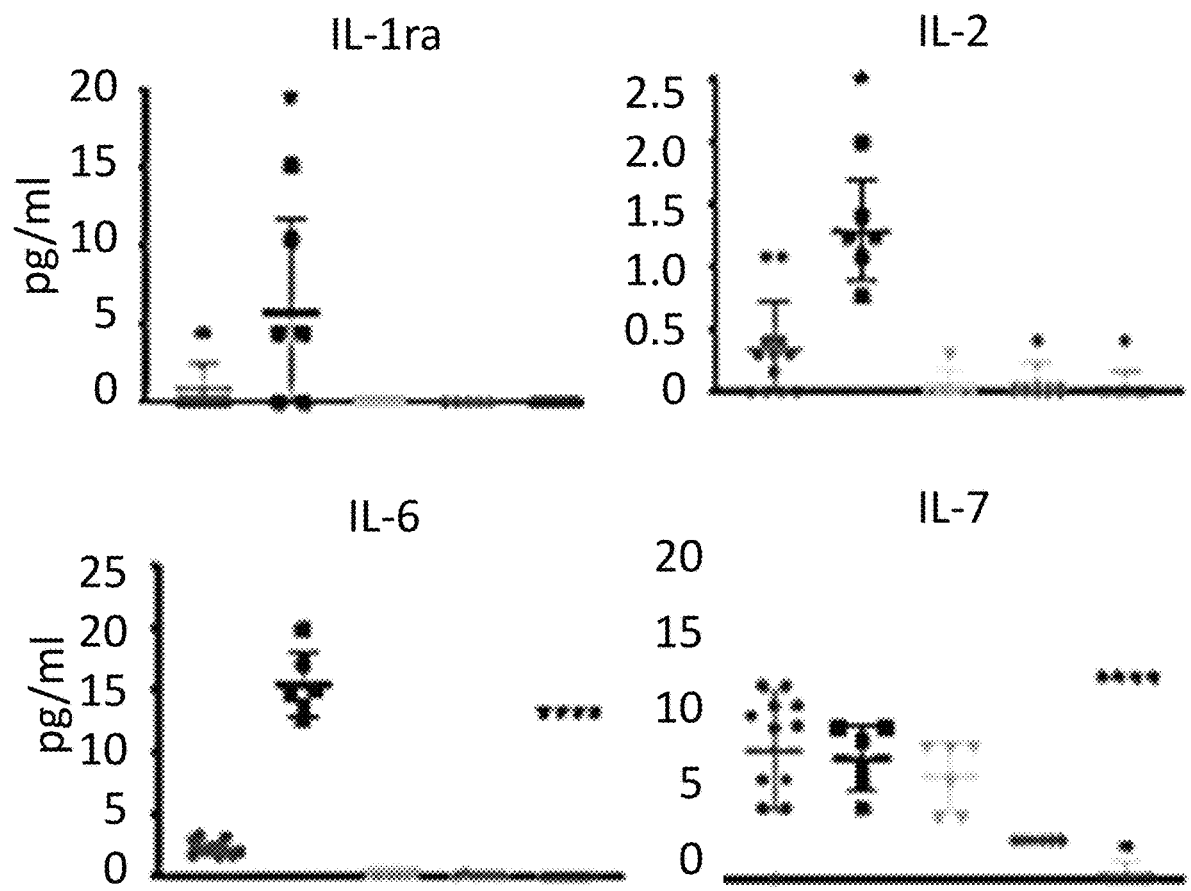
FIG. 4. Attenuated WNV NS4B mutants exhibited two different patterns of cytokine induction. Cytokine levels in NS4B mutant infected cells were compared to NY99ic infected cells using a Kruskal-Wallis ANOVA with Dunn's post-hoc correction. A WNV NS4B-P38G attenuated mutant that was previously characterized was included as an attenuated control. Six replicates of each mutant and 12 replicates of NY99ic and mock were measured, except for IFN-$\alpha$ and IFN-$\beta$ for which six replicates were tested for all viruses and controls. *$p<0.05$, $p<0.01$, *$p<0.001$, ****$p<0.0001$.
Figure 4A:
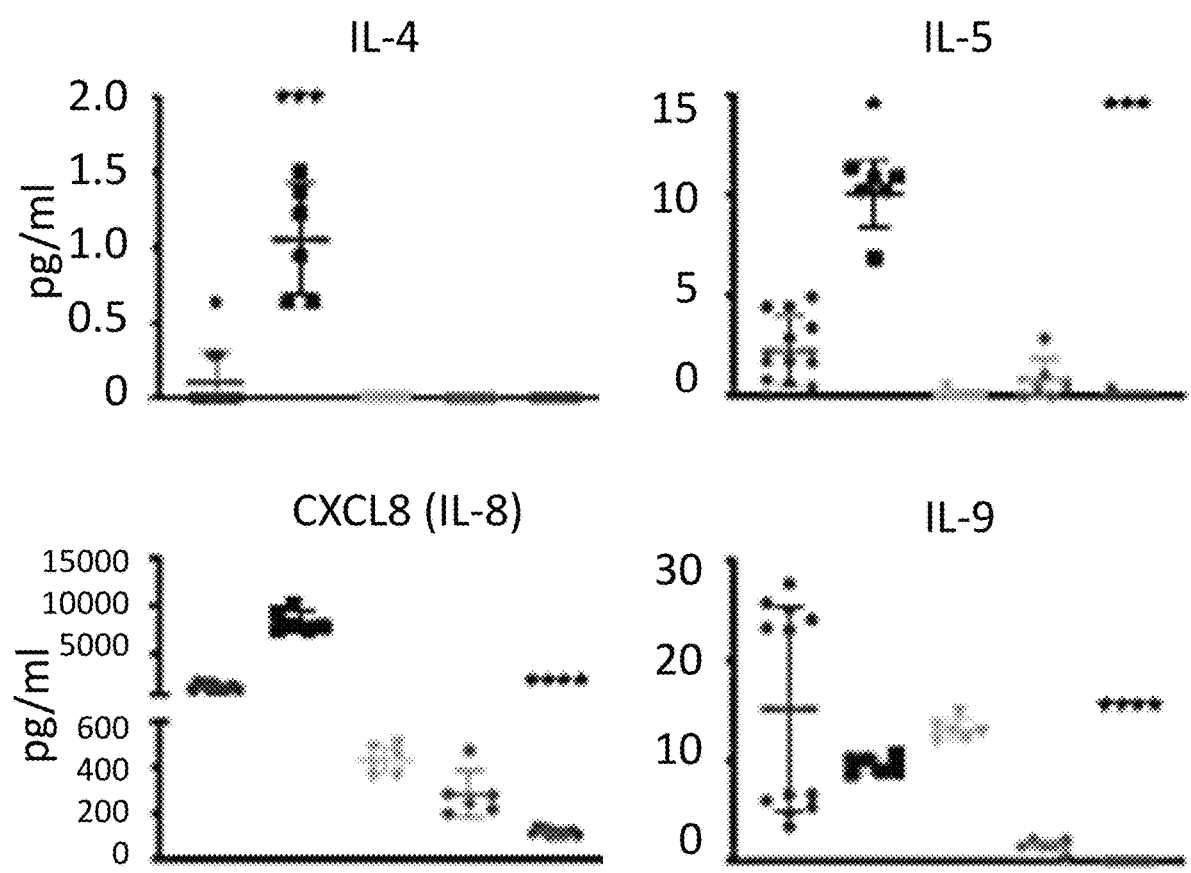
Figure 4B:
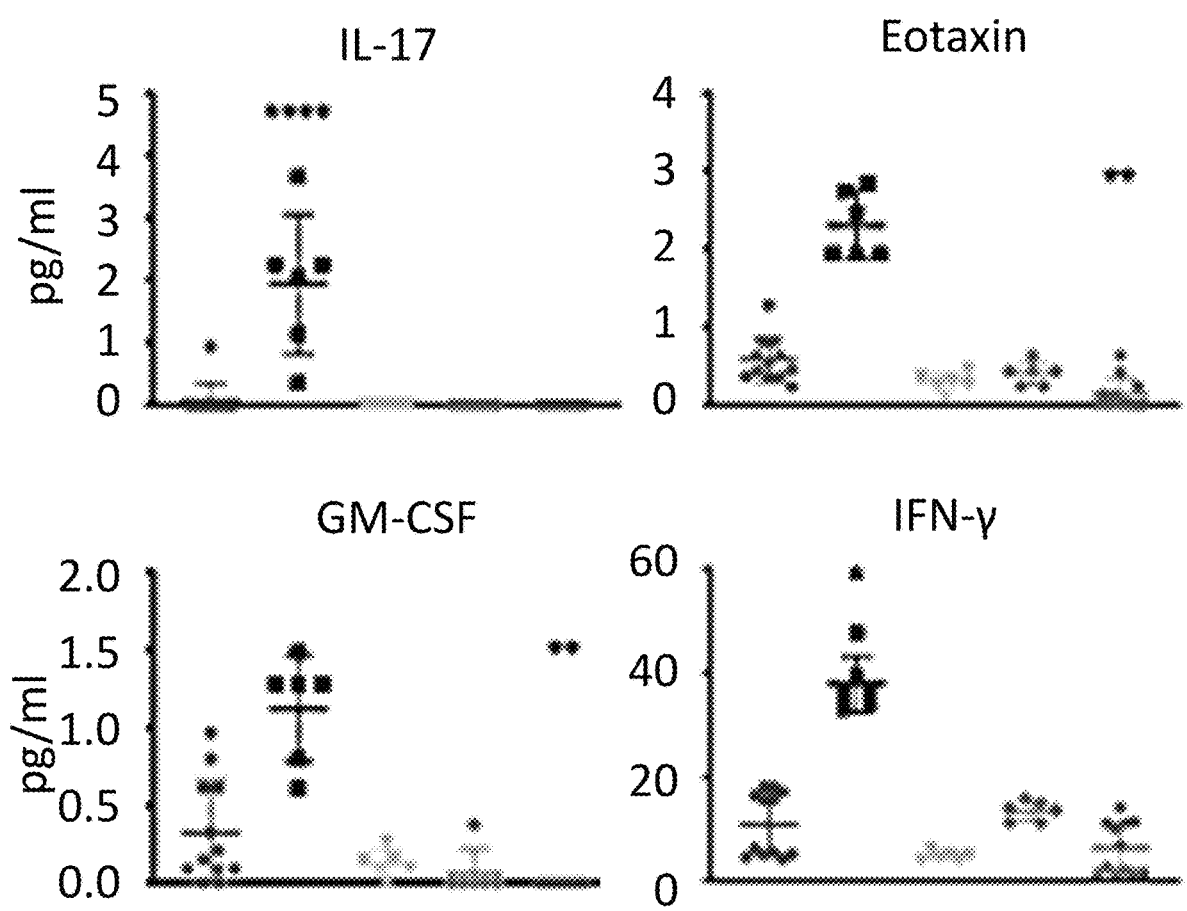
Figure 4B:
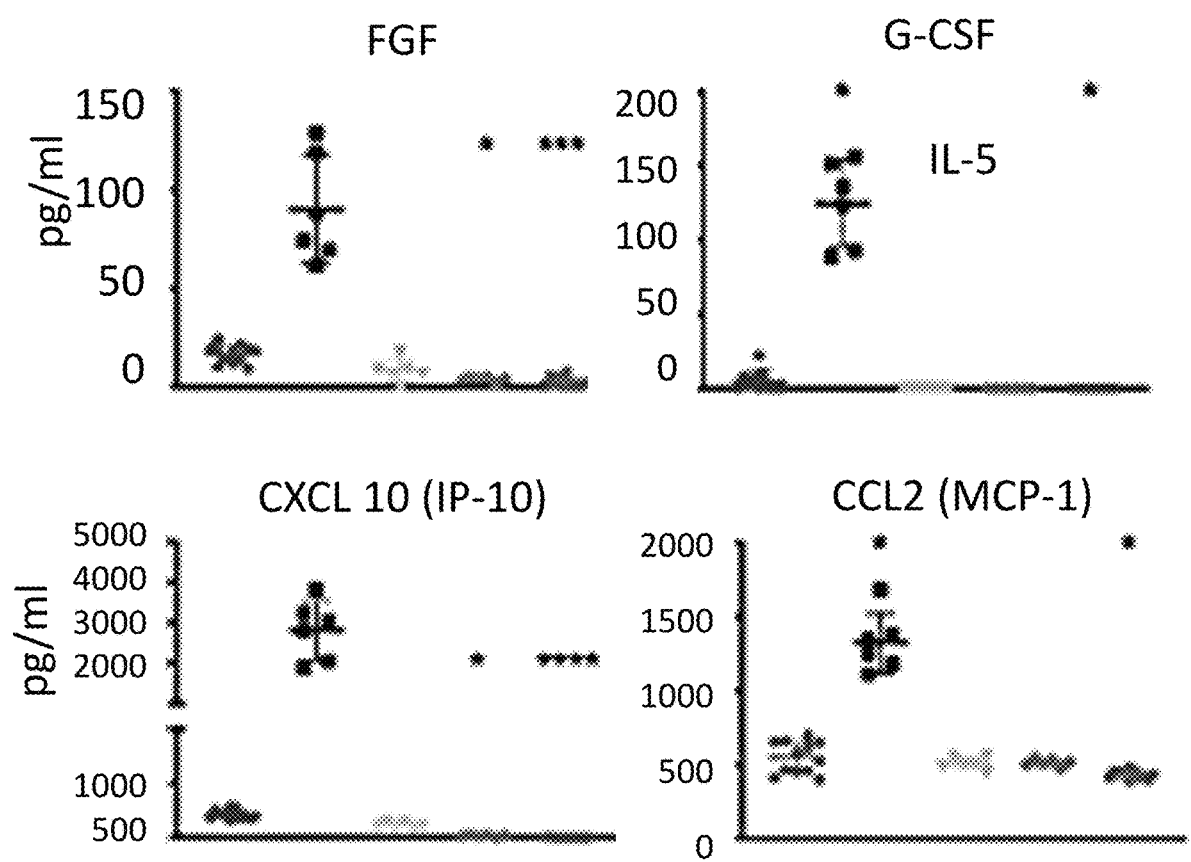
Figure 4C:
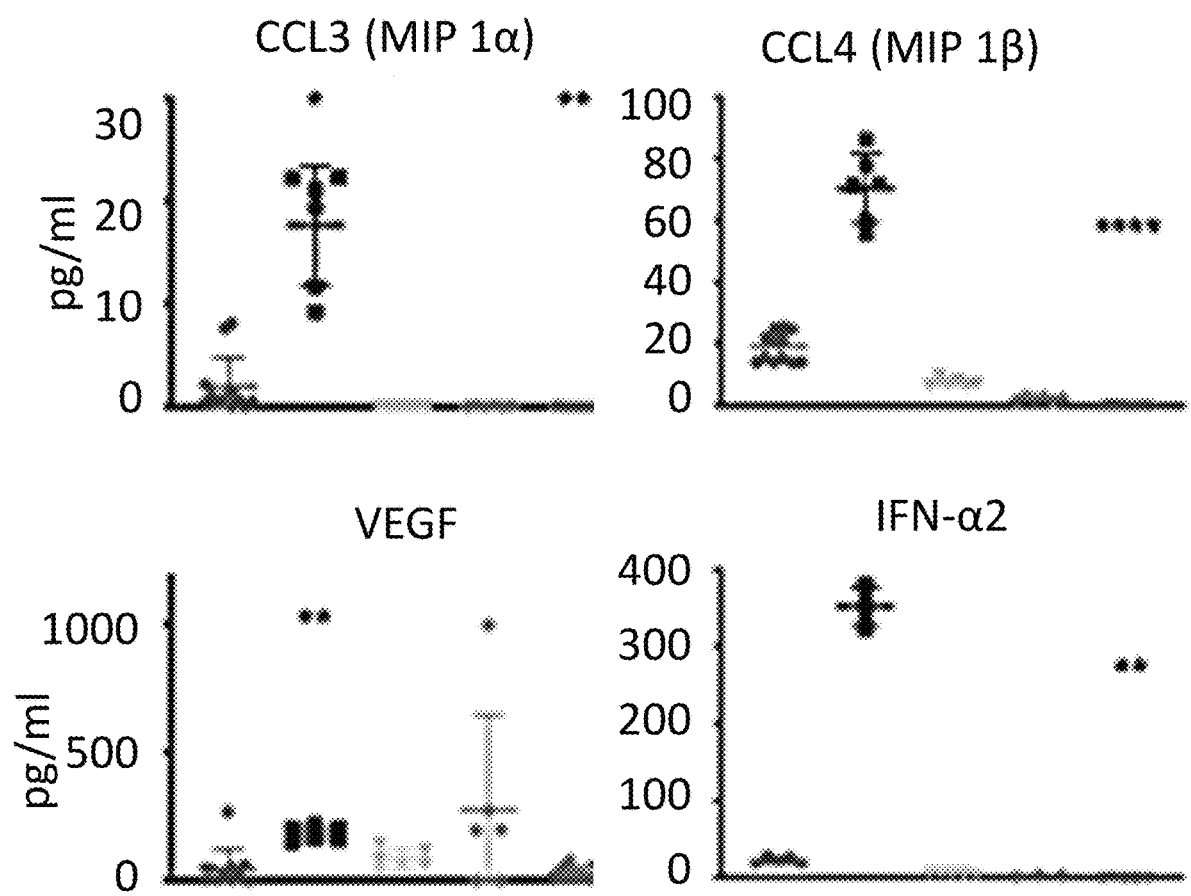
Figure 4C:
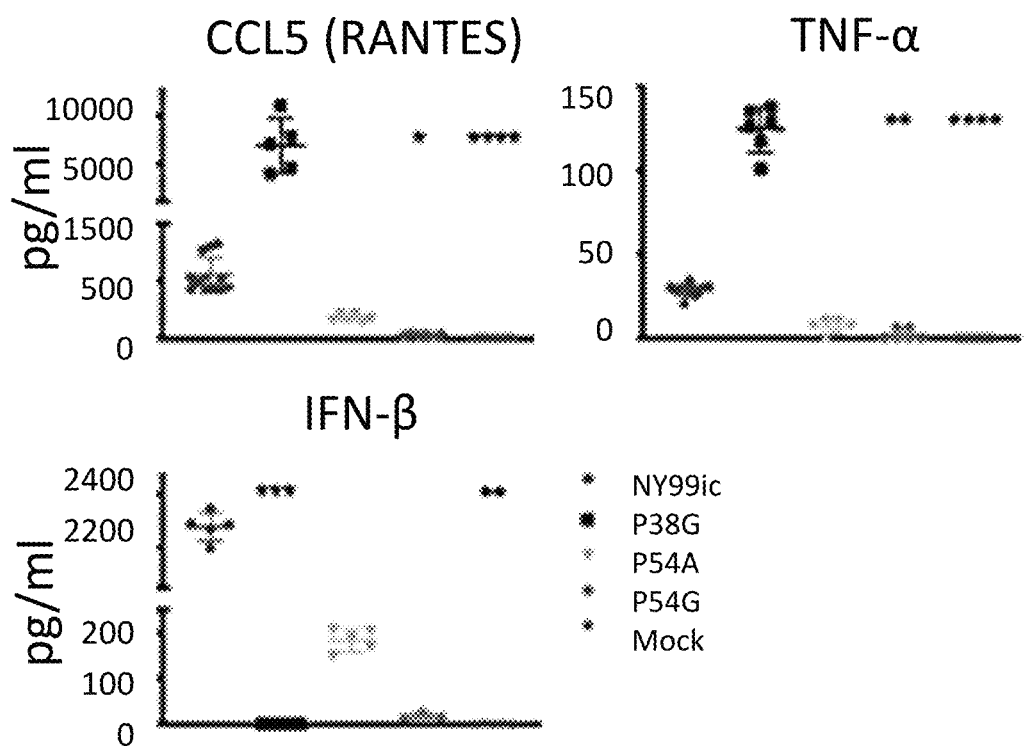

Multiplication kinetics of the NS4B-P54 mutants were compared to that of parental NY99ic using a MOI of 0.1 in both Vero (Type I Interferon [IFN-I]deficient) and A549 cells (IFN-I competent). In both cell lines, the mutants had similar multiplication kinetics to those of NY99ic (FIG. 3). The P54A mutant had the most significantly reduced kinetics compared to NY99ic. Specifically, in Vero cells the P54A mutant grew to titers >100-fold lower than those of NY99ic at early time points, but by two dpi, the mutant and NY99ic exhibited similar infectivity titers (FIG. 3A). In A549 cells, the P54A mutant multiplied to titers >10-fold below those of NY99ic at all time points between 1-4 dpi (FIG. 3B). Despite the observed differences from NY99ic, both NS4B-P54 mutants were able to multiply in each cell line to relatively high titers >6 $\log_{10}$ PFU/mL.

Example 3—Temperature Sensitivity of WNV Mutants

To investigate temperature sensitive (TS) phenotypes, infectivity titers were compared at both 37° C. and 41° C.

While the P54G mutant was similar to NY99ic in that it did not exhibit significant reduction of infectivity titer at 41° C., P54A was significantly TS (p<0.0001) (Table 1). Specifically, the P54A mutant had a 10-fold reduction in titer at 41° C. compared to 37° C.

Example 4—Mouse Neuroinvasive Phenotype of WNV Mutants

To investigate attenuation of mouse neuroinvasion, experiments were undertaken in outbred mice as they are a highly susceptible model for WNV infection. First, each of the new mutants was tested using i.p. inoculation of 500 PFU, and then were tested at a high dose by the i.p. route where the virus was administered undiluted (undiluted doses listed in Table 1).

All (5/5) mice inoculated with 500 PFU of either P54A or P54G mutants survived infection (Table 1). Furthermore, all surviving mice were challenged with 10,000 PFU of NY99ic at 36 dpi, and all challenged mice survived (Table 1); therefore, mutation of P54A and P54G conferred an attenuated phenotype and also induced protective immunity.

To investigate the attenuated phenotype further, groups of mice were inoculated with undiluted virus. P54A was tested at both 350,000 and 54 million PFU doses, and P54G was tested at both 520,000 and 15 million PFU doses. Both the P54A and P54G mutants caused no lethality (5/5 mice) following inoculation of >300,000 PFU (Table 1). All (5/5) mice survived a 54 million PFU dose of the P54A mutant, while 50% (5/10) of mice survived a 15 million PFU dose of the P54G mutant (Table 1).

Example 5—Cytokine Induction of WNV Mutants in A549 Cells

Using a BioPlex Pro 27-plex human cytokine assay and a custom IFN-α/IFN-β assay, 29 cytokines were measured in A549 cell culture supernatant at 36 hpi. Cells were infected with both new mutants, the NS4B-P38G (+NS3-N480H/NS4B-T116I) mutant as an attenuated control, NY99ic, or PBS as a mock infection. Two cytokines (IL-10 and IL-15) were not detected at all, and four cytokines (IL-1β, IL-12 p70, IL-13, and PDGF-bb) were either detected at very low levels (<1 pg/mL) or were only sporadically measured in fewer than half of the replicates, and therefore, these six cytokines were not analyzed for significance.

Several patterns were detected in the cytokine profiles of the NS4B mutants. Cells infected with the P38G (+NS3-N480H/NS4B-T116I) mutant produced higher pro-inflammatory cytokine and chemokine responses than NY99ic-infected cells (FIG. 4), which was consistent with previous studies of cytokine induction from this mutant in immune cells and a mouse model [35,36]. In comparison, both attenuated P54A and P54G mutants induced relatively low cytokine responses that were typically similar to those in mock-infected cells and lower than those in NY99ic-infected cells (FIG. 4). The only cytokine for which all attenuated mutants had a similar trend that was distinct from the virulent viruses was IFN-β, where P38 and P54 attenuated mutants decreased production compared to NY99ic, albeit the P38G mutant was the only one for which the difference was statistically significant (FIG. 4).

Example 6—Stability of WNV NS4B Mutant Genotypes

Figure 5:
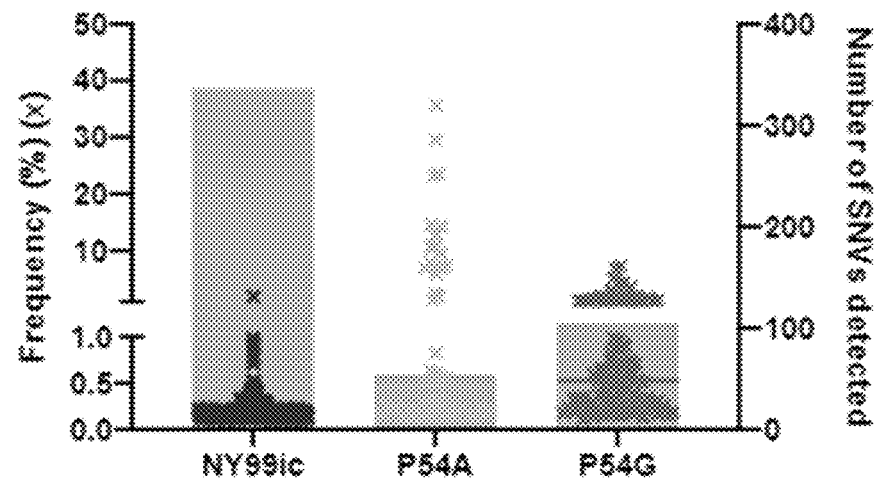

To investigate the stability of each NS4B mutation, SNVs were analyzed in the cell culture stocks of each virus. Viruses that were passaged once in Vero cells (P1) were analyzed since these were the stocks utilized in the mouse studies. Each of these stocks had similar depths of coverage of sequencing reads with the average coverage ranging from 7217-7796, therefore, stocks were analyzed without down sampling. The total number and frequency of SNVs identified varied between the different viruses, and there was no obvious pattern to correlate SNV number or frequency with attenuation (FIG. 5). Although SNVs as low as 0.1% frequency were detected, analysis was concentrated on SNVs ≥1% to focus on the variants of the greatest significance. Comparison of the SNVs of the new NS4B mutants demonstrated that there were no SNVs that were shared amongst all of the mutants and none that appeared associated with attenuated or virulent phenotypes of the mutants (Table 2).

Figure 6:
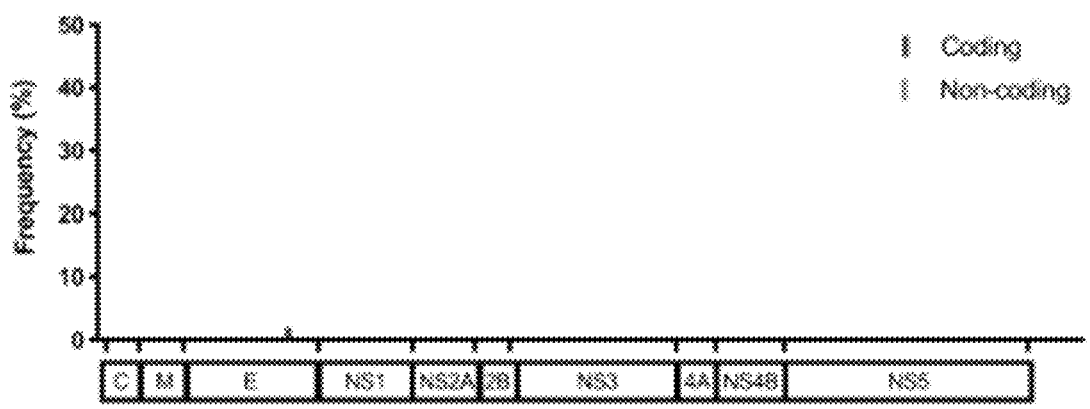
FIG. 6. WNV NS4B-P54 mutants had unique SNV frequency and genomic distribution. Each graph displays the SNVs $\geq 1\%$ frequency that were detected in the Vero cell P1 virus stocks of each virus.
Figure 6:
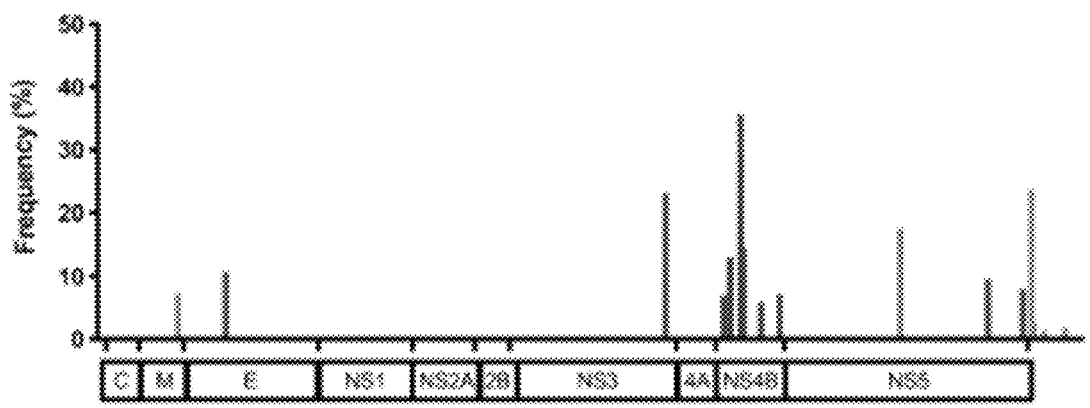
Figure 6:
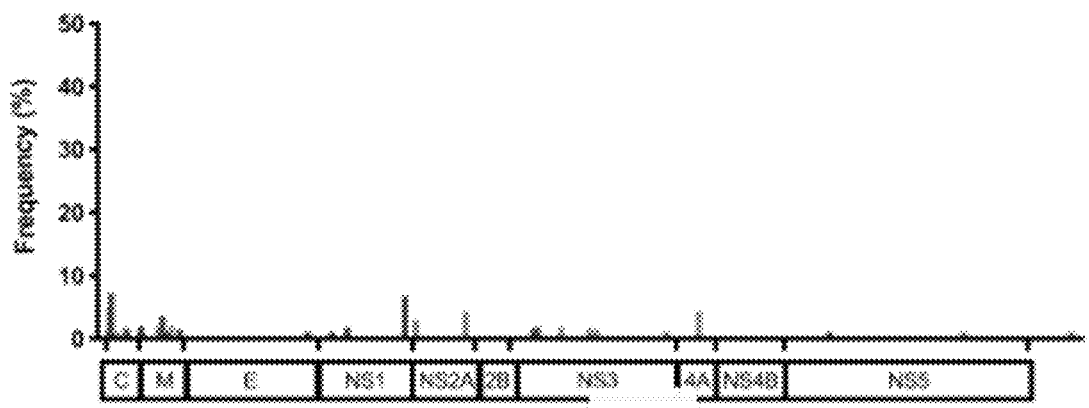
Figure 7:
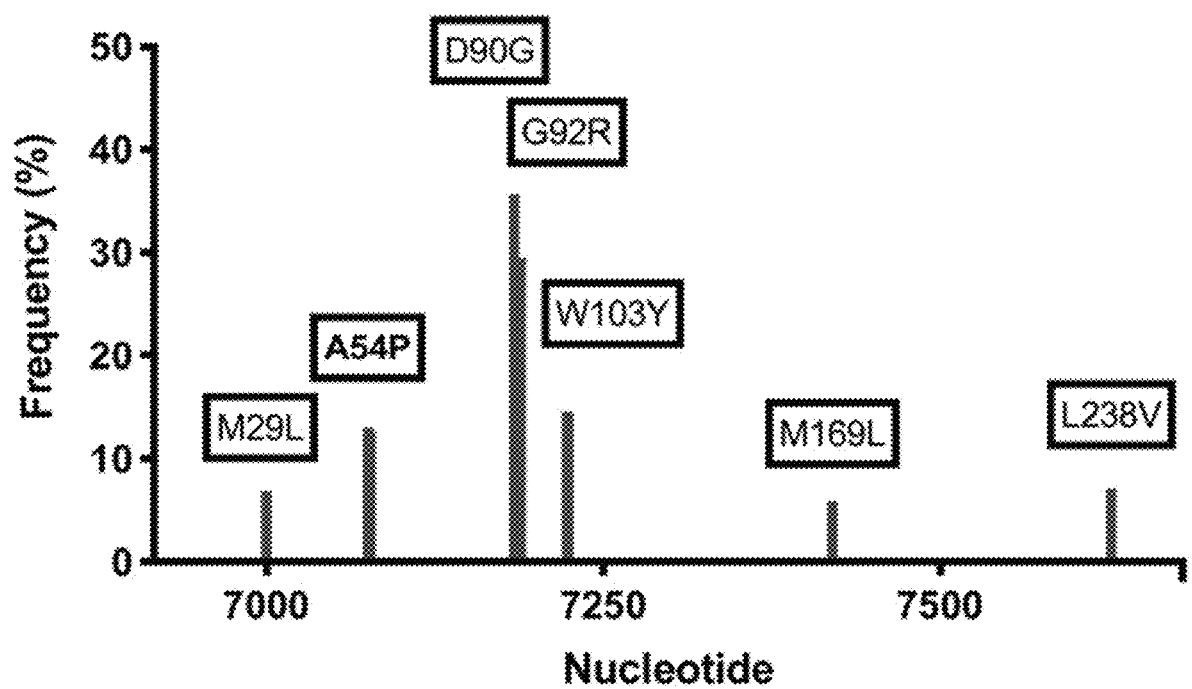
FIG. 7. The NS4B-P54A mutant had SNVs clustered in the NS4B protein, including one that encoded reversion. SNVs $\geq 1\%$ frequency in the NS4B protein of the NS4B-P54A mutant are mapped to the corresponding genomic position. The NS4B amino acid substitutions are indicated above each line.

Most SNVs detected in the P54G mutant quasispecies were approximately 1% frequency with only 10% (3/30) that were >5% frequency in the population, and none were detected in the NS4B gene (FIG. 6, Table 2). In comparison, of 20 SNVs ≥1% frequency in the P54A mutant quasispecies, 50% (10/20) had a frequency >10% and 45% (9/20) were clustered in the NS4B gene (FIG. 6, Table 2). The nine nucleotide changes in NS4B encoded seven amino acid substitutions, including one that exhibited reversion of NS4B-A54P in 13.0% of the population (FIG. 7).

TABLE 2

NS4B-P54A mutation reverted during cell culture passage, but NS4B-P54G mutation did not

| Mutant | P0 | P1 | P5 |
| --- | --- | --- | --- |
| P54A | 18.0% | 13.0% | 69.3% |
| P54G | <0.1% | <0.1% | <0.1% |

The frequency of reversion to the wild-type proline residue of NS4B-P54 mutants were measured in Vero cell P0, P1, and P5 virus stocks. The limit of detection was 0.1%.

To further investigate the stability of the P54A mutation, Vero cell P0 and P5 stocks were sequenced and variants were analyzed. The P0 stock of the P54A mutant (the virus rescued directly after transfection) had slightly lower average sequencing coverage than the other mutants analyzed (6165 compared to >7216), but regardless, the P0 stock had a similar genotype to the P1 stock. Specifically, no extra coding consensus sequence changes were identified throughout the genome and of 20 SNVs >1% frequency, one encoded reversion in 18.0% of the population (Table 3). In comparison, the P5 stock had 16 SNVs >1% frequency and had undergone consensus sequence reversion and harbored both NS4B-A54P and NS4B-D90G consensus genome mutations (Table 3). It is notable that during serial passage of the P54A mutant, the viral titer did not significantly change, but the plaque phenotype changed from medium-sized (P0 and P1) to mixed medium and large sized plaques (P5). Based on the instability of the P54A mutation, P0 and P5 stocks of the P54G mutant were also analyzed. The P0 stock had an average coverage depth of only 1729, which was significantly lower sequencing coverage depth than the other viruses analyzed (the P54G mutant P1 and P5 stocks had average coverage of 7655 and 7605 reads, respectively). Therefore, the SNV results of this stock may be biased since there were fewer viral reads. With this limitation in mind, the P0 stock of the P54G mutant was similar to the P1 stock in that it harbored 34 SNVs >1% frequency, none of which were in NS4B. The P5 stock of the P54G mutant had 18 SNVs >1% frequency, and although six were in NS4B, there was no evidence of reversion of the P54G mutation and there were no additional consensus sequence changes (Table 4). Consistent with the sequencing results, the viral titer and the medium-size plaque phenotype remained constant during five serial passages of the P54G mutant.

TABLE 3

WNV NS4B mutants exhibited distinct single nucleotide variants

|  | Nucleotide Position | Major Nucleotide | Minor Nucleotide | Viral Protein Position | Major Residue | Minor Residue | Frequency (%) |
|---|---|---|---|---|---|---|---|
| NY99ic | 2135 | A | G | E-390 | E | G | 1.9 |
| P54A | 904 | A | U | prM-147 | S | S | 7.3 |
|  | 1435 | A | G | E-157 | T | A | 10.7 |
|  | 6347 | A | G | NS3-579 | E | G | 23.2 |
|  | 7000 | A | C | NS4B-29 | M | L | 6.9 |
|  | 7075 | G | C | NS4B-54 | *A | *P | 13.0 |
|  | 7077 | C | A | NS4B-54 |  |  | 12.7 |
|  | 7184 | A | G | NS4B-90 | D | G | 35.7 |
|  | 7189 | G | A | NS4B-92 | G | R | 29.5 |
|  | 7223 | G | A | NS4B-103 | *W | *Y | 14.6 |
|  | 7224 | G | U | NS4B-103 |  |  | 14.3 |
|  | 7420 | A | C | NS4B-169 | M | L | 5.9 |
|  | 7627 | C | G | NS4B-238 | L | V | 7.1 |
|  | 8973 | A | C | NS5-431 | P | P | 10.6 |
|  | 8973 | A | U | NS5-431 | P | P | 6.9 |
|  | 9956 | U | G | NS5-759 | L | R | 9.6 |
|  | 10342 | A | C | NS5-888 | M | L | 8.0 |
|  | 10440 | A | G | 3' UTR | — | — | 23.6 |
|  | 10464 | A | G | 3' UTR | — | — | 2.5 |
|  | 10582 | G | U | 3' UTR | — | — | 1.4 |
|  | 10814 | A | U | 3' UTR | — | — | 1.9 |
| P54G | 117 | G | A | C-7 | G | G | 1.2 |
|  | 139 | A | G | C-15 | N | D | 5.0 |
|  | 155 | G | A | C-20 | G | E | 7.3 |
|  | 225 | A | G | C-43 | P | P | 1.1 |
|  | 320 | A | G | C-75 | Q | R | 1.7 |
|  | 330 | G | A | C-78 | M | I | 1.4 |
|  | 488 | G | A | prM-8 | *G | *E | 2.0 |
|  | 489 | G | A | prM-8 |  |  | 1.3 |
|  | 507 | A | G | prM-14 | V | V | 1.1 |
|  | 681 | A | G | prM-72 | S | S | 1.9 |
|  | 728 | G | A | prM-88 | R | K | 3.6 |
|  | 767 | A | G | prM-101 | E | G | 1.2 |
|  | 831 | A | G | prM-122 | V | V | 2.1 |
|  | 920 | G | A | prM-152 | R | K | 1.5 |
|  | 2346 | A | G | E-460 | I | M | 1.1 |
|  | 2624 | A | G | NS1-52 | E | G | 1.1 |
|  | 2788 | A | G | NS1-107 | T | A | 1.8 |
|  | 3440 | A | G | NS1-324 | Q | R | 6.8 |
|  | 3561 | C | U | NS2A-12 | G | G | 3.0 |
|  | 4113 | A | G | NS2A-196 | K | K | 4.4 |
|  | 4871 | A | C | NS3-87 | H | P | 1.6 |
|  | 4918 | G | A | NS3-103 | G | S | 1.9 |
|  | 5187 | G | C | NS3-192 | L | L | 1.9 |
|  | 5502 | A | U | NS3-297 | A | A | 1.7 |
|  | 5580 | A | G | NS3-323 | S | S | 1.6 |
|  | 6357 | C | U | NS3-582 | V | V | 1.2 |
|  | 6717 | A | G | NS4A-83 | G | G | 4.4 |
|  | 8179 | A | G | NS5-167 | A | A | 1.1 |
|  | 9681 | A | G | NS5-667 | G | G | 1.2 |
|  | 10888 | U | A | 3' UTR | — | — | 1.2 |

All SNVs ≥1% frequency in the P1 cell culture stock of each virus are listed.
*Two nucleotide changes occurred simultaneously, viewed on Tablet software

TABLE 4

WNV NS4B-P54G mutant harbored 18 single nucleotide variants ≥1% frequency after five Vero cell passages.

| Nucleotide Position | Major Nucleotide | Minor Nucleotide | Viral Protein Position | Major Residue | Minor Residue | Frequency (%) |
|---|---|---|---|---|---|---|
| 139 | A | G | C-15 | N | D | 3.3 |
| 155 | G | A | C-20 | G | E | 2.4 |
| 728 | A | G | prM-88 | R | K | 2.4 |
| 2743 | A | G | NS1-92 | K | E | 1.6 |
| 3440 | A | G | NS1-324 | Q | R | 46.8 |
| 3561 | C | U | NS2A-12 | G | G | 2.3 |
| 4113 | A | G | NS2A-196 | K | K | 2.6 |
| 4918 | G | A | NS3-103 | G | S | 19.1 |
| 5166 | G | A | NS3-185 | R | R | 1.0 |
| 5187 | G | C | NS3-192 | L | L | 18.7 |
| 6717 | A | G | NS4A-83 | G | G | 1.7 |
| 7081 | C | A | NS4B-56 | L | I | 16.5 |
| 7091 | U | G | NS4B-59 | L | W | 43.0 |
| 7123 | A | G | NS4B-70 | T | A | 2.1 |
| 7183 | G | A | NS4B-90 | D | N | 2.1 |
| 7193 | U | C | NS4B-93 | V | A | 1.2 |

TABLE 4-continued

WNV NS4B-P54G mutant harbored 18 single nucleotide variants ≥1% frequency after five Vero cell passages.

| Nucleotide Position | Major Nucleotide | Minor Nucleotide | Viral Protein Position | Major Residue | Minor Residue | Frequency (%) |
|---|---|---|---|---|---|---|
| 7274 | G | U | NS4B-120 | C | F | 1.6 |
| 10888 | U | A | 3' UTR | — | — | 1.2 |

The frequency of reversion to the wild-type proline residue of NS4B-P54 mutants were measured in Vero cell P0, P1, and P5 virus stocks. The limit of detection was 0.1%.

Even though the P54A mutation did not rapidly revert in mouse experiments, the SNVs identified in the P1 cell culture stock exhibited instability of the genotype with many high frequency SNVs, especially in the NS4B gene. One of these, NS4B-D90G, was selected for during cell culture passage and encoded a consensus sequence change by P5. NS4B-90 is on the ER lumen side of the protein, and while the role of this residue during WNV infection is not known, it is possible that the loss of negative charge at this position helped to compensate for changes to NS4B induced by the P54A mutation. However, NS4B-D90G mutation was not evident in the quasispecies of the P54G mutant through P5.

Example 7—Immunostaining of the Attenuated WNV NS4B-P54G Mutant

Figure 8A:
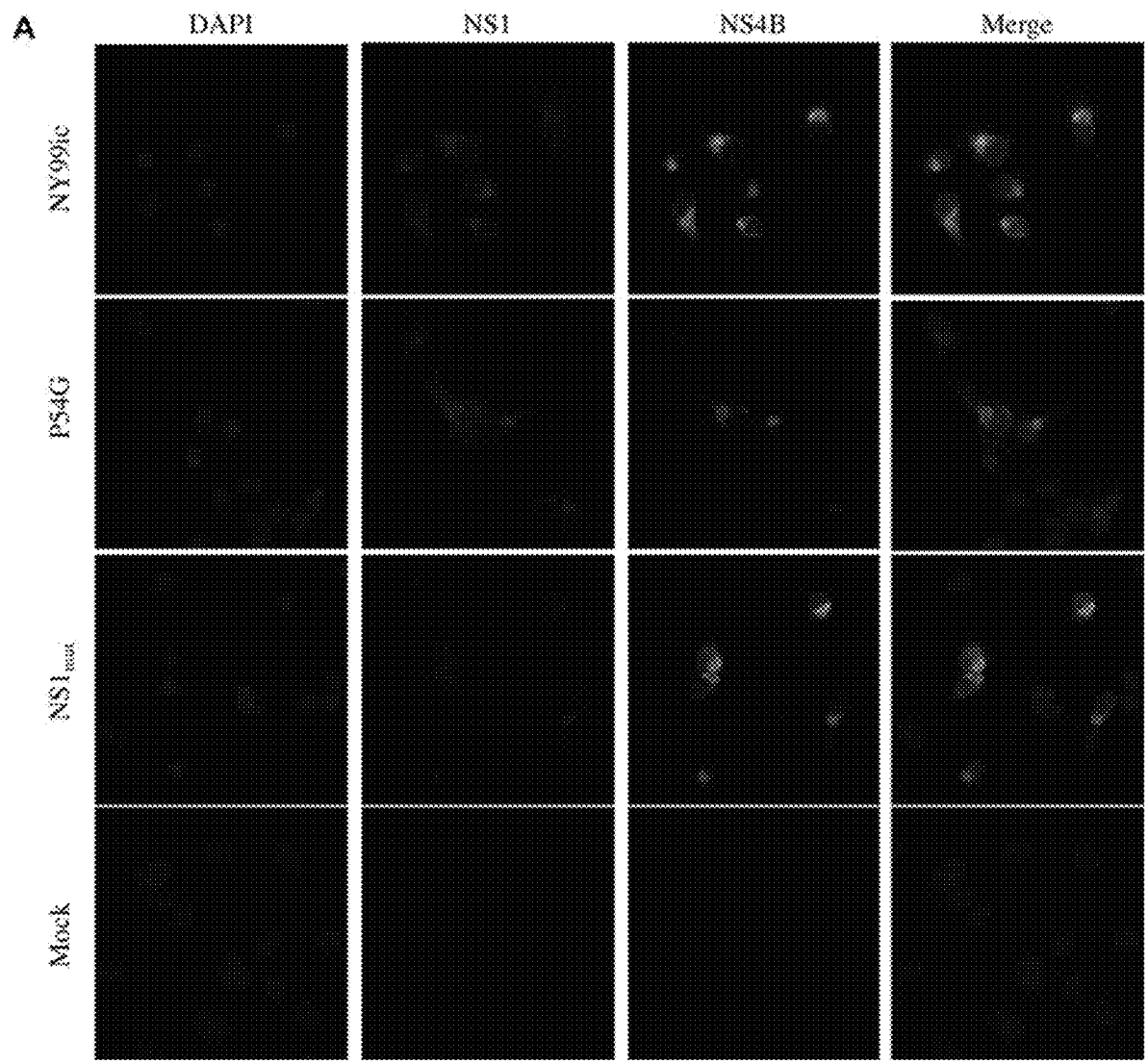
FIGS. 8A-8C. The WNV P54G mutant had reduced NS4B accumulation and NS1-NS4B colocalization in infected cells one day post infection. Vero cells were infected with a MOI of 0.1 of NY99ic, the NS4B-P54G mutant, a WNV NS1 glycosylation site mutant, or PBS as a mock infection, and fluorescence microscopy was performed one day post infection (FIG. 8A). Mean fluorescence intensity (FIG. 8B) and Pearson's correlation coefficient (FIG. 8C) were calculated on individual infected cells (n=18). Statistical difference in mean fluorescence intensity and colocalization were measured using a Kruskal-Wallis test with multiple comparisons to compare both mutants to NY99ic. *$p<0.05$, $p<0.01$, *$p<0.001$.
Figure 8B:
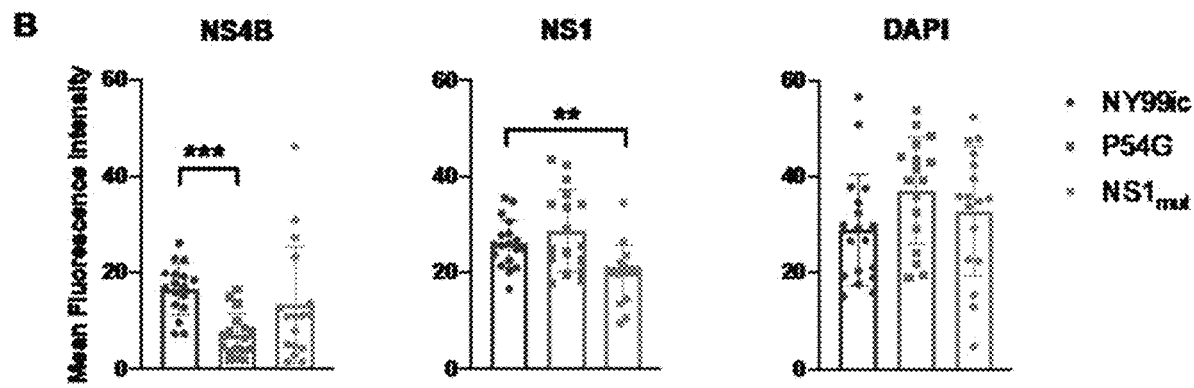
Figure 8C:
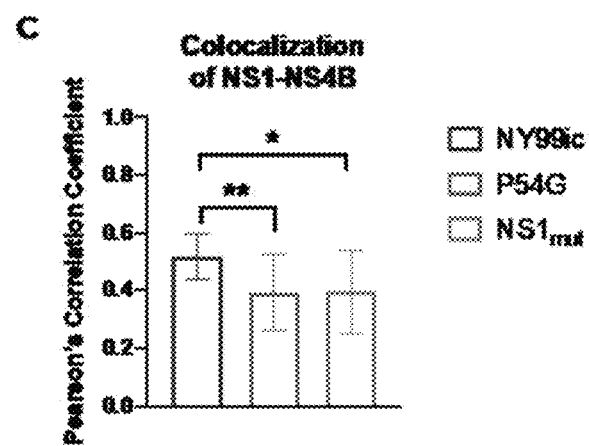

Since the P54G mutant was strongly attenuated in mice and had a stable genotype after cell culture passage, confocal microscopy was used to further investigate the mechanism of attenuation for this single site mutant. Virus-infected Vero cells were stained for both NS4B and NS1 since it is known that these two viral proteins interact [11]. Furthermore, an attenuated NS1 glycosylation site mutant (hereafter termed NS1$_{mut}$) that was used for NS1 immunostaining in previous studies [34] was used as an attenuated control virus. One day post infection, the P54G mutant had fewer infected cells than NY99ic (FIG. 8A), and this was expected based on the differences in infectivity titers (FIG. 3A). Cells infected with the P54G mutant, however, had significantly lower levels of NS4B (p=0.0002), but had similar staining of NS1 compared to NY99ic (FIG. 8B). Consistent with previous studies, the attenuated WNV NS1$_{mut}$ had lower levels of NS1 (p=0.006), but the staining of NS4B was similar to that in NY99ic infected cells (FIG. 8B). Pearson's correlation coefficient (PCC) was also calculated to compare colocalization of NS1 and NS4B in infected cells. For PCC, a value of 0 indicates no colocalization, whereas a value of 1 indicates perfect colocalization. At one dpi, all infected cells exhibited some degree of colocalization of NS1-NS4B, but both the NS4B-P54G mutant and the NS1$_{mut}$ had significantly less colocalization compared to NY99ic (p=0.004 and p=0.01, respectively) (FIG. 8C).

Figure 9A:
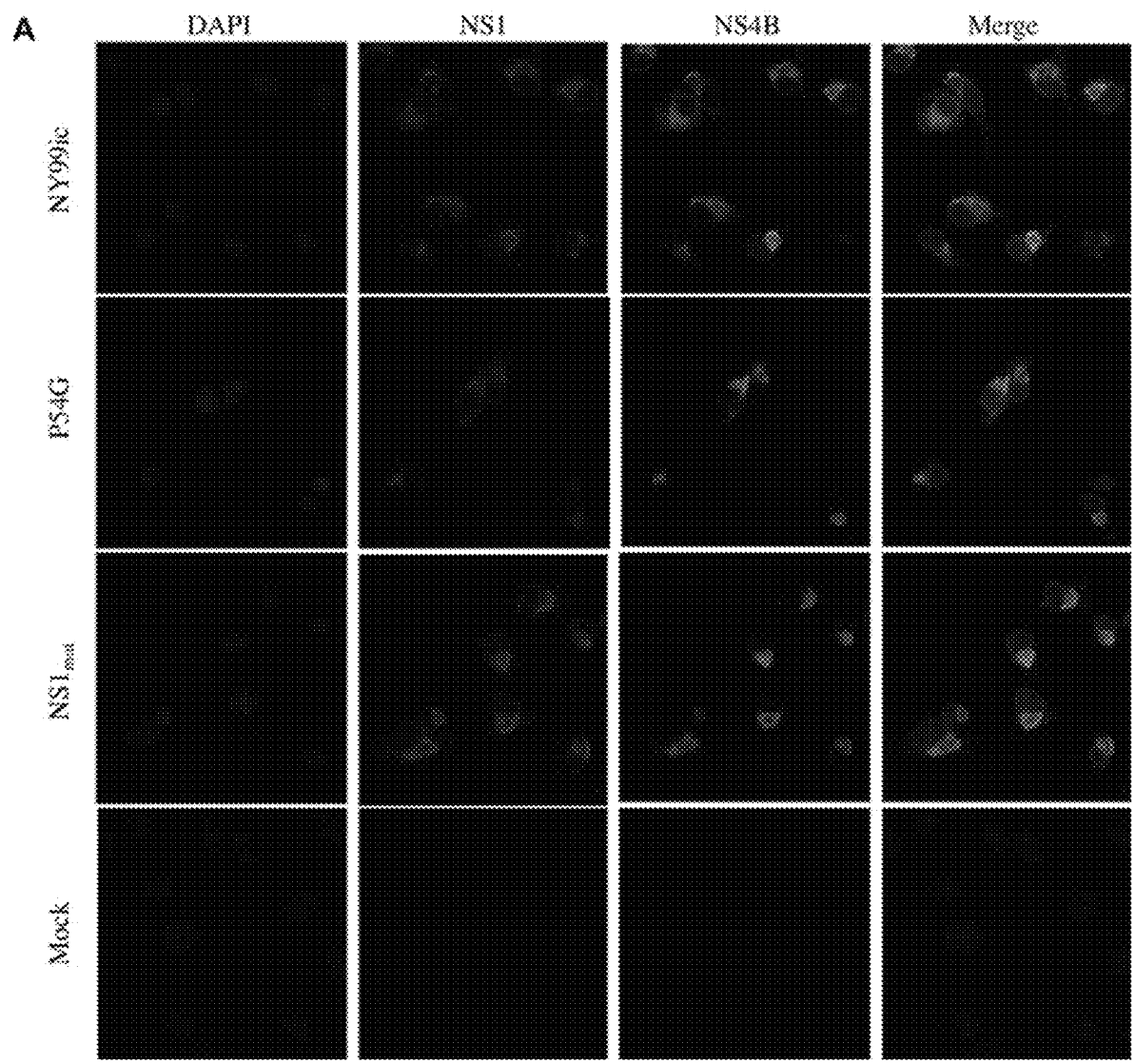
FIGS. 9A-9C. Attenuated WNV NS4B-P54G mutant exhibited lower levels of both NS4B and NS1 two days post infection. Vero cells were infected with a MOI of 0.1 of NY99ic, the NS4B-P54G mutant, a WNV NS1 glycosylation site mutant, or PBS as a mock infection, and fluorescence microscopy was performed two days post infection (FIG. 9A). Mean fluorescence intensity (FIG. 9B) and Pearson's correlation coefficient (FIG. 9B) were calculated on individual infected cells (n=19). Statistical difference in mean fluorescence intensity and colocalization were measured using a Kruskal-Wallis test with multiple comparisons to compare both mutants to NY99ic. *$p<0.05$, **$p<0.01$.
Figure 9B:
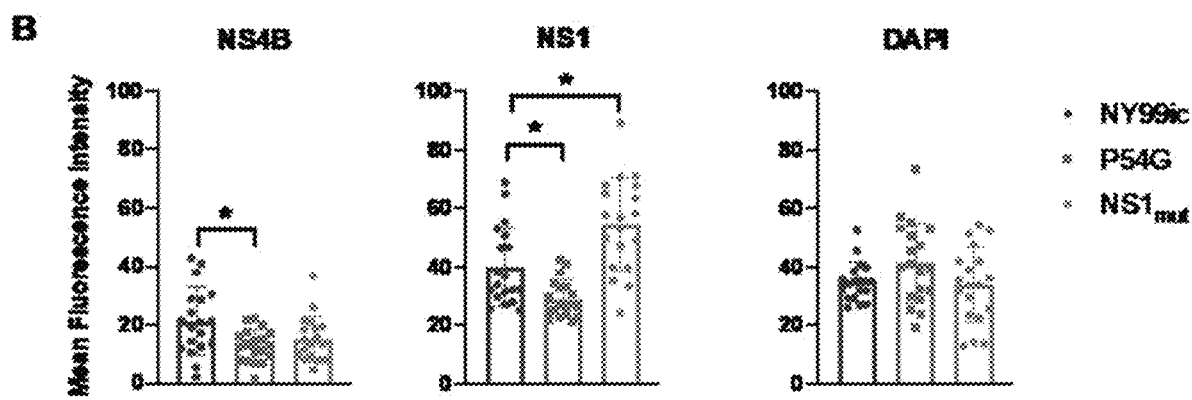
Figure 9C:
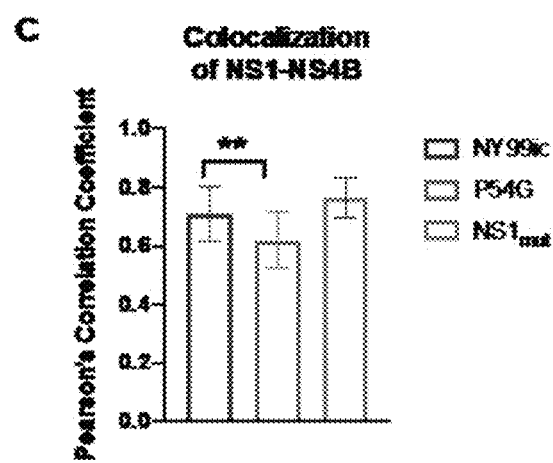

At two dpi, the P54G mutant still exhibited lower levels of NS4B compared to NY99ic (p=0.03), however, there were also significantly lower levels of NS1 staining (p=0.03) (FIG. 9A and FIG. 9B). In comparison, the NS1$_{mut}$ attenuated control had similar levels of NS4B as NY99ic and there was stronger NS1 staining compared to NY99ic (p=0.02) (FIG. 9A and FIG. 9B), which was in agreement with previous studies demonstrating that this mutant had a block of NS1 transport out of the endoplasmic reticulum [34]. At 48 hpi, NY99ic and the NS1$_{mut}$ had strong colocalization of NS1-NS4B, but the P54G mutant still exhibited a significant reduction in colocalization (p=0.009) (FIG. 9C).

Example 8—Genomic Diversity of a YFV Asibi NS4B-P52G Mutant

Figures 10A, 10B, 10C, 10D, 10E, 10F:
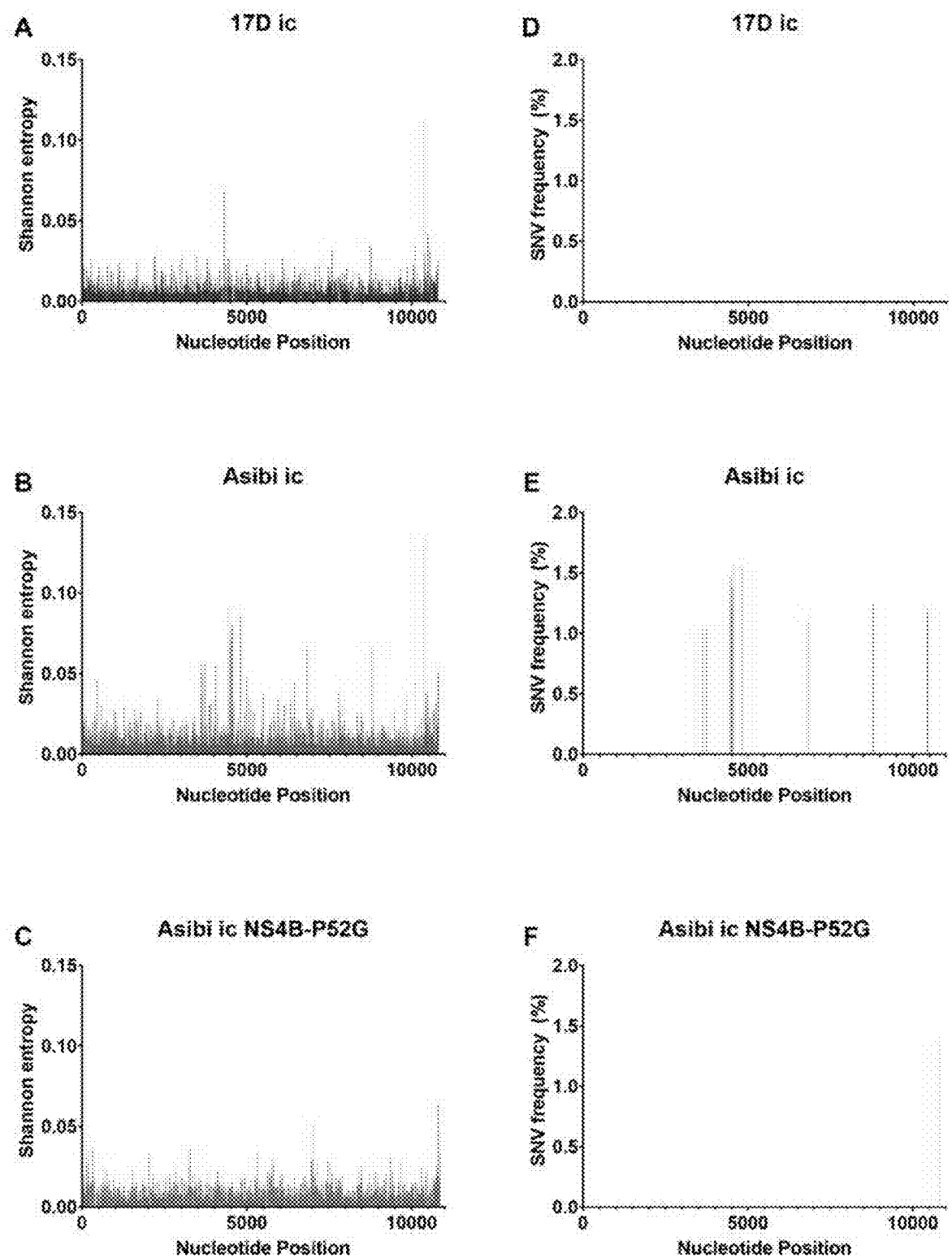
FIGS. 10A-10F. YFV NS4B-P52G mutation resulted in reduced quasispecies diversity compared to the parental Asibi strain. Shannon entropy (FIGS. 10A-10C) and SNV frequency (FIGS. 10D-10F) were utilized as two independent measurements of genomic diversity in the P0 unpassaged stocks of 17Dic, Asibi ic, and Asibi ic NS4B-P52G. YFV NS4B-P52G is homologous to WNV NS4B-P54G.

Since the WNV NS4B-P54 residue is highly conserved in the Flavivirus genus, the inventors hypothesized that the homologous mutation will also attenuate other pathogenic Flaviviruses. Therefore, the inventors investigated whether or not a YFV NS4B-P52G mutant (the equivalent residue to WNV NS4B-P54G) would demonstrate an attenuated genotype. A YFV NS4B-P52G mutant was generated based on site-directed mutagenesis of an infectious clone of the wild-type (WT) Asibi strain. The mutant genome was sequenced and had the correct mutation and no compensatory mutations. Genetic diversity (Shannon entropy and SNV frequency) of the YFV Asibi NS4B-P52G mutant was compared to the parent WT Asibi strain and an infectious clone (ic) of the live attenuated 17D vaccine strain, derived from WT strain Asibi. Previous studies demonstrated that YFV 17D had low genetic diversity compared to the virulent WT Asibi strain, which had higher levels of diversity more typical of an RNA virus [29,37]. Furthermore, the homogeneity of the 17D population is thought to contribute to viral attenuation by reducing the likelihood of reversion to virulence [38]. The coverage of the Asibi ic and YFV 17Dic sequences were down-sampled to resemble the depth of coverage of the NS4B-P52G mutant. The down-sampled coverage of sequencing reads for the Asibi ic, 17Dic, and NS4B-P52G mutant was 1426, 1436, and 1433, respectively. As expected, the Asibi ic exhibited multiple peaks of high entropy across the genome and 12 SNVs >1% frequency were detected (FIG. 10). In contrast, the 17Dic had fewer peaks of high entropy and had no detectable SNVs >1% frequency (FIG. 10). For both measurements of diversity, the YFV NS4B-P52G mutant more closely resembled the 17D ic. Specifically, the Shannon entropy of the mutant had few peaks of high entropy and had only two detectable SNVs >1% frequency (FIG. 10), supporting that the NS4B-P52G mutation induced changes to the YFV quasispecies that are characteristic of the attenuated YFV 17D vaccine strain [29,37,38].

Interestingly, for WNV the NS4B-P54G mutation generated an attenuated phenotype without reduction of genetic diversity compared to WT WNV, whereas, for YFV both the NS4B-P52G and 17D attenuated mutants were associated with loss of genetic diversity suggesting that attenuation of a neurotropic (brain) flavivirus is different than that of a viscerotropic (liver) flavivirus.

Example 9—Exemplary Methods

Cell Culture. Vero African Green Monkey kidney cells and A549 human alveolar epithelial cells were grown at 37° C. with 5% $CO_2$ in minimum essential media (MEM-Gibco) supplemented with 100 U/mL penicillin, 100 ug/mL streptomycin, 2 mM L-glutamine, 0.1 mM non-essential amino acids, and 8% fetal bovine serum (FBS).

Reverse Genetics. An infectious clone based on WNV strain NY99-flamingo382 was utilized as previously described [28]. Asibi and 17D YFV infectious clones were prepared as previously described [29]. Mutagenesis primers were designed for mutation of WNV NS4B residues P54A, P54G, as well as YFV NS4B P52G. Primer sequences are listed in Table 5.

TABLE 5

NS4B mutagenesis primers

| NS4B Mutation | Primer 1 | Primer 2 |
| --- | --- | --- |
| WNV-P54A (SEQ ID NO: 9 and 10) | acaacagcgg tcctcactgc cctgctaaag catttgatc | gatcaaatgc tttagcaggg cagtgaggac cgctgttgt |
| WNV-P54G (SEQ ID NO: 11 and 12) | Tgctttagca gtccagtgag gaccgctgtt gtcaca | tgtgacaaca gcggtcctca ctggactgct aaagca |
| YFV-P52G (SEQ ID NO: 17 and 18) | gatccagtgg tgcaacattc cagagagcat tgtaacaatg | cattgttaca atgctctctg gaatgttgca ccactggatc |

Mutagenesis was completed using the Agilent QuikChange II XL Site-Directed Mutagenesis kit (Cat. No. 200521) according to the manufacturer's protocol. After mutagenesis, plasmids were transformed into MC1061 competent E. coli cells and grown in 200 mL Luria broth (LB) with 100 ug/mL ampicillin. After growth for 14-16 hours, bacteria were pelleted and suspended in glucose-tris-EDTA buffer. Cells were lysed using 0.2 M NaOH/1% SDS, and lysis was neutralized using 3 M KOAc. After isopropanol precipitation, the plasmid was treated with RNAse A for 60 minutes, then purified using phenol:chloroform:isoamyl alcohol. The purified plasmid was ethanol precipitated, then desalted and concentrated using the QiaQuick PCR purification kit (Qiagen). Preparation, purification, and in vitro transcription were carried out for each clone as previously described [28]. Viruses were rescued in Vero cells between 4-6 days post transfection. WNV clones were passaged once in Vero cells to generate the stocks utilized for the experiments described below and P0 unpassaged YFV clones were utilized for genomic analysis described below.

Infectivity Titration. Infectivity titers were measured using plaque titration in 6-well cell culture dishes that were 90% confluent with Vero cells. Cells were washed with PBS and then ten-fold serial dilutions ($10^{-1}$-$10^{-6}$) of each virus were incubated on the cell monolayers for 30 minutes with rocking every 5 minutes. Following incubation, cells were overlaid with 4 mL of media containing 1% agarose and 1% MEM supplemented with 2% FBS, plates were incubated at 37° C. for two days (or at 41° C. for temperature sensitivity assays), and then and additional 2 mL of overlay containing 2% neutral red (Sigma) was added to each well. Plates were monitored for two days as plaques formed, and infectivity titers were calculated based upon the reciprocal dilution of plaque-containing wells.

Multiplication kinetics. Multiplication kinetics were undertaken using Vero and A549 cells at a multiplicity of infection (MOI) of 0.1. Infections were completed in duplicate flasks and virus was allowed to adsorb for 30 minutes at room temperature. Flasks were washed once with PBS, and then supplemented with MEM maintenance media containing 2% FBS. Cells were incubated at 37° C. for 4 days, and at 0, 24, 36, 48, 72, and either 84/96 hours post infection, two aliquots were collected from each flask for titration. Aliquots were centrifuged at 1,500 RPM 5 minutes to pellet cell debris, and then supernatants were stored at −80° C. until plaque titration.

Mouse virulence. Groups of outbred 4-week-old Swiss Webster mice (Taconic Farms, Germantown, NY) were used to investigate virus neuroinvasion. All viruses were inoculated via the intraperitoneal route (i.p.) into groups of five mice using an inoculum of 500 PFU, and mice were monitored for 36 days for signs of neurological disease. At 36 days post infection (dpi) surviving mice were challenged with an i.p. inoculum of $10^4$ PFU of NY99ic (≥1000 $LD_{50}$) and then monitored for 28 days post challenge. For viruses that were attenuated with the 500 PFU dose, studies were repeated using a high inoculum ranging from 520,000-39,000,000 PFU (dependent upon the infectivity titer).

Cytokine quantification. Cytokines were measured in cell culture supernatant of A549 cells at 36 hpi following infection of the cells with a MOI of 0.1. Supernatants were collected from cells infected with each of the NS4B mutants as well as NY99ic and mock infected cells. Samples were centrifuged at 1,500 RPM for 5 minutes to remove cell debris, and then stored at −80° C. until use. Supernatants were gamma irradiated to remove infectivity and then processed for multiplex assay according to the manufacturer's protocol using a Bio-Plex Pro Human Cytokine 27-plex Assay (Cat. No. M500KCAF0Y) and a Bio-Plex custom IFN-α/IFN-β assay. A Kruskal-Wallis ANOVA with Dunn's correction was utilized to compare each sample to NY99ic-infected cells.

Sequencing Analysis. RNA was extracted from Vero cell culture supernatant using the QiaAmp Viral RNA Kit (Qiagen). Paired-end reads were sequenced on the Illumina NextSeq 550 platform and Trimmomatic [30] was utilized to remove adapters and any sequences with a quality score below 30. The trimmed reads were aligned to the appropriate reference sequence (WNV NY99ic, YFV 17Dic, or YFV Asibi ic) using Bowtie2 with the very sensitive local parameter. All reads were sorted based on genome position and coordinate position using SAMtools, and PCR duplicates were marked and removed using Picard Tools (Broad Institute) with the optical duplicate pixel distance set to 0. Depth of coverage was measured with SAMtools. For the YFV 17Dic and Asibi ic, depth of coverage was randomly downsampled using Picard Tools. LoFreq was utilized to measure single nucleotide variants in the viral RNA populations [31]. Individual sequencing contigs were visualized in Tablet software (James Hutton Institute) [32]. The diversity indices for the YFV clones were calculated using the R package deepSNV (v. 1.32.0) to calculate nucleotide frequency at each position in the genome and Shannon entropy was calculated as previously described[33].

Fluorescence Microscopy. Vero cells were infected with a MOI of 0.1 of NY99ic, the NS4B-P54G mutant, a WNV NS1 glycosylation site mutant [34], or PBS as a mock infection. After 24 or 48 hpi, cells were seeded onto Teflon-coated microscope slides (Polysciences Cat. No. 18357-1). Cells were placed in the 37° C. incubator for approximately five hours to adhere and then they were fixed with a 1:1 acetone:methanol solution. Slides were stored at −20° C. until immunostaining. Prior to staining, slides were incubated in 5% normal goat serum/3% bovine serum albumin blocking buffer for 1 hour at room temperature (r.t.). Slides were washed twice with tris-buffered saline (TBS) then incubated with primary antibody for two hours at r.t. DENV NS4B monoclonal antibody 44-4-7 (kindly provided by Dr. Pei-Yong Shi) and a WNV NS1 polyclonal antibody (Genetex Cat. No. 132053) were diluted 1:500 to generate working stocks. Slides were washed twice with TBS prior to incubation with secondary antibodies (Invitrogen Cat. No. A-11001 and A-11011) for 1 hour at r.t. After washing three times with TBS, slides were incubated with 7 μg/mL DAPI for 5 minutes, and then washed again four times with TBS. Slides were mounted with Vectashield (Vector Laboratories Cat. No. H-1000) and stored at 4° C. overnight. Slides were imaged with a Zeiss LSM 880 confocal microscope using a 1.4 numerical aperture 63× oil immersion lens. Using ImageJ software, background fluorescence was subtracted uniformly from each image and mean fluorescence intensities and Pearson's correlation coefficients were calculated by drawing regions of interest around infected cells.

Statistical Analysis. ANOVA, Kruskal-Wallis tests, and calculations of standard deviation were all completed in GraphPad Prism v. 8.0.

Example 10—Yellow Fever Virus and Dengue Virus-4

Yellow fever virus (YFV) Asibi NS4B-P52G and Dengue virus-4 (DENV-4) NS4B-P47G Mutants. Since the WNV NS4B-P54 residue is highly conserved in the Flavivirus genus, the inventors contemplate that the homologous mutation will also attenuate other pathogenic flaviviruses. Demonstration of proof of principle in other flaviviruses include YFV as it genetically very different to WNV causing viscerotropic rather than neurotropic disease, and DENV-4 because it causes a febrile illness and is genetically different to both YFV and WNV.

It is shown that YFV NS4B-P52G mutant (the equivalent residue to WNV NS4B-P54G) was generated by site-directed mutagenesis of the WT Asibi strain (Asibi ic). Next Generation Sequencing (NGS) showed the mutant genome had the correct mutation and no compensatory mutations. Genetic diversity (Shannon entropy and SNV frequency) of Asibi NS4B-P52G was compared to the parent WT Asibi ic and to an ic of the 17D live attenuated vaccine strain (17D ic). YFV 17D has low genetic diversity compared to Asibi. Furthermore, the homogeneity of the 17D viral RNA population is thought to contribute to viral attenuation by reducing the likelihood of reversion to virulence. The coverage of the Asibi ic and 17Dic sequences were down-sampled to resemble the depth of coverage of the NS4B-P52G mutant. The down-sampled coverage of sequencing reads for the Asibi ic, 17Dic, and NS4B-P52G were 1426, 1436, and 1433, respectively. The Asibi ic exhibited multiple peaks of high entropy across the genome and 12 single nucleotide variants (SNVs) >1% frequency were detected. In contrast, 17Dic had fewer peaks of high entropy and had no SNVs >1% frequency. For both measurements of diversity, NS4B-P52G more closely resembled 17D ic. Specifically, the Shannon entropy of the mutant had few peaks of high entropy and had only 2 detectable SNVs >1% frequency, supporting that the NS4B-P52G mutation induced changes in genetic diversity that are characteristic of the 17D LAV, possibly via affecting the function of the RC.

YFV NS4B-P52G does not form plaques but does give cytopathic effect when used to infect monkey kidney Vero cells so it is possible to titrate the virus by an assay called 50% Tissue Culture infectious dose ($TCID_{50}$).

A DENV-4 NS4B-P47G mutant has been generated (the equivalent residue to WNV NS4B-P54G) by site-directed mutagenesis of an infectious clone of the wild-type DENV-4 strain 1036. The virus gave cytopathic effect post transfection.

REFERENCES

1. Chancey et al., *Biomed Res. Int.* 2015, 1-20.
2. Mann et al., *Int. J. Environ. Res. Public Health* 2013, 10, 5111-5129.
3. CDC West Nile Virus—Symptoms, Diagnosis, & Treatment. Available online.
4. CDC West Nile Virus—Statistics and Maps Available online.
5. Klema et al., *Viruses* 2015, 7, 4640-4656.
6. Brinton, *Viruses* 2013, 6, 13-53.
7. Zmurko et al., *Rev. Med Virol.* 2015, 25, 205-223.
8. Li et al., *BBA—Biomembr.* 2015, 1848, 3150-3157.
9. Li et al., *Angew. Chemie—Int. Ed* 2016, 55, 12068-12072.
10. Zou et al., *J. Virol.* 2014, 88, 3379-91.
11. Youn et al., *J. Virol.* 2012, 86, 7360-71.
12. Yu et al., *Virology* 2013, 446, 365-377.
13. Zou et al., *J. Virology* 2015, 89, 3471-3483.
14. Zou et al., *J. Virol.* 2015, 89, 3455-3470.
15. Kaufusi et al., *PLoS One* 2014, 9, e84040.
16. Munoz-Jordan et al., *J. Virol.* 2005, 79, 8004-8013.
17. Wang et al., *J. Virol.* 2005, 79, 1934-1942.
18. Kakumani et al., *J. Virol.* 2013, 87, 8870-8883.
19. Grant et al., *J. Virol.* 2011, 85, 7775-7787.
20. Pletnev et al., *Proc. Natl. Acad Sci.* 2002, 99, 3036-3041.
21. Orozco et al., *J. Gen. Virol.* 2012, 93, 2152-2157.
22. Dunster et al., *Virology* 1999, 318, 309-318.
23. Hahn et al., *Proc. Natl. Acad Sci. U.S.A.* 1987, 84, 2019-23.
24. Gromowski et al., *J. Virol.* 2015, 89, 6328-6337.
25. Wicker et al., *Virology* 2006, 349, 245-253.
26. Wicker et al., *Virology* 2012, 426, 22-33.
27. Davis et al., *Virology* 2004, 330, 342-350.
28. Beasley et al., *J. Virol.* 2005, 79, 8339-8347.
29. Collins et al., *MBio* 2018, 9, 1-13.
30. Bolger et al., *Bioinformatics* 2014, 30, 2114-2120.
31. Wilm et al., *Nucleic Acids Res.* 2012, 40, 11189-11201.
32. Milne et al., *Brief Bioinform.* 2012, 14, 193-202.
33. Nishijima et al., *PLoS One* 2012, 7, 1-10.
34. Whiteman et al., *J. Virol.* 2015, 89, 1474-1478.
35. Welte et al., *Vaccine* 2011, 29, 4853-4861.
36. Xie et al., *Vaccine* 2015, 33, 869-878.
37. Beck et al., *J Infect. Dis.* 2014, 209, 334-344.
38. Davis et al., *MBio* 2019, 10, 1-14.
39. Kim et al., *Protein Sci.* 1999, 8, 1492-1499.
40. Kumeta et al., *J. Cell Sci.* 2017, 131.
41. Xie et al., *Virology* 2014, 450-451, 250-257.

The invention claimed is:

1. An attenuated flavivirus genome comprising a NS4B gene segment encoding a mutant NS4B protein having an amino acid substitution analogous to an alanine or glycine substitution at proline 54 of the West Nile Virus (WNV) NS4B protein, SEQ ID NO: 19.

2. The attenuated flavivirus genome of claim 1, comprising one or more mutations in the gene segment encoding non-structural protein 1 (NS1), analogous to amino acids 792 to 1143 of SEQ ID NO: 2, the one or more mutations resulting in disruption of one or more glycosylation sites of the NS1 protein.

3. The attenuated flavivirus genome of claim 2, wherein the one or more mutations in the glycosylation sites of the NS1 protein is a substitution of one or more of wild-type amino acids asparagine 130, asparagine 131, or threonine 132 of NS1.

4. The attenuated flavivirus genome of claim 3, wherein the substitution of wild-type amino acids asparagine 130, asparagine 131, or asparagine 130 and asparagine 131 is a substitution of an asparagine residue with a polar amino acid.

5. The attenuated flavivirus genome of claim 4, wherein the polar amino acid is a glutamine residue.

6. The attenuated flavivirus genome of claim 3, wherein the substitution of amino acid threonine 132 is a substitution of the threonine residue with a nonpolar amino acid.

7. The attenuated flavivirus genome of claim 6, wherein the nonpolar amino acid is an alanine residue.

8. The attenuated flavivirus genome of claim 3, wherein the one or more mutations corresponding to one or more glycosylation sites of NS1 of the flavivirus further comprise a substitution of wild-type amino acid 175 of NS1, a substitution of wild-type amino acid 207 of NS1, or a substitution of wild-type amino acid 175 and amino acid 207 of NS1.

9. The attenuated flavivirus genome of claim 8, wherein the substitution of wild-type amino acid asparagine 175, wild-type amino acid asparagine 207, or wild-type amino acid asparagine 175 and wild-type amino acid asparagine 207 is a substitution of an asparagine residue with a nonpolar amino acid.

10. The attenuated flavivirus genome of claim 9, wherein the nonpolar amino acid is an alanine residue.

11. A nucleic acid construct encoding the genome of the attenuated flavivirus of claim 1.

12. The nucleic acid construct of claim 11, wherein the flavivirus is selected from the group consisting of West Nile virus, Japanese encephalitis virus, St. Louis encephalitis virus, tickborne encephalitis virus, Zika virus, dengue fever virus, and yellow fever virus (YFV).

13. The nucleic acid construct of claim 11, wherein the flavivirus is yellow fever virus (YFV).

14. The nucleic acid construct of claim 11, wherein the nucleic acid encoding the genome of the attenuated flavivirus further comprises one or more mutations corresponding to one or more glycosylation sites of non-structural protein 1 (NS1) of the flavivirus.

15. An immunogenic composition comprising the attenuated flavivirus encoded by claim 1 and a pharmaceutically acceptable carrier or diluent.

16. A method of inducing an immune response in a subject comprising administering an effective amount of the composition of claim 15 to the subject.

17. The method of claim 16, wherein the subject is a non-human primate, a human, a horse, or a bird.

18. A vaccine composition comprising the attenuated flavivirus genome of claim 1 or an attenuated flavivirus encoded by the attenuated genome of claim 1 and a pharmaceutically acceptable carrier or diluent.

19. The attenuated flavivirus genome of claim 1, wherein the flavivirus is selected from the group consisting of West Nile virus, Japanese encephalitis virus, St. Louis encephalitis virus, tickborne encephalitis virus, Zika virus, dengue fever virus, and yellow fever virus (YFV).

* * * * *